(12) United States Patent
Girijavallabhan et al.

(10) Patent No.: US 9,150,603 B2
(45) Date of Patent: *Oct. 6, 2015

(54) 2'-CYANO SUBSTITUTED NUCLEOSIDE DERIVATIVES AND METHODS OF USE THEREOF USEFUL FOR THE TREATMENT OF VIRAL DISEASES

(75) Inventors: Vinay Girijavallabhan, Whippany, NJ (US); F. George Njoroge, Carmel, IN (US); Stephane Bogen, Somerset, NJ (US); Angela Kerekes, Plainfield, NJ (US); Frank Bennett, Cranford, NJ (US); Ying Huang, Berkeley Heights, NJ (US); Latha Nair, Edison, NJ (US); Dmitri Pissarnitski, Scotch Plains, NJ (US); Vishal Verma, San Francisco, CA (US); Qun Dang, Westfield, NJ (US); Ian Davies, Princeton, NJ (US); David B. Olsen, Lansdale, PA (US); Andrew Stamford, Chatham, NJ (US); Joseph P. Vacca, Telford, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/111,688

(22) PCT Filed: Apr. 11, 2012

(86) PCT No.: PCT/US2012/033028
§ 371 (c)(1),
(2), (4) Date: Jan. 30, 2014

(87) PCT Pub. No.: WO2012/142093
PCT Pub. Date: Oct. 18, 2012

(65) Prior Publication Data
US 2014/0161770 A1    Jun. 12, 2014

Related U.S. Application Data

(60) Provisional application No. 61/475,071, filed on Apr. 13, 2011.

(51) Int. Cl.
| | | |
|---|---|---|
| C07H 19/06 | (2006.01) |
| C07H 19/20 | (2006.01) |
| C07H 19/10 | (2006.01) |
| C07H 19/12 | (2006.01) |
| C07H 19/16 | (2006.01) |
| C07H 19/04 | (2006.01) |
| C07H 19/207 | (2006.01) |
| C07H 19/11 | (2006.01) |
| C07H 19/213 | (2006.01) |
| A61K 31/7056 | (2006.01) |
| A61K 31/7068 | (2006.01) |
| A61K 31/7076 | (2006.01) |
| A61K 45/06 | (2006.01) |

(52) U.S. Cl.
CPC ............ *C07H 19/16* (2013.01); *A61K 31/7056* (2013.01); *A61K 31/7068* (2013.01); *A61K 31/7076* (2013.01); *A61K 45/06* (2013.01); *C07H 19/06* (2013.01); *C07H 19/10* (2013.01); *C07H 19/11* (2013.01); *C07H 19/20* (2013.01); *C07H 19/207* (2013.01); *C07H 19/213* (2013.01)

(58) Field of Classification Search
None
See application file for complete search history.

(56) References Cited

U.S. PATENT DOCUMENTS

| | | | |
|---|---|---|---|
| 3,480,613 | A | 11/1969 | Walton |
| 1,187,824 | A | 4/1970 | Walton |
| 4,211,773 | A | 7/1980 | Lopez et al. |
| 4,666,892 | A | 5/1987 | Fox et al. |
| 4,808,614 | A | 2/1989 | Hertel |
| 5,672,594 | A | 9/1997 | Weis et al. |
| 5,837,852 | A | 11/1998 | Chung et al. |
| 5,977,061 | A | 11/1999 | Holy et al. |
| 6,063,628 | A | 5/2000 | Loeb et al. |

(Continued)

FOREIGN PATENT DOCUMENTS

| | | |
|---|---|---|
| FR | 1581628 | 9/1969 |
| GB | 1209654 | 10/1970 |

(Continued)

OTHER PUBLICATIONS

Mehta, et al., Biochemistry, 1976, pp. 4329-4333, vol. 15, No. 19.

(Continued)

*Primary Examiner* — Traviss C McIntosh, III
(74) *Attorney, Agent, or Firm* — Jeffrey P. Bergman; Laura M. Ginkel

(57) ABSTRACT

The present invention relates to 2'-Cyano Substituted Nucleoside Derivatives of Formula (I): and pharmaceutically acceptable salts thereof, wherein B, X, R¹, R² and R³ are as defined herein. The present invention also relates to compositions comprising at least one 2'-Cyano Substituted Nucleoside Derivative, and methods of using the 2'-Cyano Substituted Nucleoside Derivatives for treating or preventing HCV infection in a patient.

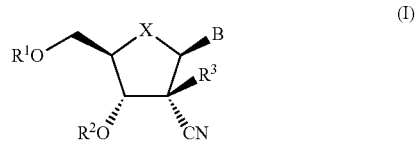

(I)

21 Claims, No Drawings

(56) References Cited

U.S. PATENT DOCUMENTS

| | | | |
|---|---|---|---|
| 6,110,901 | A | 8/2000 | Gluzman et al. |
| 6,348,587 | B1 | 2/2002 | Schinazi et al. |
| 6,777,395 | B2 | 8/2004 | Bhat et al. |
| 6,784,161 | B2 | 8/2004 | Ismaili et al. |
| 6,812,219 | B2 | 11/2004 | LaColla et al. |
| 6,914,054 | B2 | 7/2005 | Sommadossi et al. |
| 7,101,861 | B2 | 9/2006 | Sommadossi et al. |
| 7,105,499 | B2 | 9/2006 | Carroll et al. |
| 7,112,600 | B1 | 9/2006 | Hashimoto et al. |
| 7,125,855 | B2 | 10/2006 | Bhat et al. |
| 7,157,441 | B2 | 1/2007 | Sommadossi et al. |
| 7,169,766 | B2 | 1/2007 | Sommadossi et al. |
| 7,202,224 | B2 | 4/2007 | Eldrup et al. |
| 7,405,204 | B2 | 7/2008 | Roberts et al. |
| 7,429,572 | B2 | 9/2008 | Clark |
| 7,973,013 | B2 | 7/2011 | Cho et al. |
| 2002/0019363 | A1 | 2/2002 | Ismaili et al. |
| 2002/0053096 | A1 | 5/2002 | Hirschberg et al. |
| 2002/0055483 | A1 | 5/2002 | Watanabe et al. |
| 2002/0147160 | A1 | 10/2002 | Bhat et al. |
| 2002/0198171 | A1 | 12/2002 | Schinazi et al. |
| 2003/0007946 | A1 | 1/2003 | Narang et al. |
| 2003/0013089 | A1 | 1/2003 | Fisher et al. |
| 2003/0050229 | A1 | 3/2003 | Sommadossi et al. |
| 2003/0060400 | A1 | 3/2003 | LaColla et al. |
| 2004/0072788 | A1 | 4/2004 | Bhat et al. |
| 2005/0272676 | A1 | 12/2005 | Bhat et al. |
| 2006/0205686 | A1 | 9/2006 | Bhat et al. |
| 2006/0241064 | A1 | 10/2006 | Roberts et al. |
| 2007/0042988 | A1 | 2/2007 | Klumpp et al. |
| 2007/0259832 | A1 | 11/2007 | Cook et al. |
| 2007/0265222 | A1 | 11/2007 | MacCoss et al. |
| 2007/0275912 | A1 | 11/2007 | Bhat et al. |
| 2010/0021425 | A1 | 1/2010 | Butler et al. |
| 2010/0104532 | A1 | 4/2010 | Chen et al. |
| 2010/0297079 | A1 | 11/2010 | Almond et al. |
| 2010/0298257 | A1 | 11/2010 | Ross et al. |
| 2010/0316594 | A1 | 12/2010 | Sommadossi et al. |
| 2012/0009147 | A1 | 1/2012 | Cho et al. |
| 2012/0237480 | A1 | 9/2012 | Or et al. |

FOREIGN PATENT DOCUMENTS

| | | | |
|---|---|---|---|
| WO | 9318051 | | 9/1993 |
| WO | 9405687 | | 3/1994 |
| WO | 9616184 | A2 | 4/1998 |
| WO | 9943691 | | 9/1999 |
| WO | 0132153 | | 5/2001 |
| WO | 0160315 | | 8/2001 |
| WO | 0179246 | | 10/2001 |
| WO | 0190121 | | 11/2001 |
| WO | 0192282 | | 12/2001 |
| WO | 0218404 | | 3/2002 |
| WO | 0232920 | A2 | 4/2002 |
| WO | 0248165 | A2 | 6/2002 |
| WO | 0248165 | A3 | 6/2002 |
| WO | 02069903 | A2 | 9/2002 |
| WO | 02069903 | A3 | 9/2002 |
| WO | 02094289 | A1 | 11/2002 |
| WO | 02100354 | A2 | 12/2002 |
| WO | 02100354 | A3 | 12/2002 |
| WO | 02100415 | A2 | 12/2002 |
| WO | 03000200 | A2 | 1/2003 |
| WO | 03000713 | A1 | 1/2003 |
| WO | 03015798 | A1 | 2/2003 |
| WO | 03026589 | A2 | 4/2003 |
| WO | 03026675 | A1 | 4/2003 |
| WO | 03051881 | | 6/2003 |
| WO | 03051896 | | 6/2003 |
| WO | 03051897 | | 6/2003 |
| WO | 03051898 | | 6/2003 |
| WO | 03051899 | | 6/2003 |
| WO | 03062255 | | 7/2003 |
| WO | 03093290 | A2 | 11/2003 |
| WO | 2004003000 | A2 | 1/2004 |
| WO | 2004080989 | | 9/2004 |

OTHER PUBLICATIONS

CAPLUS Database, Accession No. 129:156753, Abstract of Ilyin et al., "Ribavirin Inhibits Protein Synthesis and Cell Proliferation Induced by Mitogenic Factors in Promary Human and Rat Hepatocytes", Hepatology (Philadelphia), 1998, vol. 27, pp. 1687-1694.

CAPLUS Database, Accession No. 1980:599421, Abstract of Harada et al., "The Nucleotide Sequence of Nuclear 4.8S RNA of Mouse Cells", Biochem. Biophys. Res. Commun. 1980, vol. 95, pp. 1332-1340.

Beers, et al., "The Merck Manual of Diagnosis and Therapy", 1999, Seventeenth Edition, pp. 377-386, 1132, 1280.

Chu, et al. "9-Deazaadenosine—A New Potent antitumor Agent", Biochemical Pharmacology, 1984, vol. 33, pp. 1229-1234.

Clark, et al., "Synthesis and Antiviral Activity of 2'-Deoxy-2'-Fluoro-2'-C-Methyl Purine Nucleosides as Inhibitors of Hepatitits C Virus RNA Replication", Bioorganic & Medicinal Chemistry Letters, 2006, vol. 16, pp. 1712-1715.

Dee Nord, et al., "Inhibition of Orotidylate Decarboxylase by 4(5H)-Oxo-1-B-D-Ribofuranosylpyrazolo[3,4-d] Pyrimidine-3-Thiocarboxamide (APR-TC) in B Lymphoblasts", Biochemical Pharmacology, 1988, vol. 37, pp. 4697-4705.

Eldrup, et al., "Structure—Activity Relationship of Purine Ribonucleosides for Inhibition of Hepatitis C Virus RNA-Dependent RNA Polymerase", Journal of Medicinal Chemistry, 2004, vol. 47, pp. 2283-2295.

Flockhart, et al., "ATP Analog Specificity of gAMP-Dependent Protein Kinase, cGMP-Dependent Protein Kinase, and Phosphorylase Kinase", European Journal of Biochemistry, 1984, vol. 140, pp. 289-295.

Gupta, et al., "Genetic and Biochemical Studies on Mutants of CHO Cells Resistant to 7-Deazapurine Nucleosides: Differences in the Mechanisms of Action of Toyocamycin and Tubercidin", Biochemical and Biophysical Research Communications, 1984, vol. 120, pp. 88-95.

Hoofnagle, "Therapy of Viral Hepatitis", Digest, 1998, vol. 59, pp. 563-578.

Olsen, et al., A 7-Deaza-Adenosine Analog is a Potent and Selective Inhibitor of Hepatitis C Virus Replication With Excellent Pharmacokinetic Properties, Antimicrobial Agents and Chemotherapy, 2004, vol. 48, pp. 3944-3953.

Ono, et al., "Oligodeoxynucleotides Containing 7-Deazaadenine: Synthesis and Recognition of Restriction Endonucleases", Eleventh Symposium on Nucleic Acids Chemistry, Tokyo, Japan, Nov. 1-2, 1983, published in Nucleic Acids Symposium Series No. 12, pp. 67-70.

Seela, et al., "7-(B-D-Arabinofuranosyl)-2,4-Dichlor-7H-Pyrrolo[2,3-d]Pyrimidin—Synthese, Selektiver Halogenaustausch und ElnfluB Glyconischer Schutzgruppen Auf Die Reaktivitat des Aglycons", Liebigs Annalen der Chemie, 1984, pp. 722-733.

Smee, et al., "7-Novel Pyrazolo[3,4-d]Pyrimidine Nucleoside Analog with Broad-Spectrum Antiviral Activity", Antimicrobial Agents and Chemotherapy, 1987, vol. 31, pp. 1535-1541.

Wolf., et al., "New 2'-C-Branched-Chain Sugar Nucleoside Analogs with Potential Activiral or Antitumor Activity", Synthesis, 1992, pp. 773-778.

HCAPLUS Accession No. 1958:89150, Abstract for Yukino, "Mouse Hepatitis Virus, II. Histopathological Studies of Infected Mouse Liver with Correlation to the Level of Blood Sugar and Liver Glycogen", Virus (Osaka), 1958, 8, pp. 67-72.

(56) References Cited

OTHER PUBLICATIONS

Bailly et al., "Treatment of HCV Liver disease by Recombinant Interferon Alpha", Nephrology Dialysis Transplantation, 1996, vol. 11, Suppl. 4, pp. 56-57.

Abbruzzese, James L., et al., Phase I trial of 1-(2-deoxy-2-'fluoro-1-beta-D-arabinofuranosyl)-5-methyluracil (FMAU) terminated by severe neurologic toxicity, Investigational New Drugs, 1989, vol. 7, pp. 195-201.

Chu, Chung, K., et al., "Use of 2'-Fluoro-5-Methyl-B-L-Arabinofuranosyluracil as a Novel Antiviral Agent for Hepatitis B Virus and Epstein-Barr Virus", Antimicrobial Agents and Chemotherapy, 1995, vol. 39, No. 4., pp. 979-981.

Harada, Kazuho, et al., "Nucleosides, 139, Synthesis and Antictomegalovirus and Antiherpes Simplex Virus Activity of 5-Modified Analogues of 2'-Fluoroarabinosylpyrimidine Nucleosides", J. Med. Chem., 198, vol. 30, pp. 226-229.

Merluzzi, V.J., et al., "Comparison of 2'-Fluoro-Arabinosyl Pyrimidine Nucleosides and 1-B-D-Arabinofuranosylcytosine on Immunological Parameters In Vitro", Int. J. Immunopharmacology, 1983, vol. 5, No. 5, pp. 421-425.

AN 1990:135032 for Savochkina, et al, Molekulyarnaya Biologiya (Moscow), 1989, vol. 23, No. 6.

2'-CYANO SUBSTITUTED NUCLEOSIDE DERIVATIVES AND METHODS OF USE THEREOF USEFUL FOR THE TREATMENT OF VIRAL DISEASES

CROSS-REFERENCE TO RELATED APPLICATIONS

This application is the national stage application under 35 U.S.C. 371 of International Patent Application No. PCT/US2012/033028, filed Apr. 11, 2012, which claims priority to U.S. Provisional Patent Application No. 61/475,071, filed Apr. 13, 2011. Each of the aforementioned PCT and priority applications is incorporated by reference in its entirety.

FIELD OF THE INVENTION

The present invention relates to 2'-Cyano Substituted Nucleoside Derivatives, compositions comprising at least one 2'-Cyano Substituted Nucleoside Derivative, and methods of using the 2'-Cyano Substituted Nucleoside Derivatives for treating or preventing HCV infection in a patient.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The state of the art in the treatment of HCV infection has been reviewed, and reference is made to the following publications: B. Dymock, et al., "Novel approaches to the treatment of hepatitis C virus infection," *Antiviral Chemistry & Chemotherapy*, 11:79-96 (2000); H. Rosen, et al., "Hepatitis C virus: current understanding and prospects for future therapies," *Molecular Medicine Today*, 5:393-399 (1999); D. Moradpour, et al., "Current and evolving therapies for hepatitis C," *European J. Gastroenterol. Hepatol.*, 11:1189-1202 (1999); R. Bartenschlager, "Candidate Targets for Hepatitis C Virus-Specific Antiviral Therapy," *Intervirology*, 40:378-393 (1997); G. M. Lauer and B. D. Walker, "Hepatitis C Virus Infection," *N. Engl. J. Med.*, 345:41-52 (2001); B. W. Dymock, "Emerging therapies for hepatitis C virus infection," *Emerging Drugs*, 6:13-42 (2001); and C. Crabb, "Hard-Won Advances Spark Excitement about Hepatitis C," *Science*, 06-507 (2001); the contents of all of which are incorporated by reference herein in their entirety.

Different approaches to HCV therapy have been taken, which include the inhibition of viral serine proteinase (NS3 protease), helicase, and RNA-dependent RNA polymerase (NS5B), and the development of a vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. NS5B polymerase is therefore considered to be an essential component in the HCV replication complex [see K. Ishi, et al., "Expression of Hepatitis C Virus NS5B Protein: Characterization of Its RNA Polymerase Activity and RNA Binding," *Hepatology*, 29:1227-1235 (1999) and V. Lohmann, et al., "Biochemical and Kinetic Analyses of NS5B RNA-Dependent RNA Polymerase of the Hepatitis C Virus," *Virology*, 249:108-118 (1998)]. Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in M. P. Walker et al., "Promising candidates for the treatment of chronic hepatitis C," *Expert Opin. Invest. Drugs*, 12:1269-1280 (2003) and in P. Hoffmann et al., "Recent patents on experimental therapy for hepatitis C virus infection (1999-2002)," *Expert Opin. Ther. Patents*, 13:1707-1723 (2003). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.*, 47:2283-2295 (2004).

There is a continuing need for structurally diverse nucleoside derivatives as inhibitors of HCV polymerase as therapeutic approaches for HCV therapy. This invention responds to that need.

SUMMARY OF THE INVENTION

In one aspect, the present invention provides Compounds of Formula (I):

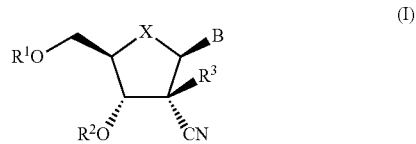

(I)

and pharmaceutically acceptable salts thereof,
wherein:
X is O, S or $CH_2$;
B is a natural or non-natural purine or pyrimidine base, or B is selected from one of the following groups:

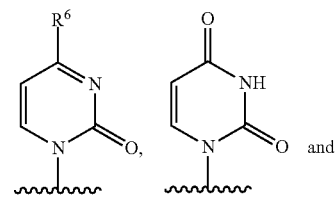

and

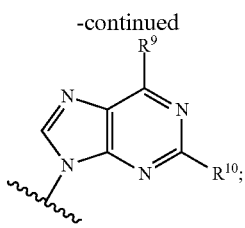

Y is N or —C(R$^{19}$)—;
R$^1$ is H,

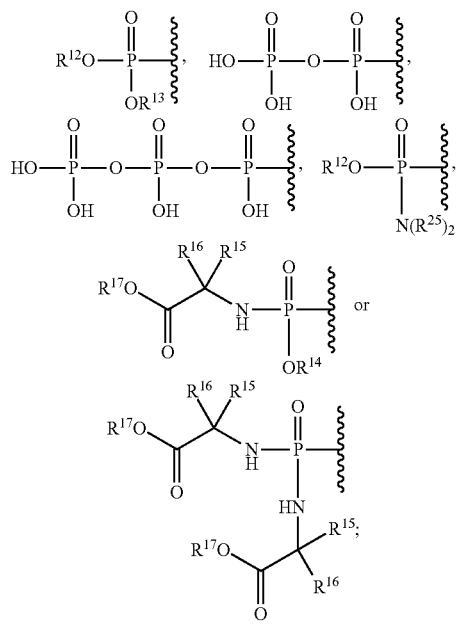

R$^2$ is H or

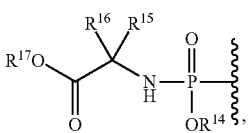

or R$^1$ and R$^2$ join to form a group having the formula:

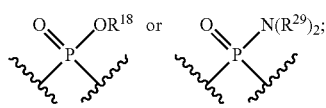

R$^3$ is C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl or C$_3$-C$_7$ cycloalkyl;

R$^4$, R$^5$, R$^7$ and R$^8$ are each independently H, C$_1$-C$_6$ alkyl, C$_1$-C$_6$ haloalkyl, C$_1$-C$_6$ hydroxyalkyl, halo, —OR$^{20}$, —SR$^{20}$ or —N(R$^{20}$)$_2$;

R$^6$, R$^9$ and R$^{10}$ are each independently selected from H, C$_1$-C$_6$ alkyl, C$_2$-C$_6$ alkenyl, C$_2$-C$_6$ alkynyl, C$_3$-C$_7$ cycloalkyl, 5- or 6-membered monocyclic heteroaryl, 9- or 10-membered bicyclic heteroaryl, halo, —OR$^{20}$, —SR$^{20}$, —S(O)R$^{20}$, —S(O)$_2$R$^{10}$, —S(O)$_2$N(R$^{20}$)$_2$, —NHC(O)OR$^{20}$, —NHC(O)N(R$^{20}$)$_2$, C$_1$-C$_6$ haloalkyl, C$_1$-C$_6$ hydroxyalkyl, —O—(C$_1$-C$_6$ haloalkyl), —CN, —NO$_2$, —N(R$^{20}$)$_2$, —NH(C$_1$-C$_6$ alkylene)-(5- or 6-membered monocyclic heteroaryl), —NH(C$_1$-C$_6$ alkylene)-(9- or 10-membered bicyclic heteroaryl), —C(O)R$^{20}$, —C(O)OR$^{20}$, —C(O)N(R$^{20}$)$_2$ and —NHC(O)R$^{20}$, wherein said C$_2$-C$_6$ alkenyl group and said C$_2$-C$_6$ alkynyl group can be optionally substituted a halo group;

R$^{12}$ is H or —(C$_1$-C$_6$ alkylene)-T-R$^{21}$;

R$^{13}$ is H or —(C$_1$-C$_6$ alkylene)-T-R$^{21}$, or R$^{12}$ and R$^{13}$ can join to form a C$_2$-C$_4$ alkylene group between the oxygen atoms that R$^{12}$ and R$^{13}$ are attached to, wherein said C$_2$-C$_4$ alkylene group is substituted with at least one C$_6$-C$_{10}$ aryl group;

R$^{14}$ is H, C$_6$-C$_{10}$ aryl, 5- or 6-membered monocyclic heteroaryl or 9- or 10-membered bicyclic heteroaryl, wherein said C$_6$-C$_{10}$ aryl group, said 5- or 6-membered monocyclic heteroaryl group and said 9- or 10-membered bicyclic heteroaryl group can be optionally substituted with R$^{22}$;

R$^{15}$ is H, C$_1$-C$_6$ alkyl, C$_3$-C$_7$ cycloalkyl, phenyl or benzyl, wherein said C$_1$-C$_6$ alkyl can be optionally substituted with a group selected from halo, —OR$^{20}$, —SR$^{20}$, guanidino, —N(R$^{20}$)$_2$, —C(O)OR$^{20}$, —C(O)N(R$^{20}$)$_2$, —NHC(O)R$^{20}$, 5- or 6-membered monocyclic heteroaryl and 9- or 10-membered bicyclic heteroaryl, and wherein said phenyl group and said benzyl group can be optionally substituted with up to 2 groups, each independently selected from C$_1$-C$_6$ alkyl, halo and —OR$^{20}$;

R$^{16}$ is H, C$_1$-C$_6$ alkyl, C$_3$-C$_7$ cycloalkyl, phenyl or benzyl, wherein said C$_1$-C$_6$ alkyl can be optionally substituted with a group selected from halo, —OR$^{20}$, —SR$^{20}$, guanidino, —N(R$^{20}$)$_2$, —C(O)OR$^{20}$, —C(O)N(R$^{20}$)$_2$, —NHC(O)R$^{20}$, 5- or 6-membered monocyclic heteroaryl and 9- or 10-membered bicyclic heteroaryl, and wherein said phenyl group and said benzyl group can be optionally substituted with up to 2 groups, each independently selected from C$_1$-C$_6$ alkyl, halo and —OR$^{20}$;

R$^{17}$ is H, C$_1$-C$_{20}$ alkyl, C$_2$-C$_{20}$ alkenyl, —(C$_1$-C$_3$ alkylene)$_m$-(C$_3$-C$_7$ cycloalkyl), —(C$_1$-C$_3$ alkylene)$_m$-(C$_6$-C$_{10}$ aryl) or adamantyl, wherein said C$_1$-C$_{20}$ alkyl group, said C$_2$-C$_{20}$ alkenyl group, said C$_6$-C$_{10}$ aryl group and said adamantyl group can be optionally substituted with up to three groups, each independently selected from halo, —OR$^{20}$, —C(O)OR$^{20}$, CN, NO$_2$, C$_1$-C$_6$ haloalkyl, C$_1$-C$_6$ hydroxyalkyl, C$_3$-C$_7$ cycloalkyl, C$_6$-C$_{10}$ aryl, 5- or 6-membered monocyclic heteroaryl, 9- or 10-membered bicyclic heteroaryl, —N(R$^{20}$)$_2$, —C(O)N(R$^{20}$)$_2$—SR$^{20}$, —S(O)R$^{20}$, —S(O)$_2$R$^{20}$, —S(O)$_2$N(R$^{20}$)$_2$, —NHC(O)R$^{20}$, —NHC(O)OR$^{20}$ and —NHC(O)N(R$^{20}$)$_2$ and;

R$^{18}$ is H, C$_1$-C$_6$ alkyl, C$_3$-C$_7$ cycloalkyl, —(C$_1$-C$_3$ alkylene)$_m$-C$_6$-C$_{10}$ aryl, 5- or 6-membered monocyclic heteroaryl, 9- or 10-membered bicyclic heteroaryl or:

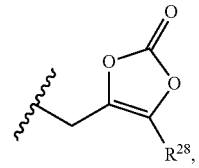

wherein said C$_6$-C$_{10}$ aryl group, said 5- or 6-membered monocyclic heteroaryl group and said 9- or 10-membered bicyclic heteroaryl group can be optionally substituted with up to five groups, each independently selected from C$_1$-C$_6$ alkyl, C$_2$-C$_6$ alkenyl, C$_2$-C$_6$ alkynyl, halo, —OR$^{20}$, —SR$^{20}$, $C_1$-$C_6$ haloalkyl, $C_1$-$C_6$ hydroxyalkyl, —O—($C_1$-$C_6$ haloalkyl), —CN, —NO$_2$, —N(R$^{20}$)$_2$, —C(O)OR$^{20}$, —C(O)N(R$^{20}$)$_2$ and —NHC(O)R$^{20}$;

R$^{19}$ is H, $C_1$-$C_6$ alkyl, $C_1$-$C_6$ haloalkyl, $C_1$-$C_6$ hydroxyalkyl, halo, —OR$^{20}$, —SR$^{20}$, N(R$^{20}$)$_2$, $C_3$-$C_7$ cycloalkyl, $C_6$-$C_{10}$ aryl, 5- or 6-membered monocyclic heteroaryl or 9- or 10-membered bicyclic heteroaryl;

each occurrence of R$^{20}$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -(5- or 6-membered monocyclic heteroaryl group or said 9- or 10-membered bicyclic heteroaryl group can be optionally substituted with R$^{26}$;

each occurrence of R$^{21}$ is independently H, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_7$ cycloalkyl, $C_3$-$C_7$ cycloalkenyl, 5- or 6-membered monocyclic heteroaryl, 9- or 10-membered bicyclic heteroaryl, —OR$^{20}$, —O—($C_1$-$C_6$ haloalkyl) or —N(R$^{20}$)$_2$, wherein said $C_2$-$C_6$ alkenyl group, said $C_2$-$C_6$ alkynyl group, said $C_3$-$C_7$ cycloalkyl group, said $C_3$-$C_7$ cycloalkenyl group, said $C_6$-$C_{10}$ aryl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —OR$^{20}$, —SR$^{20}$, $C_1$-$C_6$ haloalkyl, $C_1$-$C_6$ hydroxyalkyl, —O—($C_1$-$C_6$ haloalkyl), —CN, —NO$_2$, —N(R$^{20}$)$_2$, —C(O)R$^{20}$, —C(O)OR$^{20}$, —C(O)N(R$^{20}$)$_2$ and —NHC(O)R$^{20}$;

R$^{22}$ represents from one to five substituent groups, each independently selected from $C_1$-$C_6$ alkyl, halo, —OR$^{20}$, —SR$^{20}$, $C_1$-$C_6$ haloalkyl, $C_1$-$C_6$ hydroxyalkyl, —O—($C_1$-$C_6$ haloalkyl), —CN, —NO$_2$, —N(R$^{20}$)$_2$, —C(O)OR$^{20}$, —C(O)N(R$^{20}$)$_2$ and —NHC(O)R$^{20}$, or any two R$^{22}$ groups on adjacent ring carbon atoms can combine to form —O—R$^{23}$—O—;

R$^{23}$ is —[C(R$^{24}$)$_2$]$_n$—;

each occurrence of R$^{24}$ is independently H or $C_1$-$C_6$ alkyl;

each occurrence of R$^{25}$ is independently H, $C_1$-$C_6$ alkyl, $C_2$-$C_6$ alkenyl, $C_2$-$C_6$ alkynyl, $C_3$-$C_7$ cycloalkyl, —($C_1$-$C_3$ alkylene)$_m$-($C_6$-$C_{10}$ aryl), 4 to 7-membered heterocycloalkyl, 5- or 6-membered monocyclic heteroaryl or 9- or 10-membered bicyclic heteroaryl, wherein said $C_1$-$C_6$ alkyl group, said $C_2$-$C_6$ alkenyl group, said $C_2$-$C_6$ alkynyl group, said $C_3$-$C_7$ cycloalkyl group, said $C_6$-$C_{10}$ aryl group, said 4 to 7-membered heterocycloalkyl group, said -(5- or 6-membered monocyclic heteroaryl group or said 9- or 10-membered bicyclic heteroaryl group can be optionally substituted with R$^{26}$; or two R$^{25}$ groups, together with the common nitrogen atom to which they are attached, join to form a 4- to 7-membered heterocycloalkyl group;

R$^{26}$ represents from one to five substituent groups, each independently selected from $C_1$-$C_6$ alkyl, $C_2$-$C_6$ alkenyl, $C_2$-$C_6$ alkynyl, halo, —OR$^{27}$, —SR$^{27}$, $C_1$-$C_6$ haloalkyl, $C_1$-$C_6$ hydroxyalkyl, —O—($C_1$-$C_6$ haloalkyl), —CN, —NO$_2$, —N(R$^{27}$)$_2$, —C(O)OR$^{27}$, —C(O)N(R$^{27}$)$_2$ and —NHC(O)R$^{27}$;

each occurrence of R$^{27}$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl);

R$^{28}$ is H, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_7$ cycloalkyl, $C_3$-$C_7$ cycloalkenyl, 5- or 6-membered monocyclic heteroaryl, 9- or 10-membered bicyclic heteroaryl, —OR$^{20}$, —O—($C_1$-$C_6$ haloalkyl) or —N(R$^{20}$)$_2$, wherein said $C_2$-$C_6$ alkenyl group, said $C_2$-$C_6$ alkynyl group, said $C_3$-$C_7$ cycloalkyl group, said $C_3$-$C_7$ cycloalkenyl group, said $C_6$-$C_{10}$ aryl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —OR$^{20}$, —SR$^{20}$, $C_1$-$C_6$ haloalkyl, $C_1$-$C_6$ hydroxyalkyl, —O—($C_1$-$C_6$ haloalkyl), —CN, —NO$_2$, —N(R$^{20}$)$_2$, —C(O)R$^{20}$, —C(O)OR$^{20}$, —C(O)N(R$^{20}$)$_2$ and —NHC(O)R$^{20}$;

each occurrence of R$^{29}$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -(5- or 6-membered monocyclic heteroaryl group or said 9- or 10-membered bicyclic heteroaryl group can be optionally substituted with R$^{26}$;

each occurrence of T is independently —S—, —O—, —SC(O)—, —SC(S)—, —OC(O)— and —OC(S)—;

each occurrence of m is independently 0 or 1; and each occurrence of n is independently 1 or 2.

The Compounds of Formula (I) (also referred to herein as the "2'-Cyano Substituted Nucleoside Derivatives") and pharmaceutically acceptable salts thereof can be useful, for example, for inhibiting HCV viral replication or replicon activity, and for treating or preventing HCV infection in a patient. Without being bound by any specific theory, it is believed that the 2'-Cyano Substituted Nucleoside Derivatives inhibit HCV viral replication by inhibiting HCV NS5B.

Accordingly, the present invention provides methods for treating or preventing HCV infection in a patient, comprising administering to the patient an effective amount of at least one 2'-Cyano Substituted Nucleoside Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to 2'-Cyano Substituted Nucleoside Derivatives, compositions comprising at least one 2'-Cyano Substituted Nucleoside Derivative, and methods of using the 2'-Cyano Substituted Nucleoside Derivatives for treating or preventing HCV infection in a patient.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of 2'-Cyano Substituted Nucleoside Derivative and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood or severity of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)$$CH_2$—. In one embodiment, an alkylene group has from 1 to about 6 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

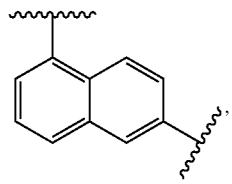 [SMILES: *c1ccc2c(*)cccc2c1]

is understood to represent both:

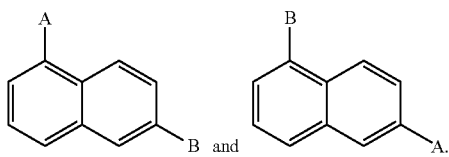

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

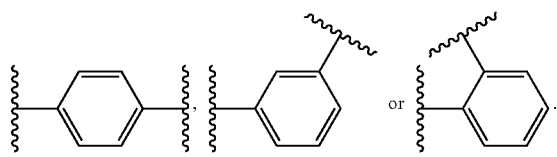

Unless otherwise indicated, an arylene group is unsubstituted.

The term "cycloalkyl," as used herein, refers to a non-aromatic mono- or multicyclic ring system comprising from 3 to about 10 ring carbon atoms. In one embodiment, a cycloalkyl contains from about 5 to about 10 ring carbon atoms. In another embodiment, a cycloalkyl contains from 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

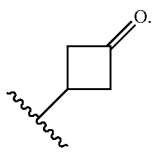

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

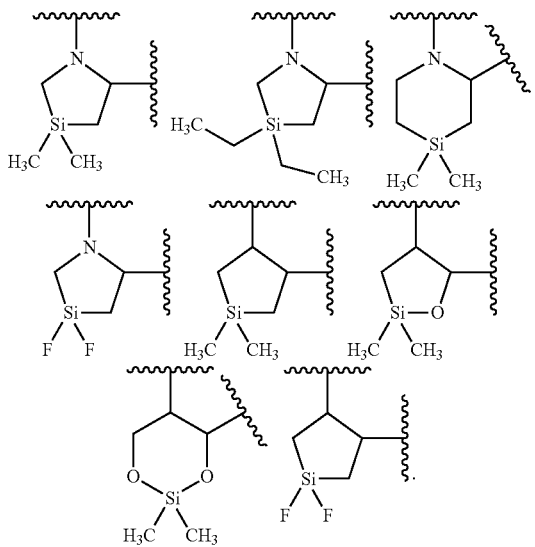

A ring carbon atom of a heterocycloalkyl group may be functionalized as a carbonyl group. An illustrative example of such a heterocycloalkyl group is:

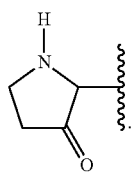

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "natural or non-natural purine or pyrimidine base" includes, but is not limited to, adenine, $N^{6-alkylpurines}$, $N^{6-acylpurines}$ (wherein acyl is C(O)(alkyl, aryl, alkylaryl, or arylalkyl), $N^{6-benzylpurine}$, $N^{6-halopurine}$, $N^{6-vinylpurine}$, $N^{6-acetylenic}$ purine, $N^{6-acyl}$ purine, $N^{6-hydroxyalkyl}$ purine, $N^{6-thioalkyl}$ purine, $N^{2-alkylpurines}$, $N^{2-alkyl-6-thiopurines}$, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^{5-alkylpyrimidines}$, $C^{5-benzylpyrimides}$, $C^{5-halopyrimidines}$, $C^{5-vinylpyrimidine}$, $C^{5-acetylenic}$ pyrimidine, $C^{5-acyl}$ pyrimidine, $C^{5-hydroxyalkyl}$ purine, $C^{5-amidopyrimidine}$, $C^{5-cyanopyrimidine}$, $C^{5-nitropyrimidine}$, $C^{5-aminopyrimidine}$, $N^{2-alkylpurines}$, $N^{2-alkyl-6-thiopurines}$, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

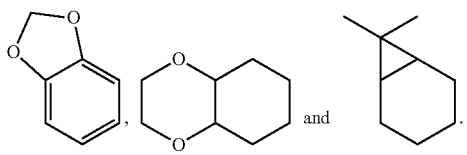

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^6$, $R^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a 2'-Cyano Substituted Nucleoside Derivative or a pharmaceutically acceptable salt of the compound. The transformation may occur by various mechanisms (e.g., by metabolic or chemical processes), such as, for example, through hydrolysis in blood.

For example, if a 2'-Cyano Substituted Nucleoside Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as 3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$) alkyl, and the like.

Similarly, if a 2'-Cyano Substituted Nucleoside Derivative contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate). Other non-limiting example of alcohol-derived prodrugs include —P(O)(OH)$_2$; —P(O)(—O—$C_1$-$C_6$alkyl)$_2$; —P(O)(—NH-(α-aminoacyl group))(—O-aryl); —P(O)(—O—($C_1$-$C_6$ alkylene)-S-acyl)(—NH-arylalkyl); any cyclic phosphate ester that forms a bridge between two ribose hydroxyl groups, such as:

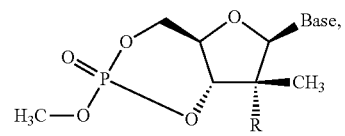

wherein the cyclic phosphate ester forms a bridge between the 3'-OH group and 5'-OH groups; and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842 (2005); Bobeck et al., *Antiviral Therapy* 15:935-950 (2010); Furman et al., Future Medicinal Chemistry, 1:1429-1452 (2009); and Erion, *Microsomes and Drug Oxidations, Proceedings of the International Symposium*, 17th, Saratoga Springs, N.Y., United States, Jul. 6-10, 2008, 7-12 (2008).

If a 2'-Cyano Substituted Nucleoside Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl; carboxy ($C_1$-$C_6$)alkyl; amino($C_1$-$C_4$)alkyl or mono-N- or di-N,N—($C_1$-$C_6$)alkylaminoalkyl; —C(Y$^4$)Y$^5$ wherein $Y^4$ is H or methyl and $Y^5$ is mono-N- or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_1$-20 alcohol or reactive derivative thereof, or by a 2,3-di ($C_{6-24}$) acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The 2'-Cyano Substituted Nucleoside Derivatives can form salts which are also within the scope of this invention. Reference to a 2'-Cyano Substituted Nucleoside Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 2'-Cyano Substituted Nucleoside Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a 2'-Cyano Substituted Nucleoside Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the 2'-Cyano Substituted Nucleoside Derivatives may be atropisomers (e.g., substituted biaryls) and are considered as part of this invention. Enantiomers can also be directly separated using chiral chromatographic techniques.

It is also possible that the 2'-Cyano Substituted Nucleoside Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a 2'-Cyano Substituted Nucleoside Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the 2'-Cyano Substituted Nucleoside Derivatives, and of the salts, solvates, hydrates, esters and prodrugs of the 2'-Cyano Substituted Nucleoside Derivatives, are intended to be included in the present invention.

In some instances, the compounds of the present invention are designated as "isomer 1" and "isomer 2." This designation refers to stereoisomers at the chiral phosphorus atom of the 5'-prodrug moiety as illustrated below for cyclic and non-cyclic prodrugs, wherein the structure:

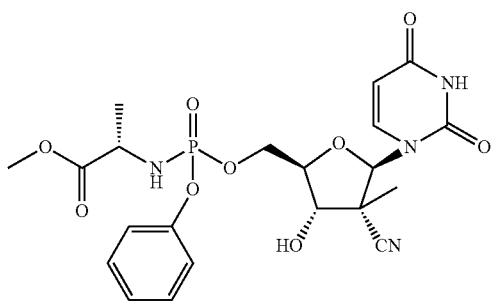 [SMILES: COC(=O)[C@H](C)NP(=O)(OC[C@H]1O[C@@H](n2ccc(=O)[nH]c2=O)[C@](C)(C#N)[C@@H]1O)Oc1ccccc1]

is understood to represent the following two phosphorus stereoisomers:

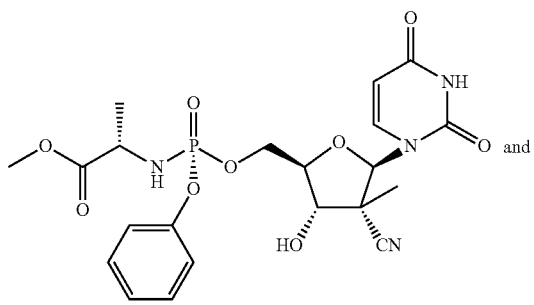

and the structure:

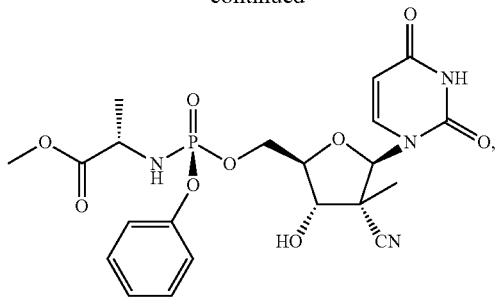

is understood to represent the following two phosphorus stereoisomers:

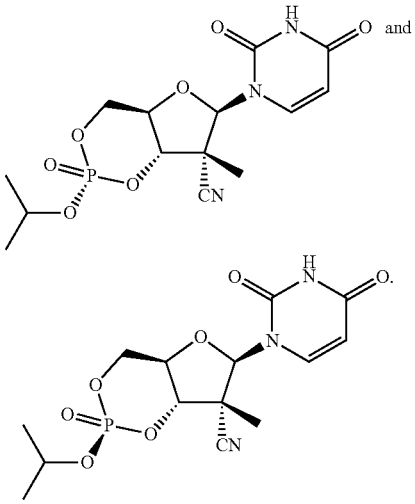

The terms "isomer 1" and "isomer 2" can be assigned to isomers of known absolute configuration or can be used to describe stereoisomers of unknown absolute configuration. Thus, the use of the terms "isomer 1" and "isomer 2" is not to be interpreted as indicating that the absolute configuration of both isomers is known.

The following abbreviations are used below and have the following meanings: Ac is acetyl or —C(O)CH$_3$, Ac$_2$O is acetic anhydride; Bu is butyl; t-BuMgCl is tert-butyl magnesium chloride; DCM is dichloromethane; Dess-Martin Periodinane is 1,1,1-triacetoxy-1,1-dihydro-1,2-benziodoxol-3 (1H)-one; DIBAL-H is diisobutylaluminum hydride; DMAP is N,N-dimethylamino pyridine; EtOAc is ethyl acetate; EtOH is ethanol; HPLC is high performance liquid chromatography; KHMDS is potassium hexamethyldisilazide;

KOBut is potassium tert-butoxide; LCMS is liquid chromatography/mass spectrometry; MeOH is methanol; NMI is N-methylimidazole; $Pd(OH)_2$ is palladium hydroxide; TBAF is tetra n-butylammonium fluoride; TEMPO is (2,2,6,6-tetramethyl-piperidin-1-yl)oxyl; THF is tetrahydrofuran; TIPDSiCl$_2$ is 1,3-dichloro-1,1,3,3-tetraisopropyldisiloxane; and TLC is thin-layer chromatography.

The Compounds of Formula (I)

The present invention provides 2'-Cyano Substituted Nucleoside Derivatives of Formula (I):

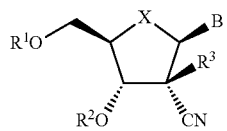
(I)

and pharmaceutically acceptable salts thereof, wherein B, X, $R^1$, $R^2$ and $R^3$ are defined above for the Compounds of Formula (I).

In one embodiment, X is O.
In another embodiment, X is S.
In another embodiment, X is $CH_2$.
In one embodiment, $R^3$ is $C_1$-$C_6$ alkyl.
In another embodiment, $R^3$ is methyl.
In one embodiment, for the Compounds of Formula (I) or (Ia), $R^1$ is H or

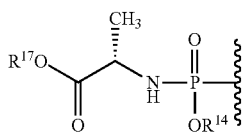

or $R^1$ and $R^2$ join to form a group having the formula:

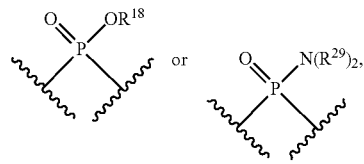

wherein $R^{14}$ is $C_6$-$C_{10}$ aryl, which can be optionally substituted as set forth in claim 1; $R^{17}$ is $C_1$-$C_6$ alkyl; $R^{18}$ is $C_1$-$C_6$ alkyl, $C_3$-$C_7$ cycloalkyl or $C_6$-$C_{10}$ aryl; and $R^{29}$ is as defined for the compounds of Formula (I).

In one embodiment, the compounds of formula (I) have the formula (Ia):

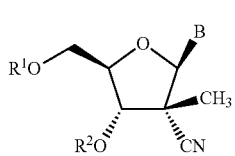
(Ia)

and pharmaceutically acceptable salts thereof, wherein:
B is:

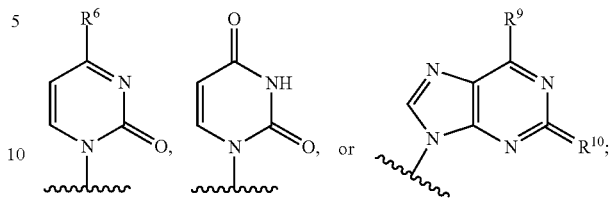

$R^1$ is H,

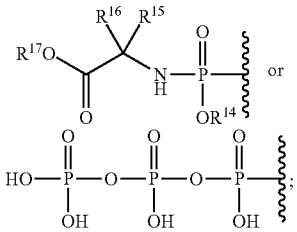

$R^2$ is H, or $R^1$ and $R^2$ join to form a group having the formula:

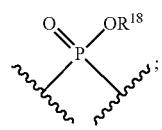

$R^6$ and $R^{10}$ are each independently $-N(R^{20})_2$;
$R^9$ is $-OH$ or $-O-(C_1-C_6$ alkyl);
$R^{14}$ is $C_6$-$C_{10}$ aryl, which can be optionally substituted with a halo group;
$R^{15}$ and $R^{16}$ are each independently H or $C_1$-$C_6$ alkyl;
$R^{17}$ is $C_1$-$C_6$ alkyl;
$R^{18}$ is $C_1$-$C_6$ alkyl, $C_3$-$C_7$ cycloalkyl or $C_6$-$C_{10}$ aryl; and
each occurrence of $R^{20}$ is independently H or $-C(O)-(C_1-C_6$ alkyl).

In one embodiment, for the Compounds of Formula (I) or (Ia), B is selected from one of the following groups:

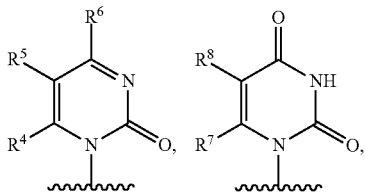

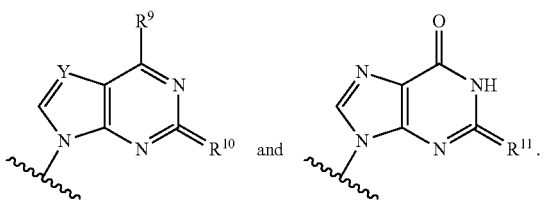

In another embodiment, for the Compounds of Formula (I) or (Ia), B is:

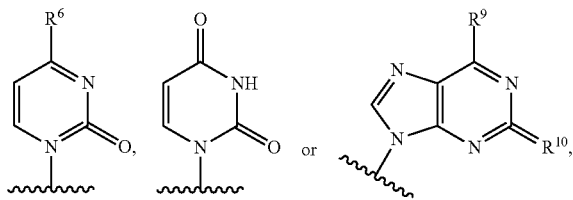

wherein $R^6$ and $R^{10}$ are each independently —$NH_2$ or —NHC(O)$CH_3$ and $R^9$ is —OH or —O—($C_1$-$C_6$ alkyl).

In another embodiment, for the Compounds of Formula (I) or (Ia), B is:

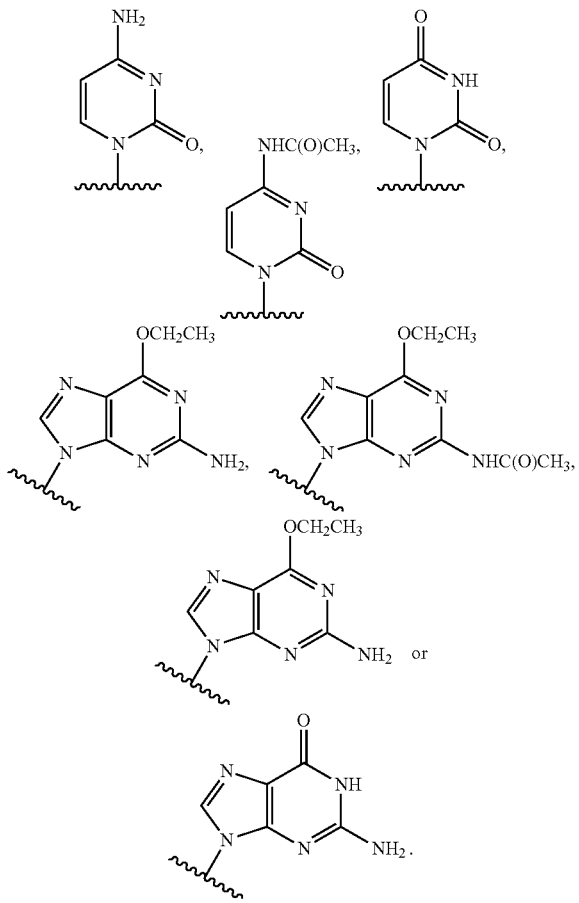

In another embodiment, for the Compounds of Formula (I) or (Ia), B is:

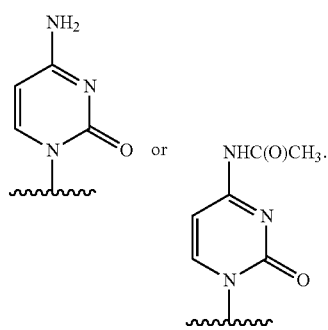

In still another embodiment, for the Compounds of Formula (I) or (Ia), B is:

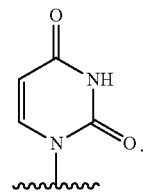

In another embodiment, for the Compounds of Formula (I) or (Ia), B is:

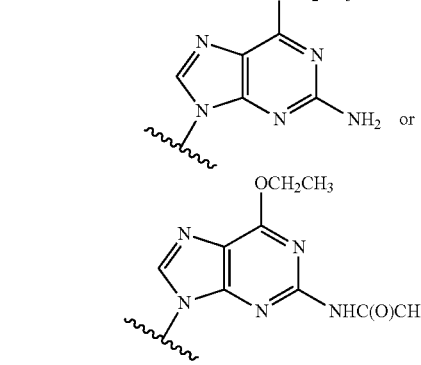

In another embodiment, for the Compounds of Formula (I) or (Ia), B is:

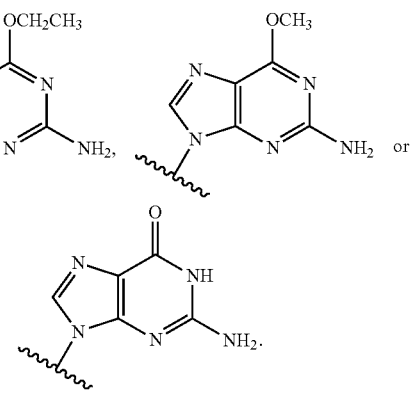

In one embodiment, for the Compounds of Formula (I) or (Ia), $R^1$ is H.

In another embodiment, for the Compounds of Formula (I) or (Ia), $R^1$ is H or

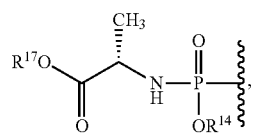

or $R^1$ and $R^2$ join to form a group having the formula:

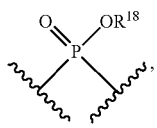

wherein $R^{14}$ is $C_6$-$C_{10}$ aryl, which can be optionally substituted as set forth in claim 1; $R^{17}$ is $C_1$-$C_6$ alkyl; and $R^{18}$ is $C_1$-$C_6$ alkyl, $C_3$-$C_7$ cycloalkyl or $C_6$-$C_{10}$ aryl.

In another embodiment, for the Compounds of Formula (I) or (Ia), $R^1$ is:

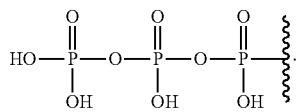

In still another embodiment, for the Compounds of Formula (I) or (Ia), $R^1$ is:

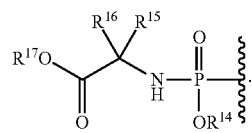

In another embodiment, for the Compounds of Formula (I) or (Ia), $R^1$ is:

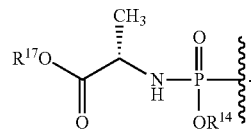

In yet another embodiment, for the Compounds of Formula (I) or (Ia), $R^1$ is:

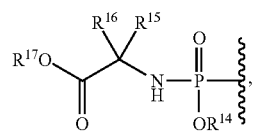

wherein $R^{14}$ is $C_6$-$C_{10}$ aryl, which can be optionally substituted as set forth in claim 1; one of $R^{15}$ and $R^{16}$ is H and the other is $C_1$-$C_6$ alkyl; and $R^{17}$ is $C_1$-$C_6$ alkyl.

In another embodiment, for the Compounds of Formula (I) or (Ia), $R^1$ is:

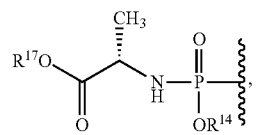

wherein $R^{14}$ is $C_6$-$C_{10}$ aryl, which can be optionally substituted as set forth in claim 1; and $R^{17}$ is $C_1$-$C_6$ alkyl.

In a further embodiment, for the Compounds of Formula (I) or (Ia), $R^1$ is:

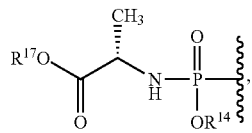

wherein $R^{14}$ is naphthyl or phenyl, which can be optionally substituted with F or Cl; and $R^{17}$ is methyl, ethyl, isopropyl, n-butyl or neopentyl.

In another embodiment, for the Compounds of Formula (I) or (Ia), $R^1$ is:

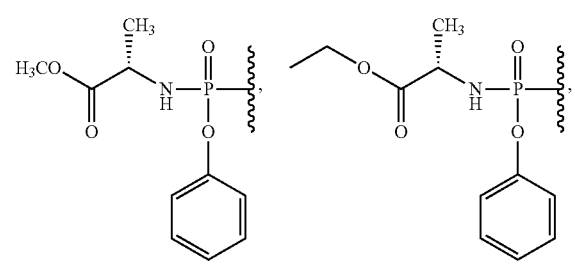

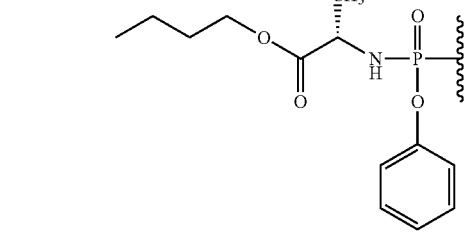

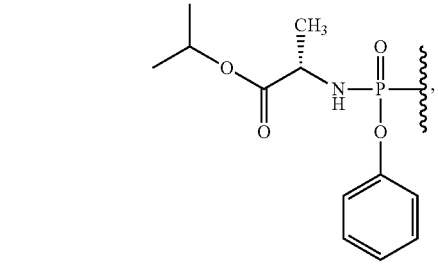

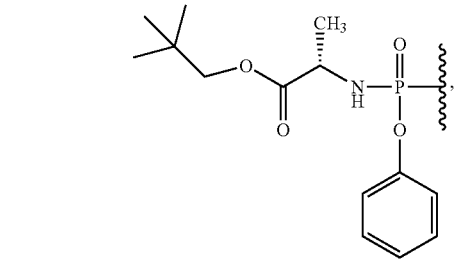

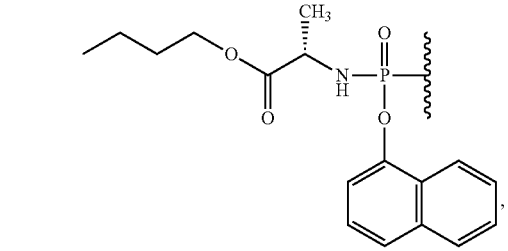

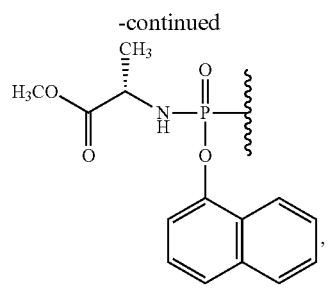

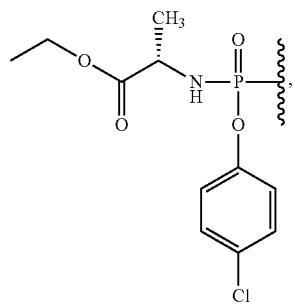

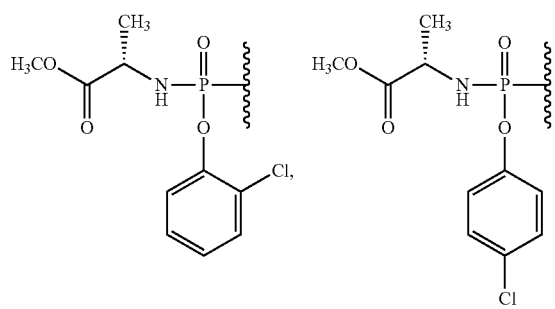

In another embodiment, for the Compounds of Formula (I) or (Ia), $R^1$ is:

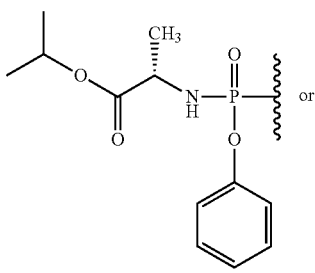

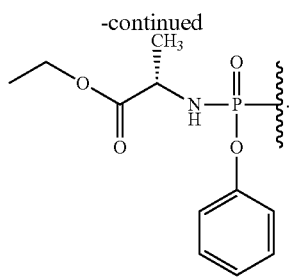

In one embodiment, for the Compounds of Formula (I) or (Ia), $R^2$ is H.

In one embodiment, for the Compounds of Formula (I) or (Ia), each of $R^1$ and $R^2$ is H.

In another embodiment, for the Compounds of Formula (I) or (Ia), $R^1$ and $R^2$ join to form a group having the formula:

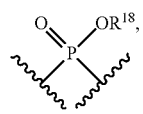

wherein $R^{18}$ is $C_1$-$C_6$ alkyl, $C_3$-$C_7$ cycloalkyl or $C_6$-$C_{10}$ aryl.

In another embodiment, for the Compounds of Formula (I) or (Ia), $R^1$ and $R^2$ join to form a group having the formula:

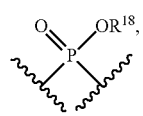

wherein $R^{18}$ is methyl, ethyl, isopropyl, cyclobutyl or phenyl.

In still another embodiment, for the Compounds of Formula (I) or (Ia), $R^1$ and $R^2$ join to form a group having the formula:

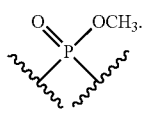

In one embodiment, for the Compounds of Formula (I) or (Ia), $R^1$ and $R^2$ join to form a group having the formula:

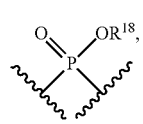

wherein $R^{18}$ is methyl, ethyl, isopropyl, cyclobutyl or phenyl.

In one embodiment, for the Compounds of Formula (I) or (Ia), $R^1$ and $R^2$ join to form a group having the formula:

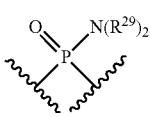

In one embodiment, the Compounds of Formula (I) or (Ia), $R^1$ is
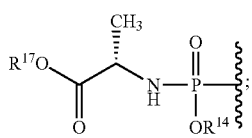
$R^{14}$ is naphthyl, phenyl or chloro-substituted phenyl; and
$R^{17}$ is methyl, ethyl, isopropyl, n-butyl or neopentyl.
In one embodiment, the Compounds of Formula (I) or (Ia), $R^2$ is H;
B is:
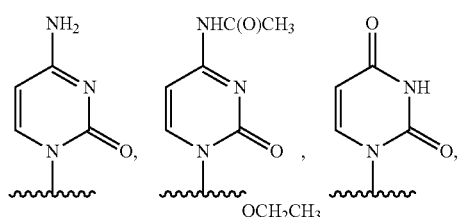
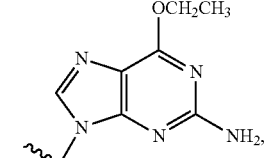
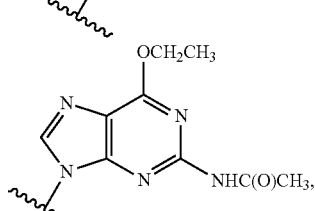
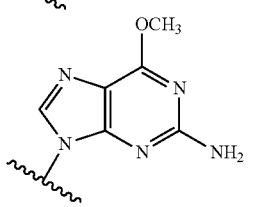
or
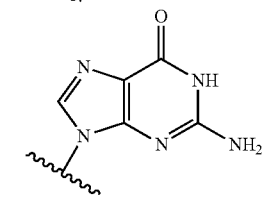
$R^1$ is:
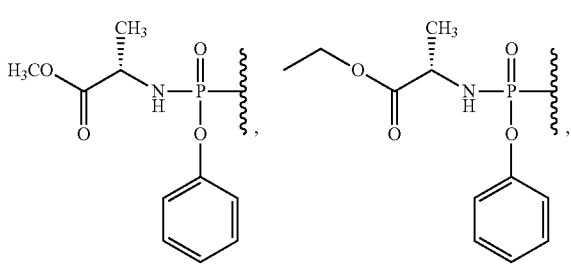
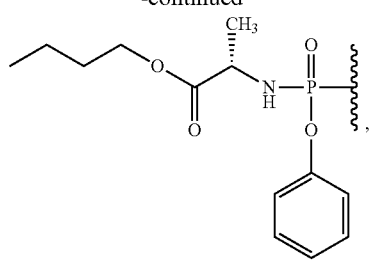
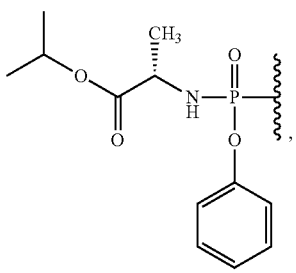
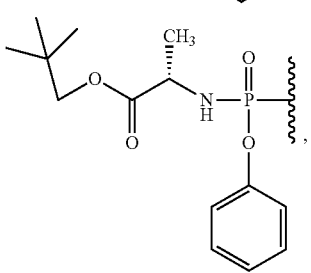
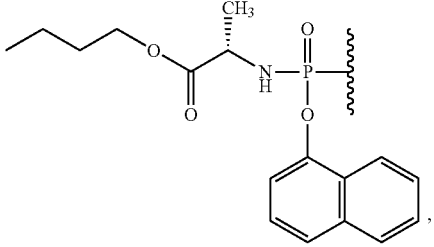
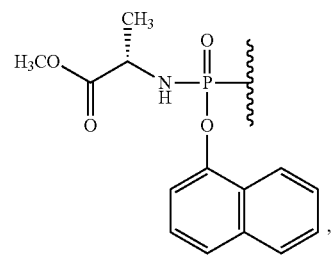
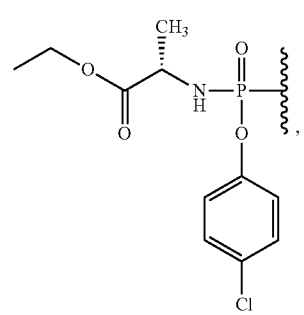

-continued
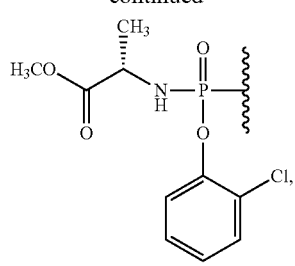
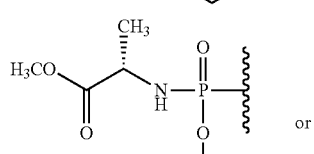
or
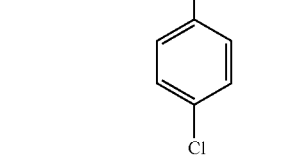
In another embodiment, the Compounds of Formula (I) or (Ia),
R² is H;
B is:
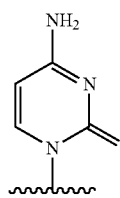 ,  , 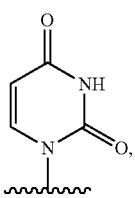
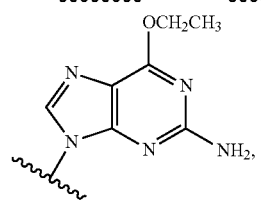
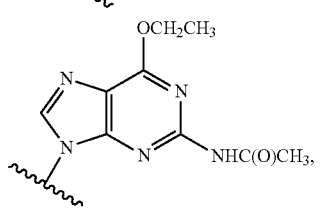
-continued
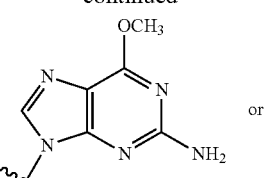
or
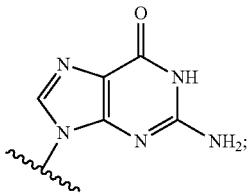 ;
R¹ is:
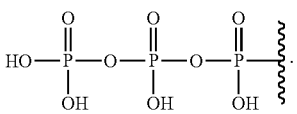 .
In another embodiment, the Compounds of Formula (I) or (Ia),
B is:
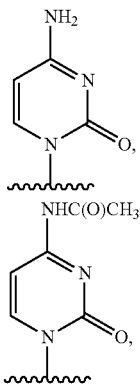
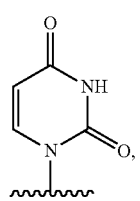
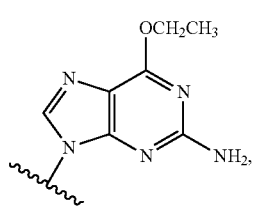

-continued
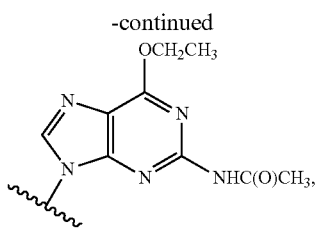
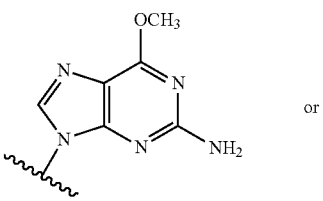
or
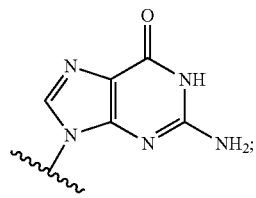
and
R¹ and R² join to form a group having the formula:
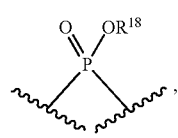
wherein R¹⁸ is methyl, ethyl, isopropyl, cyclobutyl or phenyl.
In still another embodiment, the Compounds of Formula (I) or (Ia),
R¹ and R² are each H; and
B is:
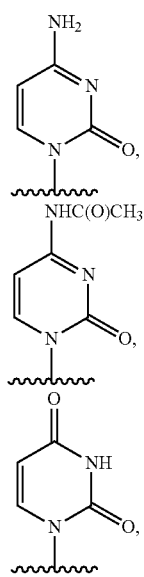
-continued
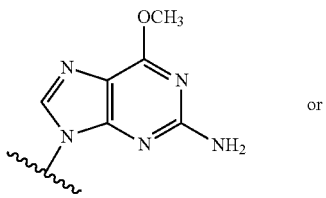
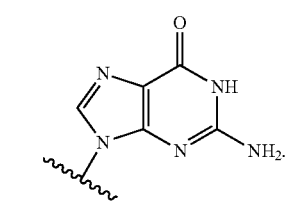
or
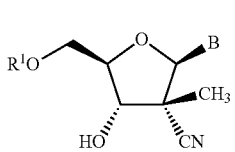
In one embodiment, the Compounds of Formula (I) have the formula (Ib):
(Ib)
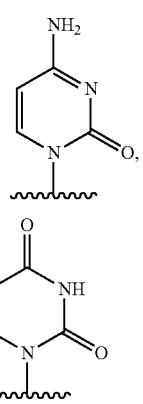
or a pharmaceutically acceptable salt thereof,
wherein:
B is:

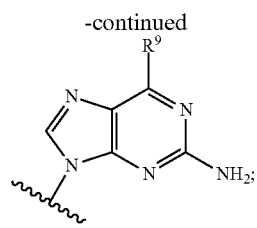

R¹ is:

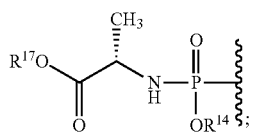

$R^9$ is —OH or —O—($C_1$-$C_6$ alkyl);
$R^{14}$ is phenyl, which can be optionally substituted with up to 2 halo groups, which can be the same or different; and
$R^{17}$ is $C_1$-$C_6$ alkyl.

In one embodiment, for the Compounds of Formula (Ib), $R^{14}$ is unsubstituted phenyl.

In another embodiment, for the Compounds of Formula (Ib), $R^{17}$ is ethyl or isopropyl.

In one embodiment, for the Compounds of Formula (Ib), $R^{14}$ is unsubstituted phenyl and $R^{17}$ is ethyl or isopropyl.

In another embodiment, for the Compounds of Formula (Ib), $R^{14}$ is unsubstituted phenyl and $R^{17}$ is ethyl.

In still another embodiment, for the Compounds of Formula (Ib), $R^{14}$ is unsubstituted phenyl and $R^{17}$ is isopropyl.

In one embodiment, the Compounds of Formula (I) have the formula (Ic):

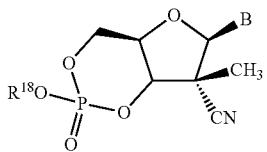
(Ic)

or a pharmaceutically acceptable salt thereof,
wherein:
B is:

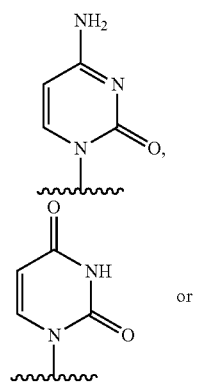

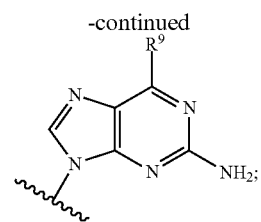

$R^9$ is —OH or —O—($C_1$-$C_6$ alkyl); and
$R^{18}$ is aryl or $C_1$-$C_6$ alkyl.

In one embodiment, for the Compounds of Formula (Ic), $R^{18}$ is $C_1$-$C_6$ alkyl.

In another embodiment, for the Compounds of Formula (Ic), $R^{18}$ is isopropyl.

In another embodiment, for the Compounds of Formula (Ic), $R^{18}$ is methyl.

In one embodiment, the Compounds of Formula (I) have the formula (Id):

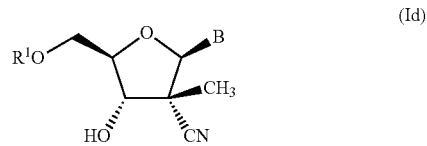
(Id)

or a pharmaceutically acceptable salt thereof,
wherein:
B is:

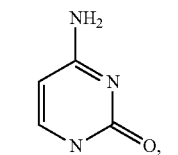

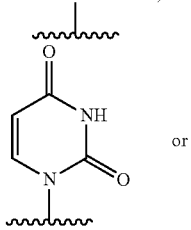
or

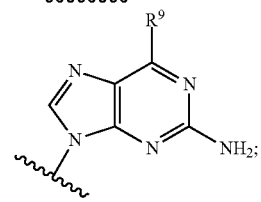

R¹ is:

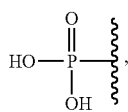

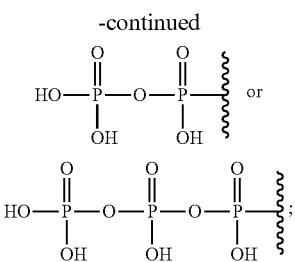

and

R⁹ is —OH or —O—(C₁-C₆ alkyl).

In one embodiment, for the Compounds of Formula (Ib), (Ic) or (Id), B is

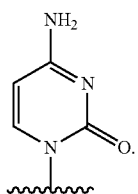 [SMILES: *n1ccc(N)nc1=O]

In another embodiment, for the Compounds of Formula (Ib), (Ic) or (Id), B is

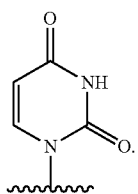 [SMILES: *n1ccc(=O)[nH]c1=O]

In another embodiment, for the Compounds of Formula (Ib), (Ic) or (Id), B is

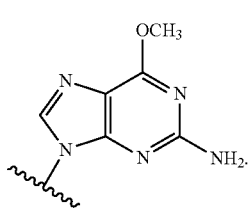 [SMILES: *n1cnc2c(OC)nc(N)nc21]

In another embodiment, for the Compounds of Formula (Ib), (Ic) or (Id), B is

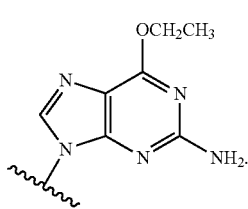 [SMILES: *n1cnc2c(OCC)nc(N)nc21]

In another embodiment, for the Compounds of Formula (Ib), (Ic) or (Id), B is

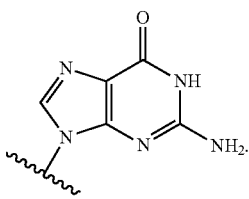 [SMILES: *n1cnc2c(=O)[nH]c(N)nc21]

In one embodiment, variables B, X, $R^1$, $R^2$ and $R^3$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, HCV NS5B polymerase inhibitors and HCV NS5A inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors, HCV NS5B polymerase inhibitors and HCV NS5A inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors, HCV NS5B polymerase inhibitors and HCV NS5A inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

In one embodiment, the present invention includes the use of a compound of the present invention, or a pharmaceutically acceptable salt thereof, in a pharmaceutical composition for inhibiting HCV NS5A activity or for preventing and/or treating infection by HCV in a patient in need thereof.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-243 as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-L below. Alternative synthetic pathways and analogous structures will be apparent to those skilled in the art of organic synthesis.

Scheme A shows a method useful for making nucleoside compounds of formula A6, which correspond to the Compounds of Formula (I), wherein X is O; $R^1$ and $R^2$ are each H; $R^3$ is methyl and B is:

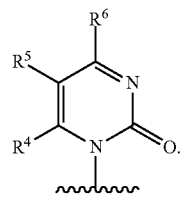

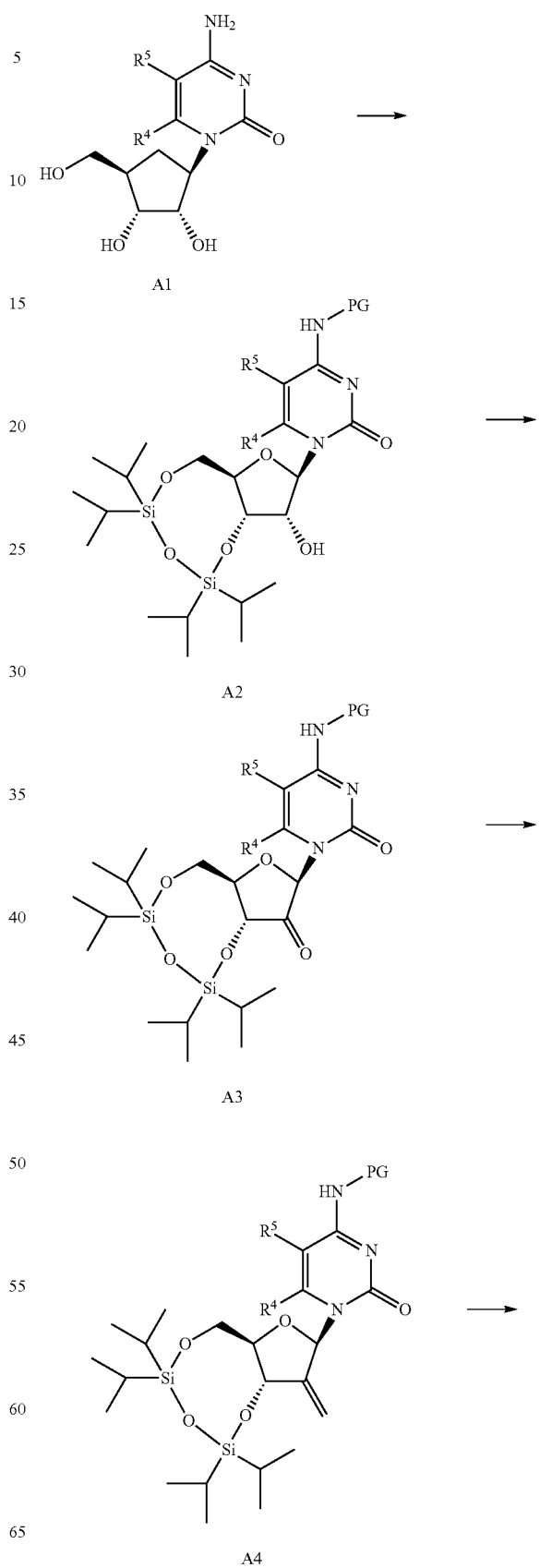

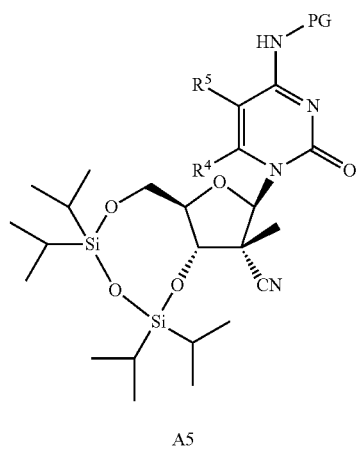

A5

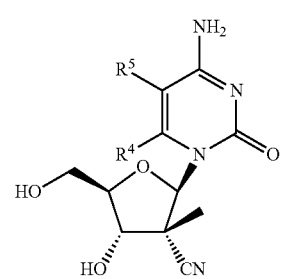

A6

Wherein PG is a protecting group and $R^4$ and $R^5$ are as defined above for the Compounds of Formula (I).

Nucleoside compounds of formula A1 can be bis-protected at the ribose 3' and 5' positions using the tetraisopropyldisiloxanyl group to provide compounds of formula A2. Compounds of formula A2 are then oxidized, using for example, the Dess-Martin Periodinane, to provide the 2'-ketone of formula A3. Wittig olefination with methyltriphenylphosphonium bromide/potassium hexamethyldisilazide provides compounds of formula A4. The olefin moiety of the compounds of formula A4 can be treated with the appropriate cobalt catalyst (synthesis described in detail in this document) in the presence of commercially available tosyl cyanide and phenylsilane to provide the 2'-CN compounds of formula A5. The silyl protecting group is then removed using tetrabutylammonium fluoride and the cytidine protecting group is then removed with methanolic ammonia to provide the compounds of formula A6.

Scheme B shows a method useful for making nucleoside compounds of formula B6, which correspond to the Compounds of Formula (I), wherein X is O; $R^1$ and $R^2$ are each H; $R^3$ is methyl and B is:

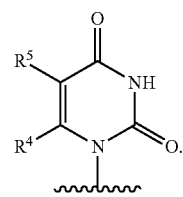

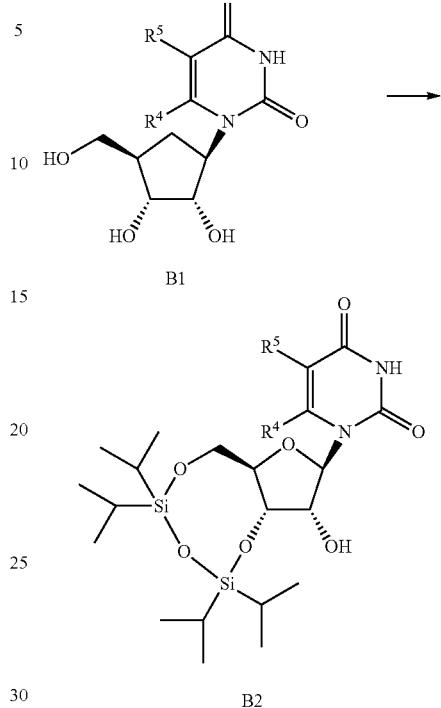

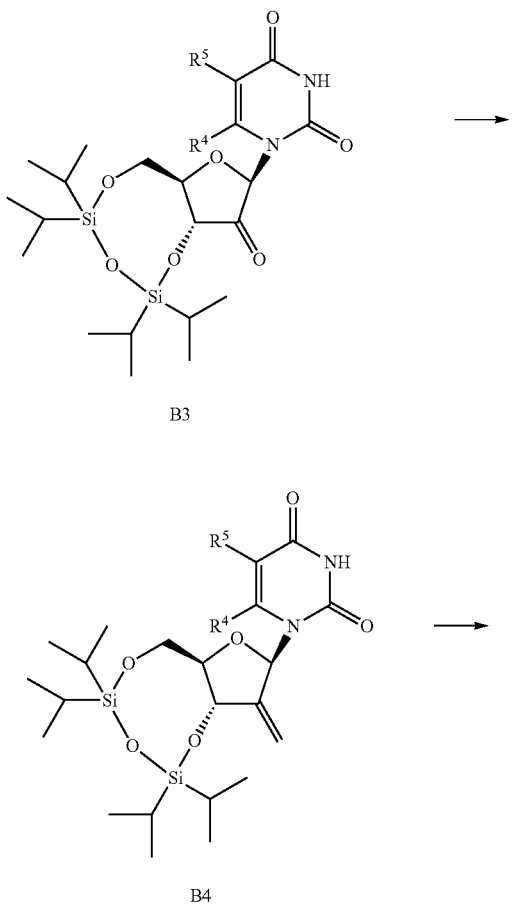

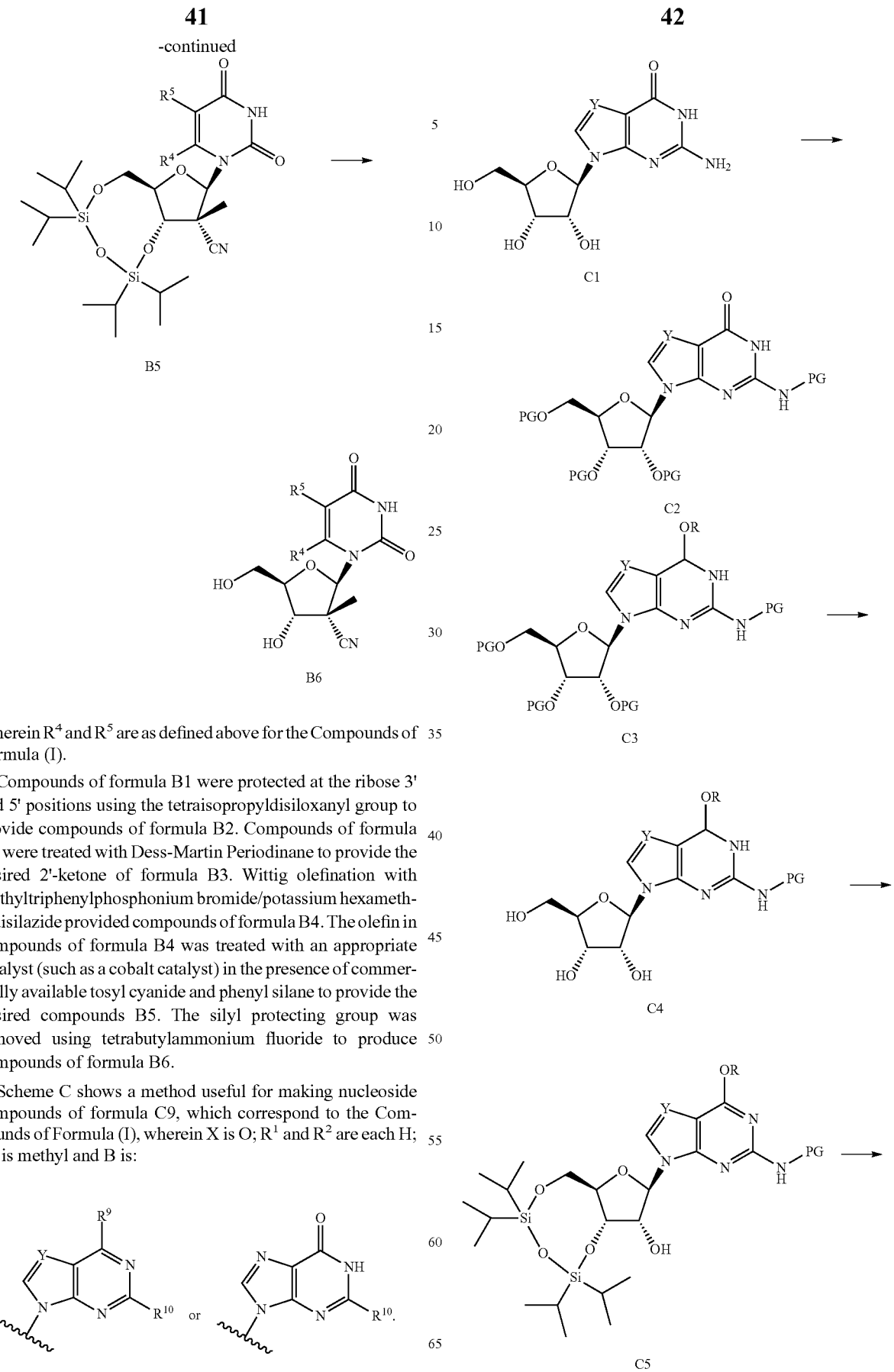

Wherein $R^4$ and $R^5$ are as defined above for the Compounds of Formula (I).

Compounds of formula B1 were protected at the ribose 3' and 5' positions using the tetraisopropyldisiloxanyl group to provide compounds of formula B2. Compounds of formula B2 were treated with Dess-Martin Periodinane to provide the desired 2'-ketone of formula B3. Wittig olefination with methyltriphenylphosphonium bromide/potassium hexamethyldisilazide provided compounds of formula B4. The olefin in compounds of formula B4 was treated with an appropriate catalyst (such as a cobalt catalyst) in the presence of commercially available tosyl cyanide and phenyl silane to provide the desired compounds B5. The silyl protecting group was removed using tetrabutylammonium fluoride to produce compounds of formula B6.

Scheme C shows a method useful for making nucleoside compounds of formula C9, which correspond to the Compounds of Formula (I), wherein X is O; $R^1$ and $R^2$ are each H; $R^3$ is methyl and B is:

-continued

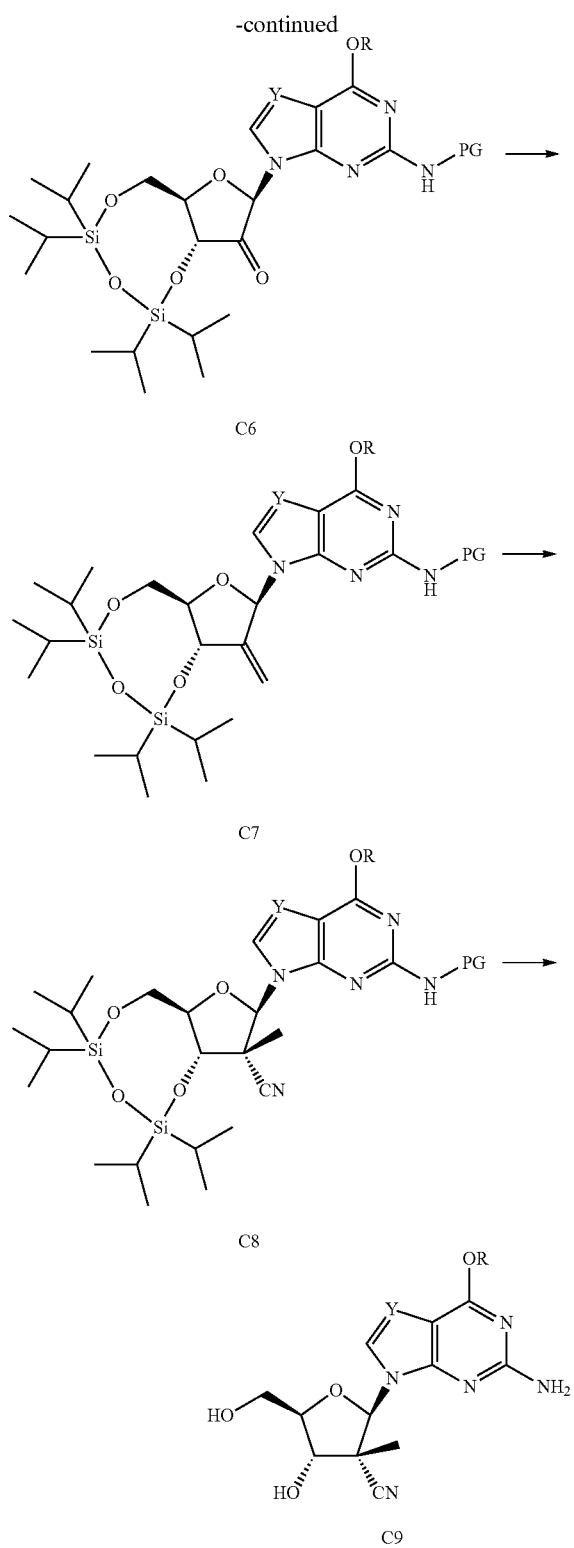

Wherein PG is a protecting group and $R^4$ and $R^5$ are as defined above for the Compounds of Formula (I).

A compound of formula C1 can have all of its hydroxyl groups protected using well known methods to provide the compounds of formula C2. A compound of formula C2 can then be subjected to Mitsunobu conditions to provide purine ethers of formula C3. The hydroxyl groups of C3 are then deprotecting to provide the compounds of formula C4, which can subsequently have their 3'-OH and 5'-OH protected using the tetraisopropyldisiloxanyl group to provide the compounds of formula C5. Compounds of formula C5 are then oxidized, using for example, the Dess-Martin Periodinane, to provide the 2'-ketone compounds of formula C6. Wittig olefination with methyltriphenylphosphonium bromide/potassium hexamethyldisilazide provides the compounds of formula C7. The olefin in compounds of formula C7 was treated with the appropriate cobalt catalyst (synthesis described in detail in this document) in the presence of commercially available tosyl cyanide and phenyl silane to provide the desired compounds C8. The silyl protecting group is then removed using tetrabutylammonium fluoride followed by deprotection of the protected aryl amine group to provide the compounds of formula C9.

Scheme D shows a method useful for making nucleoside compounds of formula D3, which correspond to the Compounds of Formula (I), wherein X is O; $R^2$ is H; $R^3$ is methyl; B is as defined above for the Compounds of Formula (I); and $R^1$ is:

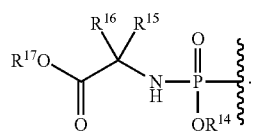

Scheme D

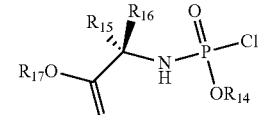

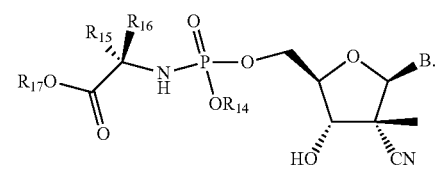

Wherein B, $R^{14}$, $R^{15}$, $R^{16}$ and $R^{17}$ are as defined above for the Compounds of Formula (I).

A compound of formula D1 can be coupled with a compound of formula D2 (compounds of formula D2 can be synthesized using methods described in U.S. Pat. No. 7,879, 815 B2) in the presence of either t-butylmagnesium bromide or N-methylimidazole to provide the compounds of formula D3.

Scheme E

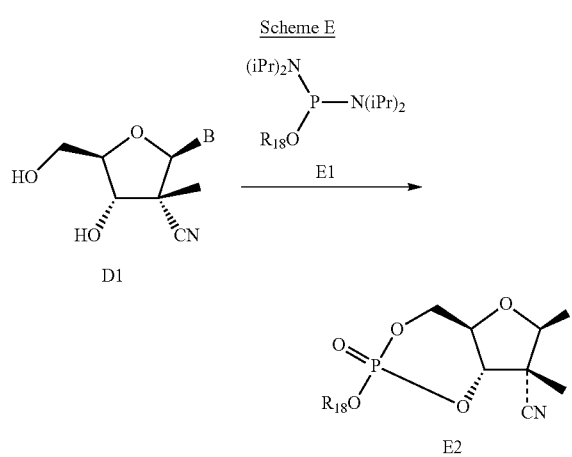

Wherein B and $R^{18}$ are as defined above for the Compounds of Formula (I).

A compound of formula D1 can be reacted with a phosphoramidate compound of formula E1 followed by oxidation with, for example, m-chloroperbenzoic acid to provide a cyclic phosphate ester of formula E2.

Scheme F

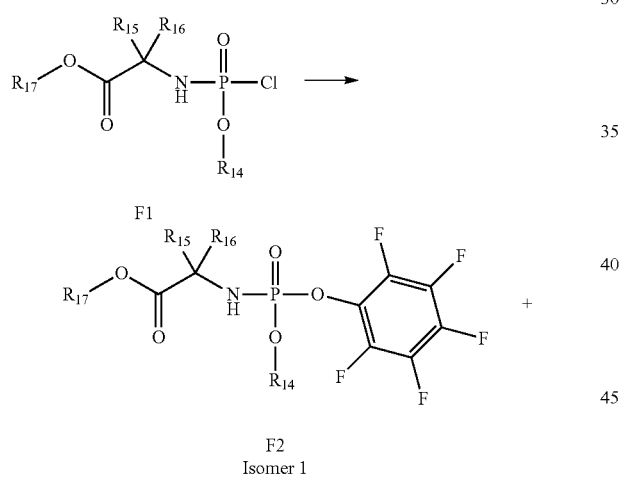

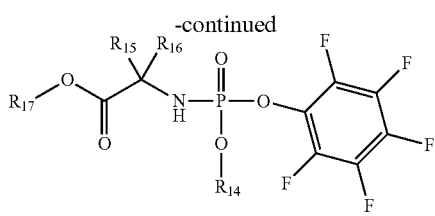

Wherein B, $R^{14}$, $R^{15}$, $R^{16}$ and $R^{17}$ are as defined above for the Compounds of Formula (I).

Compounds of type F1 can be treated with pentafluoro phenol to provide two isomers F2 and F3. These isomers can be individually reacted with F3 to provide compounds of type F4.

Scheme G

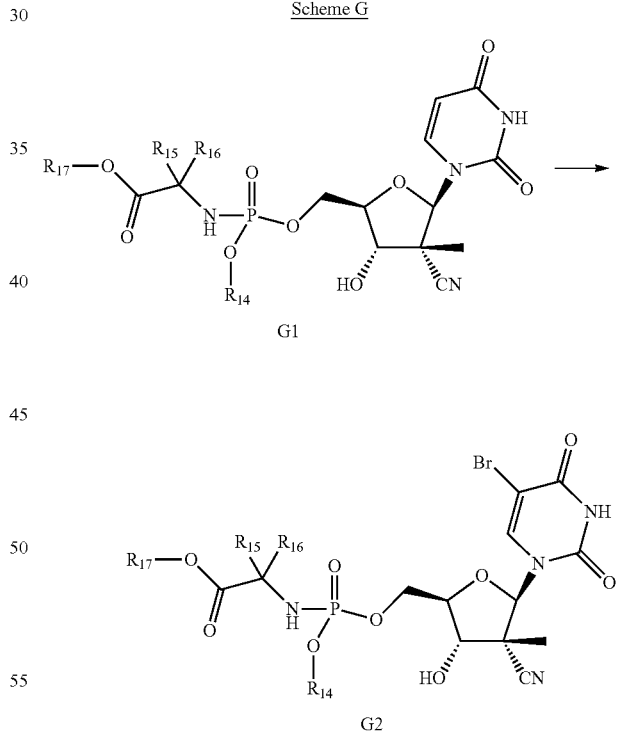

Wherein $R^{14}$, $R^{15}$, $R^{16}$ and $R^{17}$ are as defined above for the Compounds of Formula (I).

Compounds of type G1 can be brominated with reagents such as N-bromosuccinimide to provide compounds of type G2.

Scheme H

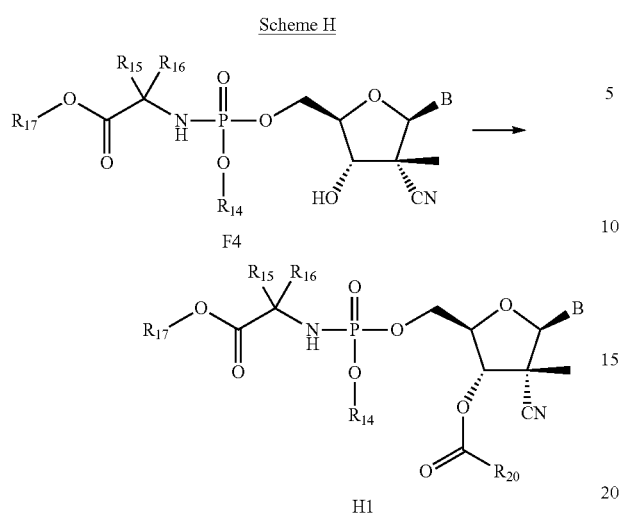

Wherein $R^{14}$, $R^{15}$, $R^{16}$, $R^{17}$ and $R^{20}$ are as defined above for the Compounds of Formula (I).

Compounds of type F4 can be reacted with a variety of acetylating reagents to provide compounds of type H1.

Scheme I

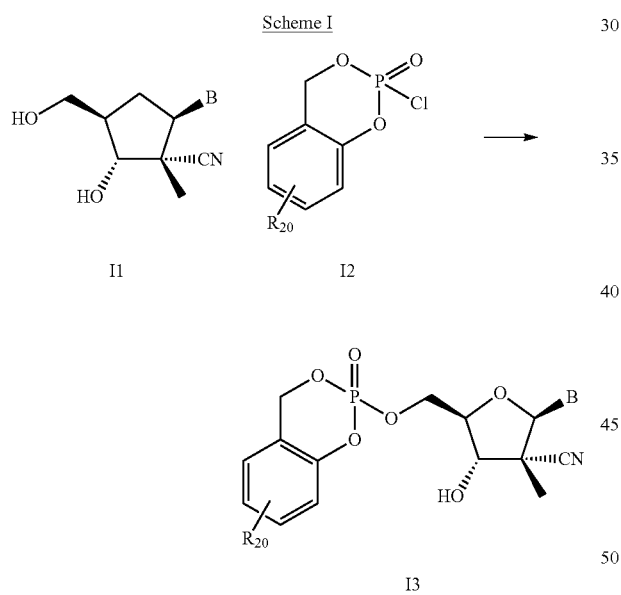

Wherein B and $R^{20}$ are as defined above for the Compounds of Formula (I).

Compounds of type I1 can be treated with compounds of type I2 to provide compounds of type I3.

Scheme J

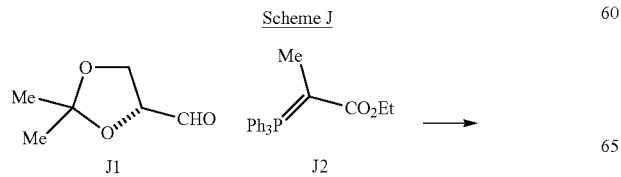

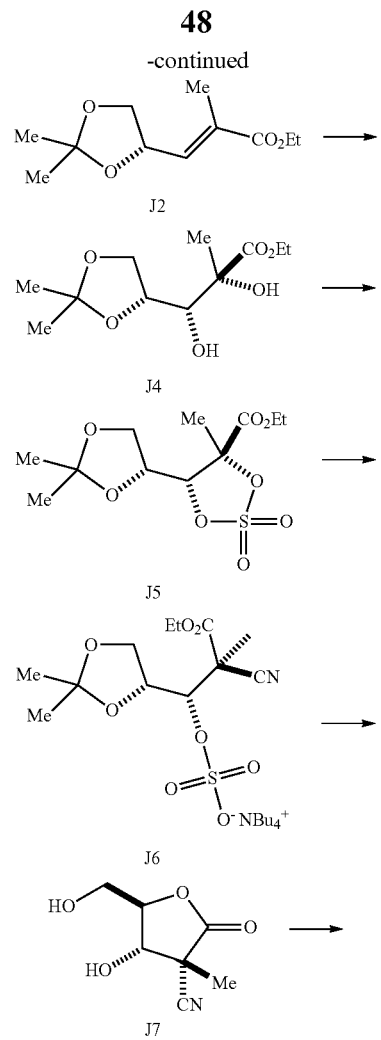

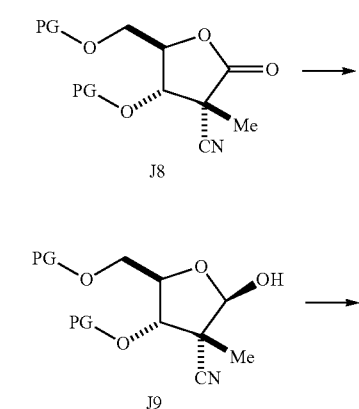

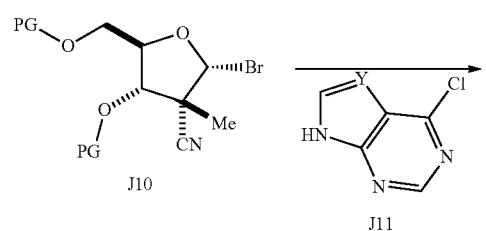

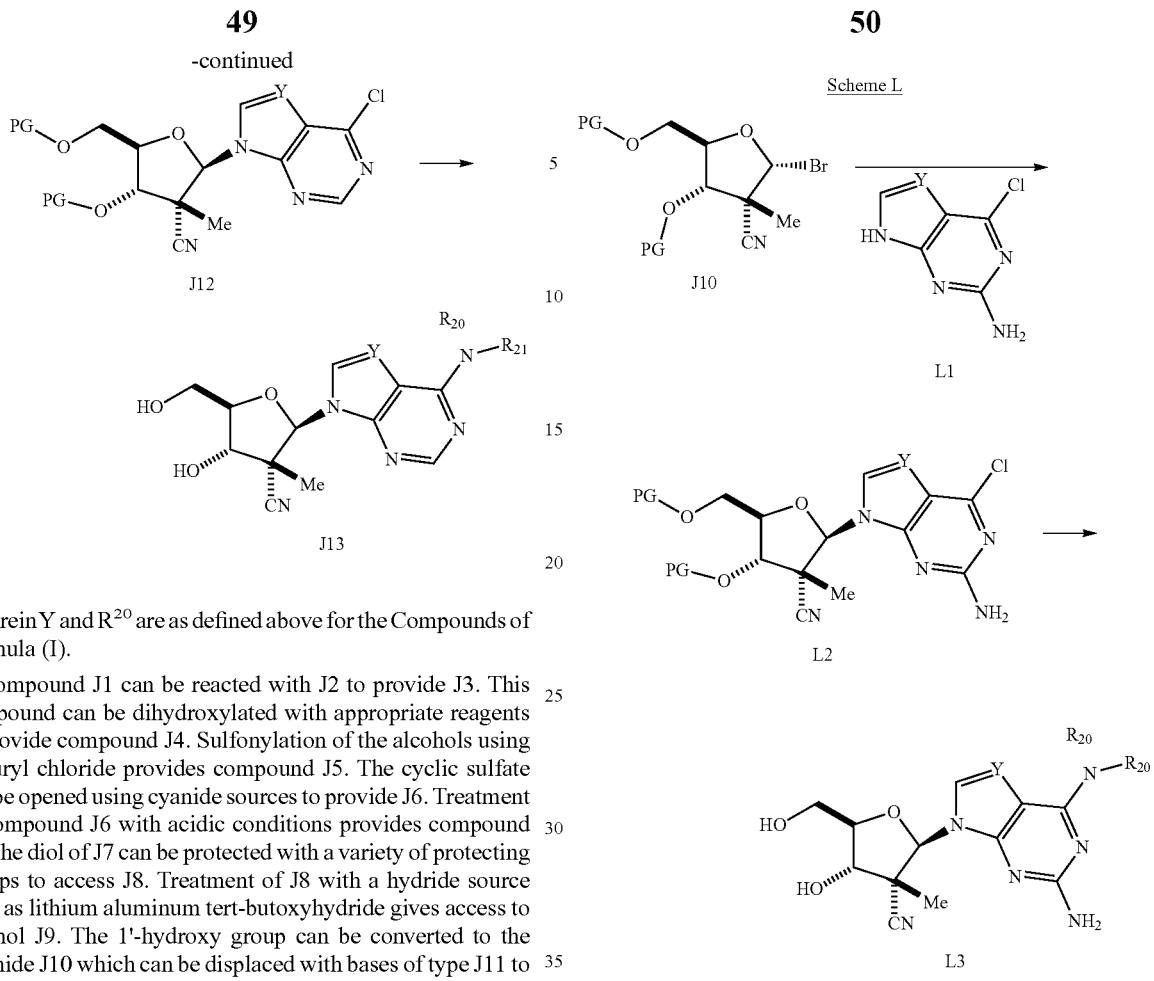

Wherein Y and R[20] are as defined above for the Compounds of Formula (I).

Compound J1 can be reacted with J2 to provide J3. This compound can be dihydroxylated with appropriate reagents to provide compound J4. Sulfonylation of the alcohols using sulfuryl chloride provides compound J5. The cyclic sulfate can be opened using cyanide sources to provide J6. Treatment of compound J6 with acidic conditions provides compound J7. The diol of J7 can be protected with a variety of protecting groups to access J8. Treatment of J8 with a hydride source such as lithium aluminum tert-butoxyhydride gives access to alcohol J9. The 1'-hydroxy group can be converted to the bromide J10 which can be displaced with bases of type J11 to produce compounds of type J12. Global deprotection of J12 provides J13.

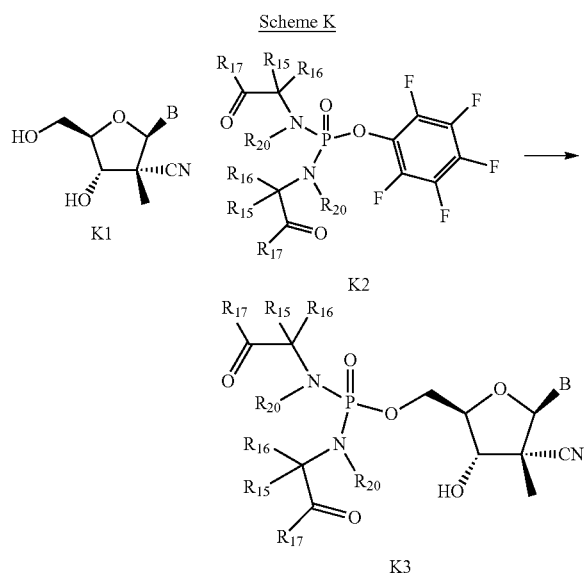

Wherein B and R[20] are as defined above for the Compounds of Formula (I).

Compounds of type K1 can be treated with compounds of type K2 to provide compounds of type K3.

Wherein R[20] is defined above for the Compounds of Formula (I).

Compounds of type J10 can be treated with compounds of type L1 to provide compounds of type L2. L2 can then be reacted with a variety of amines to provide compounds of type L3.

Compounds of formula A6, B6, C9, D3, E2, F4, G2, H1, I3, J13, K3 and L3 may be further elaborated using methods that would be well-known to those skilled in the art of organic synthesis or, for example, the methods described in the Examples below, to make the full scope of the Compounds of Formula (I).

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

The starting materials used and the intermediates prepared using the methods set forth in Schemes A-L may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The parent ion is given. Flash chromatography on silica gel was performed using pre-packed normal phase silica from Isco, Biotage, Inc. or bulk silica from Fisher Scientific. Unless otherwise indicated, flash chromatography on silica gel was performed using a gradient elution of hexanes/ethyl acetate, from 100% hexanes to 100% ethyl acetate.

Example 1

Preparation of Intermediate Compound Int-1c

Compound Int-1a (733 mg, 1.33 mmol) was suspended in ethanol (10 mL) and the resulting suspension was heated to 80° C. and allowed to stir for 5 minutes. Compound Int-1b (236 mg, 1.33 mmol) was then added and the resulting reaction was allowed to stir at 80° C. for an additional 2 hours. The reaction was then cooled to room temperature using in an ice bath and the reaction mixture was filtered. The collected red solid was dried under vacuum to provide compound Int-1c (579 mg, 72%).

Example 2

Preparation of Intermediate Compound Int-2e

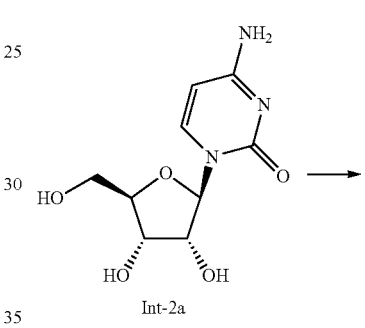

Int-2a

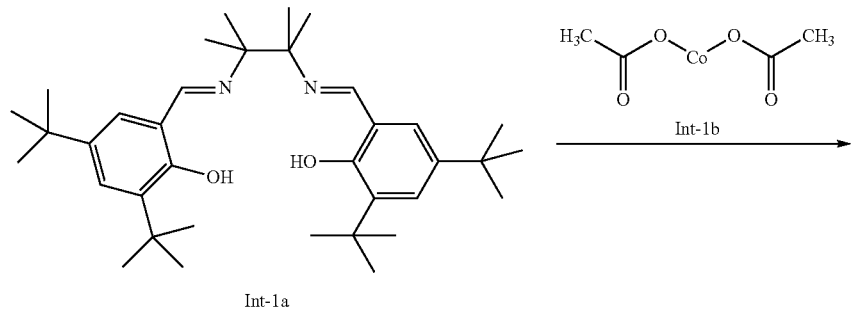

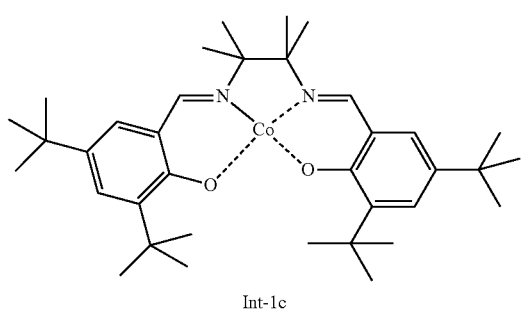

Int-1c

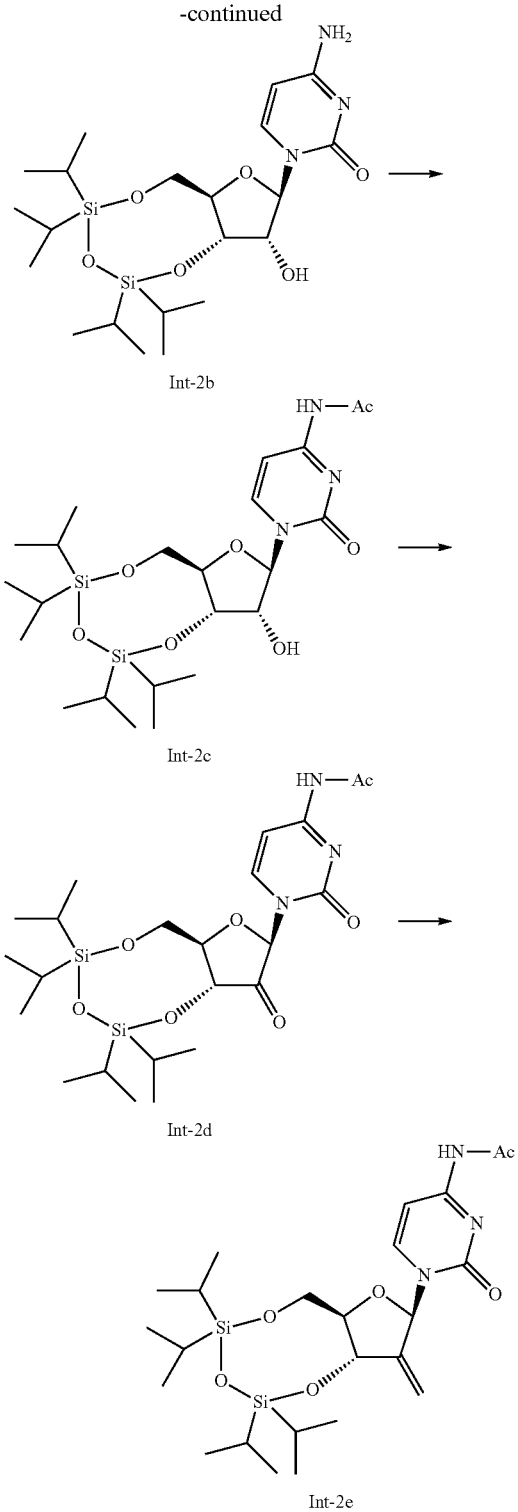

Int-2b

Int-2c

Int-2d

Int-2e

Step A—Synthesis of Compound Int-2b

Cytidine (Int-2a, 8.0 g, 32.89 mmol) was azeotroped with pyridine (2×15 mL) and then suspended in pyridine (25 mL). To the suspension was added tetraisopropyldisiloxanedichloride (12.0 mL, 35.4 mmol) dropwise over fifteen minutes and the resulting reaction was allowed to stir for about 15 hours at room temperature. The reaction mixture was diluted with water and extracted with ethyl acetate. The organic extracted were washed with brine, dried over sodium sulfate, filtered and concentrated in vacuo. The residue obtained was triturated with heptane to provide 13.5 g of compound Int-2b as a white solid [M+H]=486.5.

Step B—Synthesis of Compound Int-2c

Compound Int-2b (13.5 mmol, 27.8 mmol) was dissolved in ethanol (200 mL) and treated with acetic anhydride (10 mL). The resulting reaction was heated to 65° C. and allowed to stir at this temperature for 3 hours, then the reaction mixture was concentrated in vacuo. The residue obtained was cooled to 0° C. in an ice bath and treated with saturated sodium bicarbonate, then extracted with ethyl acetate. The organic extract was dried over sodium sulfate, filtered and concentrated in vacuo to provide 14.5 g of compound Int-2c, which was used without further purification. [M+H]=528.6

Step C—Synthesis of Compound Int-2d

A solution of compound Int-2c (8.0 g, 15.15 mmol) in methylene chloride (120 mL) was cooled to 0° C., then the Dess Martin Periodinane (15 g, 34.3 mmol) was added. The resulting reaction was allowed to stir for about 15 hours at room temperature and was then diluted with diethyl ether (400 mL). The resulting solution was washed with a mixture of saturated sodium bicarbonate and 10% sodium thiosulfate (1:1). The organic phase was collected and was dried over sodium sulfate, filtered and concentrated in vacuo to provide 7.8 g of compound Int-2d, which was used without purification. [M+H]=526.

Step D—Synthesis of Compound Int-2e

Methyltriphenylphosphonium bromide (2.72 g, 7.6 mmol) was diluted with tetrahydrofuran (25 mL) and to the resulting suspension was added KHMDS (0.5 M, 14.5 mL, 7.22 mmol). The resulting reaction was allowed to stir at room temperature for 20 minutes, then the reaction was cooled to 0° C. using an ice bath and a solution of compound Int-2d (1.0 g, 1.9 mmol) in tetrahydrofuran (5 mL) was added dropwise. The resulting reaction was warmed to room temperature and stirred for 4 hours, then the reaction was quenched with saturated ammonium chloride and extracted with ethyl acetate. The organic extract was washed with brine, dried over sodium sulfate, filtered and concentrated in vacuo. The resulting residue was purified using flash chromatography on silica gel (2:1 hexanes/ethyl acetate) to provide 750 mg of compound Int-2e. [M+H]=524.5

Example 3

Preparation of Intermediate Compound Int-3d

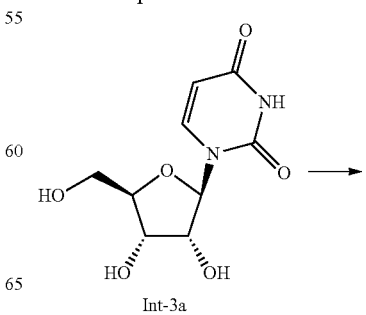

Int-3a

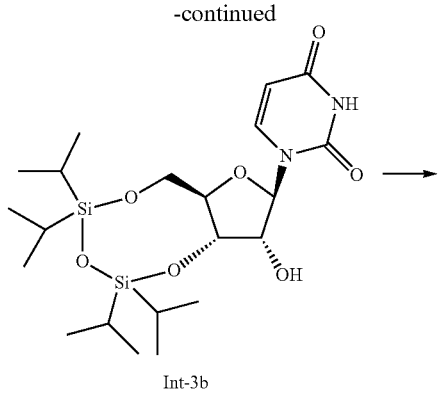

Int-3b

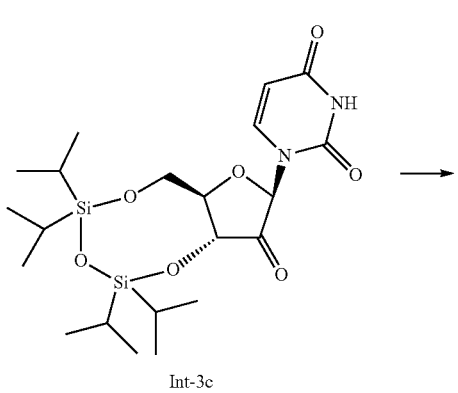

Int-3c

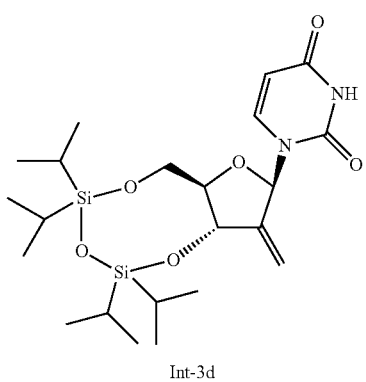

Int-3d

Step A—Synthesis of Compound Int-3b

Uridine (Int-3a, 5.0 g, 18.0 mmol) was azeotroped with pyridine (2×15 mL) and then suspended in pyridine (25 mL). Tetraisopropyldisiloxanedichloride (6.06 mL mL, 18.95 mmol) was added dropwise over fifteen minutes and the reaction was allowed to stir for about 15 hours at room temperature. The reaction was diluted with water and extracted with ethyl acetate. The organic layers were washed with brine, dried over sodium sulfate, and concentrated in vacuo. The residue was azeotroped with toluene (2×50 mL) to provide 7.8 g of compound Int-3b as a white solid that was used without purification. [M+H]=487.42.

Step B—Synthesis of Compound Int-3c

Using the method described in Example 2, Step C, compound Int-3b was converted to compound Int-3b (3.8 g). [M+H]=485.2

Step C—Synthesis of Compound Int-3d

Using the method described in Example 2, Step D, compound Int-3c was converted to compound Int-3d (750 mg) [M+H]=505.2.

Example 4

Preparation of Intermediate Compound Int-4f

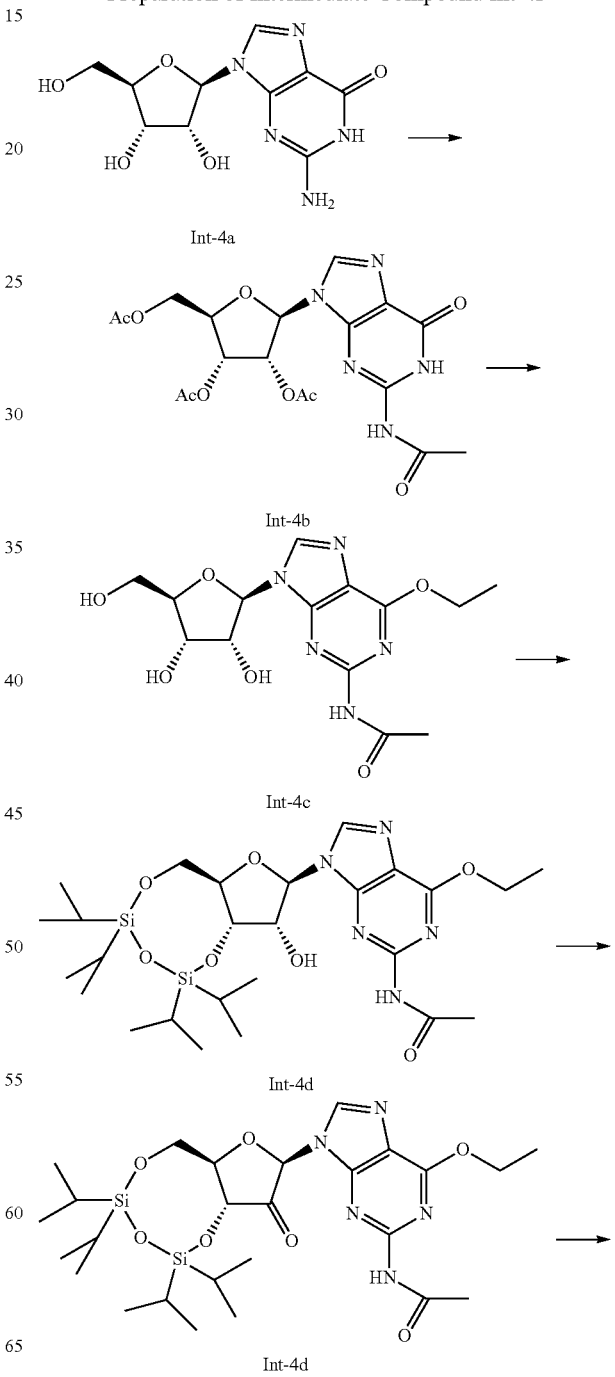

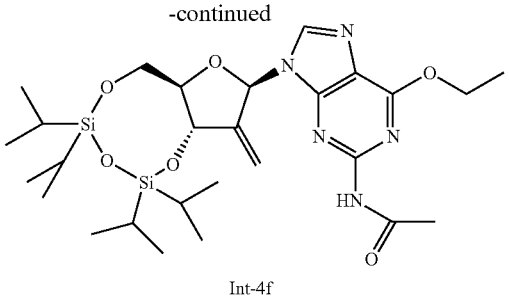

Int-4f

Step A—Synthesis of Compound Int-4b

Guanosine hydrate (Int-4a, 15 g, 53 mmol) was dissolved in pyridine (120 mL) and acetic anhydride (60 mL). N,N-dimethylaminopyridine (6.46 g, 53 mmol) was added and the reaction was heated to 70° C. and allowed to stir at this temperature for 3 hours. The reaction was then cooled in an ice bath and treated dropwise with methanol (60 mL). The reaction mixture was then partially concentrated in vacuo to half of its volume. The resulting solution was diluted with methylene chloride and washed sequentially with 0.2 M potassium dihydrogen sulfate, water, and sodium bicarbonate. The organic phase was then dried over sodium sulfate, filtered and concentrated in vacuo to provide a residue which was purified using flash chromatography on silica gel (5% methanol in methylene chloride) to provide 22 g of compound Int-4b. [M+H]=452.2

Step B—Synthesis of Compound Int-4c

Compound Int-4b (3.2 g, 7.09 mmol) was dissolved in dioxane (50 mL) and treated with triphenylphosphine (2.23 g, 8.5 mmol), diisopropylazodicarboxylate (1.65 mL, 8.5 mmol) and ethanol (391 mg, 8.5 mmol). The reaction was allowed to stir for fifteen minutes at room temperature, then the reaction mixture was concentrated in vacuo. The residue obtained was dissolved in methanol (15 mL) and ammonium hydroxide (15 mL) and stirred for 3 hours. The reaction mixture was filtered and the collected solid was dried in vacuo to provide 1.4 g of compound Int-4c. The filtrate was then concentrated in vacuo and the resulting residue was triturated with chloroform to provide an additional 0.5 g of compound Int-4c. [M+H]=354.2

Step C—Synthesis of Compound Int-4d

Compound Int-4c (1.46 g, 4.13 mmol) was azeotroped with pyridine (2×20 mL) and then suspended in pyridine (30 mL). Tetraisopropyldisiloxanedichloride (1.43 g, 4.43 mmol) was added dropwise over fifteen minutes and the reaction was allowed to stir at room temperature for 3 hours. The reaction was diluted with water (1 mL) and the resulting solution was concentrated in vacuo. The residue obtained was diluted with water and ethyl acetate and the organic layer was collected and washed with brine, dried over sodium sulfate, filtered and concentrated in vacuo. The resulting residue was azeotroped with toluene (2×50 mL) and purified using flash chromatography on silica gel (5% methanol in methylene chloride) to provided 2.25 g of compound Int-4d as a white solid [M+H]=596.2.

Step D—Synthesis of Compound Int-4e

Using the method described in Example 2, Step C, compound Int-4d was converted to compound Int-4e. The product was purified using flash chromatography on silica gel (hexanes/ethyl acetate 0%→100%) to provide 260 mg compound Int-4e. [M+H]=594.2

Step E—Synthesis of Compound Int-4f

Using the method described in Example 2, Step D, compound Int-4e was converted to compound Int-4f, which was purified using flash chromatography on silica gel (2:1 hexanes/ethyl acetate) to provide 170 mg of compound Int-4f. [M+H]=592.2

Example 5

Preparation of Compounds 1 and 2

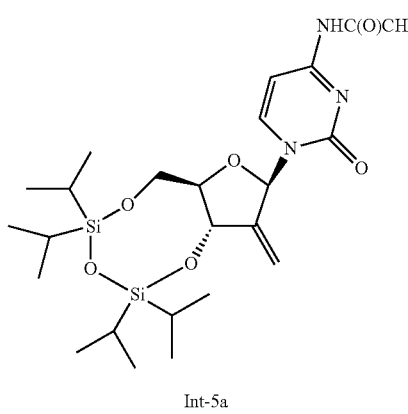

Int-5a

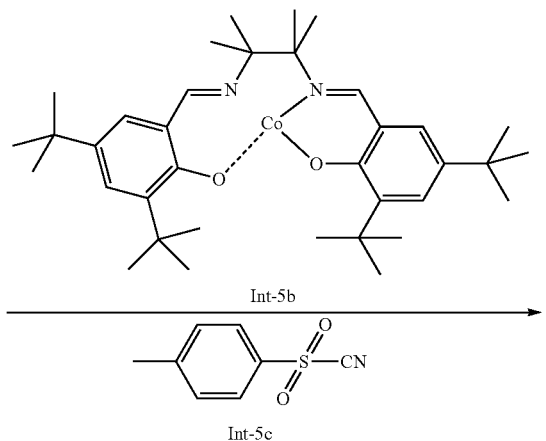

Int-5b

Int-5c

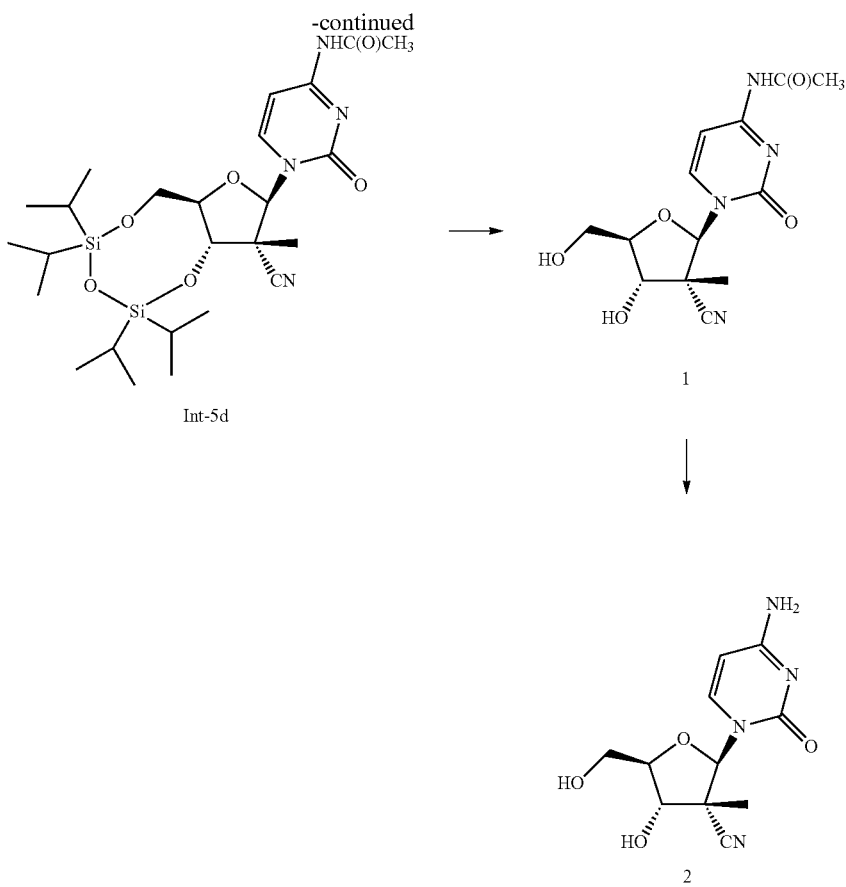

Step A—Synthesis of Compound Int-5d

Compound Int-5a (300 mg, 0.57 mmol), Compound Int-1c (10 mg), and Compound Int-5c (3.1 g, 17.1 mmol) were dissolved in dioxane (2 mL) and the resulting reaction was allowed to stir for 5 minutes at room temperature. A solution of phenylsilane (68 mg, 0.63 mmol) in ethanol (1 mL) was then added dropwise over 2 minutes and the reaction was allowed to stir for and additional 30 minutes. The reaction was then quenched with brine and extracted with ethyl acetate. The organic extract was washed with brine, dried over sodium sulfate, filtered and concentrated in vacuo. The residue obtained was purified using flash chromatography on silica gel (2:1 hexanes/ethyl acetate) to provide compound Int-5d (80 mg). [M+H]=551.5

Step B—Synthesis of Compound 1

Compound Int-5d (23 mg, 0.042 mmol) was dissolved in tetrahydrofuran (1 mL) and to the resulting solution was added TBAF (1.0 M, 0.1 mmol). The reaction was allowed to stir for 1 hour, then the reaction mixture was concentrated in vacuo and the crude residue was purified using flash chromatography on silica gel (20% methanol in methylene chloride) to provide 5.0 mg of compound 1. [M+H]=309.7

Step C—Synthesis of Compound 2

Compound 1 (3.8 mg, 0.012 mmol) was dissolved in 7M ammonia in methanol (2 mL) and stirred for 3 hours at room temperature. The reaction was concentrated in vacuo and the residue was purified using flash chromatography on silica gel (25% methanol in methylene chloride) to provide 3.0 mg of compound 2. [M+H]=267.7; $^1$H-NMR (400 MHz, CD$_3$OD): δ: 8.11 (d, 1H, J=7.58 Hz), 6.38 (s, 1H), 5.90 (bs, 1H), 4.0 (m, 3H), 3.8 (m, 1H), 1.27 (s, 3H).

The following compounds of the present invention were made using the methods described in the Example above and substituting the appropriate reactants and/or reagents.

| Compound No. | Structure | MS (M + H) |
|---|---|---|
| 3 | 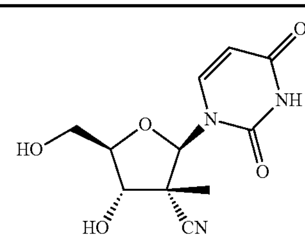 | 290.2 |

Compound 3 $^1$H-NMR (400 MHz, CD$_3$OD): δ: 8.13 (d, 1H, J=8.0 Hz), 6.33 (s, 1H), 5.7 (d, 1H, J=8.0 Hz), 4.06 (m, 1H), 4.0-3.95 (m, 2H), 3.79 (m, 1H), 1.33 (s, 3H).

Example 6

Preparation of Compounds 4 and 5

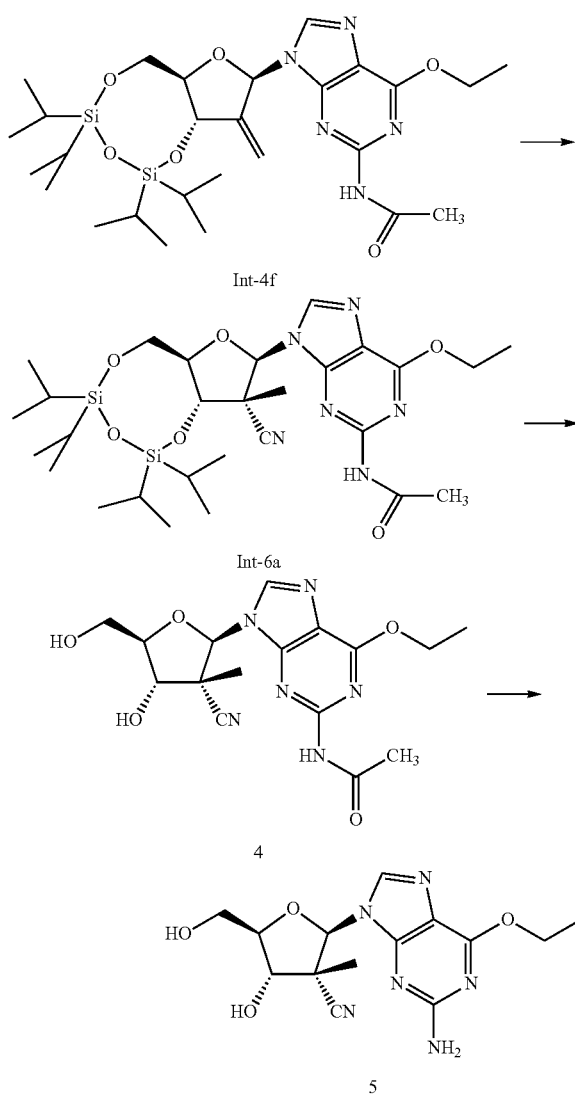

Step A—Synthesis of Compound Int-4f

Using the method described in Example 5, Step A, compound Int-4f was converted to compound Int-6a. [M+H]=619.2

Step B—Synthesis of Compound 4

Using the method described in Example 5, Step B, compound Int-6a was converted to compound 4. [M+H]=376.9

Step C—Synthesis of Compound 5

Compound 4 (8 mg, 0.021 mmol) was dissolved in 7M ammonia in methanol (3 mL) and stirred at 100 C in a pressure tube overnight. The reaction was concentrated and purified by column chromatography (CH2Cl2/MeOH, 0%→5%) to provide 6 mg of compound 5. [M+H]=335.2. $^1$H-NMR (400 MHz, CD$_3$OD): δ: 8.3 (s, 1H), 6.45 (s, 1H), 4.52 (m, 2H), 4.4 (d, 1H), 4.0 (m, 2H), 3.87 (m, 1H), 1.42 (m, 3H), 1.13 (s, 3H).

| Compound No. | Structure | MS (M + H) |
|---|---|---|
| 31 | 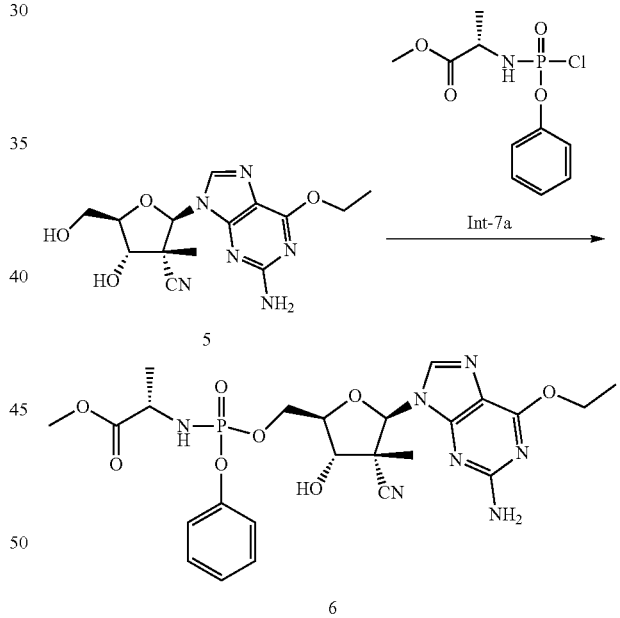 | 321.2 |

Compound 31: $^1$H-NMR (400 MHz, CD$_3$OD): δ: 8.32 (s, 1H), 6.46 (s, 1H), 4.40 (m, 1H), 4.05 (s, 3H), 4.04 (m, 2H), 3.87 (m, 1H), 1.14 (s, 3H).

Example 7

Preparation of Compound 6

To a solution of compound 5 (8 mg, 0.024 mmol) and N-methylimidazole (8 mg, 0.096 mmol) in tetrahydrofuran (2 mL) and was added dropwise a solution of compound Int-7a (26 mg, 0.096 mmol, prepared using methods described in U.S. Pat. No. 7,879,815) in tetrahydrofuran (1 mL). The resulting reaction was allowed to stir for 12 hours at room temperature, then the reaction mixture was concentrated in vacuo and the residue obtained was purified using flash chromatography on silica gel (5% methylene chloride/methanol) to provide compound 6 (3.5 mg).

The following compounds of the present invention were made using the methods described in the Example above and substituting the appropriate reactants and/or reagents.

| Compound No. | Structure | MS (M + H) |
|---|---|---|
| 7 | 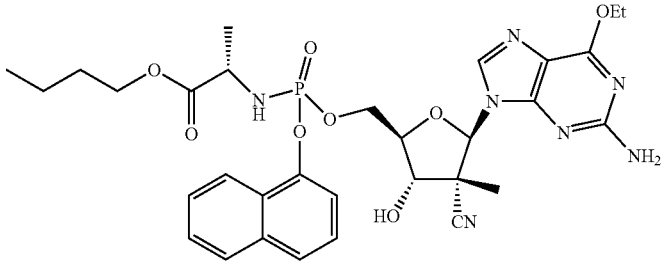 [SMILES: CCCCOC(=O)[C@H](C)NP(=O)(OC[C@H]1O[C@@H](n2cnc3c(OCC)nc(N)nc32)[C@](C)(C#N)[C@@H]1O)Oc1cccc2ccccc12] | 668.7 |
| 8 | 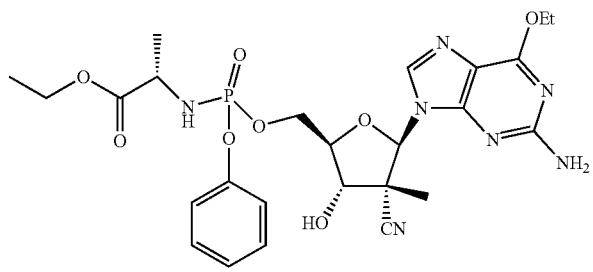 [SMILES: CCOC(=O)[C@H](C)NP(=O)(OC[C@H]1O[C@@H](n2cnc3c(OCC)nc(N)nc32)[C@](C)(C#N)[C@@H]1O)Oc1ccccc1] | 590.2 |
| 9 | 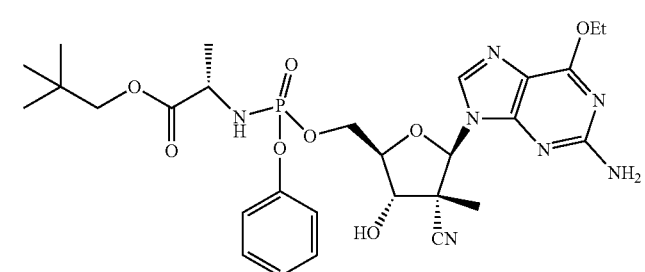 | 631.7 |
| 10 | 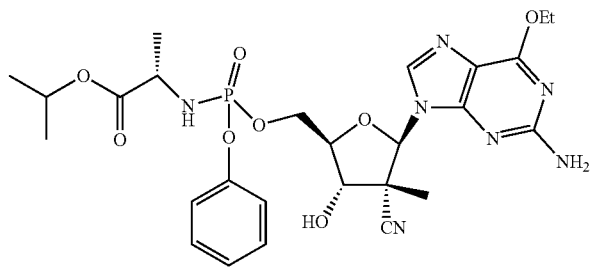 [SMILES: CCOc1nc(N)nc2c1ncn2[C@@H]1O[C@H](COP(=O)(N[C@@H](C)C(=O)OC(C)C)Oc2ccccc2)[C@@H](O)[C@@]1(C)C#N] | 603.7 |
| 11 | 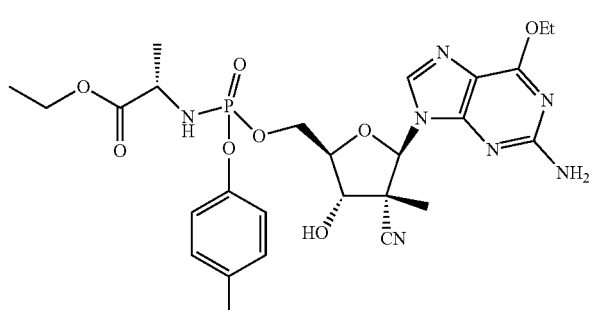 | 607.7 |

-continued

| Compound No. | Structure | MS (M + H) |
|---|---|---|
| 12 | 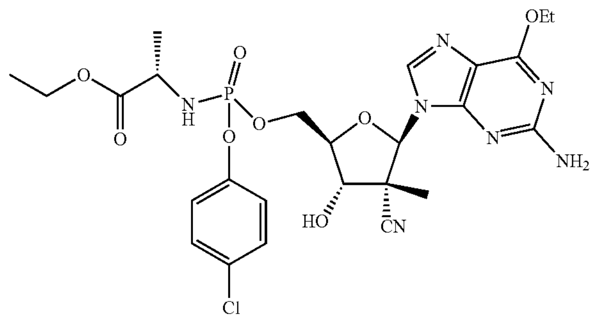 [SMILES: CCOC(=O)[C@H](C)NP(=O)(OC[C@H]1O[C@@H](n2cnc3c(OCC)nc(N)nc32)[C@](C)(C#N)[C@@H]1O)Oc1ccc(Cl)cc1] | 623.7 |
| 13 | 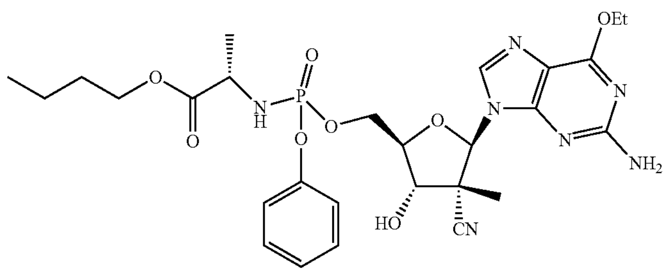 [SMILES: CCCCOC(=O)[C@H](C)NP(=O)(OC[C@H]1O[C@@H](n2cnc3c(OCC)nc(N)nc32)[C@](C)(C#N)[C@@H]1O)Oc1ccccc1] | 617.7 |
| 14 | 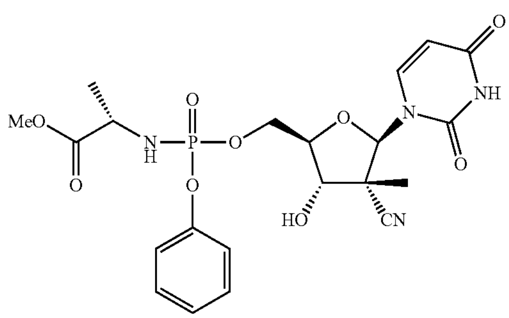 [SMILES: COC(=O)[C@H](C)NP(=O)(OC[C@H]1O[C@@H](n2ccc(=O)[nH]c2=O)[C@](C)(C#N)[C@@H]1O)Oc1ccccc1] | 509.2 |
| 15 | 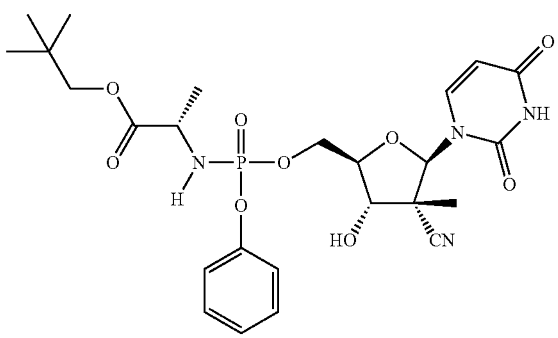 [SMILES: C[C@H](NP(=O)(OC[C@H]1O[C@@H](n2ccc(=O)[nH]c2=O)[C@](C)(C#N)[C@@H]1O)Oc1ccccc1)C(=O)OCC(C)(C)C] | 565 |
| 16 | 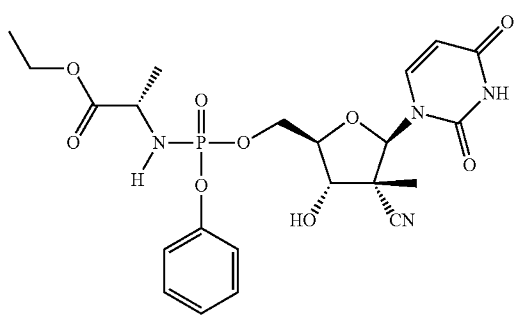 [SMILES: CCOC(=O)[C@H](C)NP(=O)(OC[C@H]1O[C@@H](n2ccc(=O)[nH]c2=O)[C@](C)(C#N)[C@@H]1O)Oc1ccccc1] | 523 |

-continued

| Compound No. | Structure | MS (M + H) |
|---|---|---|
| 17 | 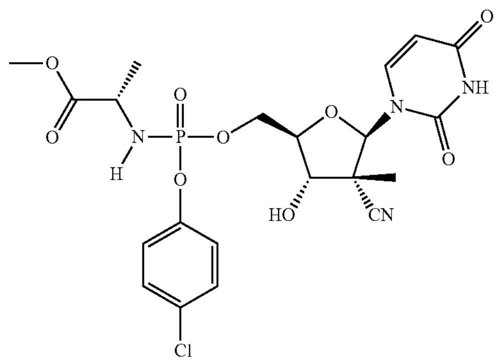 [SMILES: COC(=O)[C@H](C)NP(=O)(OC[C@H]1O[C@@H](n2ccc(=O)[nH]c2=O)[C@](C)(C#N)[C@@H]1O)Oc1ccc(Cl)cc1] | 543 |
| 18 | 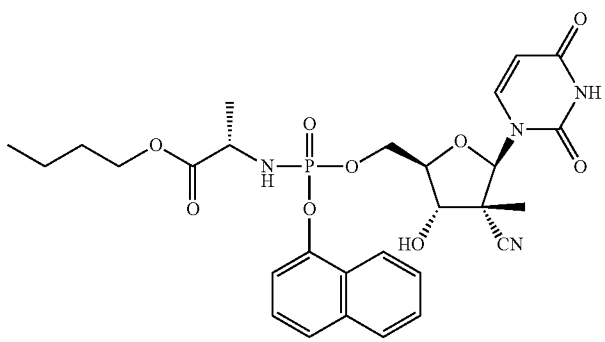 [SMILES: CCCCOC(=O)[C@H](C)NP(=O)(OC[C@H]1O[C@@H](n2ccc(=O)[nH]c2=O)[C@](C)(C#N)[C@@H]1O)Oc1cccc2ccccc12] | 601.2 |
| 19 | 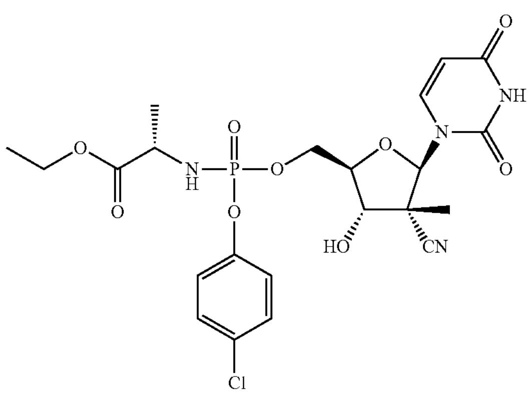 | 557.0 |
| 30 | 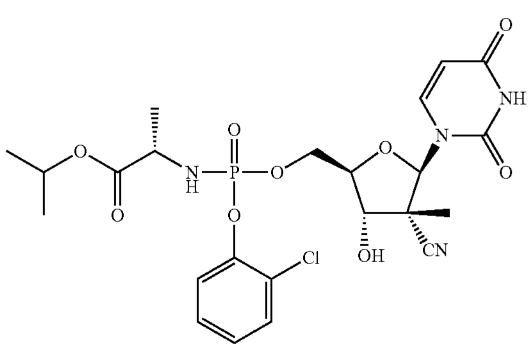 [SMILES: CC(C)OC(=O)[C@H](C)NP(=O)(OC[C@H]1O[C@@H](n2ccc(=O)[nH]c2=O)[C@](C)(C#N)[C@@H]1O)Oc1ccccc1Cl] | 571.2 |

Example 8

Preparation of Compound 20

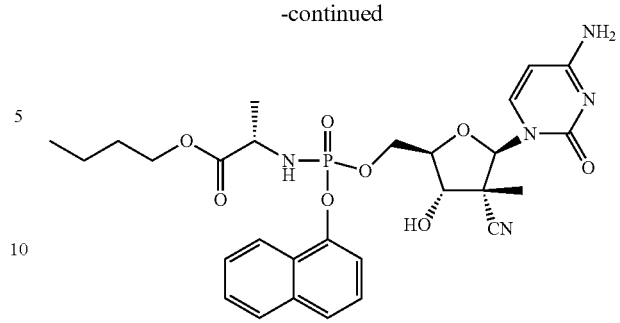

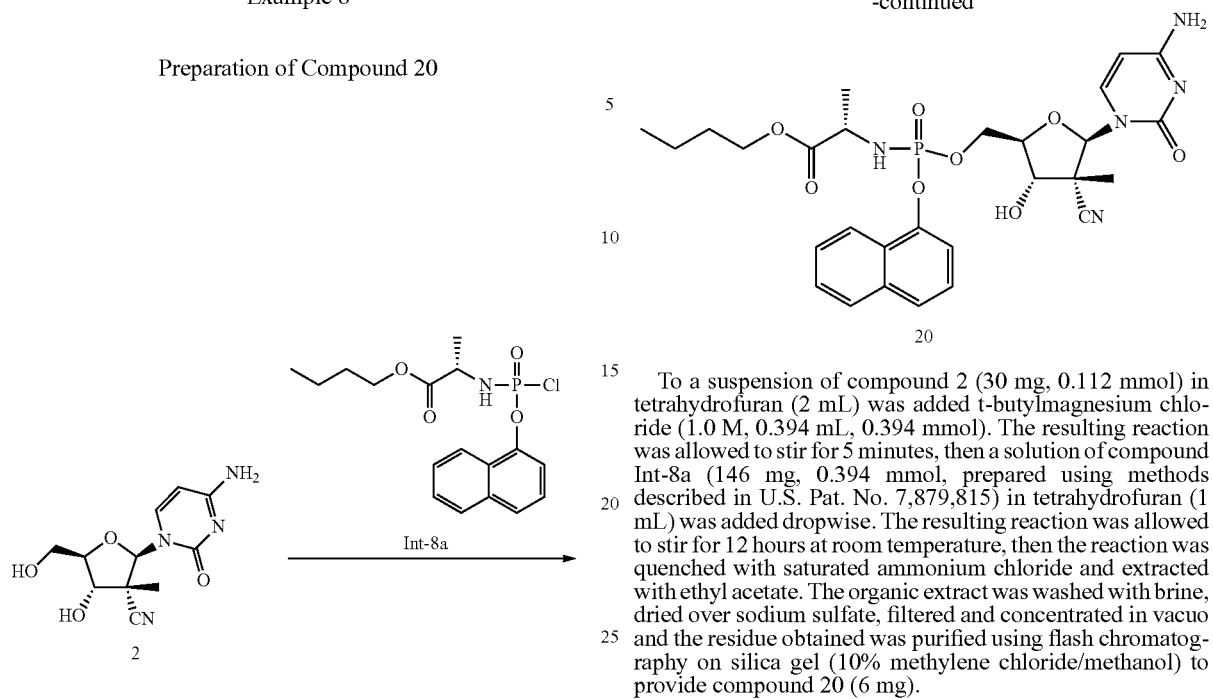

To a suspension of compound 2 (30 mg, 0.112 mmol) in tetrahydrofuran (2 mL) was added t-butylmagnesium chloride (1.0 M, 0.394 mL, 0.394 mmol). The resulting reaction was allowed to stir for 5 minutes, then a solution of compound Int-8a (146 mg, 0.394 mmol, prepared using methods described in U.S. Pat. No. 7,879,815) in tetrahydrofuran (1 mL) was added dropwise. The resulting reaction was allowed to stir for 12 hours at room temperature, then the reaction was quenched with saturated ammonium chloride and extracted with ethyl acetate. The organic extract was washed with brine, dried over sodium sulfate, filtered and concentrated in vacuo and the residue obtained was purified using flash chromatography on silica gel (10% methylene chloride/methanol) to provide compound 20 (6 mg).

The following compounds of the present invention were made using the methods described in the Example above and substituting the appropriate reactants and/or reagents.

| Compound No. | Structure | MS (M + H) |
|---|---|---|
| 21 | 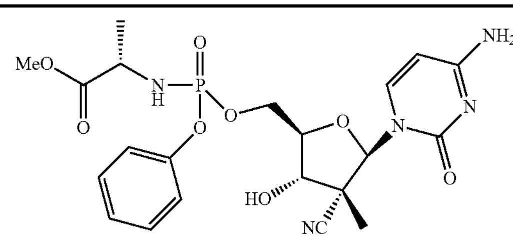 | 508.2 |
| 22 | 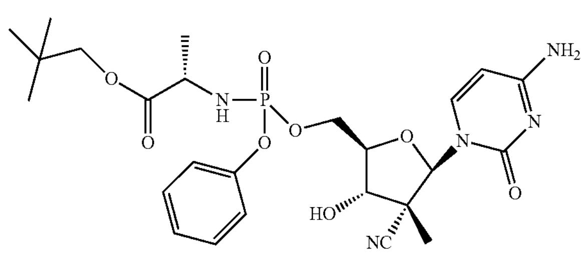 [SMILES: C[C@H](NP(=O)(OC[C@H]1O[C@@H](n2ccc(N)nc2=O)[C@](C)(C#N)[C@@H]1O)Oc1ccccc1)C(=O)OCC(C)(C)C] | 564.2 |
| 59 | 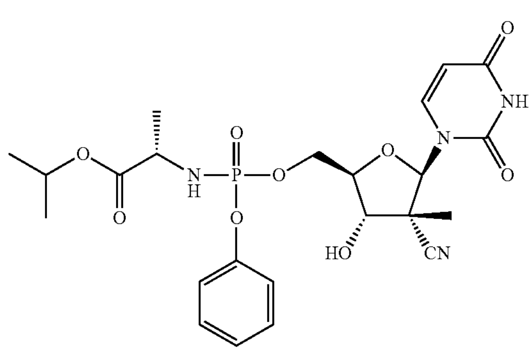 [SMILES: CC(C)OC(=O)[C@H](C)NP(=O)(OC[C@H]1O[C@@H](n2ccc(=O)[nH]c2=O)[C@](C)(C#N)[C@@H]1O)Oc1ccccc1] | 537.2 |

-continued
| Compound No. | Structure | MS (M + H) |
|---|---|---|
| 65 | 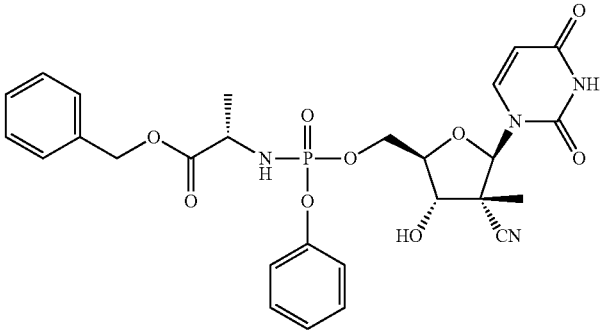 [SMILES: C[C@H](NP(=O)(OC[C@H]1O[C@@H](n2ccc(=O)[nH]c2=O)[C@](C)(C#N)[C@@H]1O)Oc1ccccc1)C(=O)OCc1ccccc1] | 585.2 |
| 68 | 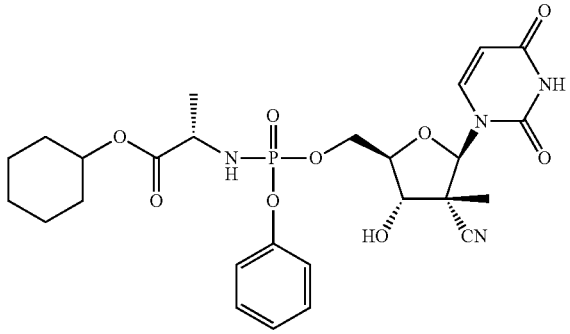 [SMILES: C[C@H](NP(=O)(OC[C@H]1O[C@@H](n2ccc(=O)[nH]c2=O)[C@](C)(C#N)[C@@H]1O)Oc1ccccc1)C(=O)OC1CCCCC1] | 577.2 |
| 71 | 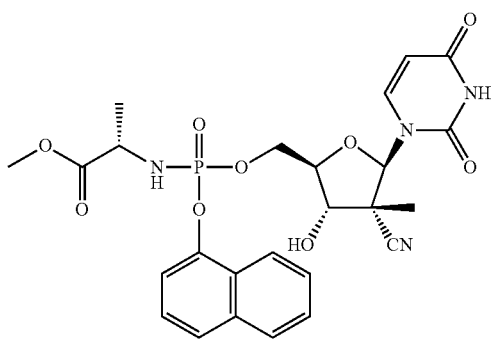 [SMILES: COC(=O)[C@H](C)NP(=O)(OC[C@H]1O[C@@H](n2ccc(=O)[nH]c2=O)[C@](C)(C#N)[C@@H]1O)Oc1cccc2ccccc12] | 559.0 |
| 78 | 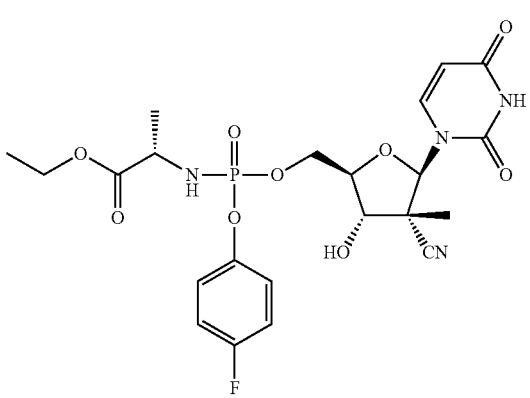 | 541.2 |

-continued

| Compound No. | Structure | MS (M + H) |
|---|---|---|
| 79 | 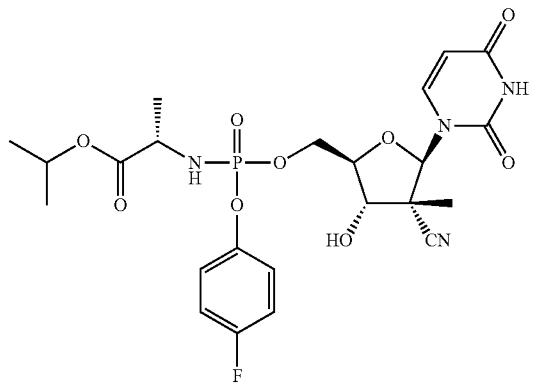 [SMILES: CCOC(=O)[C@H](C)NP(=O)(OC[C@H]1O[C@@H](n2ccc(=O)[nH]c2=O)[C@](C)(C#N)[C@@H]1O)Oc1ccc(F)cc1] | 555.0 |
| 80 | 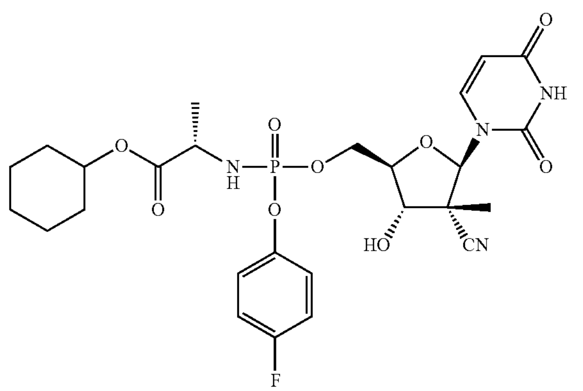 [SMILES: C[C@H](NP(=O)(OC[C@H]1O[C@@H](n2ccc(=O)[nH]c2=O)[C@](C)(C#N)[C@@H]1O)Oc1ccc(F)cc1)C(=O)OC1CCCCC1] | 595.2 |
| 81 | 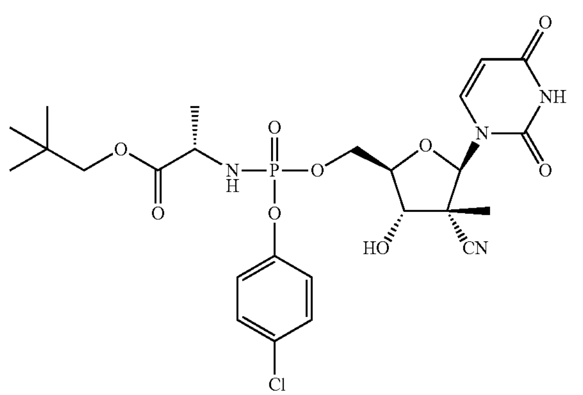 [SMILES: C[C@H](NP(=O)(OC[C@H]1O[C@@H](n2ccc(=O)[nH]c2=O)[C@](C)(C#N)[C@@H]1O)Oc1ccc(Cl)cc1)C(=O)OCC(C)(C)C] | 599.2 |
| 82 | 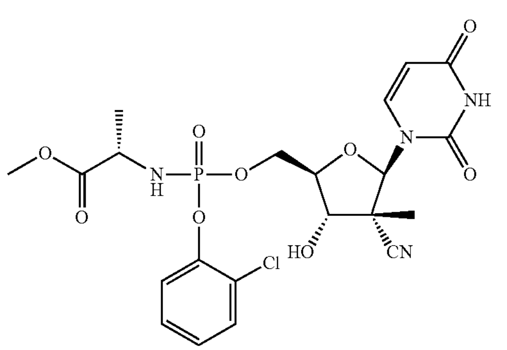 [SMILES: COC(=O)[C@H](C)NP(=O)(OC[C@H]1O[C@@H](n2ccc(=O)[nH]c2=O)[C@](C)(C#N)[C@@H]1O)Oc1ccccc1Cl] | 542.7 |

-continued

| Compound No. | Structure | MS (M + H) |
|---|---|---|
| 83 | 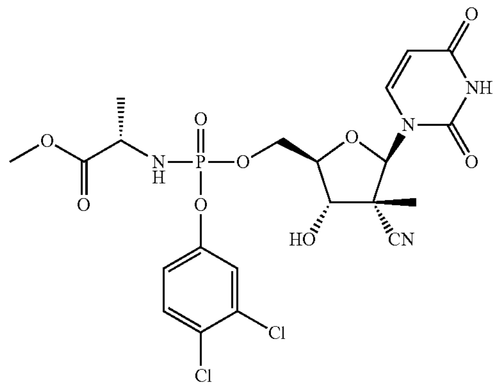 [SMILES: COC(=O)[C@H](C)NP(=O)(OC[C@H]1O[C@@H](n2ccc(=O)[nH]c2=O)[C@](C)(C#N)[C@@H]1O)Oc1ccc(Cl)c(Cl)c1] | 576.6 |
| 84 | 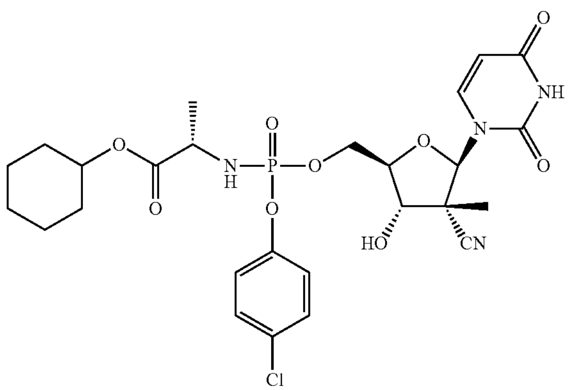 [SMILES: C[C@H](NP(=O)(OC[C@H]1O[C@@H](n2ccc(=O)[nH]c2=O)[C@](C)(C#N)[C@@H]1O)Oc1ccc(Cl)cc1)C(=O)OC1CCCCC1] | 611.0 |
| 85 | 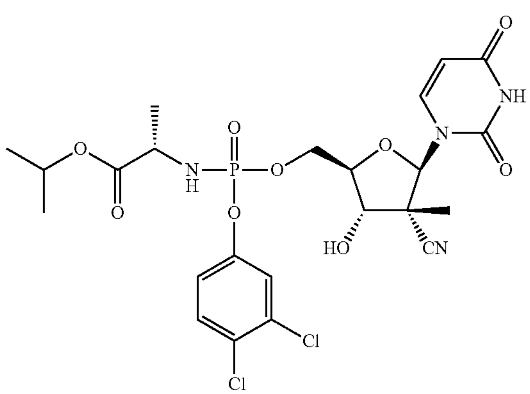 [SMILES: CC(C)OC(=O)[C@H](C)NP(=O)(OC[C@H]1O[C@@H](n2ccc(=O)[nH]c2=O)[C@](C)(C#N)[C@@H]1O)Oc1ccc(Cl)c(Cl)c1] | 605.0 |
| 86 | 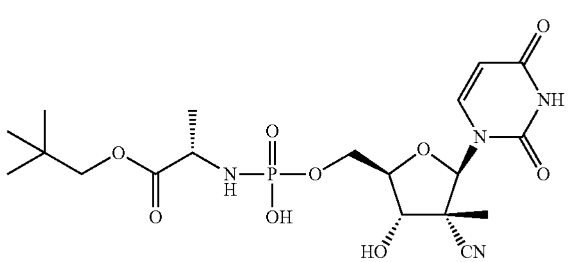 [SMILES: C[C@H](NP(=O)(O)OC[C@H]1O[C@@H](n2ccc(=O)[nH]c2=O)[C@](C)(C#N)[C@@H]1O)C(=O)OCC(C)(C)C] | 489.2 |

| Compound No. | Structure | MS (M + H) |
|---|---|---|
| 87 | 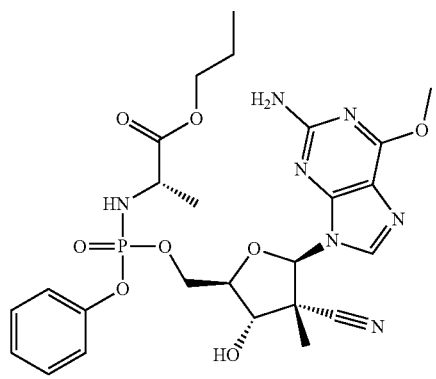 [SMILES: CCCOC(=O)[C@H](C)NP(=O)(OC[C@H]1O[C@@H](n2cnc3c(OC)nc(N)nc32)[C@](C)(C#N)[C@@H]1O)Oc1ccccc1] | 590.2 |
| 88 | 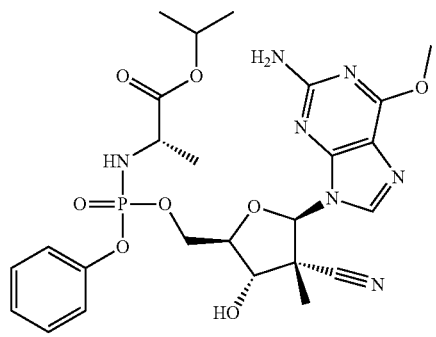 [SMILES: COc1nc(N)nc2c1ncn2[C@@H]1O[C@H](COP(=O)(N[C@@H](C)C(=O)OC(C)C)Oc2ccccc2)[C@@H](O)[C@@]1(C)C#N] | 590.2 |
| 89 | 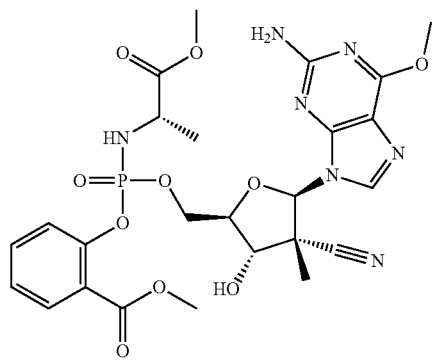 [SMILES: COC(=O)c1ccccc1OP(=O)(N[C@@H](C)C(=O)OC)OC[C@H]1O[C@@H](n2cnc3c(OC)nc(N)nc32)[C@](C)(C#N)[C@@H]1O] | 620.2 |
| 96 | 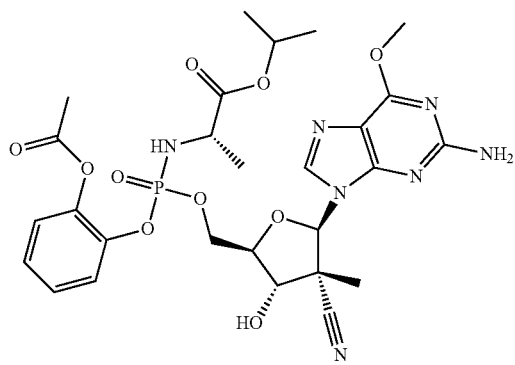 [SMILES: COc1nc(N)nc2c1ncn2[C@@H]1O[C@H](COP(=O)(N[C@@H](C)C(=O)OC(C)C)Oc2ccccc2OC(C)=O)[C@@H](O)[C@@]1(C)C#N] | 648.2 |

-continued

| Compound No. | Structure | MS (M + H) |
|---|---|---|
| 104 | 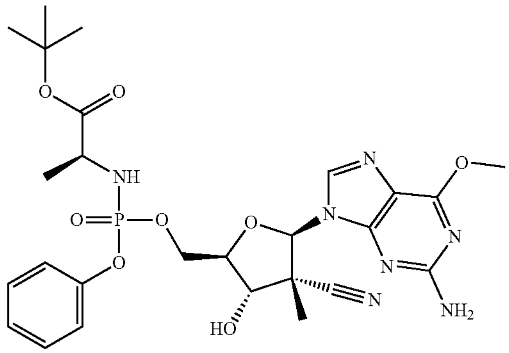 [SMILES: COc1nc(N)nc2c1ncn2[C@@H]1O[C@H](COP(=O)(N[C@@H](C)C(=O)OC(C)(C)C)Oc2ccccc2)[C@@H](O)[C@@]1(C)C#N] | 604.2 |
| 105 | 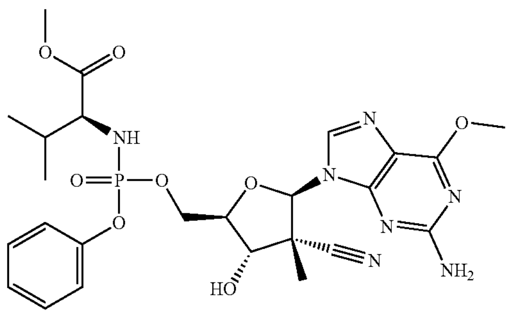 [SMILES: COC(=O)[C@@H](NP(=O)(OC[C@H]1O[C@@H](n2cnc3c(OC)nc(N)nc32)[C@](C)(C#N)[C@@H]1O)Oc1ccccc1)C(C)C] | 590.2 |
| 108 | 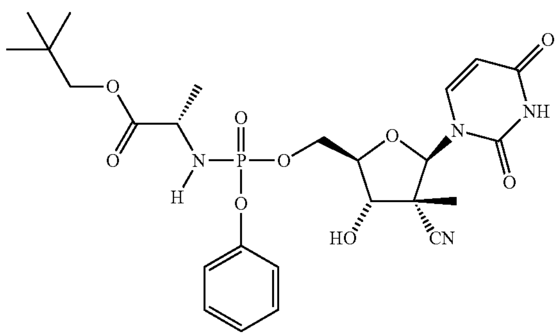 [SMILES: C[C@H](NP(=O)(OC[C@H]1O[C@@H](n2ccc(=O)[nH]c2=O)[C@](C)(C#N)[C@@H]1O)Oc1ccccc1)C(=O)OCC(C)(C)C] | 565 |
| 111 | 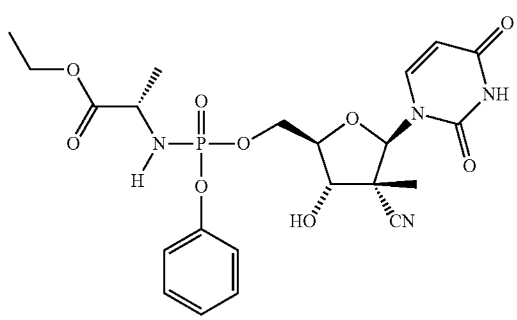 [SMILES: CCOC(=O)[C@H](C)NP(=O)(OC[C@H]1O[C@@H](n2ccc(=O)[nH]c2=O)[C@](C)(C#N)[C@@H]1O)Oc1ccccc1] | 523 |

-continued
| Compound No. | Structure | MS (M + H) |
|---|---|---|
| 112 | 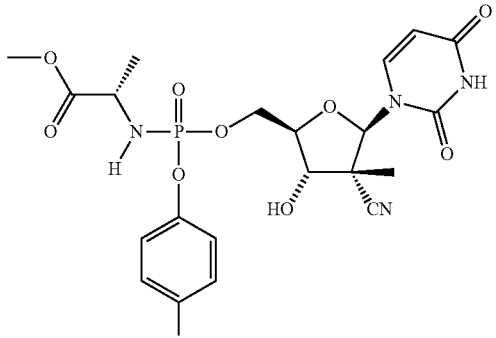 | 543 |
| 115 | 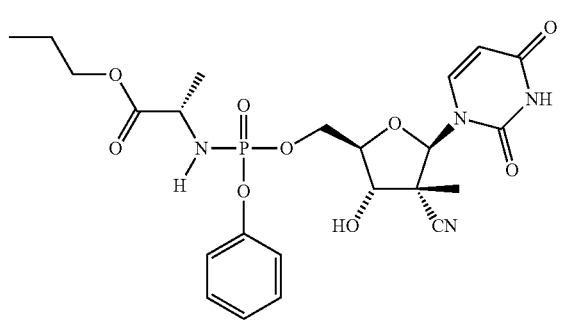 [SMILES: CCCOC(=O)[C@H](C)NP(=O)(OC[C@H]1O[C@@H](n2ccc(=O)[nH]c2=O)[C@](C)(C#N)[C@@H]1O)Oc1ccccc1] | 537 |
| 116 | 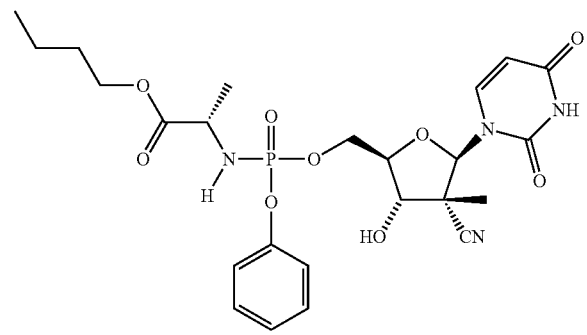 [SMILES: CCCCOC(=O)[C@H](C)NP(=O)(OC[C@H]1O[C@@H](n2ccc(=O)[nH]c2=O)[C@](C)(C#N)[C@@H]1O)Oc1ccccc1] | 551 |
| 117 | 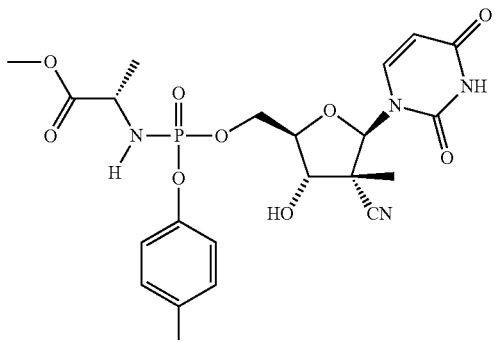 | 527 |

-continued

| Compound No. | Structure | MS (M + H) |
|---|---|---|
| 118 | 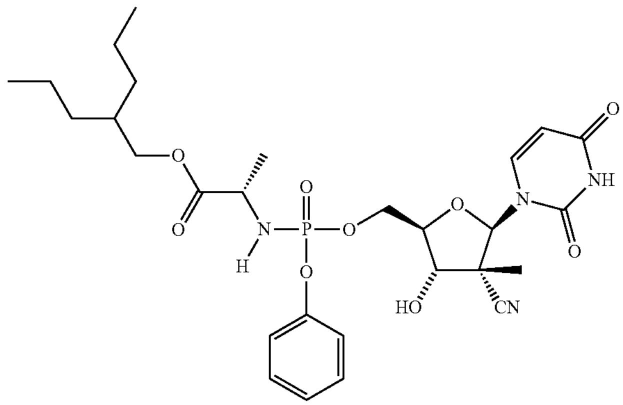 [SMILES: CCCC(CCC)COC(=O)[C@H](C)NP(=O)(OC[C@H]1O[C@@H](n2ccc(=O)[nH]c2=O)[C@](C)(C#N)[C@@H]1O)Oc1ccccc1] | 607 |
| 119 | 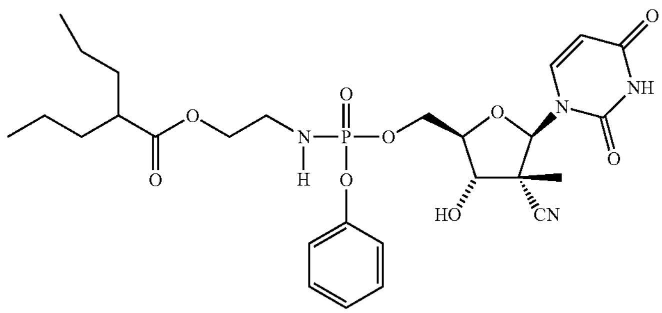 [SMILES: CCCC(CCC)C(=O)OCCNP(=O)(OC[C@H]1O[C@@H](n2ccc(=O)[nH]c2=O)[C@](C)(C#N)[C@@H]1O)Oc1ccccc1] | 593 |
| 122 | 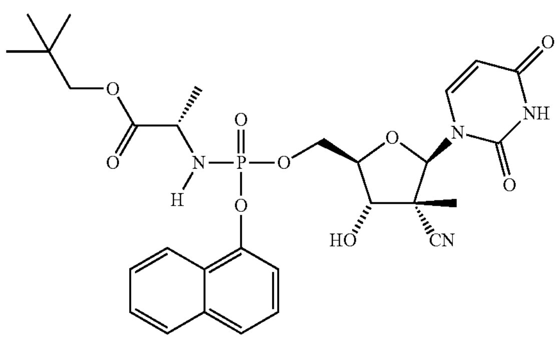 [SMILES: C[C@H](NP(=O)(OC[C@H]1O[C@@H](n2ccc(=O)[nH]c2=O)[C@](C)(C#N)[C@@H]1O)Oc1cccc2ccccc12)C(=O)OCC(C)(C)C] | 615 |
| 124 | 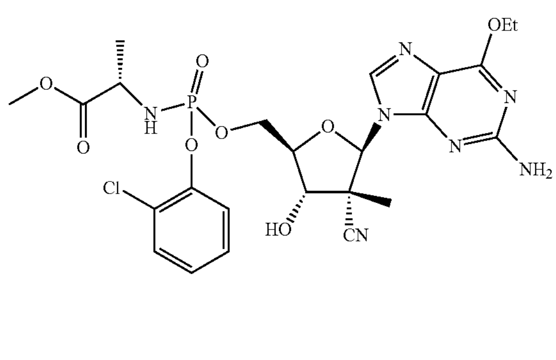 [SMILES: CCOc1nc(N)nc2c1ncn2[C@@H]1O[C@H](COP(=O)(N[C@@H](C)C(=O)OC)Oc2ccccc2Cl)[C@@H](O)[C@@]1(C)C#N] | 610.0 |

-continued

| Compound No. | Structure | MS (M + H) |
|---|---|---|
| 125 | 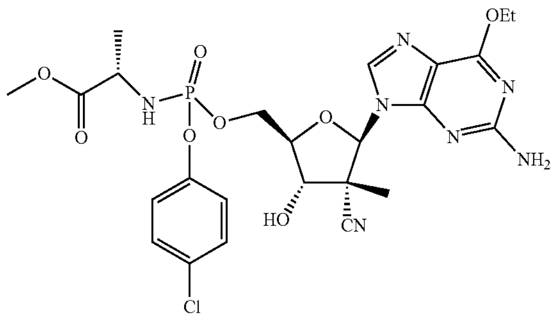 [SMILES: CCOc1nc(N)nc2c1ncn2[C@@H]1O[C@H](COP(=O)(N[C@@H](C)C(=O)OC)Oc2ccc(Cl)cc2)[C@@H](O)[C@@]1(C)C#N] | 610.6 |
| 126 | 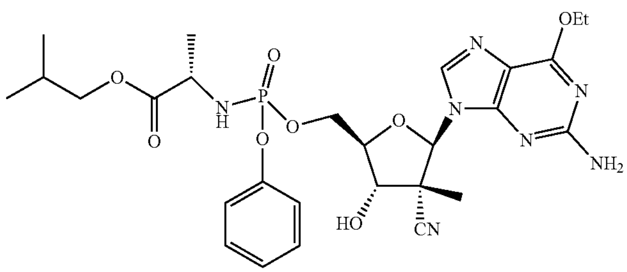 [SMILES: CCOc1nc(N)nc2c1ncn2[C@@H]1O[C@H](COP(=O)(N[C@@H](C)C(=O)OCC(C)C)Oc2ccccc2)[C@@H](O)[C@@]1(C)C#N] | 619.2 |
| 129 | 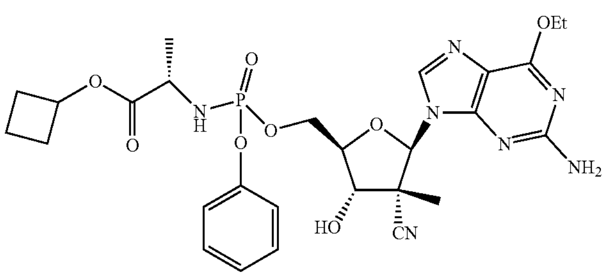 [SMILES: CCOc1nc(N)nc2c1ncn2[C@@H]1O[C@H](COP(=O)(N[C@@H](C)C(=O)OC2CCC2)Oc2ccccc2)[C@@H](O)[C@@]1(C)C#N] | 616.2 |
| 131 | 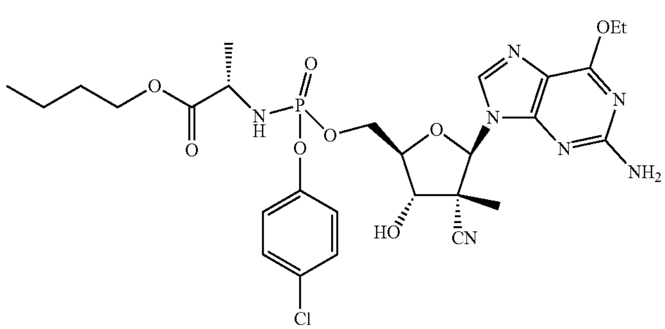 [SMILES: CCCCOC(=O)[C@H](C)NP(=O)(OC[C@H]1O[C@@H](n2cnc3c(OCC)nc(N)nc32)[C@](C)(C#N)[C@@H]1O)Oc1ccc(Cl)cc1] | 652.7 |

-continued

| Compound No. | Structure | MS (M + H) |
|---|---|---|
| 132 | 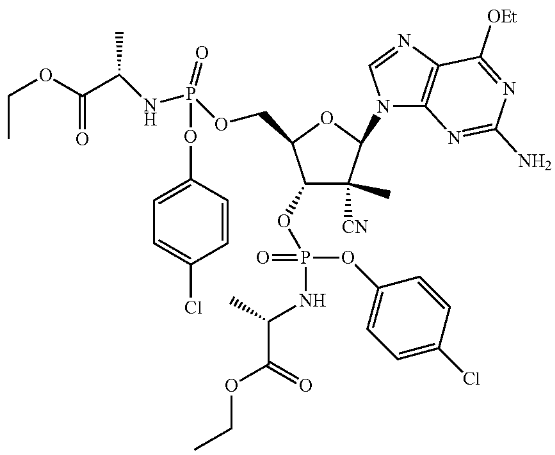 [SMILES: CCOC(=O)[C@H](C)NP(=O)(OC[C@H]1O[C@@H](n2cnc3c(OCC)nc(N)nc32)[C@](C)(C#N)[C@@H]1OP(=O)(N[C@@H](C)C(=O)OCC)Oc1ccc(Cl)cc1)Oc1ccc(Cl)cc1] | 914.5 |
| 133 | 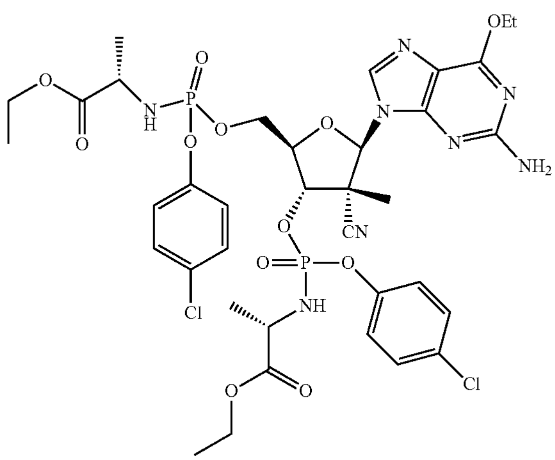 [SMILES: CCOC(=O)[C@H](C)NP(=O)(OC[C@H]1O[C@@H](n2cnc3c(OCC)nc(N)nc32)[C@](C)(C#N)[C@@H]1OP(=O)(N[C@@H](C)C(=O)OCC)Oc1ccc(Cl)cc1)Oc1ccc(Cl)cc1] | 914.5 |
| 140 | 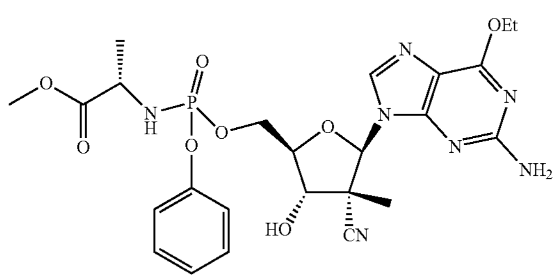 [SMILES: CCOc1nc(N)nc2c1ncn2[C@@H]1O[C@H](COP(=O)(N[C@@H](C)C(=O)OC)Oc2ccccc2)[C@@H](O)[C@@]1(C)C#N] | 562.1 |
| 143 | 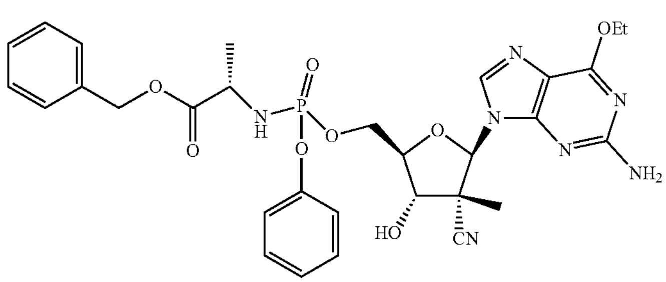 [SMILES: CCOc1nc(N)nc2c1ncn2[C@@H]1O[C@H](COP(=O)(N[C@@H](C)C(=O)OCc2ccccc2)Oc2ccccc2)[C@@H](O)[C@@]1(C)C#N] | 638.2 |

-continued

| Compound No. | Structure | MS (M + H) |
|---|---|---|
| 147 | 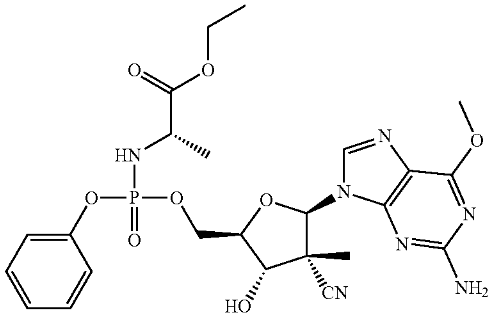 [SMILES: CCOC(=O)[C@H](C)NP(=O)(OC[C@H]1O[C@@H](n2cnc3c(OC)nc(N)nc32)[C@](C)(C#N)[C@@H]1O)Oc1ccccc1] | 575.9 |
| 150 | 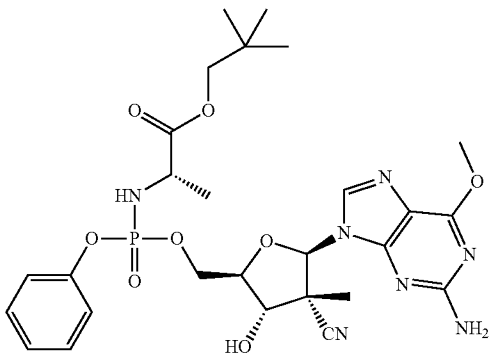 [SMILES: COc1nc(N)nc2c1ncn2[C@@H]1O[C@H](COP(=O)(N[C@@H](C)C(=O)OCC(C)(C)C)Oc2ccccc2)[C@@H](O)[C@@]1(C)C#N] | 618.2 |
| 153 | 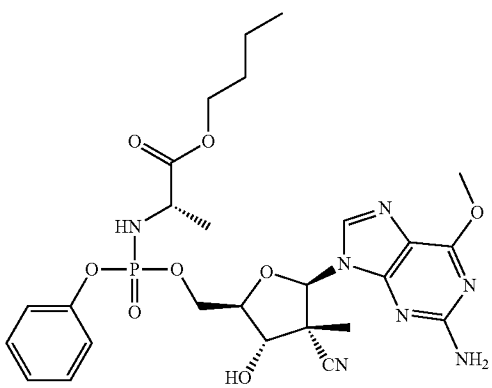 [SMILES: CCCCOC(=O)[C@H](C)NP(=O)(OC[C@H]1O[C@@H](n2cnc3c(OC)nc(N)nc32)[C@](C)(C#N)[C@@H]1O)Oc1ccccc1] | 604.2 |
| 156 | 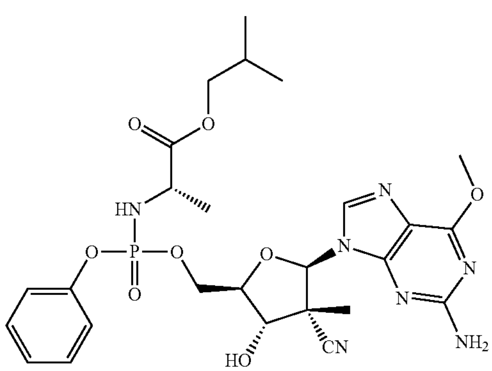 [SMILES: COc1nc(N)nc2c1ncn2[C@@H]1O[C@H](COP(=O)(N[C@@H](C)C(=O)OCC(C)C)Oc2ccccc2)[C@@H](O)[C@@]1(C)C#N] | 604.2 |

-continued

| Compound No. | Structure | MS (M + H) |
|---|---|---|
| 157 | 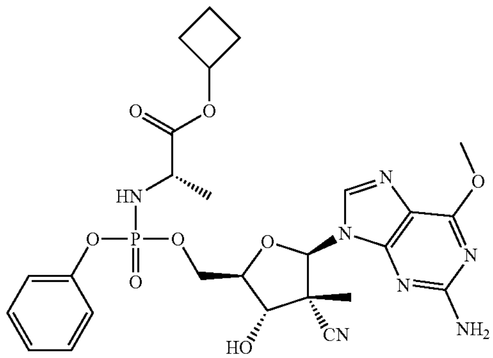 [SMILES: COc1nc(N)nc2c1ncn2[C@@H]1O[C@H](COP(=O)(N[C@@H](C)C(=O)OC2CCC2)Oc2ccccc2)[C@@H](O)[C@@]1(C)C#N] | 602.2 |
| 158 | 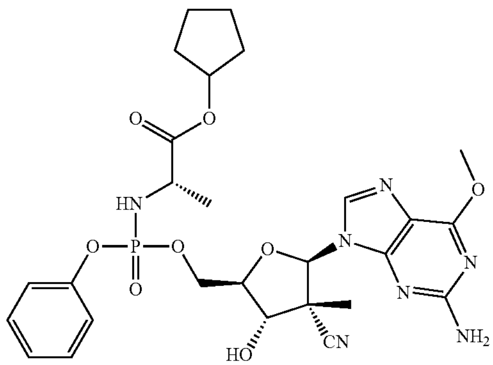 [SMILES: COc1nc(N)nc2c1ncn2[C@@H]1O[C@H](COP(=O)(N[C@@H](C)C(=O)OC2CCCC2)Oc2ccccc2)[C@@H](O)[C@@]1(C)C#N] | 616.2 |
| 161 | 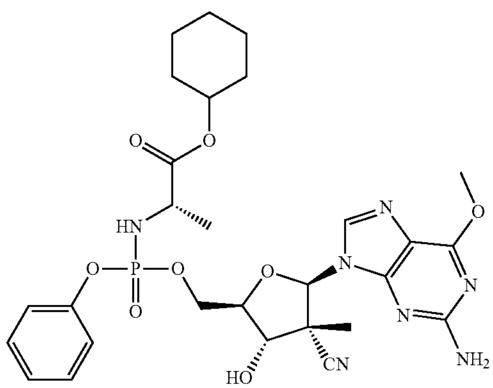 [SMILES: COc1nc(N)nc2c1ncn2[C@@H]1O[C@H](COP(=O)(N[C@@H](C)C(=O)OC2CCCCC2)Oc2ccccc2)[C@@H](O)[C@@]1(C)C#N] | 630.2 |
| 162 | 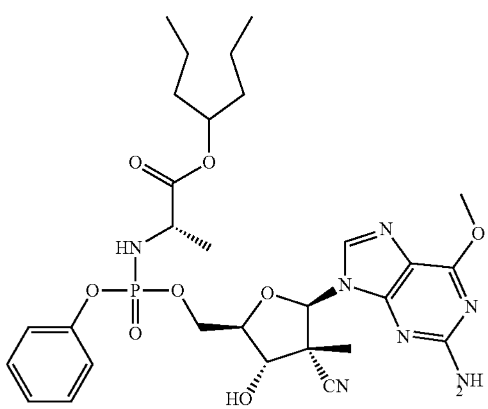 [SMILES: CCCC(CCC)OC(=O)[C@H](C)NP(=O)(OC[C@H]1O[C@@H](n2cnc3c(OC)nc(N)nc32)[C@](C)(C#N)[C@@H]1O)Oc1ccccc1] | 660.2 |

-continued

| Compound No. | Structure | MS (M + H) |
|---|---|---|
| 165 | 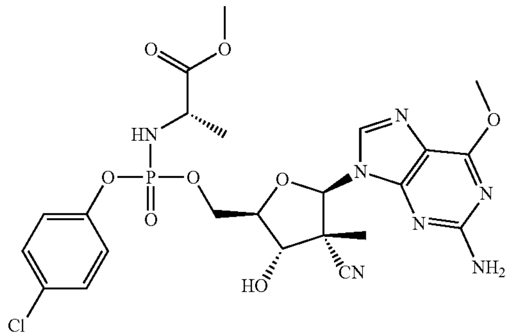 [SMILES: COC(=O)[C@H](C)NP(=O)(OC[C@H]1O[C@@H](n2cnc3c(OC)nc(N)nc32)[C@](C)(C#N)[C@@H]1O)Oc1ccc(Cl)cc1] | 596.2 |
| 168 | 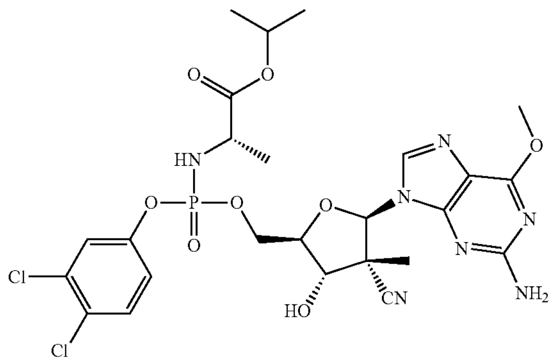 [SMILES: COc1nc(N)nc2c1ncn2[C@@H]1O[C@H](COP(=O)(N[C@@H](C)C(=O)OC(C)C)Oc2ccc(Cl)c(Cl)c2)[C@@H](O)[C@@]1(C)C#N] | 660.0 |
| 169 | 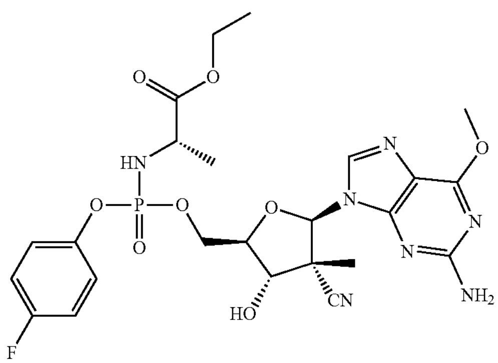 [SMILES: CCOC(=O)[C@H](C)NP(=O)(OC[C@H]1O[C@@H](n2cnc3c(OC)nc(N)nc32)[C@](C)(C#N)[C@@H]1O)Oc1ccc(F)cc1] | 594.2 |
| 170 | 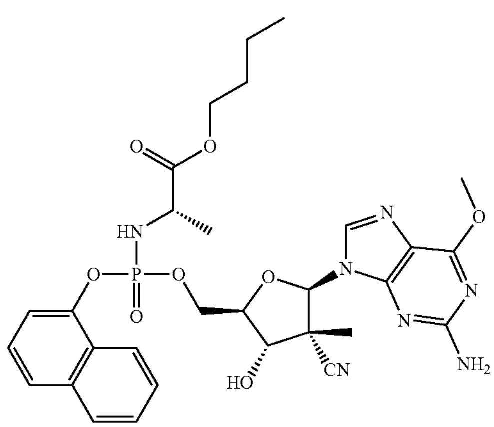 [SMILES: CCCCOC(=O)[C@H](C)NP(=O)(OC[C@H]1O[C@@H](n2cnc3c(OC)nc(N)nc32)[C@](C)(C#N)[C@@H]1O)Oc1cccc2ccccc12] | 654.2 |

-continued

| Compound No. | Structure | MS (M + H) |
|---|---|---|
| 173 | 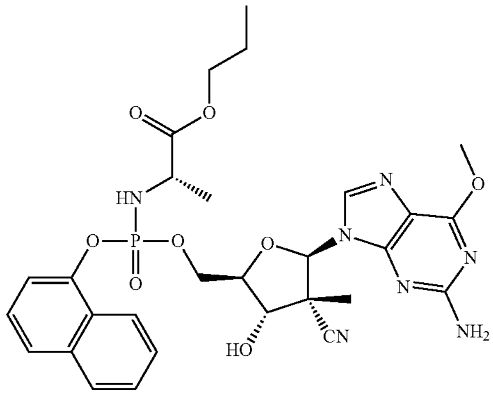 [SMILES: CCCOC(=O)[C@H](C)NP(=O)(OC[C@H]1O[C@@H](n2cnc3c(OC)nc(N)nc32)[C@](C)(C#N)[C@@H]1O)Oc1cccc2ccccc12] | 640.2 |
| 174 | 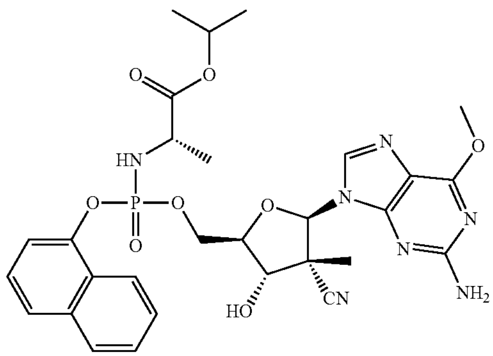 [SMILES: COc1nc(N)nc2c1ncn2[C@@H]1O[C@H](COP(=O)(N[C@@H](C)C(=O)OC(C)C)Oc2cccc3ccccc23)[C@@H](O)[C@@]1(C)C#N] | 640.2 |
| 175 | 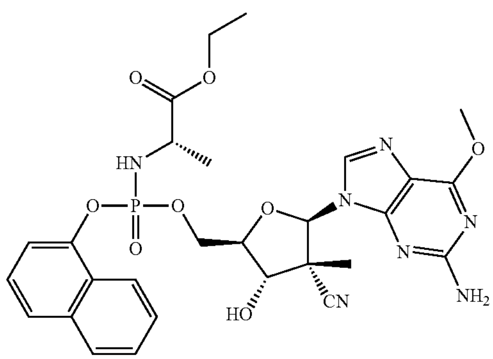 [SMILES: CCOC(=O)[C@H](C)NP(=O)(OC[C@H]1O[C@@H](n2cnc3c(OC)nc(N)nc32)[C@](C)(C#N)[C@@H]1O)Oc1cccc2ccccc12] | 626.2 |
| 178 | 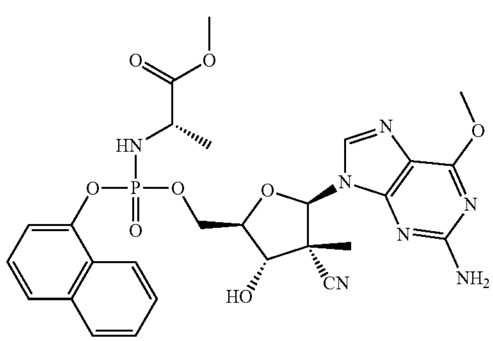 [SMILES: COC(=O)[C@H](C)NP(=O)(OC[C@H]1O[C@@H](n2cnc3c(OC)nc(N)nc32)[C@](C)(C#N)[C@@H]1O)Oc1cccc2ccccc12] | 612.2 |

-continued

| Compound No. | Structure | MS (M + H) |
|---|---|---|
| 181 | 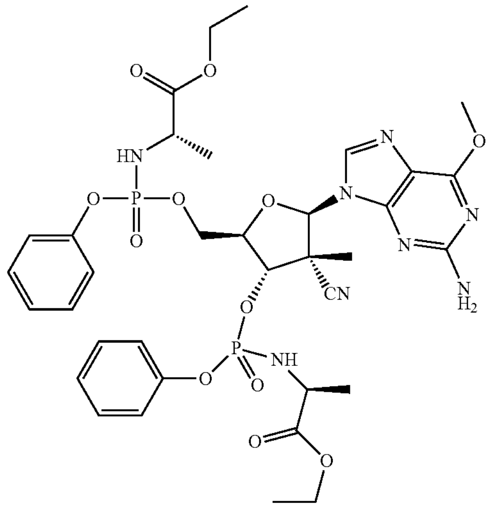 [SMILES: CCOC(=O)[C@H](C)NP(=O)(OC[C@H]1O[C@@H](n2cnc3c(OC)nc(N)nc32)[C@](C)(C#N)[C@@H]1OP(=O)(N[C@@H](C)C(=O)OCC)Oc1ccccc1)Oc1ccccc1] | 831.2 |
| 182 | 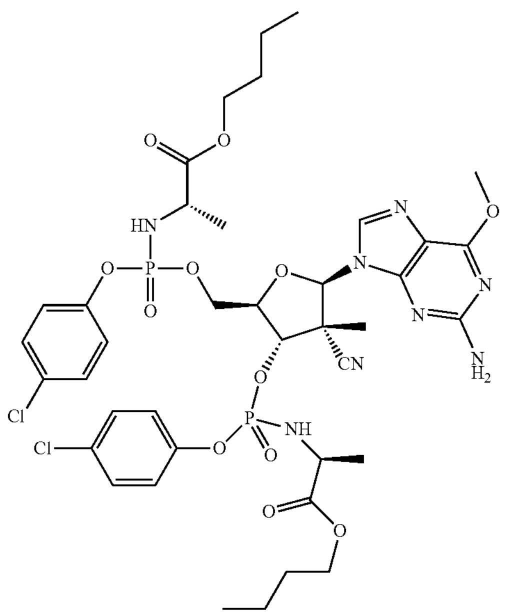 [SMILES: CCCCOC(=O)[C@H](C)NP(=O)(OC[C@H]1O[C@@H](n2cnc3c(OC)nc(N)nc32)[C@](C)(C#N)[C@@H]1OP(=O)(N[C@@H](C)C(=O)OCCCC)Oc1ccc(Cl)cc1)Oc1ccc(Cl)cc1] | 955.2 |
| 183 | 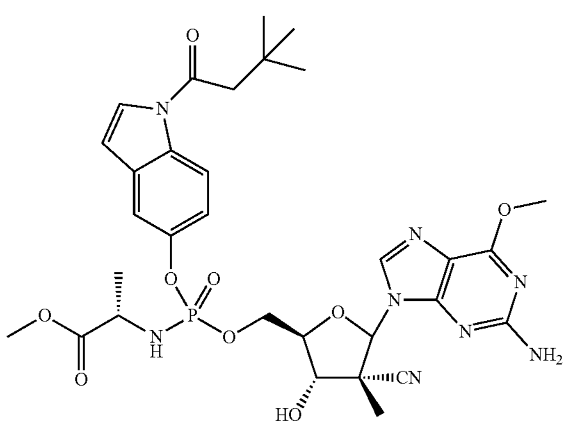 | 700.8 |

-continued

| Compound No. | Structure | MS (M + H) |
|---|---|---|
| 184 | 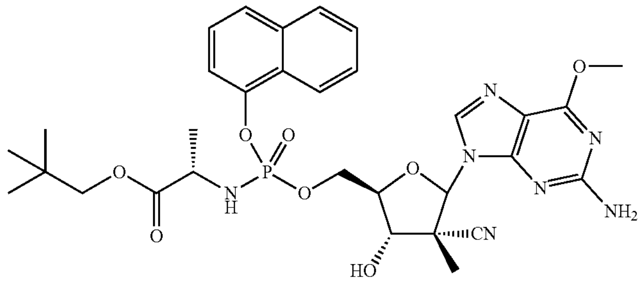 [SMILES: COc1nc(N)nc2c1ncn2C1O[C@H](COP(=O)(N[C@@H](C)C(=O)OCC(C)(C)C)Oc2cccc3ccccc23)[C@@H](O)[C@@]1(C)C#N] | 668.2 |
| 187 | 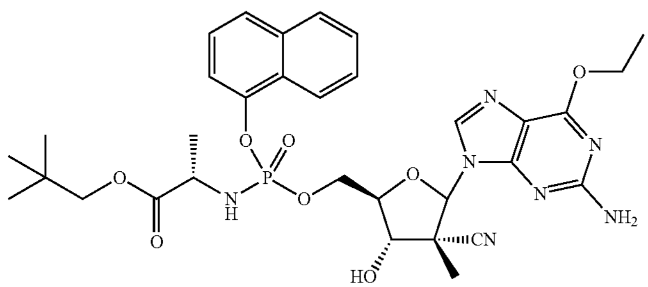 [SMILES: CCOc1nc(N)nc2c1ncn2C1O[C@H](COP(=O)(N[C@@H](C)C(=O)OCC(C)(C)C)Oc2cccc3ccccc23)[C@@H](O)[C@@]1(C)C#N] | 682.3 |
| 194 | 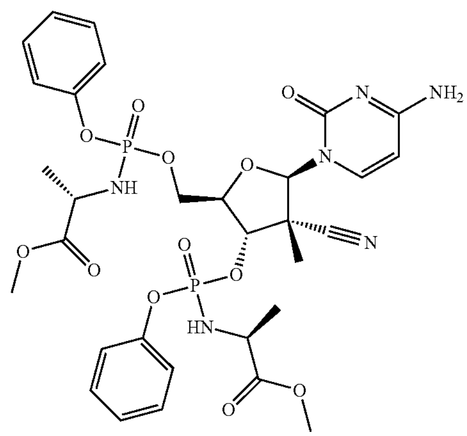 [SMILES: COC(=O)[C@H](C)NP(=O)(OC[C@H]1O[C@@H](n2ccc(N)nc2=O)[C@](C)(C#N)[C@@H]1OP(=O)(N[C@@H](C)C(=O)OC)Oc1ccccc1)Oc1ccccc1] | 749.1 |
| 200 | 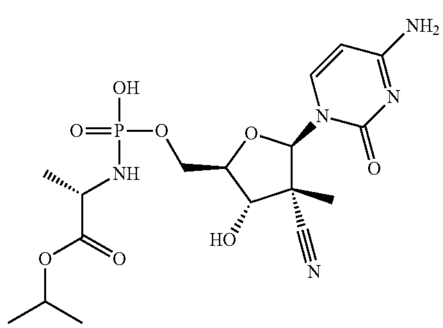 [SMILES: CC(C)OC(=O)[C@H](C)NP(=O)(O)OC[C@H]1O[C@@H](n2ccc(N)nc2=O)[C@](C)(C#N)[C@@H]1O] | 460.2 |

-continued
| Compound No. | Structure | MS (M + H) |
|---|---|---|
| 201 | 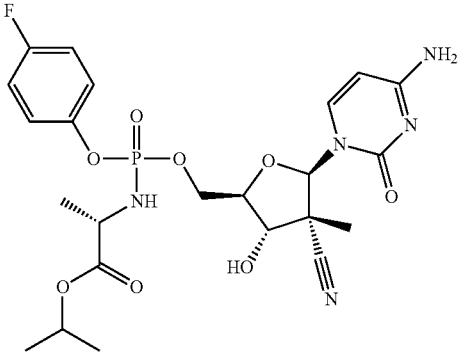 [SMILES: CC(C)OC(=O)[C@H](C)NP(=O)(OC[C@H]1O[C@@H](n2ccc(N)nc2=O)[C@](C)(C#N)[C@@H]1O)Oc1ccc(F)cc1] | 554.2 |
| 202 | 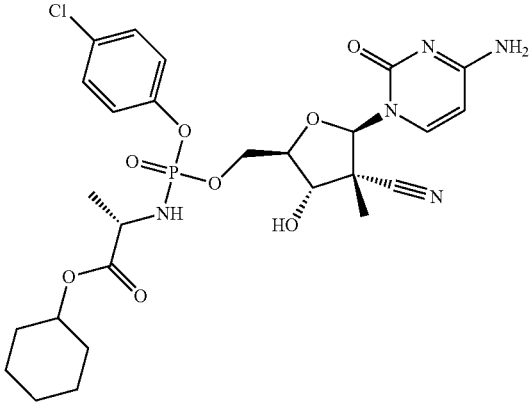 [SMILES: C[C@H](NP(=O)(OC[C@H]1O[C@@H](n2ccc(N)nc2=O)[C@](C)(C#N)[C@@H]1O)Oc1ccc(Cl)cc1)C(=O)OC1CCCCC1] | 610.2 |
| 204 | 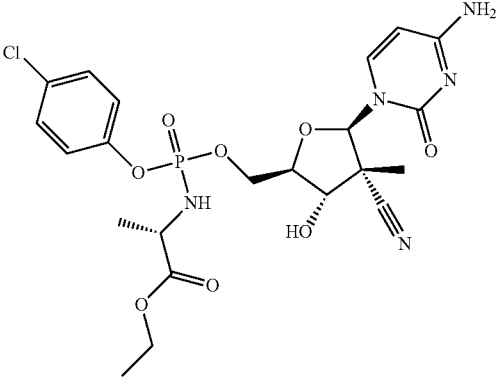 [SMILES: CCOC(=O)[C@H](C)NP(=O)(OC[C@H]1O[C@@H](n2ccc(N)nc2=O)[C@](C)(C#N)[C@@H]1O)Oc1ccc(Cl)cc1] | 556.2 |
| 205 | 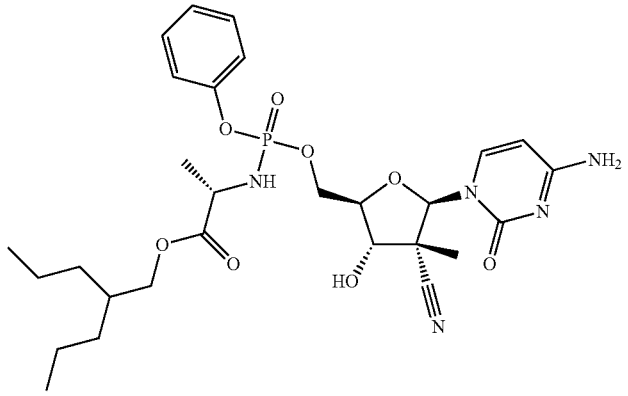 [SMILES: CCCC(CCC)COC(=O)[C@H](C)NP(=O)(OC[C@H]1O[C@@H](n2ccc(N)nc2=O)[C@](C)(C#N)[C@@H]1O)Oc1ccccc1] | 606.2 |

-continued
| Compound No. | Structure | MS (M + H) |
|---|---|---|
| 207 | 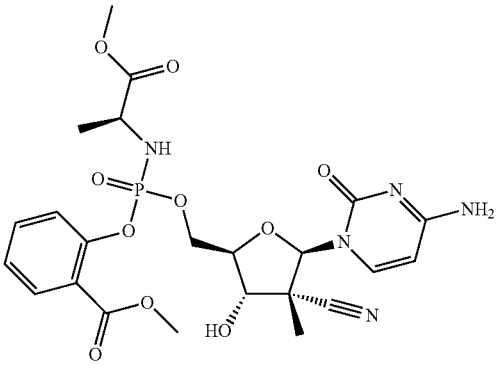 [SMILES: COC(=O)c1ccccc1OP(=O)(N[C@@H](C)C(=O)OC)OC[C@H]1O[C@@H](n2ccc(N)nc2=O)[C@](C)(C#N)[C@@H]1O] | 566 |
| 208 | 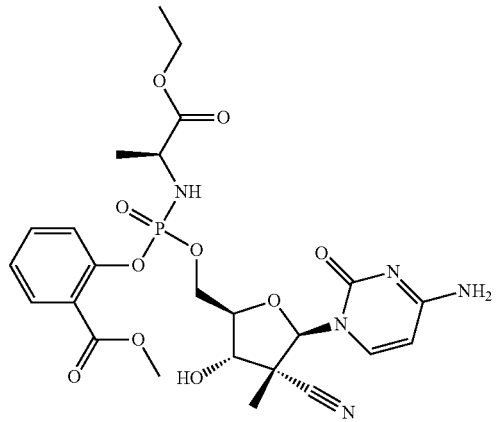 [SMILES: CCOC(=O)[C@H](C)NP(=O)(OC[C@H]1O[C@@H](n2ccc(N)nc2=O)[C@](C)(C#N)[C@@H]1O)Oc1ccccc1C(=O)OC] | 580 |
| 211 | 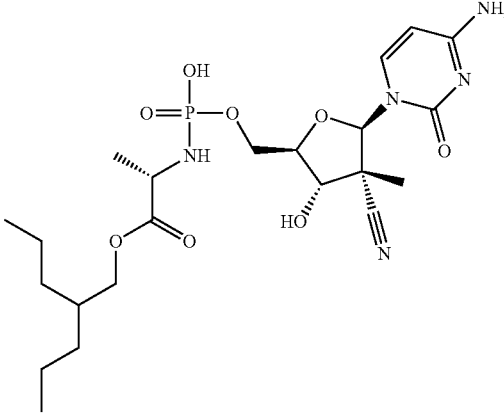 | 529.8 |
| 213 | 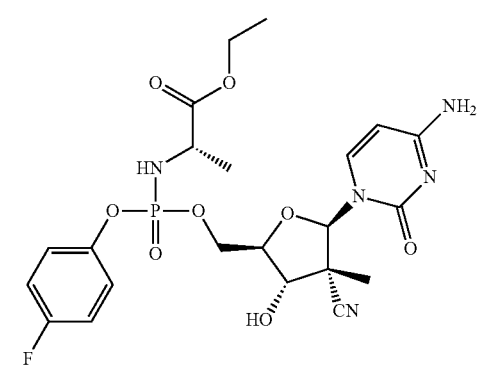 [SMILES: CCOC(=O)[C@H](C)NP(=O)(OC[C@H]1O[C@@H](n2ccc(N)nc2=O)[C@](C)(C#N)[C@@H]1O)Oc1ccc(F)cc1] | 540.2 |

-continued
| Compound No. | Structure | MS (M + H) |
|---|---|---|
| 215 | 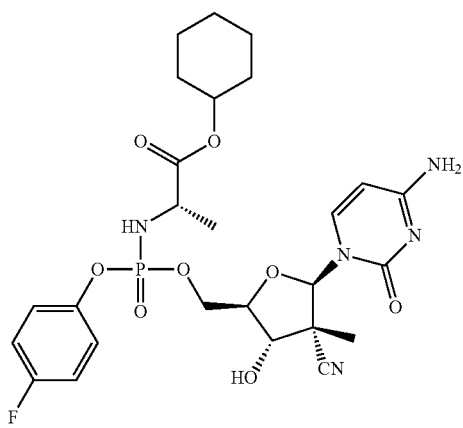 [SMILES: C[C@H](NP(=O)(OC[C@H]1O[C@@H](n2ccc(N)nc2=O)[C@](C)(C#N)[C@@H]1O)Oc1ccc(F)cc1)C(=O)OC1CCCCC1] | 594.2 |
| 216 | 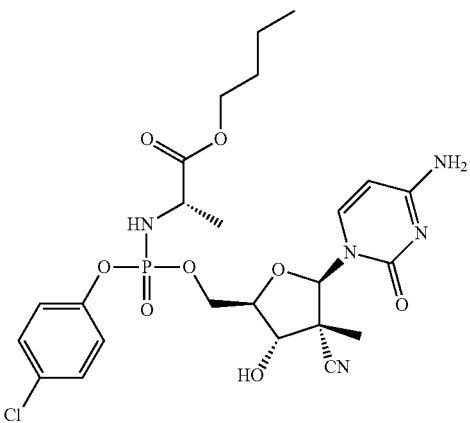 [SMILES: CCCCOC(=O)[C@H](C)NP(=O)(OC[C@H]1O[C@@H](n2ccc(N)nc2=O)[C@](C)(C#N)[C@@H]1O)Oc1ccc(Cl)cc1] | 584.2 |
| 224 | 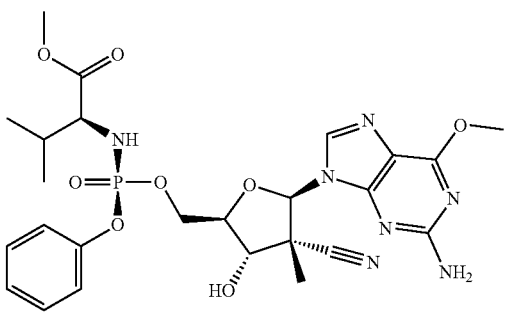 [SMILES: COC(=O)[C@@H](N[P@@](=O)(OC[C@H]1O[C@@H](n2cnc3c(OC)nc(N)nc32)[C@](C)(C#N)[C@@H]1O)Oc1ccccc1)C(C)C] | 590.2 |
| 225 | 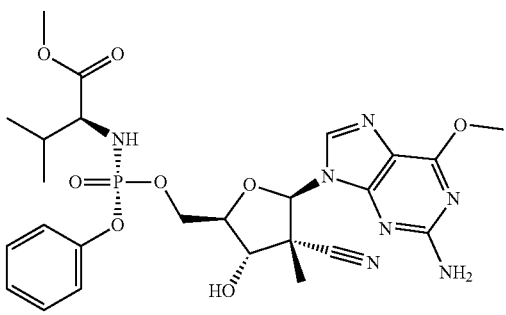 [SMILES: COC(=O)[C@@H](N[P@](=O)(OC[C@H]1O[C@@H](n2cnc3c(OC)nc(N)nc32)[C@](C)(C#N)[C@@H]1O)Oc1ccccc1)C(C)C] | 590.2 |

-continued

| Compound No. | Structure | MS (M + H) |
|---|---|---|
| 226 | 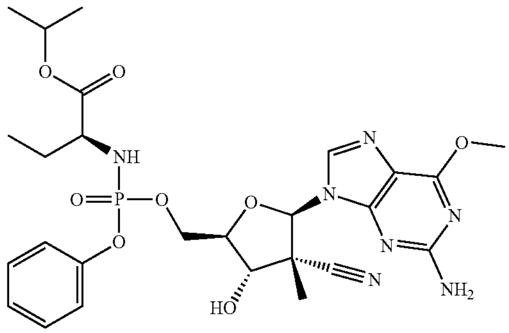 [SMILES: CC[C@H](NP(=O)(OC[C@H]1O[C@@H](n2cnc3c(OC)nc(N)nc32)[C@](C)(C#N)[C@@H]1O)Oc1ccccc1)C(=O)OC(C)C] | 604.2 |
| 227 | 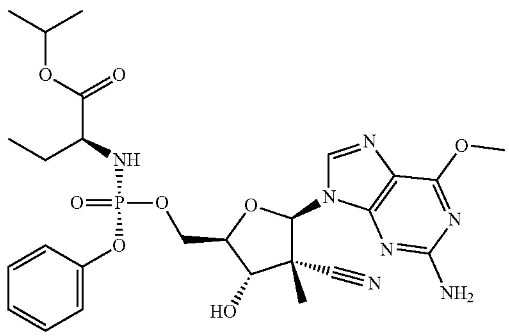 [SMILES: CC[C@H](N[P@](=O)(OC[C@H]1O[C@@H](n2cnc3c(OC)nc(N)nc32)[C@](C)(C#N)[C@@H]1O)Oc1ccccc1)C(=O)OC(C)C] | 604.2 |

Example 9

Preparation of Compound 23

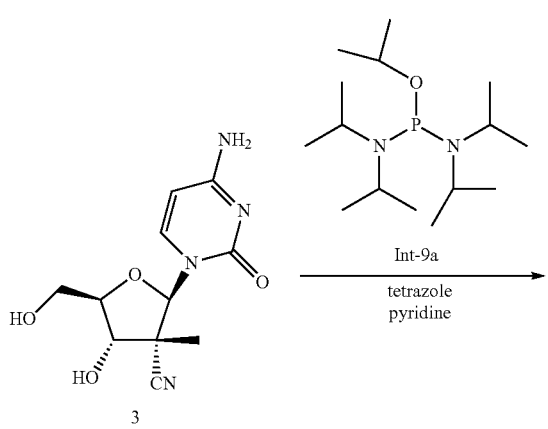

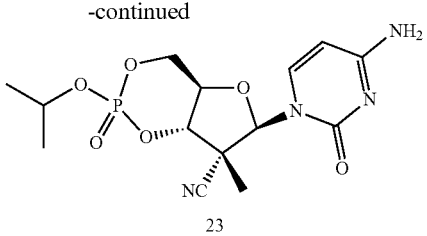

23

Step A—Synthesis of Compound Int-9b

To a solution of compound 3 (44 mg, 0.165 mmol) in pyridine (1 mL) was added a solution of tetrazole (0.92 mL, 0.413 mmol) in acetonitrile (1 mL), followed by 1-isopropoxy-N,N,N',N'-tetraisopropylphosphinediamine (Int-9a). The reaction mixture was allowed to stir for 2 hours, then the reaction mixture was concentrated in vacuo and the residue obtained was triturated with EtOAc. The precipitate that formed was removed by filtration and the filtrate was concentrated in vacuo to provide a residue which was purified using flash chromatography on silica gel on silica gel (dichloromethane/methanol) to provide compound Int-9b (20 mg) as a white solid which was used without further purification.

Step B—Synthesis of Compound 23

To a solution of compound Int-9b (20 mg, 0.056 mmol) in dichloromethane (2 mL), was added m-chloroperbenzoic acid (15.2 mg, 0.068 mmol), and the resulting reaction was allowed to stir at room temperature for 10 minutes. The reaction mixture was then diluted with water and extracted with dichloromethane (2×10 mL). The combined organic extracts were concentrated in vacuo and the residue obtained was purified using flash chromatography on silica gel on silica gel (dichloromethane/methanol) to provide a white solid product. The white solid product was dissolved in CH$_3$CN (0.8 mL) and methanol (0.2 mL) and repurified using reverse phase HPLC to provide compound 23 (1.8 mg), M+H=371.2.

The following compounds of the present invention were made using the methods described in the Example above and substituting the appropriate reactants and/or reagents.

| Compound No. | Structure | MS (M + H) |
|---|---|---|
| 24 | 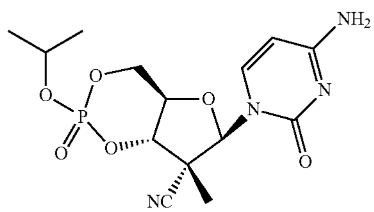 | 371.2 |
| 25 | 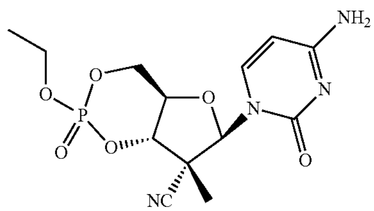 | 357.2 |
| 26 | 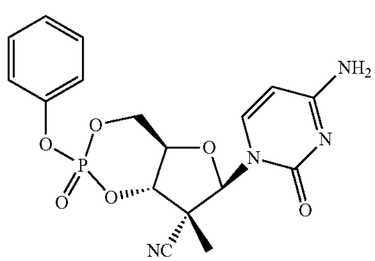 | 405.2 |
| 27 | 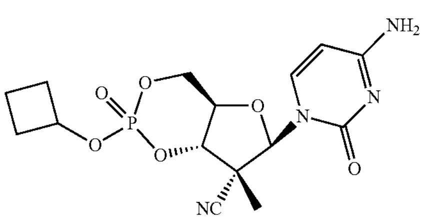 | 383.2 |
| 28 | 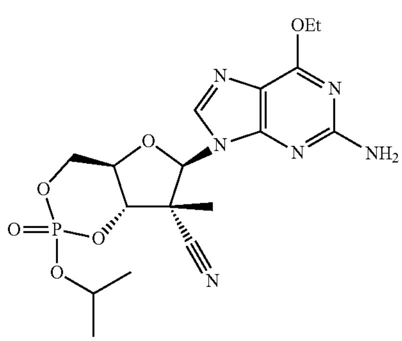 | 438.9 |
| 32 | Isomer 1 | 420.0 |
| 33 | Isomer 2 | 420.0 |
| 34 | Isomer 2 | 371.2 |
| 35 | Isomer 1 | 424.3 |

-continued
| Compound No. | Structure | MS (M + H) |
|---|---|---|
| 36 | 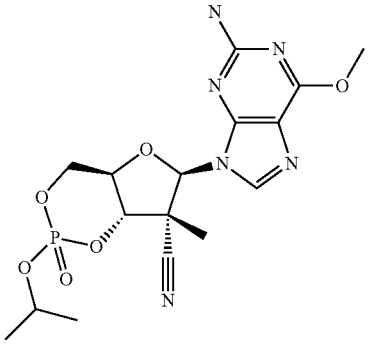 Isomer 2 | 424.3 |
| 37 | 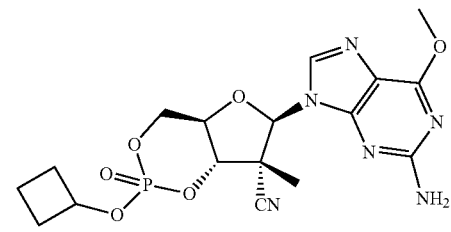 Isomer 1 | 437.2 |
| 38 | 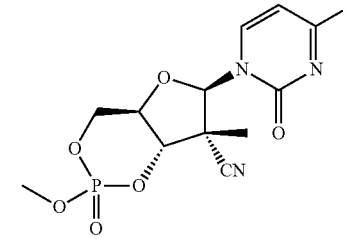 Isomer 1 | 343.2 |
| 39 | 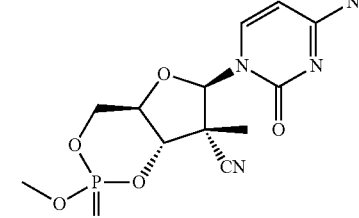 Isomer 1 | 343.3 |
| 40 | 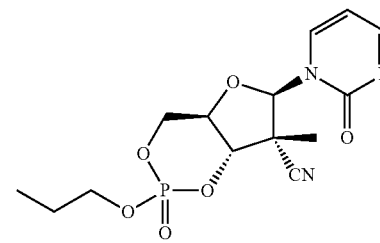 Isomer 1 | 371.2 |
-continued
| Compound No. | Structure | MS (M + H) |
|---|---|---|
| 41 | 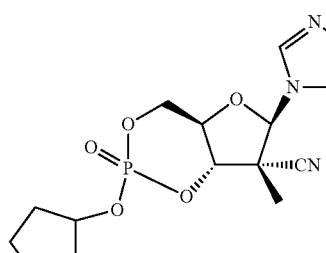 Isomer 1 | 451.0 |
| 42 | 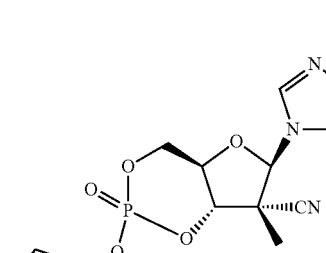 Isomer 2 | 451.0 |
| 43 | 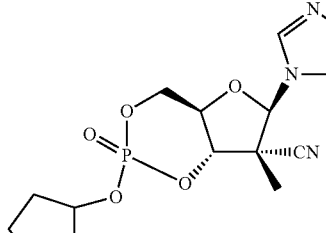 Isomer 1 | 465.0 |
| 44 | 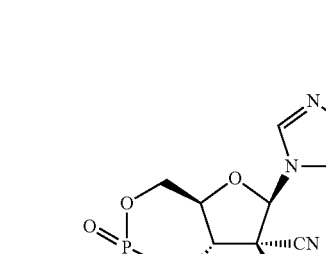 Isomer 2 | 465.0 |

| Compound No. | Structure | MS (M + H) |
|---|---|---|
| 45 | Isomer 1 | 451.0 |
| 46 | Isomer 2 | 451.0 |
| 47 | Isomer 1 | 394.2 (M + Na) |
| 48 | Isomer 2 | 394.2 (M + Na) |
| 49 | Isomer 1 | 380.2 (M + Na) |
| 50 | Isomer 2 | 380.2 (M + Na) |

Example 10

Preparation of Compound 29

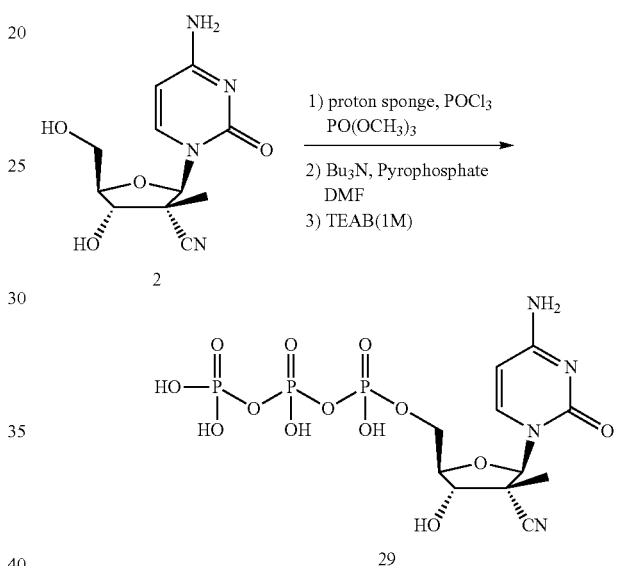

A solution of 1-[(2R,3R,4S,5R)-3-cyano-4-hydroxy-5-(hydroxymethyl)-3-methyloxolan-2-yl]-1,2,3,4-tetrahydropyrimidine-2,4-dione (2, 15 mg, 0.05 mmol, 1.00 equiv) in trimethylphosphate (1.0 mL) was placed under nitrogen atmosphere. To this solution was added proton sponge (17 mg, 0.08 mmol, 1.50 equiv) and the resulting reaction was cooled to 0° C. To the cooled solution was added phosphoryl trichloride (32 mg, 0.21 mmol, 4.50 equiv) and the resulting reaction was allowed to stir for 4 hours at 0° C. Pyrophosphate (200 mg, 0.37 mmol, 5.00 equiv), N,N-dimethylformamide (1.0 mL) and tributylamine (0.03 mL, 10.00 equiv) were then added to the reaction mixture and the resulting reaction was allowed to stir for an additional 1 hour at 0° C. The reaction was then quenched by the addition of 3.0 mL of triethylammonium bicarbonate buffer (IM) and the resulting solution was concentrated in vacuo. The residue obtained was purified using Prep-HPLC as follows: (1#-Pre-HPLC-001(SHIMADZU)): Column, 1#-PrepC-008(Atlantis HILIC Silica 19*150 186003959 0110182551kk 03), mobile phase: acetonitrile and water with 50 mmol ammonium bicarbonate; Detector, UV 220 & 254 nm. This provided 0.7 mg of compound 29 as a light yellow solid. $^1$H-NMR (400 MHz, D$_2$O): δ 7.96 (d, 1H), 6.45 (s, 1H), 6.16 (d, 1H), 4.39 (m, 1H), 4.31 (m, 2H), 4.28 (m, 1H), 1.31 (s, 3H).
$^{31}$P-NMR (162 MHz, D$_2$O): δ −10.01 (d, 1P), −10.62 (d, 1P), −22.28 (t, 1P) MS (ESI) m/z 506.7 [M]

The following compounds of the present invention were made using the methods described in the Example above and substituting the appropriate reactants and/or reagents.

| Compound No. | Structure | MS (M + H) |
|---|---|---|
| 51 | 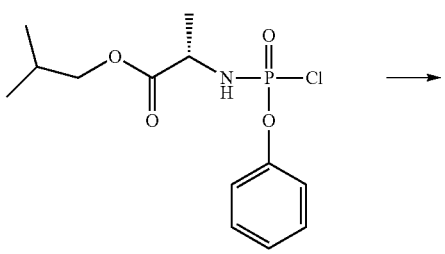 | 507.0 |
| 52 | 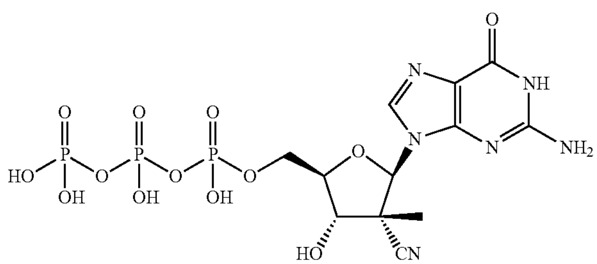 [SMILES: C[C@@]1(C#N)[C@H](O)[C@@H](COP(=O)(O)OP(=O)(O)OP(=O)(O)O)O[C@H]1n1cnc2c(=O)[nH]c(N)nc21] | 545.8 |
NMR Compound 51:
$^1$H-NMR (400 MHz, D$_2$0): δ 7.95 (d, 1H), 6.43 (s, 1H), 5.97 (d, 1H), 4.38 (m, 1H), 4.34 (m, 1H), 4.32 (m, 1H), 4.19 (m, 1H), 1.38 (s, 3H).
$^{31}$P-NMR (162 MHz, D$_2$0): δ −9.72 (bs, 1P), −10.7 (d, 1P), −22.3 (t, 1P)
MS (ESI) m/z 506.9 [M].
NMR Compound 52:
$^1$H-NMR (400 MHz, D$_2$0): δ 8.09 (s, 1H), 6.5 (s, 1H), 4.62 (m, 1H), 4.39 (m, 2H), 4.28 (m, 1H), 1.23 (s, 3H).
$^{31}$P-NMR (162 MHz, D$_2$0): δ −9.57 (bs, 1P), −10.6 (d, 1P), −22.18 (t, 1P) MS (ESI) m/z 546.5 [M].
Example 11
Preparation of Compound 53, 54
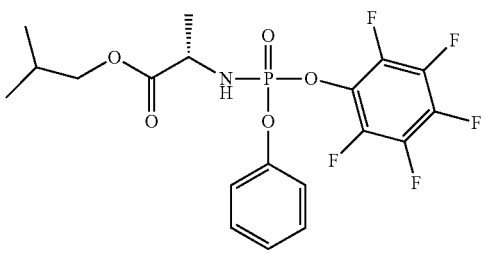
Int-11a
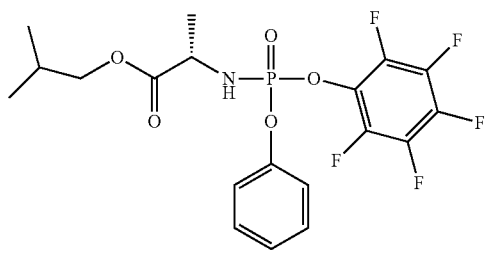
Int-11b
Isomer 1
Int-11c
Isomer 2

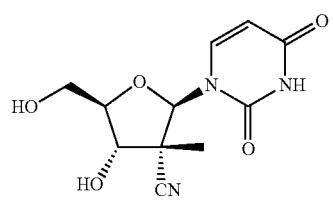

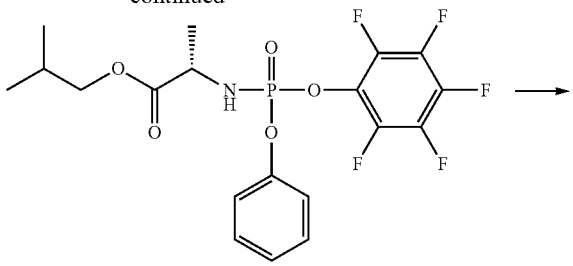

3

Int-11c

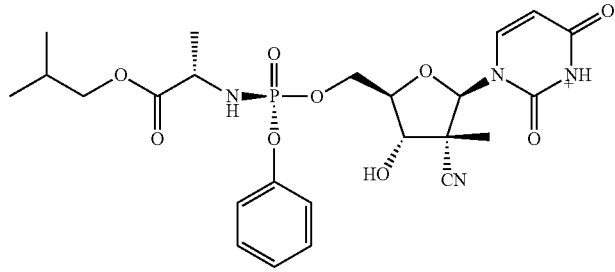

53

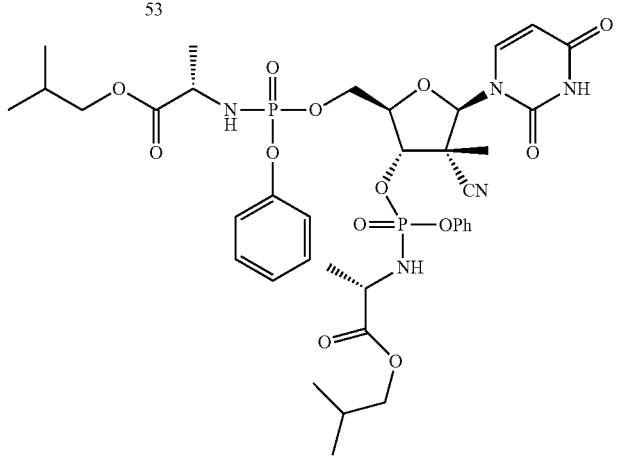

54

Step A: Synthesis of Int-11b and 11c

Phosphorylamino chloride reactants of type Int-11a can be be made using the methods described in U.S. Pat. No. 7,879,815.

To a stirred solution of Int-11a (14.2 g, 46.4 mmol) in dichloromethane (112 mL) was added pentafluorophenol (8.55 g, 46.4 mmol) in one portion. The solution was cooled to 0° C. and triethylamine (6.47 mL, 46.4 mmol) was added dropwise under nitrogen. The reaction was stirred overnight at room temperature. LCMS shows mainly product. The reaction mixture was washed with water (50 mL), dried over sodium sulfate, filtered, and concentrated in vacuo. The residue was purified by silica gel chromatography (0-30% ethyl acetate/hexanes) to provide 12.56 g of a white solid. The solid was recrystallized using 10% MBTE/hexanes to provide 6.15 g of Int-11b as a white solid. The mother liquor was concentrated in vacuo and was purified by silica gel chromatography (1:1 hexanes/ethyl acetate) to provide 4.04 g of isomer Int-11c and 805 mg of additional Int-11b.

Step B: Synthesis of 53 and 54

A solution of nucleoside 3 (500 mg, 1.87 mmol) in THF (10 mL) at 0° C. was treated with a solution of tert-butylmagnesium chloride (4.49 mL, 4.49 mmol). The reaction was stirred at 0° C. for 15 minutes and then a solution of Int-11c (962 mg, 2.06 mmol) in THF (13 mL) was added dropwise. The reaction was allowed to slowly warm to room temperature and stir for 18 hours. The reaction was quenched with saturated $NH_4Cl$ solution (20 mL) and extracted with EtOAc (2×20 mL). The organic phase was dried over $Na_2SO_4$, filtered and concentrated in vacuo. Purification by $SiO_2$ chromatography (0-10% MeOH/DCM) gave 694.3 mg (67% yield) of 53, 98.4 mg (6% yield) of 54, and 55.5 mg (11%) of recovered 3. $^1H$ NMR 53 (400 MHz, $CD_3OD$) δ 7.66 (d, J=8.0 Hz, 1H), 7.40-7.36 (m, 2H), 7.28-7.21 (m, 3H), 6.34 (s, 1H), 5.65 (d, J=8.0 Hz), 4.50 (ddd, J=12.0, 6.4, 2.0 Hz, 1H), 4.38 (ddd, J=8.8, 6.4, 3.6 Hz, 1H), 4.13-4.00 (m, 1H), 4.03-3.97 (m, 2H), 3.93-3.84 (m, 2H), 1.91 (m, 1H), 1.38 (d, J=6.8 Hz, 3H), 1.30 (s, 3H), 0.93 (d, J=6.8 Hz, 6H). Mass calculated for formula $C_{24}H_{31}N_4O_9P$ 550.2; observed $MH^+$ (LCMS) 551.0 (m/z).

The following compounds of the present invention were made using the methods described in the Example above and substituting the appropriate reactants and/or reagents. Note that the designation of isomers is arbitrary and only suggests that the compound is a single isomer.

| Compound No. | Structure | MS (M + H) |
|---|---|---|
| 55 | 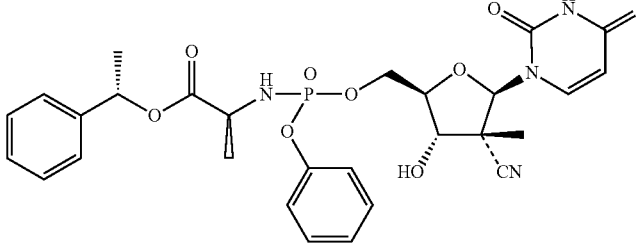<br>Isomer 1 | 620.7 |
| 56 | 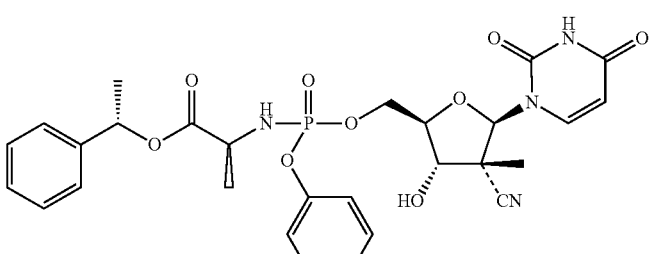<br>Isomer 2 | 620.8 |
| 57 | 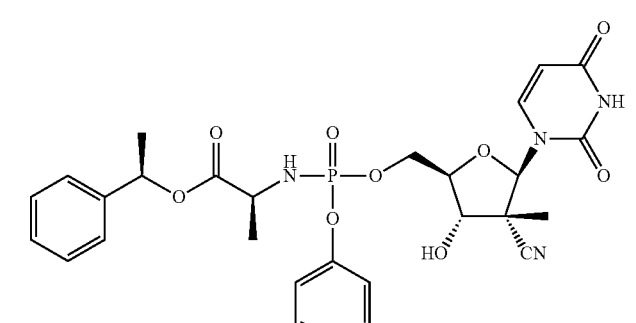<br>Isomer 1 | 621.2<br>(M + Na) |
| 58 | 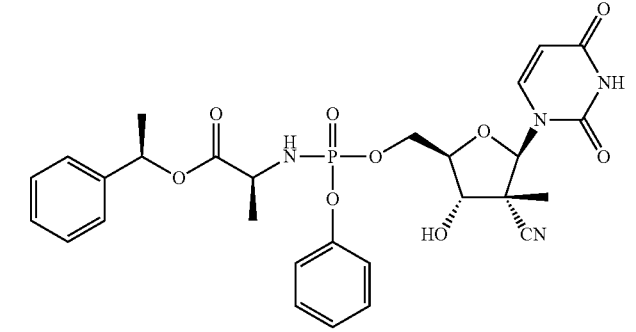 [SMILES: C[C@H](NP(=O)(OC[C@H]1O[C@@H](n2ccc(=O)[nH]c2=O)[C@](C)(C#N)[C@@H]1O)Oc1ccccc1)C(=O)O[C@H](C)c1ccccc1]<br>Isomer 2 | 621.2<br>(M + Na) |

-continued

| Compound No. | Structure | MS (M + H) |
|---|---|---|
| 60 | Isomer 1 | 537.2 |
| 61 | Isomer 2 | 537.2 |
| 63 | Isomer 1 | 550.5 |
| 66 | Isomer 1 | 585.2 |

-continued

| Compound No. | Structure | MS (M + H) |
|---|---|---|
| 67 | Isomer 2 | 585.2 |
| 69 | Isomer 1 | 577.0 |
| 70 | Isomer 2 | 577.0 |
| 72 | Isomer 1 | 558.8 |

| Compound No. | Structure | MS (M + H) |
|---|---|---|
| 73 | 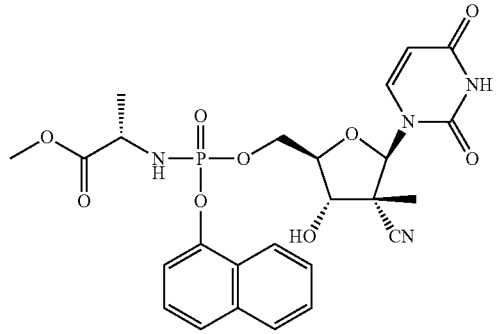 [SMILES: COC(=O)[C@H](C)NP(=O)(OC[C@H]1O[C@@H](n2ccc(=O)[nH]c2=O)[C@](C)(C#N)[C@@H]1O)Oc1cccc2ccccc12]<br>Isomer 2 | 558.8 |
| 74 | 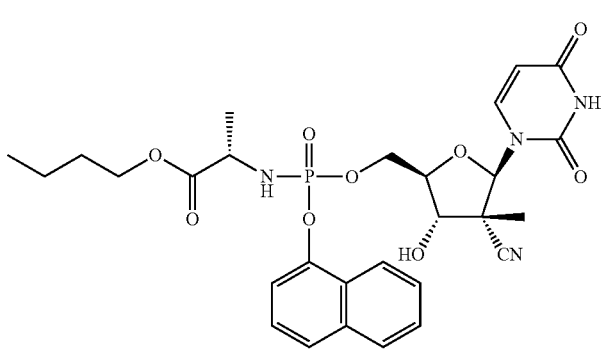 [SMILES: CCCCOC(=O)[C@H](C)NP(=O)(OC[C@H]1O[C@@H](n2ccc(=O)[nH]c2=O)[C@](C)(C#N)[C@@H]1O)Oc1cccc2ccccc12]<br>Isomer 1 | 601.0 |
| 75 | 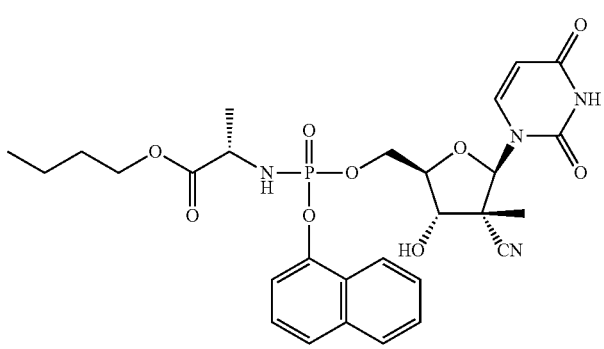 [SMILES: CCCCOC(=O)[C@H](C)NP(=O)(OC[C@H]1O[C@@H](n2ccc(=O)[nH]c2=O)[C@](C)(C#N)[C@@H]1O)Oc1cccc2ccccc12]<br>Isomer 2 | 601.0 |
| 76 | 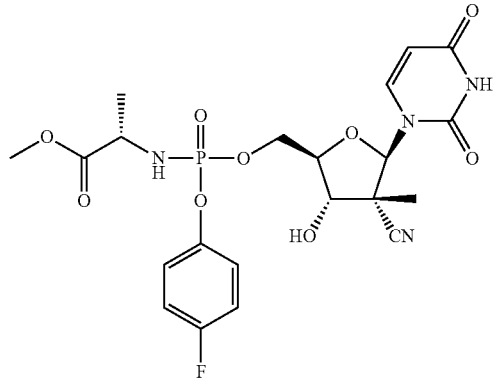 [SMILES: COC(=O)[C@H](C)NP(=O)(OC[C@H]1O[C@@H](n2ccc(=O)[nH]c2=O)[C@](C)(C#N)[C@@H]1O)Oc1ccc(F)cc1]<br>Isomer 1 | 527.0 |

| Compound No. | Structure | MS (M + H) |
|---|---|---|
| 77 | 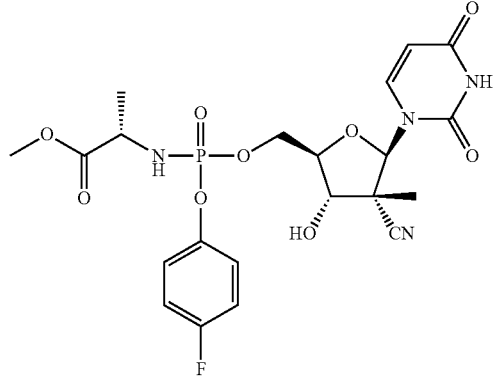 [SMILES: COC(=O)[C@H](C)NP(=O)(OC[C@H]1O[C@@H](n2ccc(=O)[nH]c2=O)[C@](C)(C#N)[C@@H]1O)Oc1ccc(F)cc1]\nIsomer 2 | 527.0 |
| 90 | 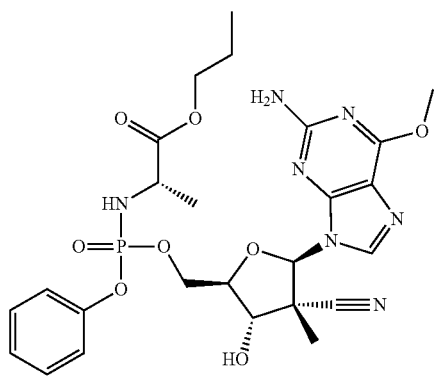 [SMILES: CCCOC(=O)[C@H](C)NP(=O)(OC[C@H]1O[C@@H](n2cnc3c(OC)nc(N)nc32)[C@](C)(C#N)[C@@H]1O)Oc1ccccc1]\nIsomer 1 | 590.2 |
| 91 | 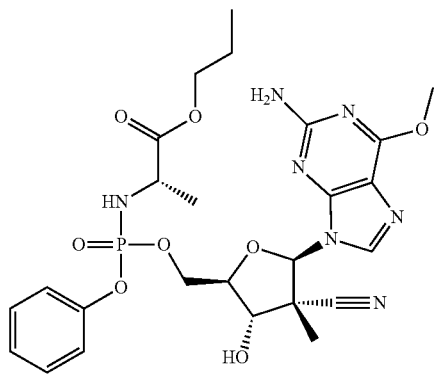 [SMILES: CCCOC(=O)[C@H](C)NP(=O)(OC[C@H]1O[C@@H](n2cnc3c(OC)nc(N)nc32)[C@](C)(C#N)[C@@H]1O)Oc1ccccc1]\nIsomer 2 | 590.2 |

|Compound No.|Structure|MS (M + H)|
|---|---|---|
|92|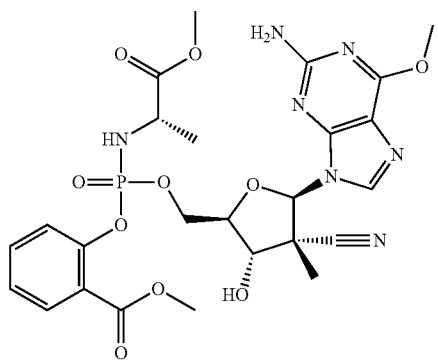 [SMILES: COC(=O)c1ccccc1OP(=O)(N[C@@H](C)C(=O)OC)OC[C@H]1O[C@@H](n2cnc3c(OC)nc(N)nc32)[C@](C)(C#N)[C@@H]1O]<br>Isomer 1|620.2|
|93|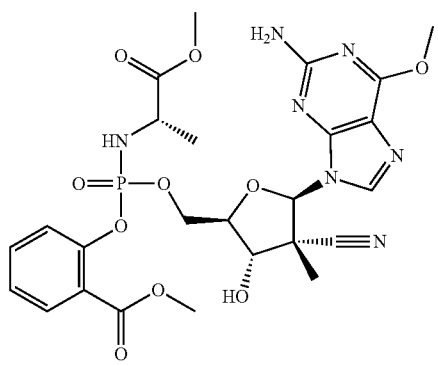 [SMILES: COC(=O)c1ccccc1OP(=O)(N[C@@H](C)C(=O)OC)OC[C@H]1O[C@@H](n2cnc3c(OC)nc(N)nc32)[C@](C)(C#N)[C@@H]1O]<br>Isomer 2|620.2|
|94|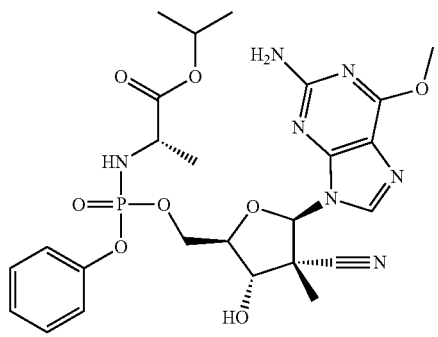 [SMILES: COc1nc(N)nc2c1ncn2[C@@H]1O[C@H](COP(=O)(N[C@@H](C)C(=O)OC(C)C)Oc2ccccc2)[C@@H](O)[C@@]1(C)C#N]<br>Isomer 1|590.2|

-continued
| Compound No. | Structure | MS (M + H) |
|---|---|---|
| 95 | 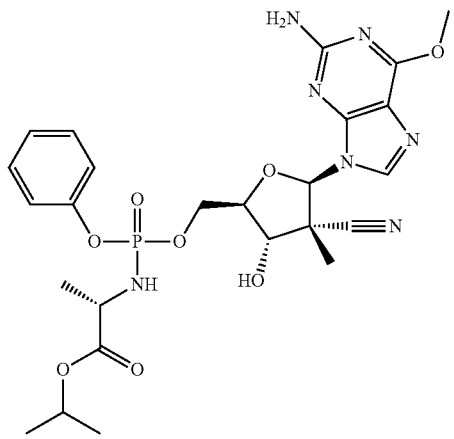 [SMILES: COc1nc(N)nc2c1ncn2[C@@H]1O[C@H](COP(=O)(N[C@@H](C)C(=O)OC(C)C)Oc2ccccc2)[C@@H](O)[C@@]1(C)C#N]<br>Isomer 2 | 590.2 |
| 97 | 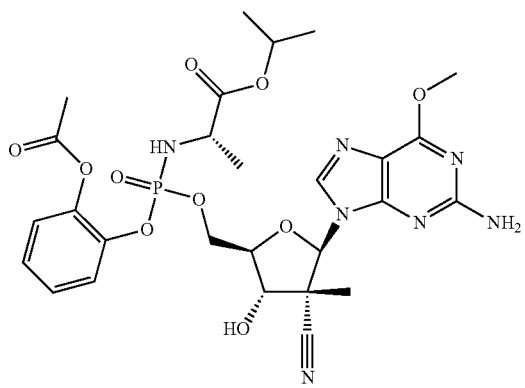 [SMILES: COc1nc(N)nc2c1ncn2[C@@H]1O[C@H](COP(=O)(N[C@@H](C)C(=O)OC(C)C)Oc2ccccc2OC(C)=O)[C@@H](O)[C@@]1(C)C#N]<br>Isomer 1 | 648.2 |
| 98 | 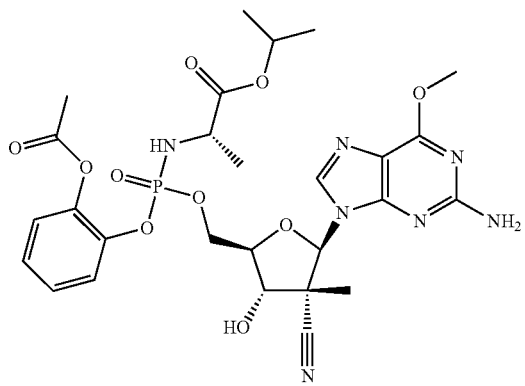 [SMILES: COc1nc(N)nc2c1ncn2[C@@H]1O[C@H](COP(=O)(N[C@@H](C)C(=O)OC(C)C)Oc2ccccc2OC(C)=O)[C@@H](O)[C@@]1(C)C#N]<br>Isomer 2 | 648.2 |

-continued
| Compound No. | Structure | MS (M + H) |
|---|---|---|
| 99 | 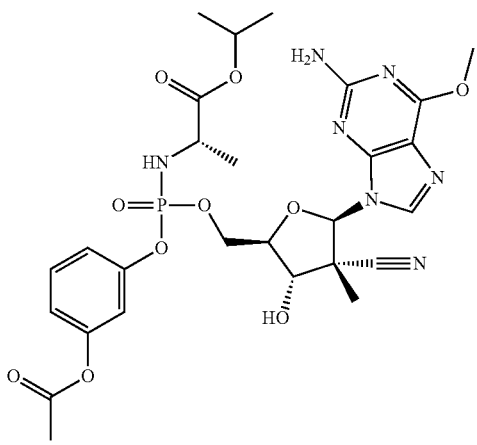 [SMILES: COc1nc(N)nc2c1ncn2[C@@H]1O[C@H](COP(=O)(N[C@@H](C)C(=O)OC(C)C)Oc2cccc(OC(C)=O)c2)[C@@H](O)[C@@]1(C)C#N]<br>Isomer 1 | 648.2 |
| 100 | 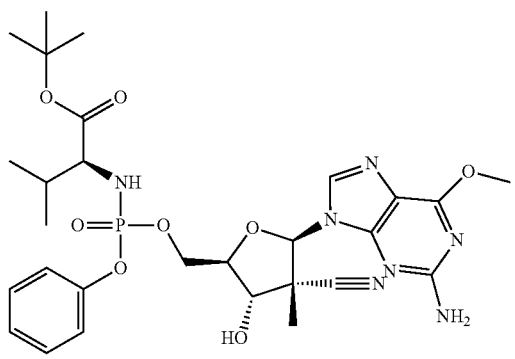 [SMILES: COc1nc(N)nc2c1ncn2[C@@H]1O[C@H](COP(=O)(N[C@H](C(=O)OC(C)(C)C)C(C)C)Oc2ccccc2)[C@@H](O)[C@@]1(C)C#N]<br>Isomer 1 | 618.2 |
| 101 | 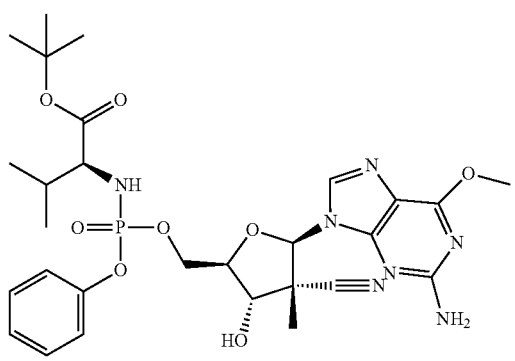 [SMILES: COc1nc(N)nc2c1ncn2[C@@H]1O[C@H](COP(=O)(N[C@H](C(=O)OC(C)(C)C)C(C)C)Oc2ccccc2)[C@@H](O)[C@@]1(C)C#N]<br>Isomer 2 | 618.2 |

-continued
| Compound No. | Structure | MS (M + H) |
|---|---|---|
| 102 | 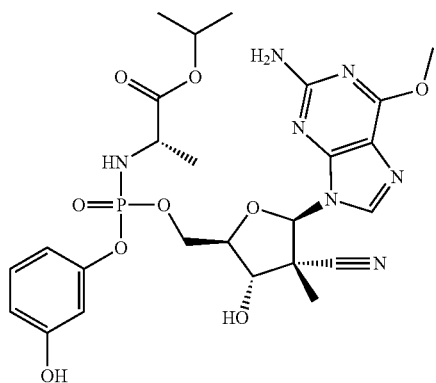 [SMILES: COc1nc(N)nc2c1ncn2[C@@H]1O[C@H](COP(=O)(N[C@@H](C)C(=O)OC(C)C)Oc2cccc(O)c2)[C@@H](O)[C@@]1(C)C#N]<br>Isomer 1 | 606.2 |
| 103 | 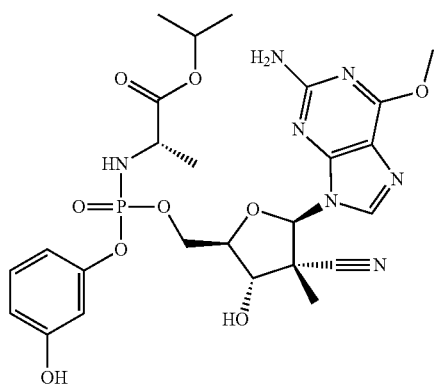 [SMILES: COc1nc(N)nc2c1ncn2[C@@H]1O[C@H](COP(=O)(N[C@@H](C)C(=O)OC(C)C)Oc2cccc(O)c2)[C@@H](O)[C@@]1(C)C#N]<br>Isomer 2 | 606.2 |
| 106 | 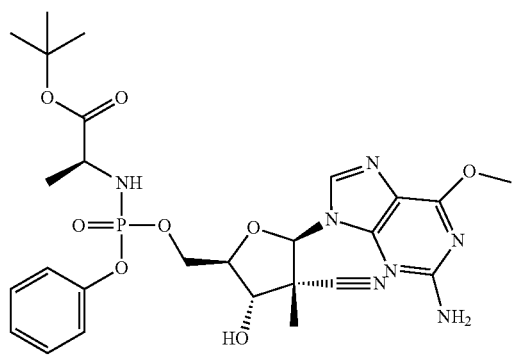 [SMILES: COc1nc(N)nc2c1ncn2[C@@H]1O[C@H](COP(=O)(N[C@@H](C)C(=O)OC(C)(C)C)Oc2ccccc2)[C@@H](O)[C@@]1(C)C#N]<br>Isomer 1 | 604.2 |

-continued

| Compound No. | Structure | MS (M + H) |
|---|---|---|
| 107 | Isomer 2 | 604.2 |
| 109 | isomer 1 | 565 |
| 110 | isomer 2 | 565 |
| 113 | isomer 1 | 543 |

| Compound No. | Structure | MS (M + H) |
|---|---|---|
| 114 | 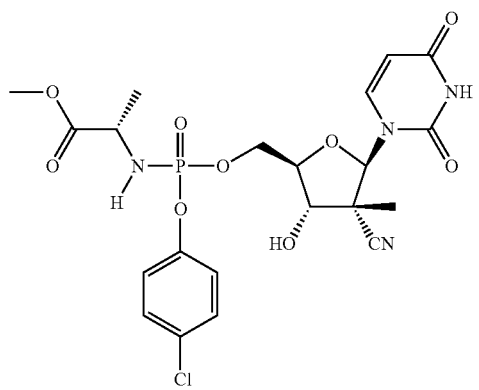 [SMILES: COC(=O)[C@H](C)NP(=O)(OC[C@H]1O[C@@H](n2ccc(=O)[nH]c2=O)[C@](C)(C#N)[C@@H]1O)Oc1ccc(Cl)cc1] isomer 2 | 543 |
| 120 | 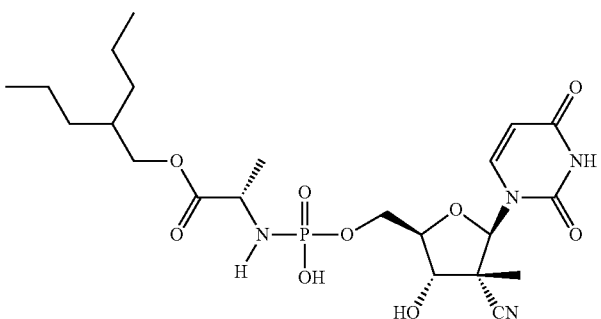 [SMILES: CCCC(CCC)COC(=O)[C@H](C)NP(=O)(O)OC[C@H]1O[C@@H](n2ccc(=O)[nH]c2=O)[C@](C)(C#N)[C@@H]1O] Isomer 1 | 531 |
| 121 | 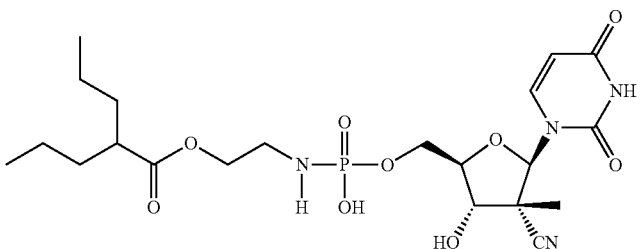 [SMILES: CCCC(CCC)C(=O)OCCNP(=O)(O)OC[C@H]1O[C@@H](n2ccc(=O)[nH]c2=O)[C@](C)(C#N)[C@@H]1O] Isomer 2 | 517 |
| 127 | 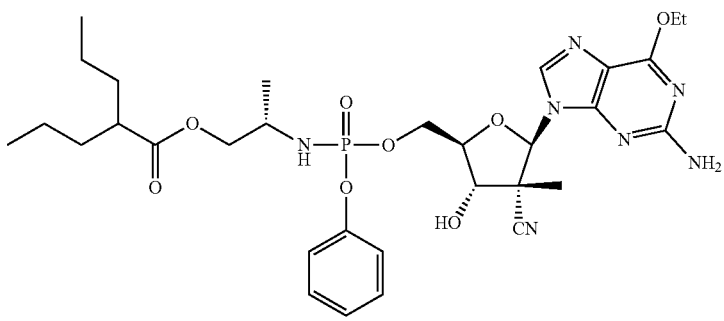 [SMILES: CCCC(CCC)C(=O)OC[C@H](C)NP(=O)(OC[C@H]1O[C@@H](n2cnc3c(OCC)nc(N)nc32)[C@](C)(C#N)[C@@H]1O)Oc1ccccc1] Isomer 1 | 674.1 |

-continued
| Compound No. | Structure | MS (M + H) |
|---|---|---|
| 128 | 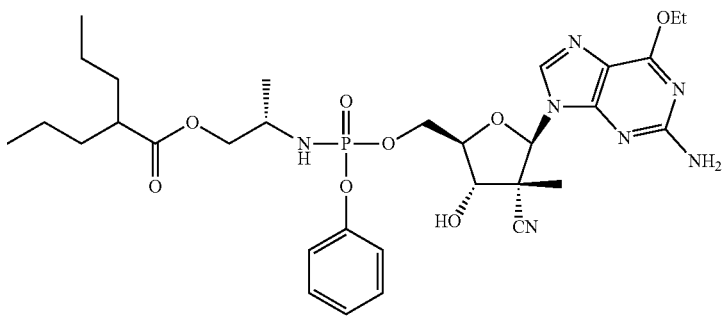 [SMILES: CCCC(CCC)C(=O)OC[C@H](C)NP(=O)(OC[C@H]1O[C@@H](n2cnc3c(OCC)nc(N)nc32)[C@](C)(C#N)[C@@H]1O)Oc1ccccc1]<br>Isomer 2 | 674.1 |
| 130 | 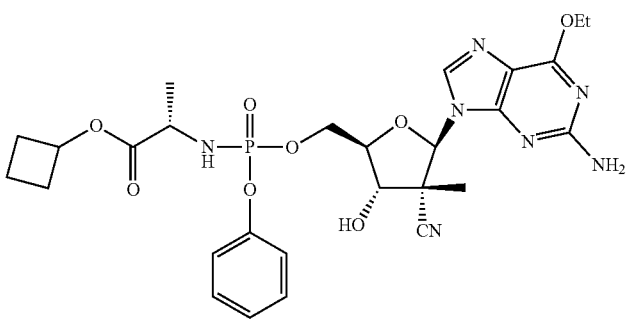 [SMILES: CCOc1nc(N)nc2c1ncn2[C@@H]1O[C@H](COP(=O)(N[C@@H](C)C(=O)OC2CCC2)Oc2ccccc2)[C@@H](O)[C@@]1(C)C#N]<br>Isomer 1 | 616.2 |
| 134 | 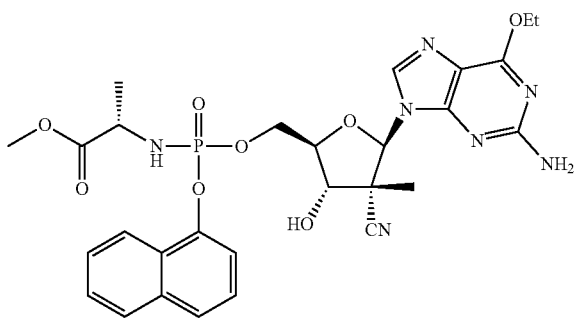 [SMILES: CCOc1nc(N)nc2c1ncn2[C@@H]1O[C@H](COP(=O)(N[C@@H](C)C(=O)OC)Oc2cccc3ccccc23)[C@@H](O)[C@@]1(C)C#N]<br>Isomer 1 | 626.1 |
| 135 | 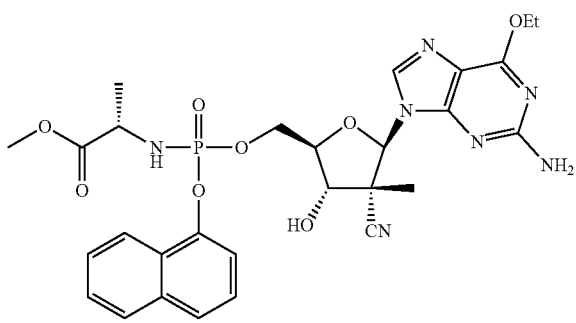 [SMILES: CCOc1nc(N)nc2c1ncn2[C@@H]1O[C@H](COP(=O)(N[C@@H](C)C(=O)OC)Oc2cccc3ccccc23)[C@@H](O)[C@@]1(C)C#N]<br>Isomer 2 | 626.2 |

-continued
| Compound No. | Structure | MS (M + H) |
|---|---|---|
| 136 | 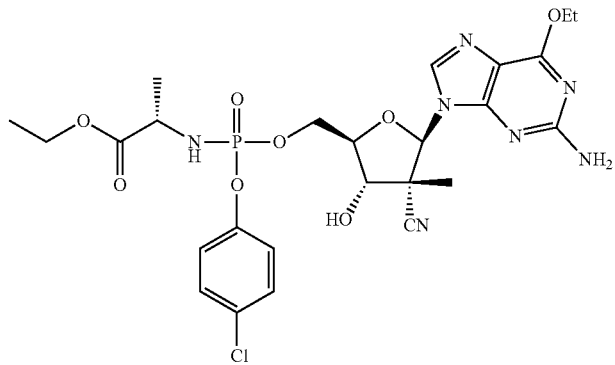 [SMILES: CCOC(=O)[C@H](C)NP(=O)(OC[C@H]1O[C@@H](n2cnc3c(OCC)nc(N)nc32)[C@](C)(C#N)[C@@H]1O)Oc1ccc(Cl)cc1] Isomer 1 | 623.7 |
| 137 | 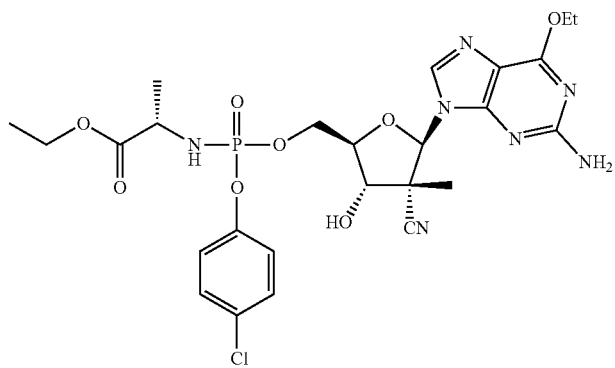 [SMILES: CCOC(=O)[C@H](C)NP(=O)(OC[C@H]1O[C@@H](n2cnc3c(OCC)nc(N)nc32)[C@](C)(C#N)[C@@H]1O)Oc1ccc(Cl)cc1] Isomer 2 | 623.7 |
| 138 | 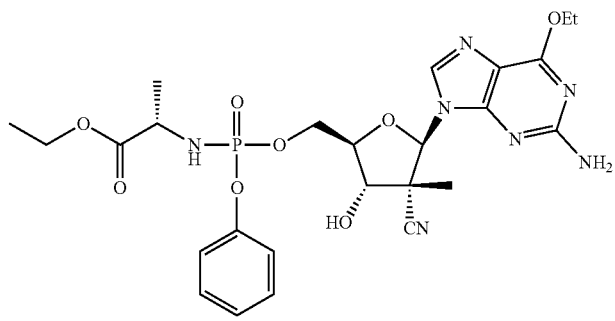 [SMILES: CCOC(=O)[C@H](C)NP(=O)(OC[C@H]1O[C@@H](n2cnc3c(OCC)nc(N)nc32)[C@](C)(C#N)[C@@H]1O)Oc1ccccc1] Isomer 1 | 589.7 |
| 139 | 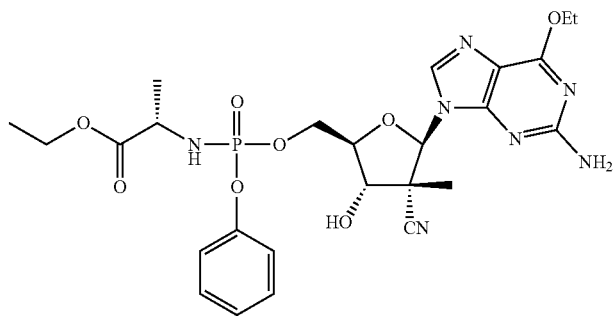 [SMILES: CCOC(=O)[C@H](C)NP(=O)(OC[C@H]1O[C@@H](n2cnc3c(OCC)nc(N)nc32)[C@](C)(C#N)[C@@H]1O)Oc1ccccc1] Isomer 2 | 589.7 |

-continued
| Compound No. | Structure | MS (M + H) |
|---|---|---|
| 141 | 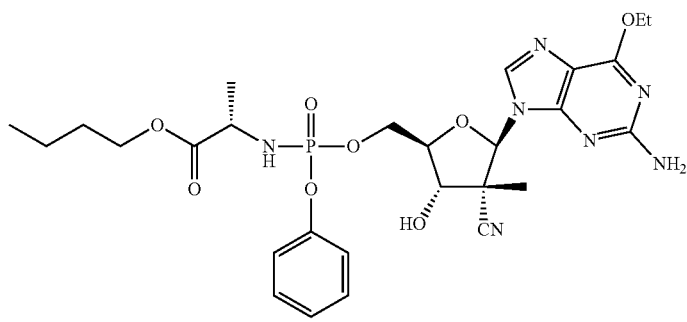 [SMILES: CCCCOC(=O)[C@H](C)NP(=O)(OC[C@H]1O[C@@H](n2cnc3c(OCC)nc(N)nc32)[C@](C)(C#N)[C@@H]1O)Oc1ccccc1]<br>Isomer 1 | 617.7 |
| 142 | 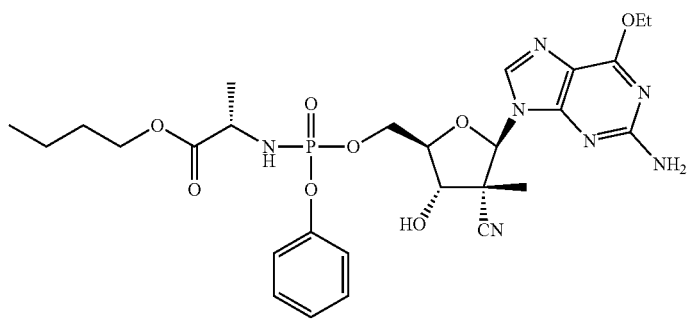 [SMILES: CCCCOC(=O)[C@H](C)NP(=O)(OC[C@H]1O[C@@H](n2cnc3c(OCC)nc(N)nc32)[C@](C)(C#N)[C@@H]1O)Oc1ccccc1]<br>Isomer 2 | 617.7 |
| 144 | 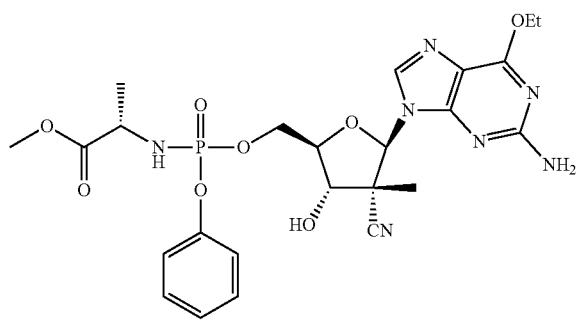 [SMILES: CCOc1nc(N)nc2c1ncn2[C@@H]1O[C@H](COP(=O)(N[C@@H](C)C(=O)OC)Oc2ccccc2)[C@@H](O)[C@@]1(C)C#N]<br>Isomer 1 | 562.0 |
| 145 | 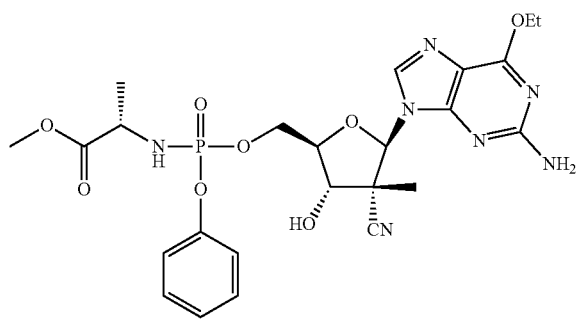 [SMILES: CCOc1nc(N)nc2c1ncn2[C@@H]1O[C@H](COP(=O)(N[C@@H](C)C(=O)OC)Oc2ccccc2)[C@@H](O)[C@@]1(C)C#N]<br>Isomer 2 | 562.0 |

| Compound No. | Structure | MS (M + H) |
|---|---|---|
| 146 | 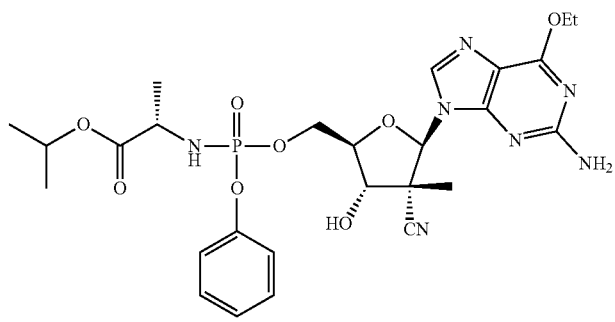 [SMILES: CCOc1nc(N)nc2c1ncn2[C@@H]1O[C@H](COP(=O)(N[C@@H](C)C(=O)OC(C)C)Oc2ccccc2)[C@@H](O)[C@@]1(C)C#N]<br>Isomer 1 | 604, 626.2 [M + Na] |
| 148 | 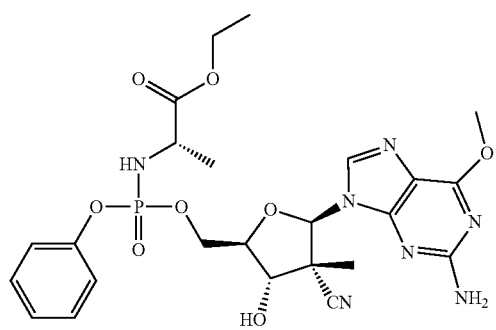 [SMILES: CCOC(=O)[C@H](C)NP(=O)(OC[C@H]1O[C@@H](n2cnc3c(OC)nc(N)nc32)[C@](C)(C#N)[C@@H]1O)Oc1ccccc1]<br>Isomer 1 | 576.2 |
| 149 | 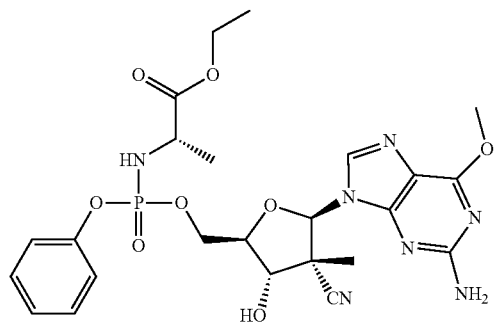 [SMILES: CCOC(=O)[C@H](C)NP(=O)(OC[C@H]1O[C@@H](n2cnc3c(OC)nc(N)nc32)[C@](C)(C#N)[C@@H]1O)Oc1ccccc1]<br>Isomer 2 | 576.2 |
| 151 | 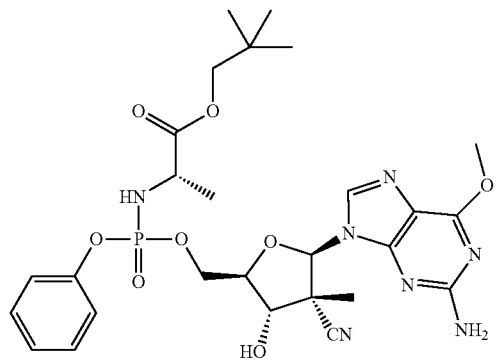 [SMILES: COc1nc(N)nc2c1ncn2[C@@H]1O[C@H](COP(=O)(N[C@@H](C)C(=O)OCC(C)(C)C)Oc2ccccc2)[C@@H](O)[C@@]1(C)C#N]<br>Isomer 1 | 618.2 |

-continued
| Compound No. | Structure | MS (M + H) |
|---|---|---|
| 152 | 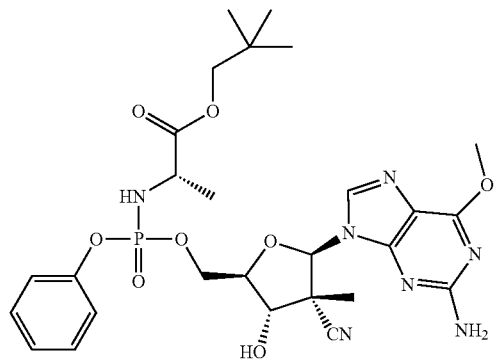 [SMILES: COc1nc(N)nc2c1ncn2[C@@H]1O[C@H](COP(=O)(N[C@@H](C)C(=O)OCC(C)(C)C)Oc2ccccc2)[C@@H](O)[C@@]1(C)C#N] Isomer 2 | 618.2 |
| 154 | 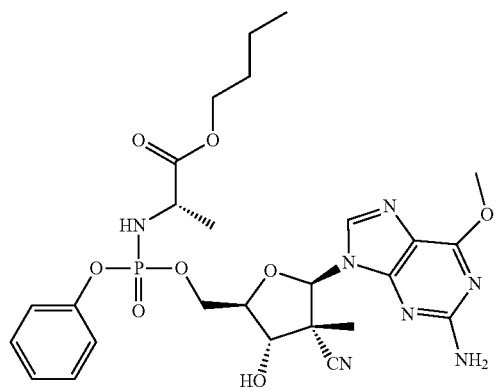 [SMILES: CCCCOC(=O)[C@H](C)NP(=O)(OC[C@H]1O[C@@H](n2cnc3c(OC)nc(N)nc32)[C@](C)(C#N)[C@@H]1O)Oc1ccccc1] Isomer 1 | 604.2 |
| 155 | 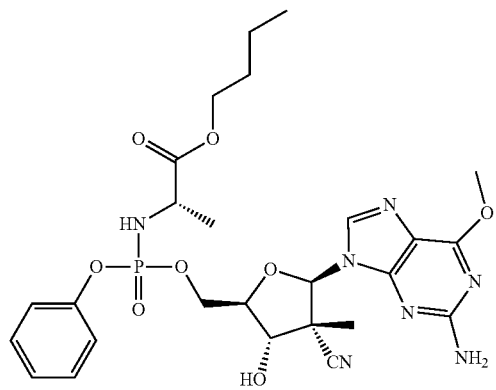 [SMILES: CCCCOC(=O)[C@H](C)NP(=O)(OC[C@H]1O[C@@H](n2cnc3c(OC)nc(N)nc32)[C@](C)(C#N)[C@@H]1O)Oc1ccccc1] Isomer 2 | 604.2 |

-continued
| Compound No. | Structure | MS (M + H) |
|---|---|---|
| 159 | 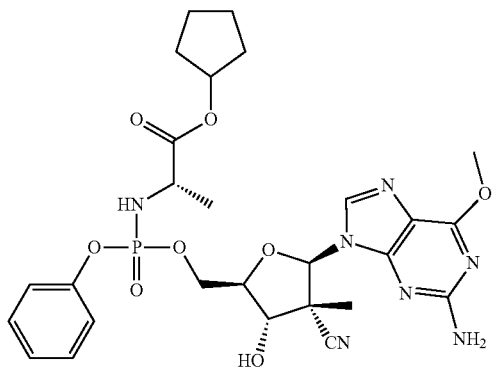 [SMILES: COc1nc(N)nc2c1ncn2[C@@H]1O[C@H](COP(=O)(N[C@@H](C)C(=O)OC2CCCC2)Oc2ccccc2)[C@@H](O)[C@@]1(C)C#N] Isomer 1 | 616.2 |
| 160 | 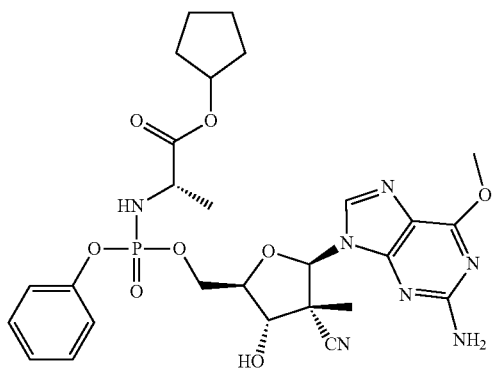 [SMILES: COc1nc(N)nc2c1ncn2[C@@H]1O[C@H](COP(=O)(N[C@@H](C)C(=O)OC2CCCC2)Oc2ccccc2)[C@@H](O)[C@@]1(C)C#N] Isomer 2 | 616.2 |
| 163 | 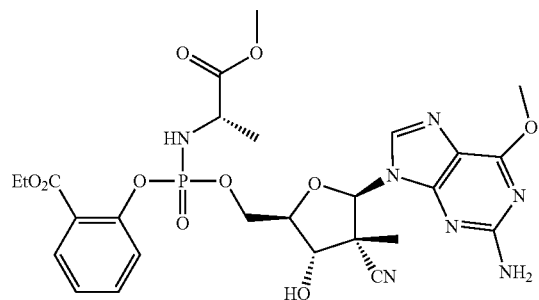 [SMILES: CCOC(=O)c1ccccc1OP(=O)(N[C@@H](C)C(=O)OC)OC[C@H]1O[C@@H](n2cnc3c(OC)nc(N)nc32)[C@](C)(C#N)[C@@H]1O] Isomer 1 | 634.2 |
| 164 | 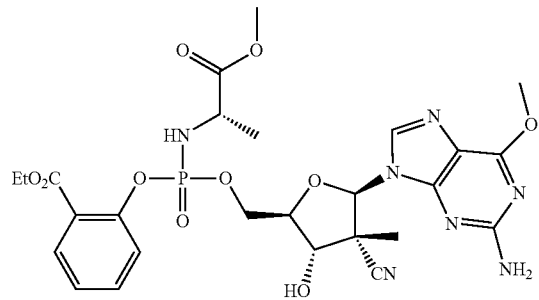 [SMILES: CCOC(=O)c1ccccc1OP(=O)(N[C@@H](C)C(=O)OC)OC[C@H]1O[C@@H](n2cnc3c(OC)nc(N)nc32)[C@](C)(C#N)[C@@H]1O] Isomer 2 | 634.2 |

-continued
| Compound No. | Structure | MS (M + H) |
|---|---|---|
| 166 | 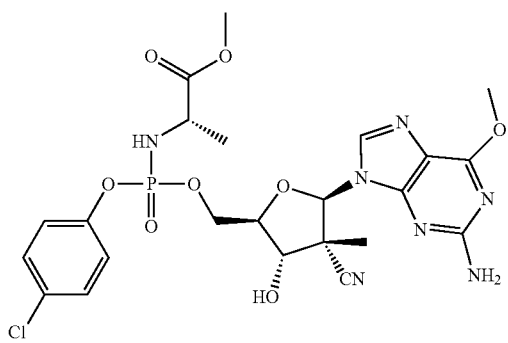 [SMILES: COC(=O)[C@H](C)NP(=O)(OC[C@H]1O[C@@H](n2cnc3c(OC)nc(N)nc32)[C@](C)(C#N)[C@@H]1O)Oc1ccc(Cl)cc1] Isomer 1 | 596.2 |
| 167 | 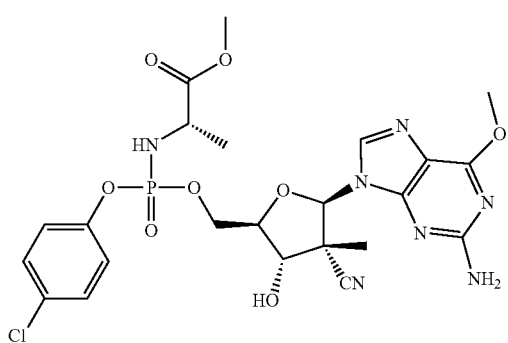 [SMILES: COC(=O)[C@H](C)NP(=O)(OC[C@H]1O[C@@H](n2cnc3c(OC)nc(N)nc32)[C@](C)(C#N)[C@@H]1O)Oc1ccc(Cl)cc1] Isomer 2 | 596.2 |
| 171 | 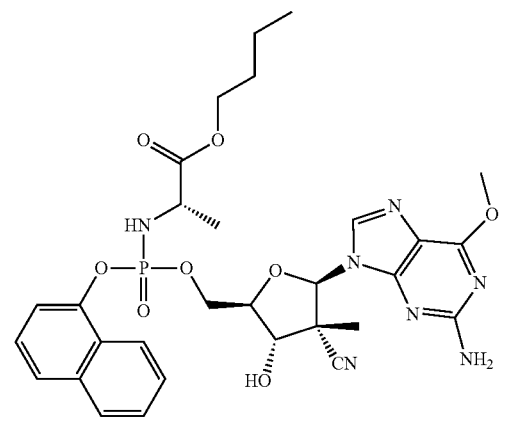 [SMILES: CCCCOC(=O)[C@H](C)NP(=O)(OC[C@H]1O[C@@H](n2cnc3c(OC)nc(N)nc32)[C@](C)(C#N)[C@@H]1O)Oc1cccc2ccccc12] Isomer 1 | 654.2 |

| Compound No. | Structure | MS (M + H) |
|---|---|---|
| 172 | 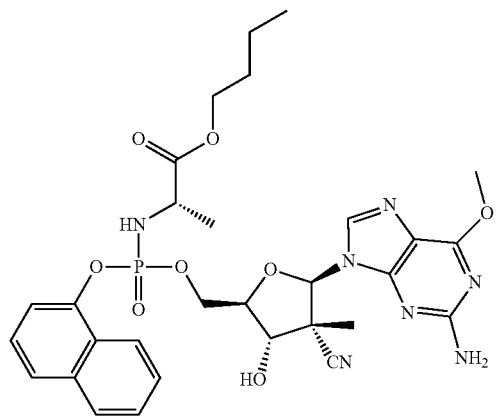 [SMILES: CCCCOC(=O)[C@H](C)NP(=O)(OC[C@H]1O[C@@H](n2cnc3c(OC)nc(N)nc32)[C@](C)(C#N)[C@@H]1O)Oc1cccc2ccccc12]<br>Isomer 2 | 654.2 |
| 176 | 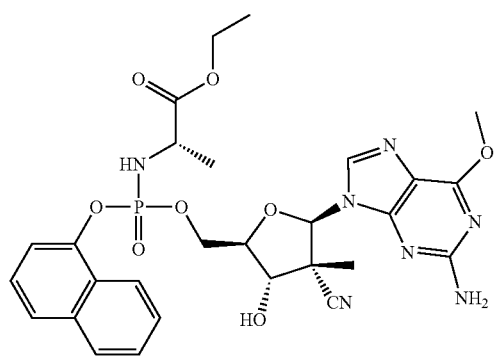 [SMILES: CCOC(=O)[C@H](C)NP(=O)(OC[C@H]1O[C@@H](n2cnc3c(OC)nc(N)nc32)[C@](C)(C#N)[C@@H]1O)Oc1cccc2ccccc12]<br>Isomer 1 | 626.2 |
| 177 | 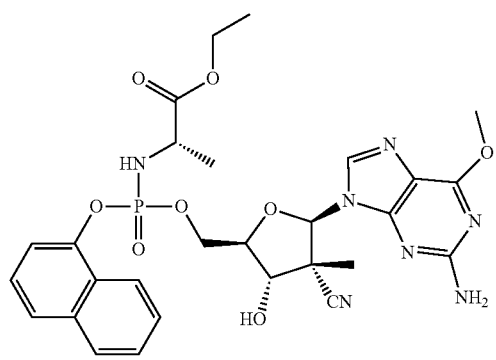 [SMILES: CCOC(=O)[C@H](C)NP(=O)(OC[C@H]1O[C@@H](n2cnc3c(OC)nc(N)nc32)[C@](C)(C#N)[C@@H]1O)Oc1cccc2ccccc12]<br>Isomer 2 | 626.2 |

-continued
| Compound No. | Structure | MS (M + H) |
|---|---|---|
| 179 | 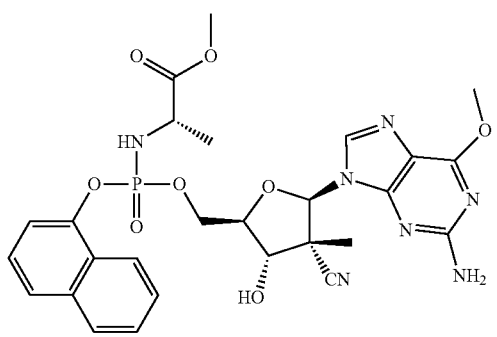 [SMILES: COC(=O)[C@H](C)NP(=O)(OC[C@H]1O[C@@H](n2cnc3c(OC)nc(N)nc32)[C@](C)(C#N)[C@@H]1O)Oc1cccc2ccccc12] Isomer 1 | 612.2 |
| 180 | 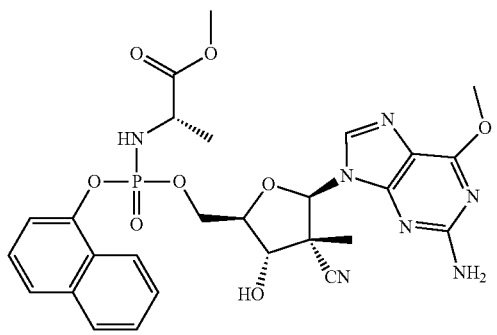 [SMILES: COC(=O)[C@H](C)NP(=O)(OC[C@H]1O[C@@H](n2cnc3c(OC)nc(N)nc32)[C@](C)(C#N)[C@@H]1O)Oc1cccc2ccccc12] Isomer 2 | 612.2 |
| 185 | 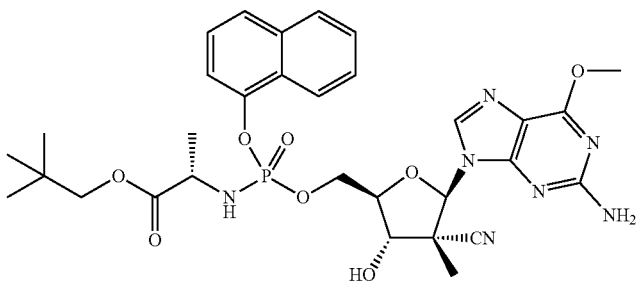 [SMILES: COc1nc(N)nc2c1ncn2[C@@H]1O[C@H](COP(=O)(N[C@@H](C)C(=O)OCC(C)(C)C)Oc2cccc3ccccc23)[C@@H](O)[C@@]1(C)C#N] Isomer 1 | 668.2 |
| 186 | 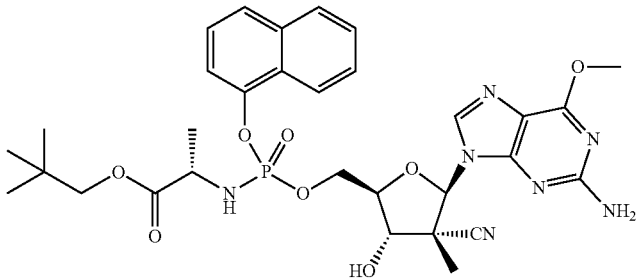 [SMILES: COc1nc(N)nc2c1ncn2[C@@H]1O[C@H](COP(=O)(N[C@@H](C)C(=O)OCC(C)(C)C)Oc2cccc3ccccc23)[C@@H](O)[C@@]1(C)C#N] Isomer 2 | 668.2 |

-continued
| Compound No. | Structure | MS (M + H) |
|---|---|---|
| 188 | 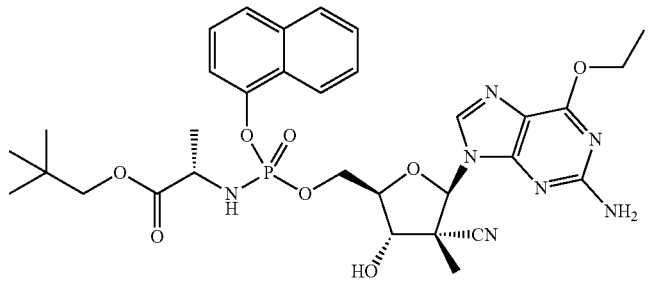 [SMILES: CCOc1nc(N)nc2c1ncn2[C@@H]1O[C@H](COP(=O)(N[C@@H](C)C(=O)OCC(C)(C)C)Oc2cccc3ccccc23)[C@@H](O)[C@@]1(C)C#N]  Isomer 1 | 682.3 |
| 189 | 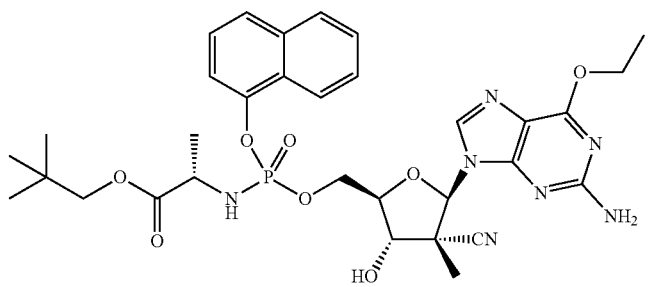 [SMILES: CCOc1nc(N)nc2c1ncn2[C@@H]1O[C@H](COP(=O)(N[C@@H](C)C(=O)OCC(C)(C)C)Oc2cccc3ccccc23)[C@@H](O)[C@@]1(C)C#N]  Isomer 2 | 682.3 |
| 228 | 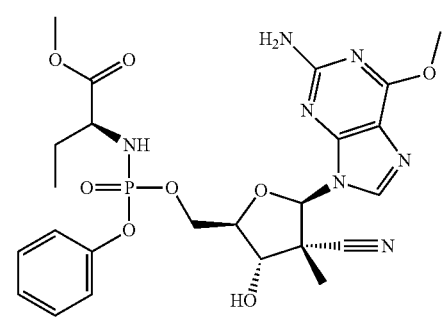 [SMILES: CC[C@H](NP(=O)(OC[C@H]1O[C@@H](n2cnc3c(OC)nc(N)nc32)[C@](C)(C#N)[C@@H]1O)Oc1ccccc1)C(=O)OC]  Isomer 1 | 576.19 |
Example 12
Preparation of Compound 190
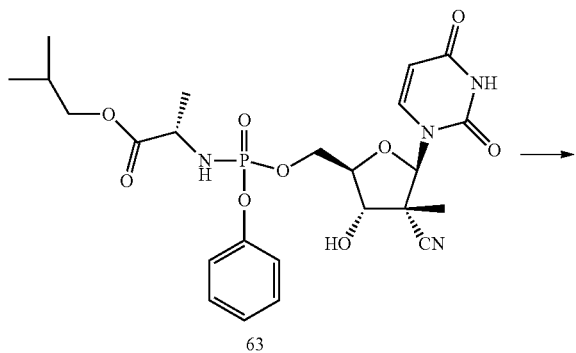
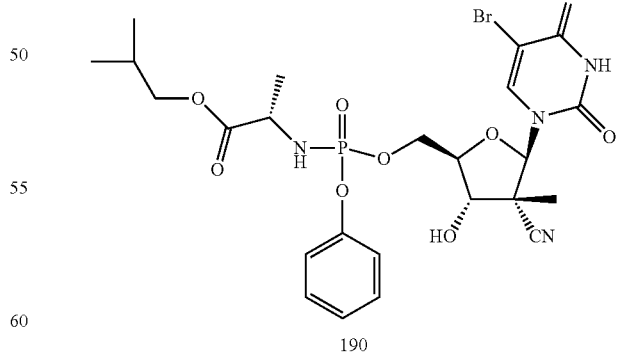
To a stirred solution of compound 63 (21 mg, 0.038 mmol) in DMF (2 mL) that had been cooled in an ice bath was added NBS (10.18 mg, 0.57 mmol). The reaction was quenched with ethyl acetate (50 mL) and water (50 mL). The organic layer was dried over sodium sulfate, filtered and concentrated in vacuo. The residue was purified by silica gel column chromatography (0-10% methanol/methylene chloride) to provide 190. (20.5 mg, 85%)

Example 13

Preparation of Compound 191

Step A: Synthesis of Int-13a

To a stirred solution of Int-5d (337 mg, 0.61 mmol) in a mixture solvent of tetrahydrofuran (1.1 mL) and water (0.37 mL) at 0° C. was added TFA (0.68 mL, 9.2 mmol) dropwise. The mixture was stirred at 0° C. for 3 hours. The reaction was diluted with EtOAc (10 mL), and then sat. $NaHCO_3$ was added to pH 6. The mixture was extracted with EtOAc (2×30 mL). The organic layers were combined, dried over $MgSO_4$,

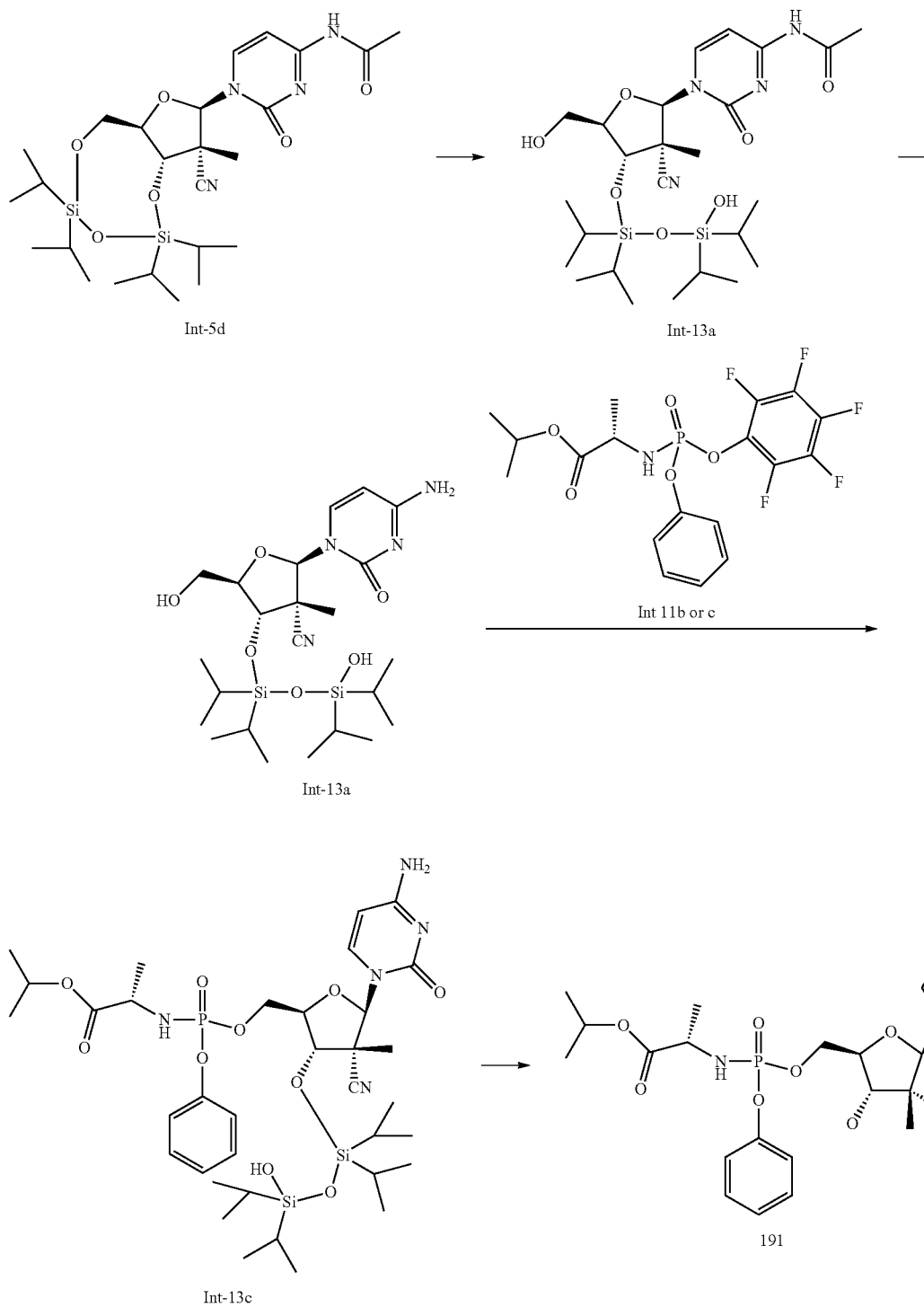

Step B: Synthesis of Int-13b

Ammonia (7 M in MeOH, 8 mL, 58 mmol) was added to the starting material Int-13a (330 mg, 0.58 mmol) at room temperature and the mixture was stirred at room temperature for 4 hours. The mixture was concentrated in vacuo. The residue was purified by silica gel column chromatography eluting with 10% methanol/methylene chloride in 1 hour to provide Int-13b as a white solid (250 mg, 82%).

Step C: Synthesis of Int-13c

To a solution of mono protected nucleoside Int-13b (550 mg, 1.04 mmol) in a mixture of NMP (6.0 mL) and THF (33 mL) was added tert-Butyl magnesium chloride (1 M in THF, 2.71 mL) at 0° C. and the reaction was stirred for 30 minutes. A solution of Int-11b or 11c (471 mg, 1.04 mmol) in THF (2 mL) was added and the reaction was stirred for 2 hours. The reaction was quenched with saturated aq. $NH_4Cl$ (20 mL), extracted with EtOAc (2×20 mL), dried over $MgSO_4$, filtered and concentrated in vacuo. The residue was purified by silica gel column chromatography 0-10% MeOH/DCM to provide the desired white solid product Int-13c (715 mg, 86%).

Step D: Synthesis of Compound 191

To a stirred solution of starting material Int-13c (980 mg, 1.23 mmol) in tetrahydrofuran (22.0 mL) and MeOH (26.0 mL) at room temperature was added formic acid (8.0 mL, 209 mmol). CsF (1.12 g, 7.39 mmol) was added to the reaction mixture and stirred at 50° C. for 8 hours. The reaction mixture was extracted with ethyl acetate (3×30 mL), washed with water and brine, dried over $MgSO_4$, filtered and concentrated in vacuo. The residue was purified by silica gel chromatography eluting with 0-10% MeOH/$CH_2Cl_2$ to provide product 191 which was lyophilized over night to provide a white dry powder (293 mg, 44%). $^1H$ NMR: 7.66 (1H, d, J=7.58), 7.38 (2H, m), 7.27 (2H, m), 7.21 (1H, m), 6.37 (1H, s), 5.85 (1H, d, J=7.57), 4.96 (1H, m), 4.52 (1H, m), 4.37 (1H. m), 4.10 (1H, m), 3.93 (2H, m), 1.35 (3H, d, J=7.14), 1.22 (6H, s), 1.20 (3H, s).

The following compounds of the present invention were made using the methods described in the Example above and substituting the appropriate reactants and/or reagents. Note that the designation of isomers is arbitrary and only suggests that the compound is a single isomer.

| Compound No. | Structure | MS (M + H) |
|---|---|---|
| 193 | 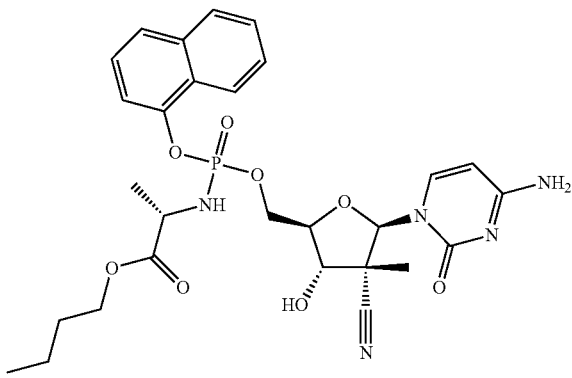 [SMILES: CCCCOC(=O)[C@H](C)NP(=O)(OC[C@H]1O[C@@H](n2ccc(N)nc2=O)[C@](C)(C#N)[C@@H]1O)Oc1cccc2ccccc12] Isomer 1 | 600.2 |
| 195 | 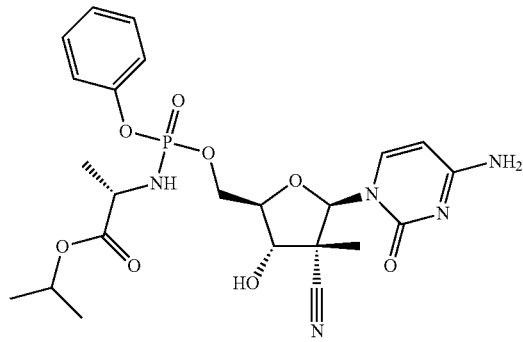 [SMILES: CC(C)OC(=O)[C@H](C)NP(=O)(OC[C@H]1O[C@@H](n2ccc(N)nc2=O)[C@](C)(C#N)[C@@H]1O)Oc1ccccc1] Isomer 1 | 536.2 |

-continued
| Compound No. | Structure | MS (M + H) |
|---|---|---|
| 196 | 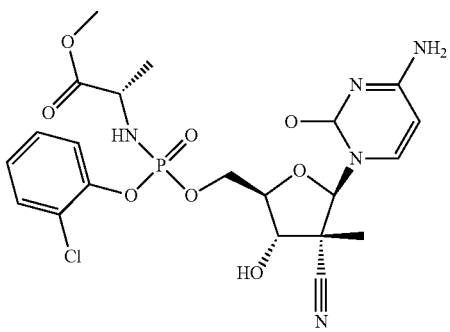 [SMILES: COC(=O)[C@H](C)NP(=O)(OC[C@H]1O[C@@H](N2C=CC(N)=NC2O)[C@](C)(C#N)[C@@H]1O)Oc1ccccc1Cl]  Isomer 1 | 542.2 |
| 197 | 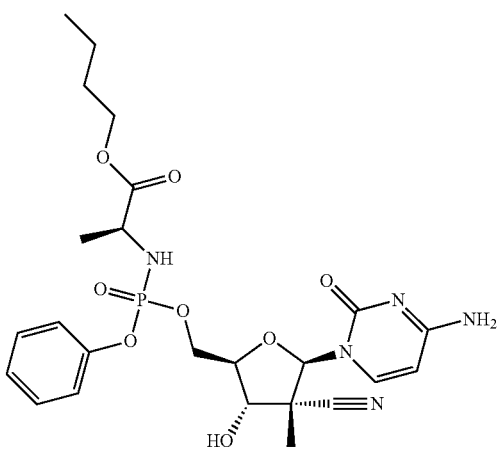 [SMILES: CCCCOC(=O)[C@H](C)NP(=O)(OC[C@H]1O[C@@H](n2ccc(N)nc2=O)[C@](C)(C#N)[C@@H]1O)Oc1ccccc1]  Isomer 1 | 550.2 |
| 198 | 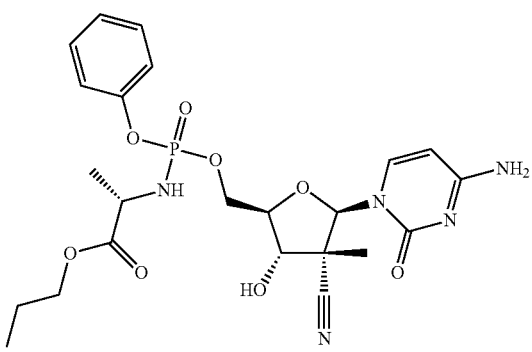 [SMILES: CCCOC(=O)[C@H](C)NP(=O)(OC[C@H]1O[C@@H](n2ccc(N)nc2=O)[C@](C)(C#N)[C@@H]1O)Oc1ccccc1]  Isomer 1 | 536.2 |

-continued
| Compound No. | Structure | MS (M + H) |
|---|---|---|
| 199 | 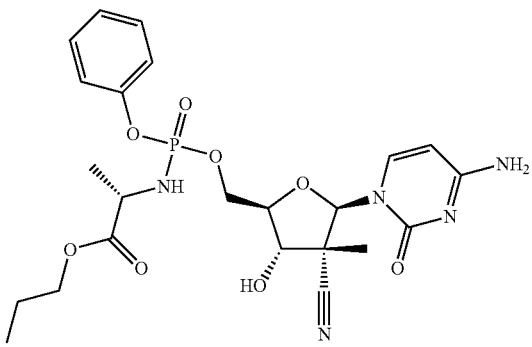 [SMILES: CCCOC(=O)[C@H](C)NP(=O)(OC[C@H]1O[C@@H](n2ccc(N)nc2=O)[C@](C)(C#N)[C@@H]1O)Oc1ccccc1]<br>Isomer 2 | 536.2 |
| 203 | 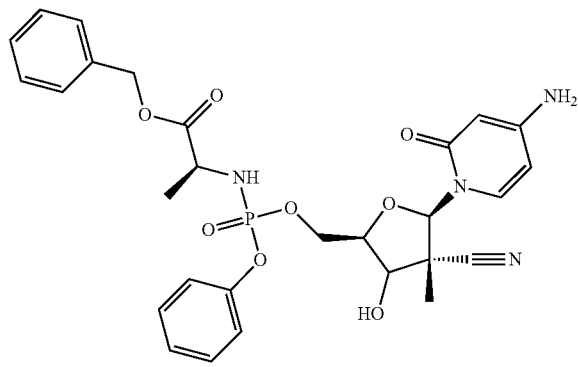 [SMILES: C[C@H](NP(=O)(OC[C@H]1O[C@@H](n2ccc(N)cc2=O)[C@](C)(C#N)C1O)Oc1ccccc1)C(=O)OCc1ccccc1]<br>Isomer 1 | 584.2 |
| 209 | 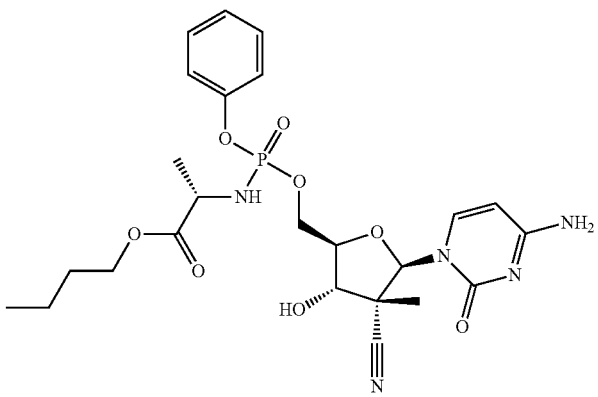 [SMILES: CCCCOC(=O)[C@H](C)NP(=O)(OC[C@H]1O[C@@H](n2ccc(N)nc2=O)[C@](C)(C#N)[C@@H]1O)Oc1ccccc1]<br>Isomer 1 | 549.8 |

-continued

| Compound No. | Structure | MS (M + H) |
|---|---|---|
| 210 | Isomer 1 | 535.8 |
| 212 | Isomer 2 | 535.8 |
| 214 | Isomer 1 | 522.2 |
| 217 | Isomer 1 | 558.1 |

-continued

| Compound No. | Structure | MS (M + H) |
|---|---|---|
| 229 | 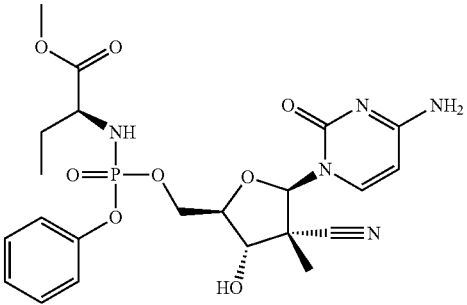 [SMILES: CC[C@H](NP(=O)(OC[C@H]1O[C@@H](n2ccc(N)nc2=O)[C@](C)(C#N)[C@@H]1O)Oc1ccccc1)C(=O)OC]<br>Isomer 1 | 576.19 |
| 230 | 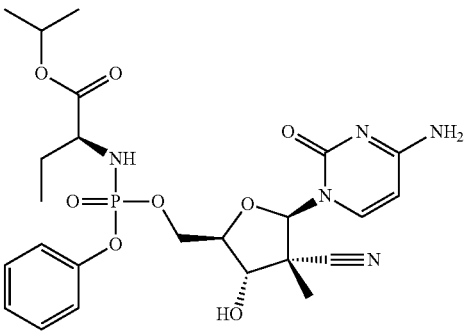 [SMILES: CC[C@H](NP(=O)(OC[C@H]1O[C@@H](n2ccc(N)nc2=O)[C@](C)(C#N)[C@@H]1O)Oc1ccccc1)C(=O)OC(C)C]<br>Isomer 1 | 550.2 |

Example 14

Preparation of Compound 218

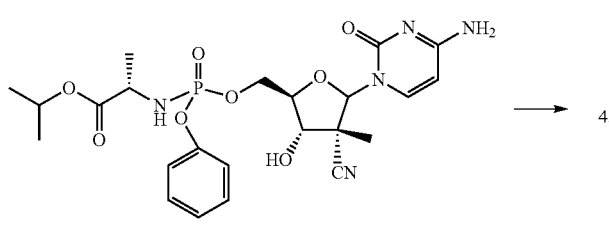

To a stirred mixture of starting material 210 (20 mg, 0.037 mmol) and DMAP (0.502 mg, 4.11 µmol) in tetrahydrofuran (1.0 mL) at 0° C. was added Et₃N (0.016 mL, 0.112 mmol) and water (0.7 mL) and the mixture was stirred at 0° C. for 5 minutes. Isobutyryl chloride (0.037 mmol) was added to the reaction mixture slowly. The reaction was stirred for 30 minutes at 0° C. and then acidified with aqueous HCl (IM) to pH 6-7. The mixture was extracted with EtOAc (2×20 mL), washed with water and brine, dried over MgSO₄, filtered, and concentrated in vacuo. The residue was purified by silica gel preparatory TLC, eluting with 10% MeOH/DCM in 45 minutes to provide a white solid. Lyophilization of the solid from acetonitrile/water provided the dry powder 218 (17 mg, 75%).

Example 15

Preparation of Compound 219

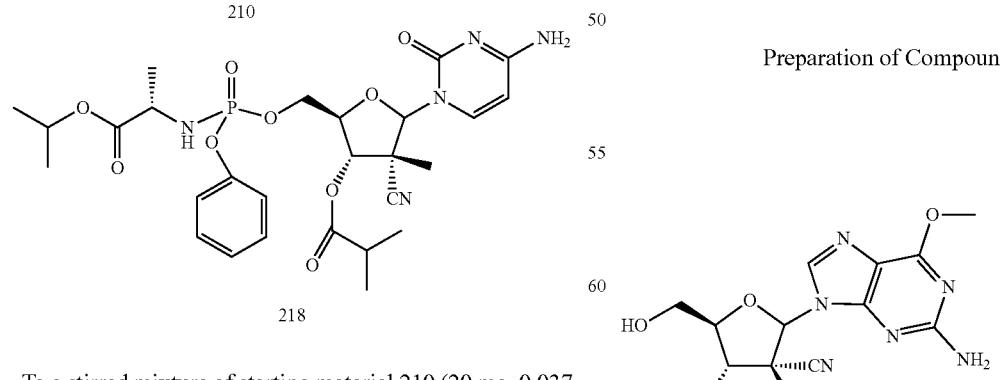

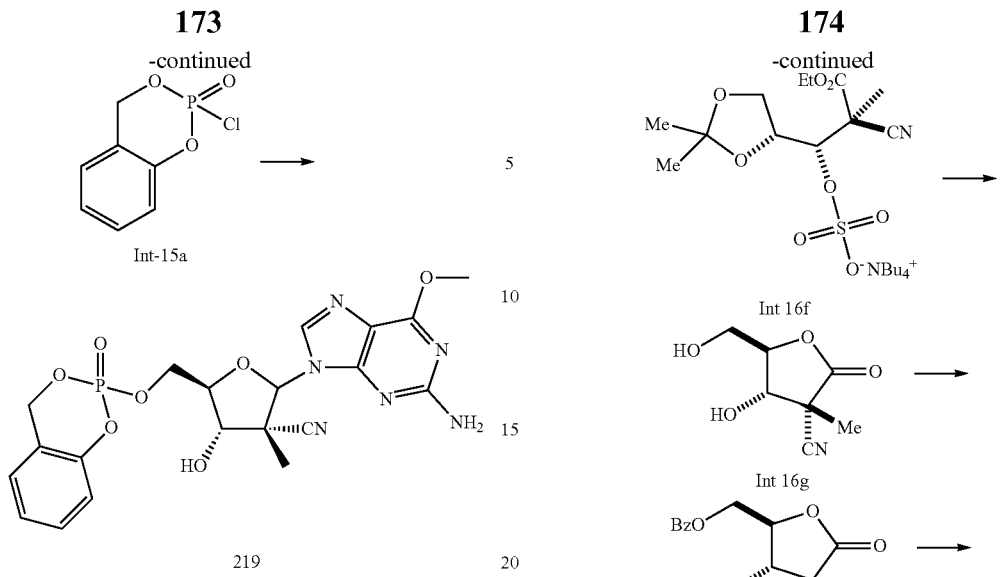

To a stirred mixture of starting material 31 (20 mg, 0.062 mmol) in tetrahydrofuran (1 mL) at room temperature was added N-methylimidazole (0.035 mL, 0.437 mmol) and the mixture was stirred at 35° C. for 3 minutes. Phosphorochloridate Int-15a (51 mg, 0.25 mmol in 0.5 ml THF) was added dropwise and the reaction mixture was stirred for 1 hour at 35° C. The reaction was quenched with water (20 mL) and the mixture was extracted with ethyl acetate (2×30 mL), washed with brine (25 mL), back extract aqueous layer with EtOAc (30 mL). The combined organic layers were dried with MgSO$_4$, filtered and concentrated. The residue was purified by silica gel preparatory TLC (10% MeOH/DCM) to provide desired product 219 (4.1 mg, 13.4%).

Example 16

Preparation of Compound 220

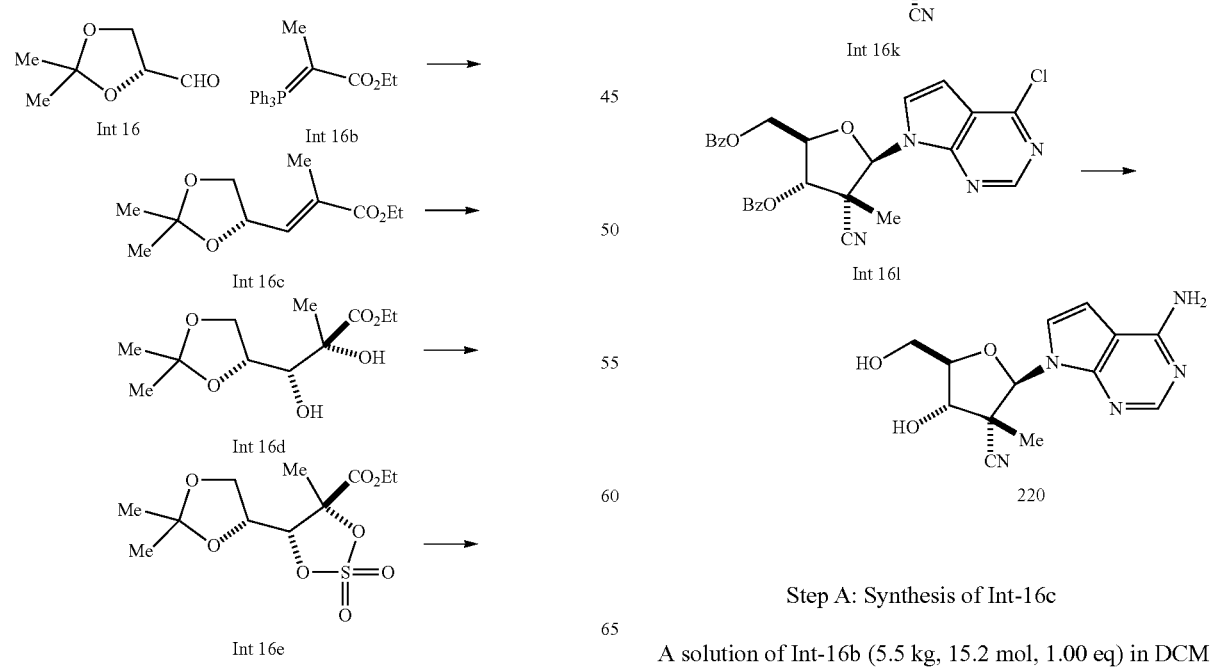

Step A: Synthesis of Int-16c

A solution of Int-16b (5.5 kg, 15.2 mol, 1.00 eq) in DCM (15.4 L) was placed into a 50 L reactor, and a solution of Int-16a (2.35 kg, 18.1 mol, 1.19 eq) in DCM (2.8 L) was added into above solution while maintaining the temperature at −5° C. for about 0.5 hour to complete addition). The mixture was allowed to react for 3 hours at −5° C. until LCMS showed the content of Int-16a is not more than 5%. The reaction solution was concentrated in vacuo at 40° C. The residue was treated with petroleum ether (5 L) and the insoluble solid was filtered out and washed with EtOAc:PE (1:15, 3×5 L). The filtrate was concentrated in vacuo at 40° C. The residue was purified by distillation under vacuum (10 mm Hg) and the fraction was collected >90° C. to provide white oil Int-16c (2.6 kg, yield: 81%). The material was used to next step without any further purification.

Step B: Synthesis of 16d

A solution of Int-16c (2.6 kg, 12.15 mol, 1.00 eq) in acetone (40 L) was treated with a solution of ethane-1,2-diol (3.0 kg, 12.76 mol, 4.00 eq) and NaHCO$_3$ (3.06 kg, 36.45 mol, 3.00 eq) in H$_2$O (5.2 L). KMnO$_4$ (2.02 kg, 12.76 mol, 1.05 eq) was added in several portions into the above solution while maintaining the temperature at −15° C.~−10° C. (about 1 hour to complete addition). The mixture was allowed to react for 1 hour at −15° C.~−10° C. until the SM was consumed completely. The resulting solution was quenched with NaHSO$_3$ (aqueous 25% w/w, 5 L) while maintaining the temperature below 4° C. A filtration was performed and the filter cake was washed with acetone (3×1.0 L). The filtrate was concentrated in vacuo and the residue was extracted with EtOAc (1×10 L, 2×5 L). The organic layers were combined, dried over Na$_2$SO$_4$ (3.0 kg), filtered and concentrated in vacuo. The residue was treated with toluene (1.5 L) and petroleum ether (9 L). The slurry was stirred for 10 hours at −10° C.~0° C. The solid was collected, dried at 40° C. to provide pure product Int-16d (1.8 kg, yield: 60%) as a white solid.

Step C: Synthesis of 16e

A solution of Int-16d (1.73 kg, 6.97 mol, 1.00 eq) in DCM (17 L) was treated with TEA (2.11 kg, 20.93 mol, 3.00 eq). The reaction was then treated with SOCl$_2$ (1.08 kg, 9.06 mol, 1.30 eq) dropwise while maintaining the temperature at −5° C.~15° C. (about 0.5 hour to complete addition). The mixture was stirred for 1 hour at 15° C.~25° C. The resulting solution was quenched with water (20 L). The separated organic layer was washed with saturated NaHCO$_3$ (1×10 L). The organic layer was placed into 50 L reactor and diluted with MeCN (1.8 L), followed by the dropwise addition of aqueous NaOCl (6.9%, 20 L) while maintaining the temperature at 5° C.~20° C. (about 1 hour to complete addition). Then the mixture was allowed to react for 40 hours at 15° C.~25° C. The resulting solution was quenched with aqueous Na$_2$SO$_3$ (15%, 10 L). The separated organic layer was washed with water (6×5 L), saturated NaHCO$_3$ (1×15 L) and saturated brine (1×15 L), dried over Na$_2$SO$_4$, filtered and concentrated in vacuo to provide product Int-16e (1.6 kg, yield:74%) as oil.

Step D: Synthesis of 16f

A solution of Int-16e (900 g, 2.9 mol, 1.00 eq) in DMF (8.1 L) and H$_2$O (900 mL) was added was treated with KCN (226 g, 3.5 mol, 1.20 eq). The mixture was warmed to 50° C. and allowed to react for 5 hours until TLC showed Int-16e was consumed completely. The resulting solution was cooled to 30° C. with water bath and K$_2$HPO$_4$ (782 g, 4.5 mol, 1.55 eq) and Bu$_4$NHSO$_4$ (1.08 kg, 3.2 mol, 1.10 eq) were added in one portion. The mixture was allowed to react overnight. The reaction mixture was diluted with EtOAc (20 L) and water (10 L). The water layer was extracted with EtOAc (2×5 L). The organic layers were combined, dried over sodium sulfate, filtered and concentrated in vacuo to provide the crude product Int-16f (1.3 kg, the content of DMF is 28% w/w, isolated yield: 65%) as brown oil which was used to next step without any further purification.

Step E: Synthesis of 16g

A solution of Int-16f (1.3 kg, 1.6 mol, 1.00 eq) in EtOH (7.8 L) was treated with HCl (10 M, 233 g, 2.3 mol, 1.42 eq). The mixture was allowed to react for 15 hours at 20° C.~30° C. The reaction progress was monitored by TLC until Int-16f was consumed completely. The resulting solution was quenched with a solution of NaHCO$_3$ (193 g, 2.3 mol, 1.42 mol) in water (193 g). The resulting solution was concentrated in vacuo to remove most EtOH. The residue was extracted with EtOAc (2×3 L, 2×1.3 L). The organic layers were combined, dried over Na$_2$SO$_4$, filtered and concentrated in vacuo to provide crude product Int-16g (550 g, theoretic yield: 277 g) as a brown oil which was used to next step without any further purification.

Step F: Synthesis of Int-16h

A solution of Int-16 g (550 g, theoretic yield: 277 g, 1.6 mol, 1.00 eq) in CH$_3$CN (1.4 L) was treated with TEA (360 g, 3.6 mol, 1.00 eq) and DMAP (12.2 g, 0.1 mol, 0.06 eq). BzCl (508 g, 3.6 mol, 2.20 eq) was added dropwise to the above solution while maintaining the temperature at 0~25° C. (about 1.5 hours to complete addition). The mixture was allowed to react for 1 hour at 10° C.~25° C. until LCMS showed the Int-16g was consumed completely. The resulting solution was diluted with water (5 L), then extracted with EtOAc (4×2 L). The organic layers were combined, washed with brine (35%, 1×1 L), dried over Na$_2$SO$_4$, filtered and concentrated in vacuo. The residue (600 g) was treated with propan-2-ol (6 L) and stirred for 1 hour at 20° C.~30° C. A filtration was performed and the filter cake (300 g) was purified by recrystallization from EtOAc (600 mL) and propan-2-ol (6000 mL) to provide pure product Int-16h (270 g, yield: 44%, purity:97.6%) as a white solid.

Step G: Synthesis of Int-16i

To a solution of Int-16h (1 g, 2.64 mmol, 1.00 equiv) in THF (15 mL) was added a solution of Li(t-BuO)$_3$AlH (1 g, 3.92 mmol, 1.50 equiv) in THF (10 mL) dropwise with stirring at −30° C. The resulting solution was stirred for 2 hours at −30° C. in a liquid nitrogen bath. The reaction was then quenched by the addition of saturated NH$_4$Cl (30 mL). The resulting solution was extracted with EtOAc (3×50 mL). The organic layers were combined, dried over anhydrous Na$_2$SO$_4$, filtered and concentrated in vacuo. The residue was applied onto a silica gel column and eliuted with 10-20% EtOAc/hexane to provide Int-16i as a white solid. (800 mg, 80%). $^1$H-NMR-Int-16i (300 MHz, CD$_3$OD, ppm): δ 8.14-8.17 (m, 2H), 8.02-8.05 (m, 2H), 7.39-7.65 (m, 6H), 5.62-5.63 (m, 1H), 5.41-5.42 (m, 1H), 4.61-4.83 (m, 3H), 1.66 (s, 3H).

Step H: Synthesis of 16j

To a solution of Int-16i (3 g, 7.87 mmol, 1.00 equiv) in toluene (60 mL) was added TEA (3.2 g, 31.62 mmol, 4.00 equiv) and diphenyl chlorophosphonate (4.2 g, 15.63 mmol, 2.00 equiv). After the resulting solution was stirred for 5 hours at room temperature, it was diluted with DCM (200 mL). The reaction was then quenched by the addition of saturated $Na_2CO_3$ (40 mL). The resulting solution was extracted with DCM (3×50 mL). The organic layers were combined, dried over anhydrous $Na_2SO_4$, filtered and concentrated in vacuo. The residue was applied onto a silica gel column and eluted with 10-20% EtOAc/hexane to provide Int-16j as colorless oil (5.0 g). $^1$H-NMR-Int-16j: (300 MHz, $CDCl_3$, ppm): δ 8.10-8.12 (m, 2H), 7.99-8.00 (m, 2H), 7.53-7.69 (m, 2H), 7.43-7.52 (m, 4H), 7.14-7.37 (m, 10H), 6.02 (d, J=1.5 Hz, 1H), 5.21 (d, J=1.5 Hz, 1H), 4.61-4.66 (m, 2H), 4.31 (q, J=1.5 Hz, 1H), 1.68 (s, 3H).

Step I: Synthesis of 16k

Into a 25-mL round-bottom flask purged and maintained with an inert atmosphere of argon, was placed Int-16j (500 mg, 0.81 mmol, 1.00 equiv) and 33% hydrogen bromide/acetic acid (5 mL). The resulting solution was stirred for 3 hours at room temperature, and then diluted with DCM (50 mL). The reaction was then quenched by the addition of water/ice and the resulting solution was extracted with DCM (50 mL). The organic layers were combined, washed with saturated $Na_2CO_3$ (50 mL), dried over anhydrous $Na_2SO_4$, filtered, and concentrated in vacuo. The residue was applied onto a silica gel column and eluted with (5-20%) EtOAc/hexane to provide of Int-16k as a off-white foam (0.25 g, 69%). $^1$H-NMR-Int-16k: (300 MHz, $CDCl_3$, ppm): δ 8.25 (d, J=11.4 Hz, 2H), 8.17 (d, J=5.3 Hz, 2H), 7.59-7.77 (m, 2H), 7.44-7.50 (m, 4H), 6.39 (s, 1H), 5.35 (d, J=2.0 Hz, 1H), 4.73-4.92 (m, 3H), 1.76 (s, 3H).

Step J: Synthesis of 16l

To a stirred solution of 4-chloro-7H-pyrrolo[2,3-d]pyrimidine (2.0 g, 13.02 mmol, 1.00 equiv) in acetonitrile (10 mL) was added a solution of KOBt (1.46 g, 1.30 equiv) in tert-Butanol (10 mL). The resulting solution was stirred for 30 minutes at room temperature. A solution of Int-16k (4.4 g, 9.90 mmol, 1.30 equiv) in acetonitrile (10 mL) was added to the mixture. The resulting solution was stirred for an additional 3.5 hours while the temperature was maintained at 50° C. in an oil bath. The reaction mixture was then cooled down to room temperature. The resulting solution was diluted with dichloromethane (100 mL) and the reaction was then quenched by the addition of saturated $NH_4Cl$ (50 mL). The resulting solution was extracted with DCM (3×50 mL). The organic layers were combined, dried over anhydrous $Na_2SO_4$, filtered, and concentrated in vacuo. The residue was applied onto a silica gel column and eluted with 5-30% EtOAc/petroleum ether to provide 2.9 g (43%) of Int-16l as a white solid.

$^1$H-NMR-Int-16l: (300 MHz, $CDCl_3$, ppm): δ 8.73 (s, 1H), 8.14-8.19 (m, 2H), 8.06-8.09 (m, 2H), 7.60-7.70 (m, 2H), 7.46-7.55 (m, 5H), 6.97 (s, 1H), 6.66 (d, J=1.5 Hz, 1H), 5.79-5.81 (m, 1H), 4.92-4.96 (m, 1H), 4.71-4.79 (m, 2H), 1.60 (s, 3H).

Step K: Synthesis of 220

Into a 25-mL sealed tube, was placed a solution Int-16l (50 mg, 0.10 mmol, 1.00 equiv) in ammonia saturated i-PrOH (10 mL). The resulting solution was stirred for 2 days at 50° C. in an oil bath. The resulting mixture was concentrated in vacuo. The crude product (40 mg) was purified by Prep-HPLC with the following conditions (1#-Pre-HPLC-011(Waters)): Column, SunFire Prep C18, 19*150 mm 5 μm; mobile phase, Water and $CH_3CN$ (5.0% $CH_3CN$ up to 23.0% in 6 min, up to 83.0% in 4 min, up to 100.0% in 1 min, down to 3.0% in 2 min); Detector, UV 254 & 220 nm. This provided compound 220 as an off-white solid. (20 mg, 71%) LC-MS-220(ES, m/z): 290 [M+H]$^{+1}$H-NMR-220: (300 MHz, $CD_3OD$, ppm): δ 8.12 (s, 1H), 7.59 (d, J=1.8 Hz, 1H), 6.70 (s, 1H), 6.65 (d, J=1.8 Hz, 1H), 4.30-4.35 (m, 1H), 3.98-4.06 (m, 2H), 4.85-3.90 (m, 1H), 0.99 (s, 3H).

The following compounds of the present invention were made using the methods described in the Example above and substituting the appropriate reactants and/or reagents.

| Compound No. | Structure | (M + H) |
|---|---|---|
| 222 | 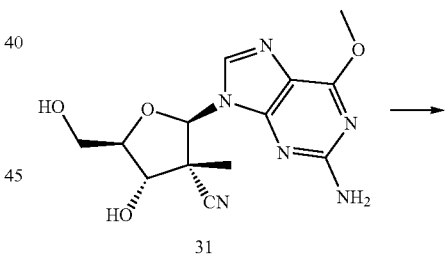 | 308 |

Example 17

Preparation of Compound 221

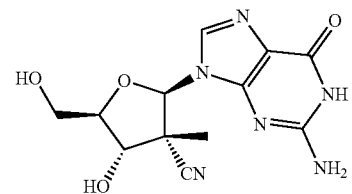

31

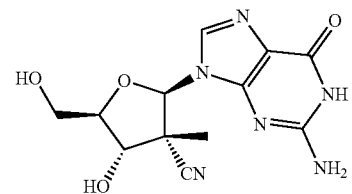

221

To a stirred solution of compound 31 (110 mg, 0.343 mmol) in THF (6 mL) was added 1N HCl (6 mL). The solution was heated at 50° C. for 48 hours. The solvent was removed in vacuo. The residue was purified by HPLC (5% water/acetonitrile) to provide compound 221. (71 mg).

[M+H]=307.0; $^1$H-NMR (400 MHz, CD$_3$OD): δ: 8.48 (s, 1H), 6.41 (s, 1H), 4.33 (m, 1H), 4.05-4.0 (m, 2H), 3.85 (m, 1H), 1.19 (s, 3H).

Example 18

Preparation of Compound 223

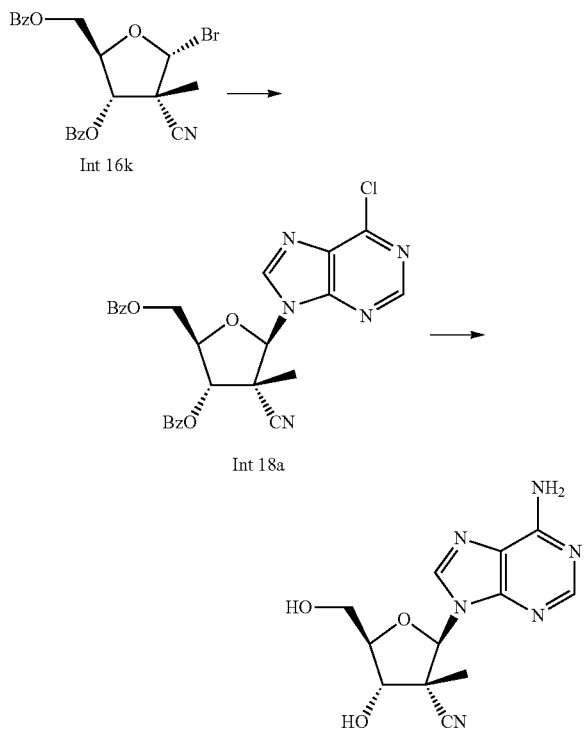

Step A: Synthesis of Int-18a

To a stirred solution of 6-chloro-9H-purine (348 mg, 2.25 mmol, 2.00 equiv) in tert-Butanol (5 mL) was added t-BuOK (253 mg, 2.26 mmol, 2.00 equiv). The resulting solution was stirred for 30 minutes at room temperature. Then a solution of Int-16k (500 mg, 1.13 mmol, 1.00 equiv) in MeCN (5 mL) was added. The resulting solution was stirred for an additional 2.0 hours at room temperature. The pH value of the solution was adjusted to 7 with 1N HCl and then concentrated in vacuo. The resulting solution was diluted with ethyl acetate (10 mL), washed with saturated NH$_4$Cl (2×10 mL) and saturated NaCl (2×10 mL). The organic phase was dried over anhydrous Na$_2$SO$_4$, filtered and concentrated in vacuo. The residue was applied onto a silica gel column and eluted with EtOAc/petroleum ether (1:3) to provide Int-18a as an off-white solid. (180 mg, 31%). $^1$H-NMR-Int-18a: (300 MHz, CDCl$_3$, ppm): δ 8.82 (s, 1H), 8.32 (s, 1H), 8.18-8.13 (m, 2H), 8.10-8.02 (m, 2H), 7.77-7.42 (m, 7H), 6.75 (s, 1H), 5.91 (d, J=6.0 Hz, 1H), 5.31 (s, 1H), 4.95-4.72 (m, 3H), 1.39 (s, 3H).

Step B: Synthesis of 223

Into a 10-mL sealed tube, was placed Int-18a (180 mg, 0.35 mmol, 1.00 equiv) and solution of NH$_3$(l) (8 mL) in i-PrOH (2 mL). The resulting solution was stirred for 2 days at 50° C. in an oil bath, and then concentrated in vacuo. The crude product (80 mg) was purified by Prep-HPLC with the following conditions (1#-Pre-HPLC-001(SHIMADZU)): Column, 1#-PrepC-014(Atlantis T3 19*150 186003698 012139334114 02), N; mobile phase, Water and CH$_3$CN (2.0% CH$_3$CN up to 25.0% in 7 min, up to 100.0% in 1 min, down to 2.0% in 2 min); Detector, UV 254 & 220 nm. This provided compound 223 as a white solid. (50 mg, 50%)

LC-MS-223: (ES, m/z): 291 [M+H]$^+$.
$^1$H-NMR-223: (300 MHz, CD$_3$OD, ppm): δ 8.65 (s, 1H), 8.23 (s, 1H), 6.63 (s, 1H), 4.46 (d, J=6.0 MHz, 1H), 4.13-4.04 (m, 2H), 3.98-3.88 (m, 1H), 1.13 (s, 3H).

Example 19

Preparation of Compound 71

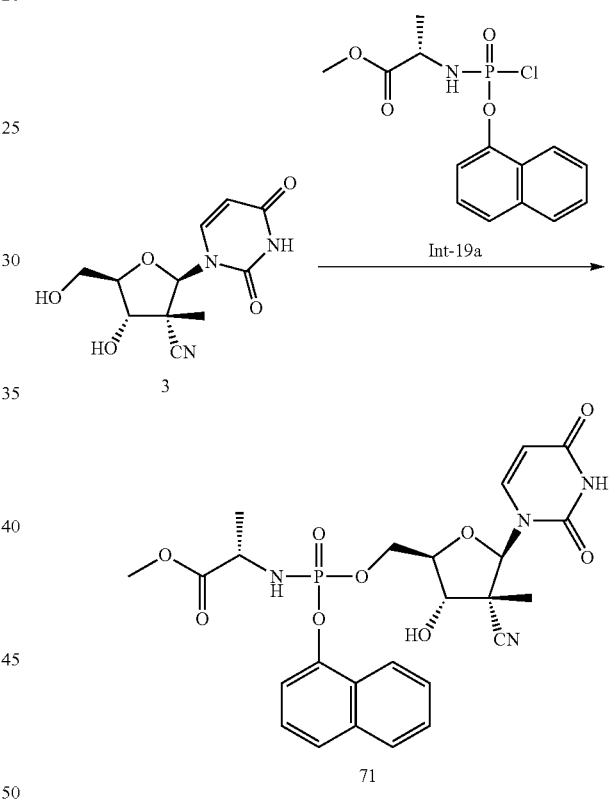

A solution of compound 3 (75.8 mg, 0.28 mmol) in tetrahydrofuran (2.5 mL) at 0° C. was treated with methyl imidazole (0.19 mL, 2.29 mmol) dropwise. The reaction was allowed to stir for 5 minutes, then a solution of prodrug Int-19a (499 mg, 1.52 mmol, made using the methods described in Example 11) in tetrahydrofuran (1.0 mL) was added dropwise. The reaction was allowed to warm to room temperature and stirred for 1.5 hours. The reaction was concentrated in vacuo. The crude material was purified via preparative TLC eluting with 10% methanol/dichloromethane. The material was further purified by reverse phase HPLC to provide a mixture of diastereomers that were separated by SFC separation to provide compound 71 (36.5 mg) as an off-white solid. $^1$H NMR (400 MHz, CD$_3$OD) δ 8.19-8.18 (m, 1H), 7.92-7.89 (m, 1H), 7.73 (d, J=8.0 Hz, 1H), 7.60-7.55 (m, 2H), 7.52-7.43 (m, 3H), 6.29 (s, 1H), 5.35 (d, J=8.0 Hz, 1H), 4.62 (ddd, J=12.0, 4.8, 2.0 Hz, 1H), 4.50 (ddd, J=12.0, 6.4, 3.2 Hz, 1H), 4.15-4.12 (m, 1H), 4.09-4.01 (m, 1H), 3.94 (d, J=8.4 Hz, 1H), 3.66 (s, 3H), 1.35 (d, J=7.2 Hz, 3H), 1.18 (s, 3H). Mass calculated for formula $C_{25}H_{27}N_4O_9P$ 558.5; observed MH+ (LCMS) 559.0 (m/z).

Example 20

Preparation of Compounds 49 and 50

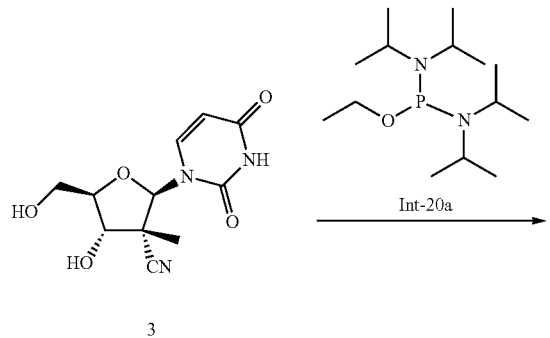
Int-20a

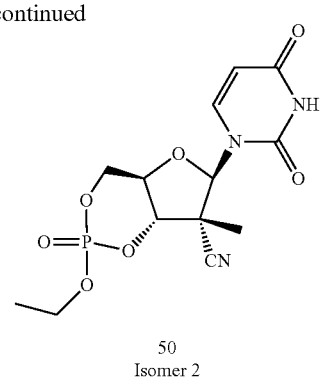
50
Isomer 2

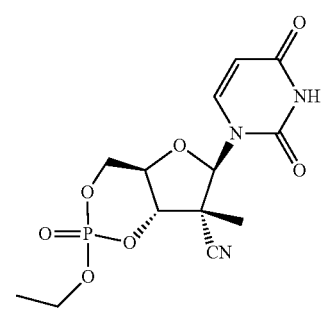
49
Isomer 1

Compound 3 (50.0 mg, 0.19 mmol) was added to a sealed tube and dissolved in tetrahydrofuran (1.5 mL). Intermediate 20a (67.2 mg, 0.24 mmol) was dissolved in tetrahydrofuran (2.0 mL) and added to the sealed tube followed by 5-(ethylthio)-1H-tetrazole (24.3 mg, 0.187 mmol). The tube was sealed and heated to 100° C. for 2.5 hours. The reaction was cooled to room temperature and t-butyl hydrogen peroxide (2.34 mL, 18.7 mmol) was added to the reaction. The reaction continued to stir for 16 hours. The reaction was transferred to a round bottom flask and concentrated in vacuo. The material was purified via preparative TLC in 5% methanol/dichloromethane yielding a mixture of diastereomers. The diastereomers were separated by SFC to afford compounds 49 (8.4 mg) and 50 (16.3 mg). $^1$H NMR: 49 (400 MHz, CD$_3$OD) δ 7.65 (d, J=8.0 Hz, 1H), 6.60 (s, 1H), 5.77 (d, J=8.0 Hz, 1H), 4.84-4.77 (m, 1H), 4.70-4.62 (m, 2H), 4.50-4.47 (m, 1H), 4.33-4.25 (m, 2H), 1.43 (s, 3H), 1.41 (t, J=7.2 Hz, 3H); LC-MS: 49: (ES, m/z): 358.2. $^1$H NMR: 50 (400 MHz, CD$_3$OD) δ 7.67 (d, J=8.0 Hz, 1H), 6.56 (s, 1H), 5.74 (d, J=8.0 Hz, 1H), 4.78-4.68 (m, 1H), 4.63-4.58 (m, 2H), 4.43-4.40 (m, 1H), 4.32-4.22 (m, 2H), 1.43-1.39 (m, 6H); LC-MS: 50: (ES, m/z): 358.2.

Example 21

Preparation of Compound 206

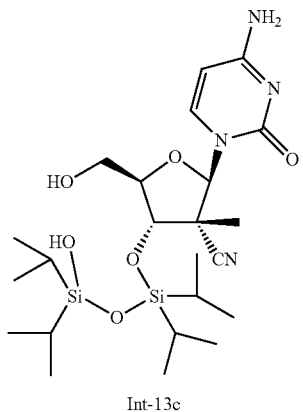
Int-13c

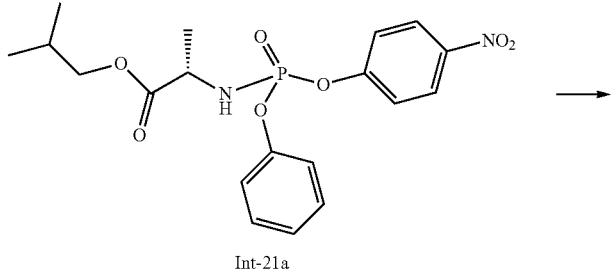
Int-21a

-continued

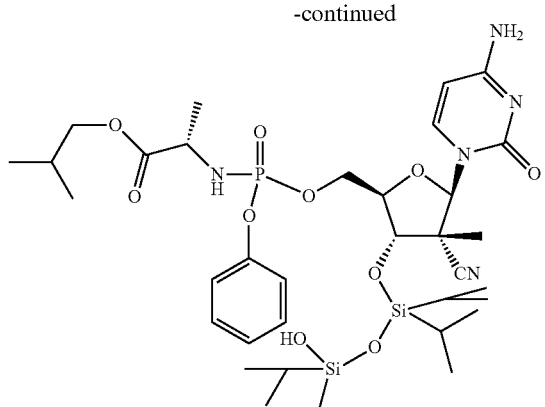

Int-21b

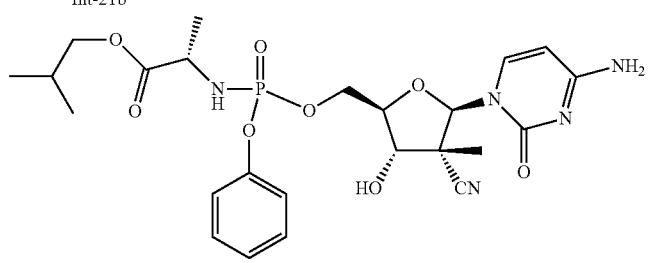

206

Step A: Synthesis of Int-21b

To a solution of compound Int-13c (350 mg, 0.664 mmol) in a mixture solvent of NMP (1.0 mL) and THF (5 mL) was added tert-butyl magnesium chloride (1.99 mL, 1M in THF) at 0° C. The solution was stirred at 0° C. for 30 minutes under nitrogen. A solution of Int-21a (561 mg, 1.33 mmol, made using the methods described in Example 11) in THF (2 mL) was added. The solution was stirred under $N_2$ at 0° C. to room temperature for 3 hours. The reaction was quenched with aq. $NH_4Cl$ (10 mL), extracted with EtOAc (2×40 mL), dried ($MgSO_4$), filtered, and concentrated. The crude product was purified by silica gel column chromatography (0-10% MeOH/$CH_2Cl_2$) in 1 hour and continue hold for 30 minutes to provide a white solid Int-21b (480 mg, 89%).

Step B: Synthesis of compound 206

To a stirred mixture of starting material Int-21b (478 mg, 0.59 mmol) in tetrahydrofuran (2.3 mL) and MeOH (4.3 mL) at room temperature was added formic acid (3.92 mL, 102 mmol). CsF (448 mg, 2.95 mmol) was added to the reaction mixture and stirred at 50° C. for 6 hours. The reaction mixture was quenched with water (10 mL) and extracted with ethyl acetate (3×30 mL), washed with water and brine, dried ($MgSO_4$), filtered and concentrated. The residue was purified by silica gel column chromatography eluting with 0-10% MeOH/$CH_2Cl_2$ in 45 minutes to provide desired product. The product was dissolved in 0.3 ml $CH_3CN$ and 2.0 ml water, lyophilized for over night to provide a white powder product 206 (128 mg, 39.5%). $^1H$ NMR: 7.64 (d, 1H, J=7.56), 7.37 (m, 2H), 7.24 (m, 3H), 6.36 (s, 1H), 5.84 (d, 1H, J=7.57), 4.51 (m, 1H), 4.37 (m, 1H), 4.09 (m, 1H), 3.8-4.0 (m, 4H), 1.90 (m, 1H), 1.37 (d, 3H, J=7.18), 1.22 (s, 3H), 0.93 (s, 3H), 0.90 (s, 3H).

Example 22

Preparation of Compounds 188 and 189

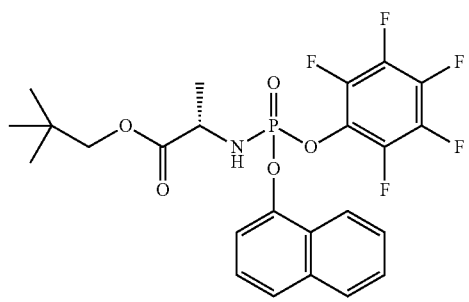

Int-22a

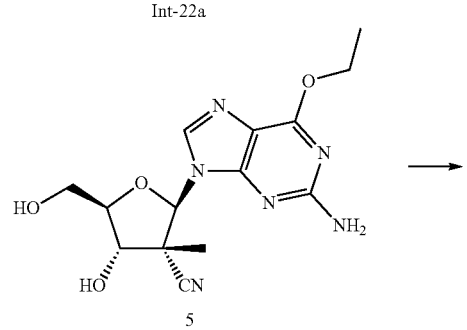

5

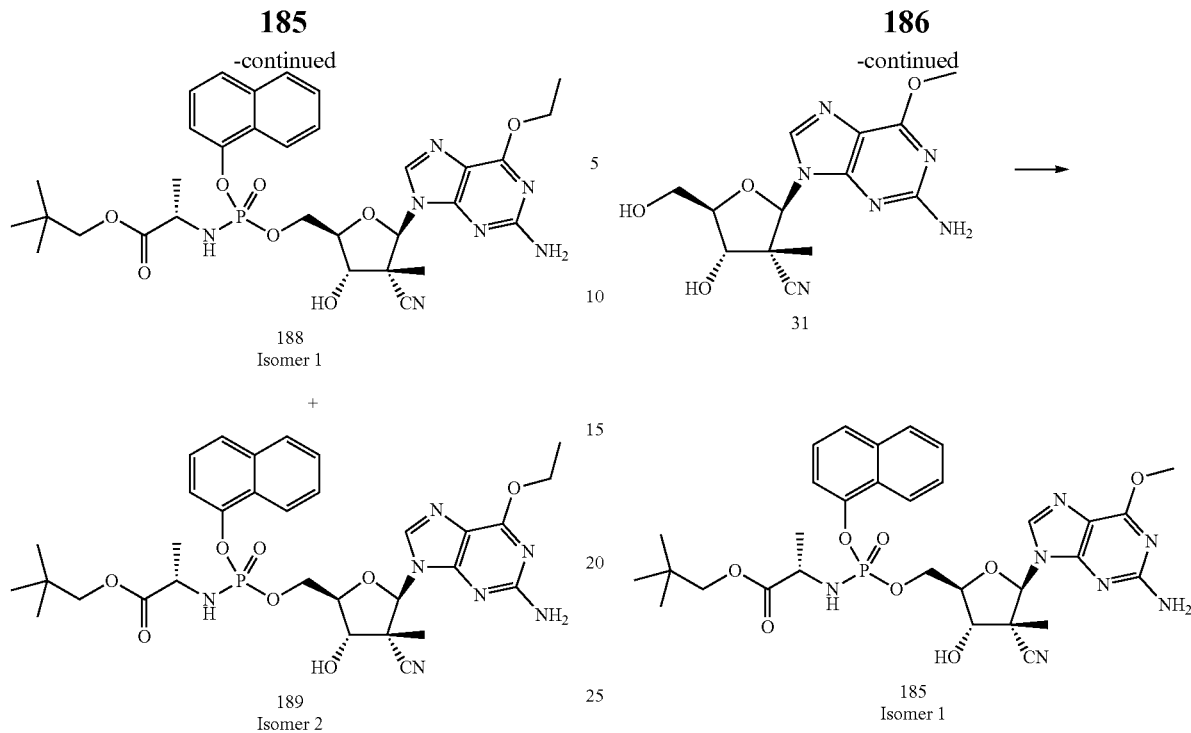

188
Isomer 1

+

189
Isomer 2

A solution of compound 5 (100 mg, 0.299 mmol) in NMP (1.5 mL) and THF(9 mL) was cooled in an ice bath under nitrogen. To the reaction was added tert-butylmagnesium chloride (1.017 mL, 1.017 mmol) and the reaction was stirred at 0° C. for 20 minutes. A solution of Int 22a (175 mg, 0.329 mmol, made using the methods described in Example 11) dissolved in THF(1 mL) was added to this mixture dropwise. The reaction mixture was stirred at room temperature for 1.5 hours. The reaction was diluted with ethyl acetate (20 mL) and washed with water (20 mL), saturated NH$_4$Cl (20 mL). The organic layer was dried over anhydrous sodium sulfate, filtered and concentrated in vacuo. The residue was purified by column chromatography on 20 g silica gel column, eluting with (0-7% MeOH/CH$_2$Cl$_2$) in 40 minutes, then 10 minutes in 7% MeOH/DCM to provide 100 mg of product. The two isomers were separated by super critical fluid separation to provide 188 (26 mg) and 189 (43 mg). $^1$H NMR 188: (400 MHz, CDCl$_3$): δ 8.12-8.08 (m, 1H), 7.66 (s, 0.5H), 7.64 (s, 0.5H), 7.54-7.49 (m, 3H), 7.48-7.44 (m, 1H), 7.37 (t, J=7.86 Hz, 1H), 6.24 (s, 1H), 5.21 (s, 1H), 4.96-4.81 (m, 3H), 4.50 (s, 1H), 4.48 (s, 1H), 4.46-4.41 (m, 2H), 4.17-4.10 (m, 1H), 3.82-3.66 (m, 3H), 1.42 (t, J=7.09 Hz, 3H), 1.30 (d, J=7.13 Hz, 3H), 1.09 (s, 3H), 0.86 (s, 9H)

Example 23

Preparation of Compounds 185 and 186

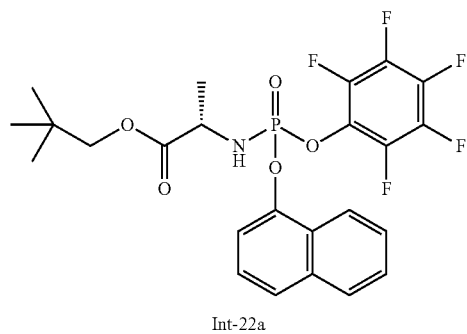

Int-22a

31

185
Isomer 1

186
Isomer 2

A solution of compound 31 (50 mg, 0.156 mmol) in NMP (4 mL) and THF(16 mL) was cooled in an ice bath and treated with t-butyl magnesium chloride (0.531 mL, 0.531 mmol). After the solution was stirred for 20 minutes, Int 22a (100 mg, 0.187 mmol, made using the methods described in Example 11) dissolved in THF(1 mL) and added to this mixture dropwise. The reaction mixture was stirred at room temperature for 1.5 hours. The reaction was diluted with ethyl acetate (20 mL) and washed with water (20 mL), saturated NH$_4$Cl (20 mL). The organic layer was dried over anhydrous sodium sulfate, filtered and concentrated in vacuo. The residue was purified by column chromatography on a 20 g silica gel column, eluting with (0-10% MeOH/CH$_2$Cl$_2$) in 40 minutes, then 10 minutes in 7% MeOH/DCM to provide 43 mg of a mixture of two diastereomers. The two isomers were separated by super critical fluid separation to provide 185 (6.1 mg) and 186 (24 mg). $^1$H NMR 185: (400 MHz, CDCl$_3$): δ 8.11-8.09 (m, 1H), 7.84-7.81 (m, 1H), 7.67-7.63 (m, 1H), 7.54-7.50 (m, 3H), 7.49-7.44 (m, 1H), 7.39-7.32 (m, 1H), 6.25 (s, 1H), 5.25 (s, 1H), 4.92-4.84 (m, 1H), 4.80-4.77 (m, 1H), 4.48-4.42 (m, 1H), 4.29-4.24 (m, 1H), 4.15-4.10 (m, 1H), 4.02 (s, 3H), 3.82 (s, 0.5H), 3.79 (s, 0.5H), 3.77-3.72 (m, 1H), 3.70 (s, 0.5H), 3.67 (s, 0.5H), 1.34-1.26 (m, 3H), 1.07 (s, 3H), 0.86 (s, 9H).

Example 24

Preparation of Compounds 43 and 44

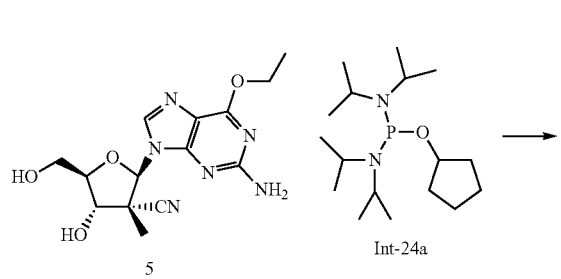

Int-24a

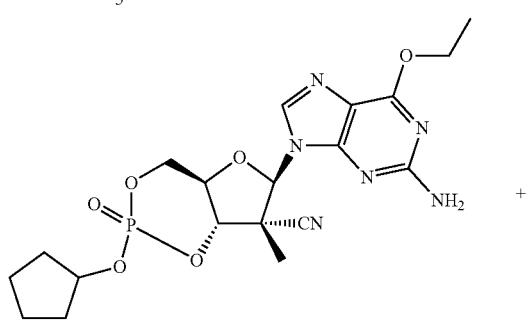

43

Isomer 1

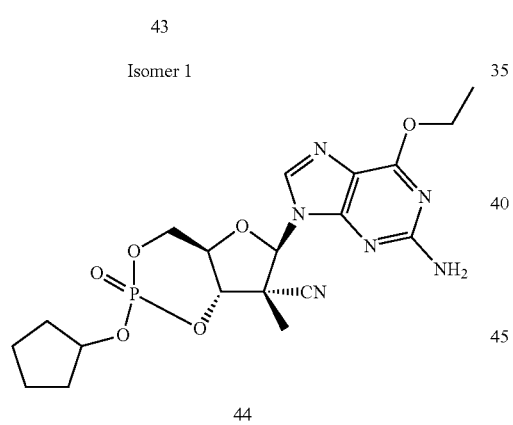

44

Isomer 2

The mixture of compound 5 (20 mg, 0.060 mmol) and Int-24a (49.2 mg, 0.156 mmol) in tetrahydrofuran (1 mL) was treated with 5-(ethylthio)-1H-tetrazole (7.79 mg, 0.060 mmol). The reaction was heated in a sealed tube at 93° C. for 2.5 hours. The reaction mixture was cooled to room temperature and was treated with t-butyl hydroperoxide (0.828 mL, 5.98 mmol). After stirring overnight the mixture was diluted with water (10 mL) and extracted with EtOAc (2×20 mL). The organic layers were washed with brine (20 mL), dried over sodium sulfate, filtered and concentrated in vacuo. The residue was purified by preparative HPLC, eluting with Acetonitrile/Water+0.1% TFA (10~95~30%) to provide compound 43 (3.82 mg) and compound 44 (2.5 mg). $^1$H NMR 43: (400 MHz, CDCl$_3$): δ 7.55 (s, 1H), 6.34 (s, 1H), 5.11-5.06 (m, 1H), 4.84 (s, 2H), 4.67-4.57 (m, 1H), 4.56-4.48 (m, 2H), 4.39-4.35 (m, 1H), 1.99-1.86 (m, 4H), 1.83-1.72 (m, 2H), 1.73-1.55 (m, 4H), 1.45 (t, J=7.04 Hz, 3H), 1.27 (s, 3H)

Example 25

Preparation of Compound 34

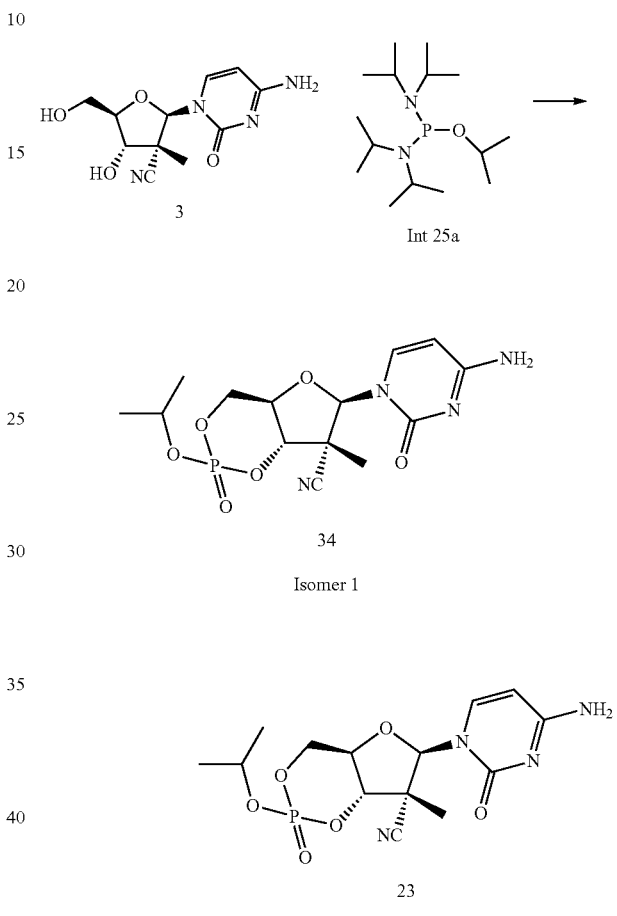

A suspension of compound 3 (263 mg, 0.988 mmol), Int 25a (516 mg, 1.778 mmol) and 5-(ethylthio)-1H-tetrazole (141 mg, 1.08 mmol) in 18.8 mL of acetonitrile was heated at 80° C. for 2 hours in a sealed tube. The mixture was cooled to room temperature and treated with tert-butyl hydroperoxide (70% solution in t-BuOH, 636 mg, 4.94 mmol). The mixture was stirred 30 minutes and diluted with DCM (20 mL) and saturated NaHCO$_3$ (20 mL). The organic phase was dried over Na$_2$SO$_4$, filtered, and concentrated in vacuo. The diastereomers were separated using reverse-phase chromatography on C-18 column using a gradient water-acetonitrile with 0.1 formic acid added as a modifier to provide compound 34 (38 mg) and compound 23 (73 mg).

$^1$H NMR 34: (400 MHz, CD$_3$OD) δ 7.70 (d, J=4.0 Hz, 1H), 6.58 (s, 1H), 5.95 (m, 1H), 4.80 (m, 2H), 4.61 (m, 1H), 4.3 (m, 2H), 1.4 (m, 6H), 1.3 (s, 3H). ESI MS [M+H]=371.2

¹H NMR 23: NMR (400 MHz, CD₃OD) δ 7.66 (d, J=4.0 Hz, 1H), 6.60 (s, 1H), 5.94 (m, 1H), 4.80 (m, 2H), 4.70 (m, 1H), 4.45 (m, H), 4.40 (m, 1H), 1.4 (m, 6H), 1.3 (s, 3H). ESI MS [M+H]=371.2

Example 26

Preparation of Compounds 243

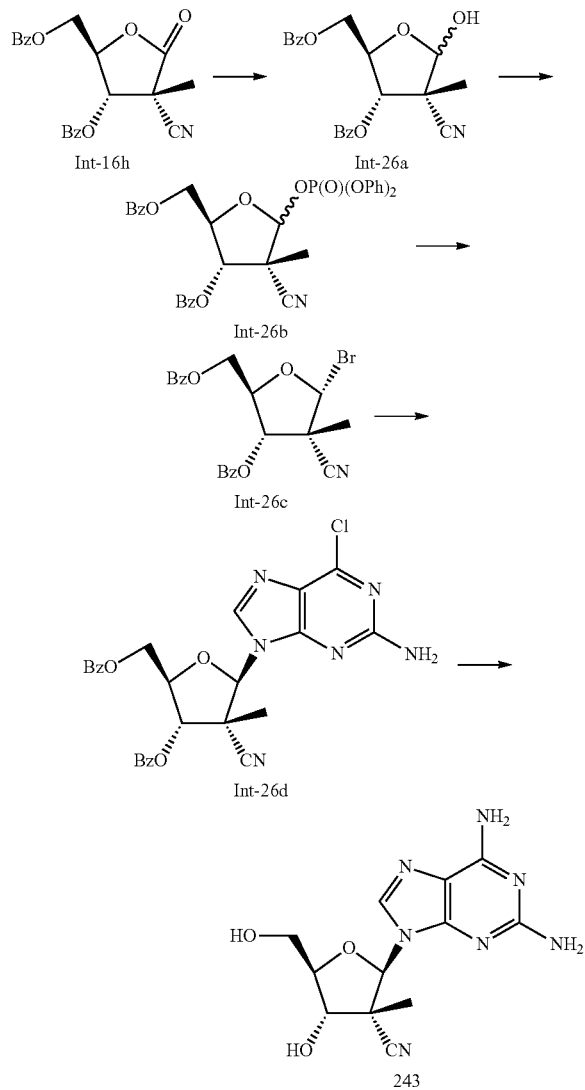

Step A: Synthesis of Int-26a

A solution of Int-16h(1 g, 2.64 mmol, 1.00 equiv) in oxolane (15 mL) was treated with the addition of a solution of 2-(tert-butoxy)-2-methylpropane oxo-2-alumanyl tert-butyl-lithium hydrate (1 g, 3.92 mmol, 1.50 equiv) in oxolane (10 mL) dropwise with stirring at −30° C. The resulting solution was stirred for 2 hours at −30° C. in a liquid nitrogen bath. The reaction was then quenched by the addition of a saturated aqueous solution of ammonium chloride (30 mL) and extracted with ethyl acetate (3×50 mL). The organic layers were combined, dried over anhydrous Na₂SO₄ filtered and concentrated in vacuo. The residue was applied onto a silica gel column and eluted with ethyl acetate/petroleum ether (10-20%) to provide 800 mg (80%) of Int-26a as a white solid.

¹H-NMR (300 MHz, CD₃OD, ppm): δ 8.14-8.17 (m, 2H), 8.02-8.05 (m, 2H), 7.39-7.65 (m, 6H), 5.62-5.63 (m, 1H), 5.41-5.42 (m, 1H), 4.61-4.83 (m, 3H), 1.66 (s, 3H).

Step B: Synthesis of Int-26b

A solution of Int-26a (3 g, 7.87 mmol) in toluene (60 mL) was treated with triethylamine (3.2 g, 31.62 mmol) and diphenyl chlorophosphonate (4.2 g, 15.63 mmol). The resulting solution was stirred for 5 hours at room temperature, then diluted with dichloromethane (200 mL) and quenched by the addition of saturated Na₂CO₃ (40 mL). The resulting solution was extracted with dichloromethane (3×50 mL). The organic layers were combined, dried over anhydrous sodium sulfate filtered and concentrated in vacuo. The residue was applied onto a silica gel column and eluted with ethyl acetate/petroleum ether (5-20%) to provide 5 g of Int-26b as colorless oil.

¹H-NMR-Int-26b: (300 MHz, CDCl₃, ppm): δ 8.10-8.12 (m, 2H), 7.99-8.00 (m, 2H), 7.53-7.69 (m, 2H), 7.43-7.52 (m, 4H), 7.14-7.37 (m, 10H), 6.02 (d, J=1.5 Hz, 1H), 5.21 (d, J=1.5 Hz, 1H), 4.61-4.66 (m, 2H), 4.31 (q, J=1.5 Hz, 1H), 1.68 (s, 3H).

Step C: Synthesis of Int-26c

Into a 25-mL round-bottom flask purged and maintained with an inert atmosphere of argon, was placed Int-26b (500 mg, 0.81 mmol, 1.00 equiv) and 33% hydrogen bromide/acetic acid (5 mL). The resulting solution was stirred for 3 hours at room temperature, then diluted with dichloromethane (50 mL) and quenched by the addition of water/ice. The resulting solution was extracted with dichloromethane (50 mL). The organic layers were combined, washed with saturated Na₂CO₃ (aq), dried over anhydrous Na₂SO₄, filtered and concentrated in vacuo. The residue was applied onto a silica gel column and eluted with ethyl acetate/petroleum ether (5-20%) to provide 0.25 g (69%) of Int-26c as a off-white foam.

¹H-NMR-Int-26c: (300 MHz, CDCl₃, ppm): δ 8.25 (d, J=11.4 Hz, 2H), 8.17 (d, J=5.3 Hz, 2H), 7.59-7.77 (m, 2H), 7.44-7.50 (m, 4H), 6.39 (s, 1H), 5.35 (d, J=2.0 Hz, 1H), 4.73-4.92 (m, 3H), 1.76 (s, 3H).

Step D: Synthesis of Int-26d

A solution of 6-chloro-9H-purin-2-amine (382 mg, 2.25 mmol) in KOBu-t (2.25 mL, 1N in tert-Butanol) was stirred for 30 minutes at room temperature. A solution of Int-26c (500 mg, 1.13 mmol) in acetonitrile (5 mL) was added to the mixture at room temperature. After the resulting solution was stirred for an additional 2 days while the temperature was maintained at 50° C. in an oil bath, the resulting solution was diluted with dichloromethane (30 mL) and the reaction was quenched by the addition of saturated NH₄Cl (30 mL). The resulting solution was extracted with dichloromethane (3×50 mL). The organic layers were combined, dried over anhydrous Na₂SO₄ filtered and concentrated in vacuo. The residue was applied onto a silica gel column and eluted with dichloromethane/methanol (2-10%) to provide 390 mg (65%) of Int-26d as a off-white solid.

¹H-NMR-Int-26d: (CDCl₃, 400 MHz, ppm): 8.09-8.14 (m, 2H), 7.98-8.06 (m, 2H), 7.91 (s, 1H), 7.64-7.67 (m, 1H), 7.44-7.58 (m, 2H), 7.36-7.42 (m, 2H), 6.50 (s, 1H), 6.12 (d, J=3.6 Hz, 1H), 5.72 (br s, 2H), 5.05-5.10 (m, 1H), 4.68-4.75 (m, 2H), 1.39 (s, 3H).

Step E: Synthesis of Compound 243

A solution of Int-26d (140 mg, 0.26 mmol) in propan-2-ol (2 mL) was treated with ammonia (10 mL). The resulting solution was stirred for 2 days at 50° C. in an oil bath. The resulting mixture was concentrated in vacuo. The residue was applied onto a silica gel column and eluted with dichloromethane/methanol (2-20%). This resulted in 30 mg (37%) of compound 243 as a off-white solid.

LC-MS-243: (ES, m/z): 306 [M+H]$^+$ $^1$H-NMR-243: (CD$_3$OD, 400 MHz, ppm): 8.23 (s, 1H), 6.43 (s, 1H), 4.45 (d, J=2.4 Hz, 1H), 4.04-4.08 (m, 2H), 3.88-3.91 (m, 1H), 1.13 (s, 3H).

Example 27

Preparation of Compounds 242

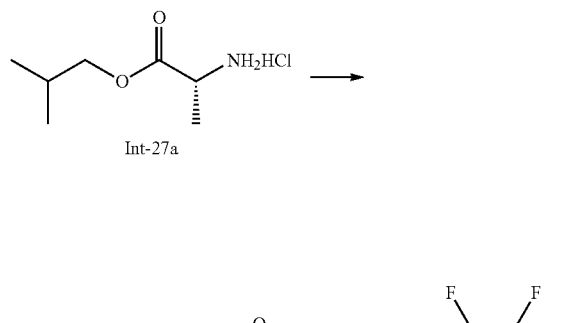

Int-27a

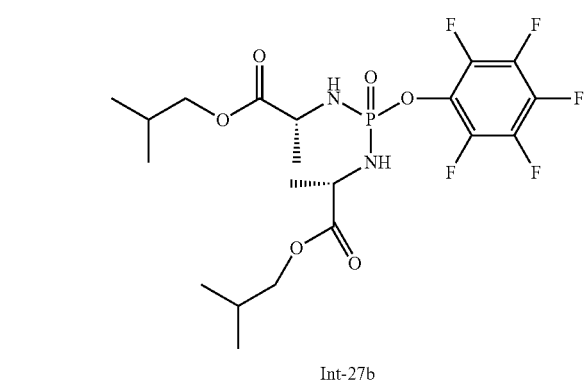

Int-27b

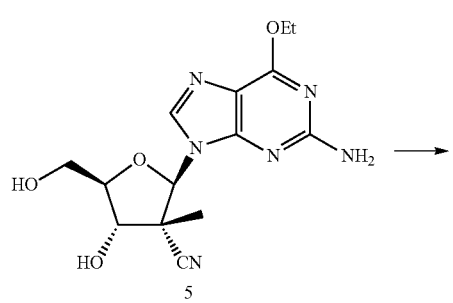

5

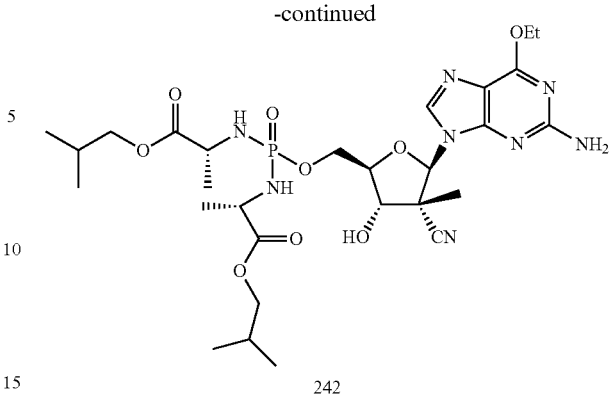

242

Step A: Synthesis of Int-27b

A solution of Int-27a (2.0 g, 11.01 mmol) in dichloromethane (20 mL) was treated with the dropwise addition of phosphorylchloride (840 mg, 5.48 mmol) with stirring at −78° C. To this was added the first batch of N,N-diisopropylethylamine (1.41 g, 2.00 equivalents) at −78° C. The resulted mixture was stirred at −78° C. for 30 minutes. To this was added the second batch of N,N-diisopropylethylamine (1.41 g, 2.00 equivalents) −78° C. The resulting mixture was stirred at room temperature for 2 hours. To the mixture was added a solution of pentafluorophenol (907 mg, 4.93 mmol) in dichloromethane (2 mL) dropwise with stirring at 0° C. and N,N-diisopropylethylamine (637 mg, 4.93 mmol) was then added dropwise with stirring at 0° C. The resulting solution was stirred overnight at 25° C., then concentrated in vacuo. The residue was dissolved in 50 mL of ether. The solids were filtered out and the filtration was concentrated under vacuum. The residue was applied onto a silica gel column and eliuted with ethyl acetate/petroleum ether (1:1) to provide 900 mg (32%) of Int-27b as a white solid.

LCMS04-Int-27b: 519[M+H]

$^1$H-NMR Int-27b: (300 MHz, CD$_3$OD, ppm): 4.05-4.16 (m, 2H), 3.86-3.98 (m, 4H), 3.69-3.77 (m, 2H), 1.87-2.00 (m, 2H), 1.42-1.60 (m, 6H), 0.79-1.00 (m, 12H) $^{31}$P-NMR Int-27b (300 MHz, CD$_3$OD, ppm): 10.012(s)

Step B: Synthesis of Compound 242

A solution of compound 5 (50 mg, 0.15 mmol, 1.00 equiv) in DMF (8 mL) was treated with tert-butylmagnesium chloride (0.09 mL, 1.7M) dropwise with stirring at 0° C. The resulted mixture was stirred at 0° C. for 30 minutes. To this was added a solution of Int-27b (78 mg, 0.15 mmol, 1.01 equiv) in DMF (2 mL) dropwise with stirring at 0° C. The resulting solution was stirred overnight at 0° C., then diluted with 30 mL of dichloromethane and washed with 10 mL of saturated ammonium chloride. The organic phase was concentrated in vacuo. The crude product (70 mg) was purified by Prep-HPLC with the following conditions (1#-Pre-HPLC-011(Waters)): Column, SunFire Prep C18, 19*150 mm 5 um; mobile phase, water and acetonitrile (20.0% acetonitrile up to 71.0% in 8 min, up to 100.0% in 2 min, down to 20.0% in 1 min); Detector, UV 254 & 220 nm. This resulted in 24.1 mg (24%) of compound 242 as a white solid.

LCMS-242: (ES, m/z): 669 [M+H]$^+$ $^1$H-NMR 242: (300 MHz, CD$_3$OD, ppm): 7.95 (s, 1H), 6.44 (s, 1H), 4.47-4.58 (m, 3H), 4.34-4.37 (m, 2H), 4.15-4.18 (m, 1H), 3.71-3.94 (m, 6H), 1.83-1.91 (m, 2H), 1.29-1.42 (m, 9H), 1.15 (s, 3H), 0.85-0.91 (m, 12H) $^{31}$P NMR-242: (300 MHz, CD3OD, ppm): 14.053(s)

The following compounds of the present invention were made using the methods described in the Example above and substituting the appropriate reactants and/or reagents.

| Compound No. | Structure | MS (M + H) |
|---|---|---|
| 41 | 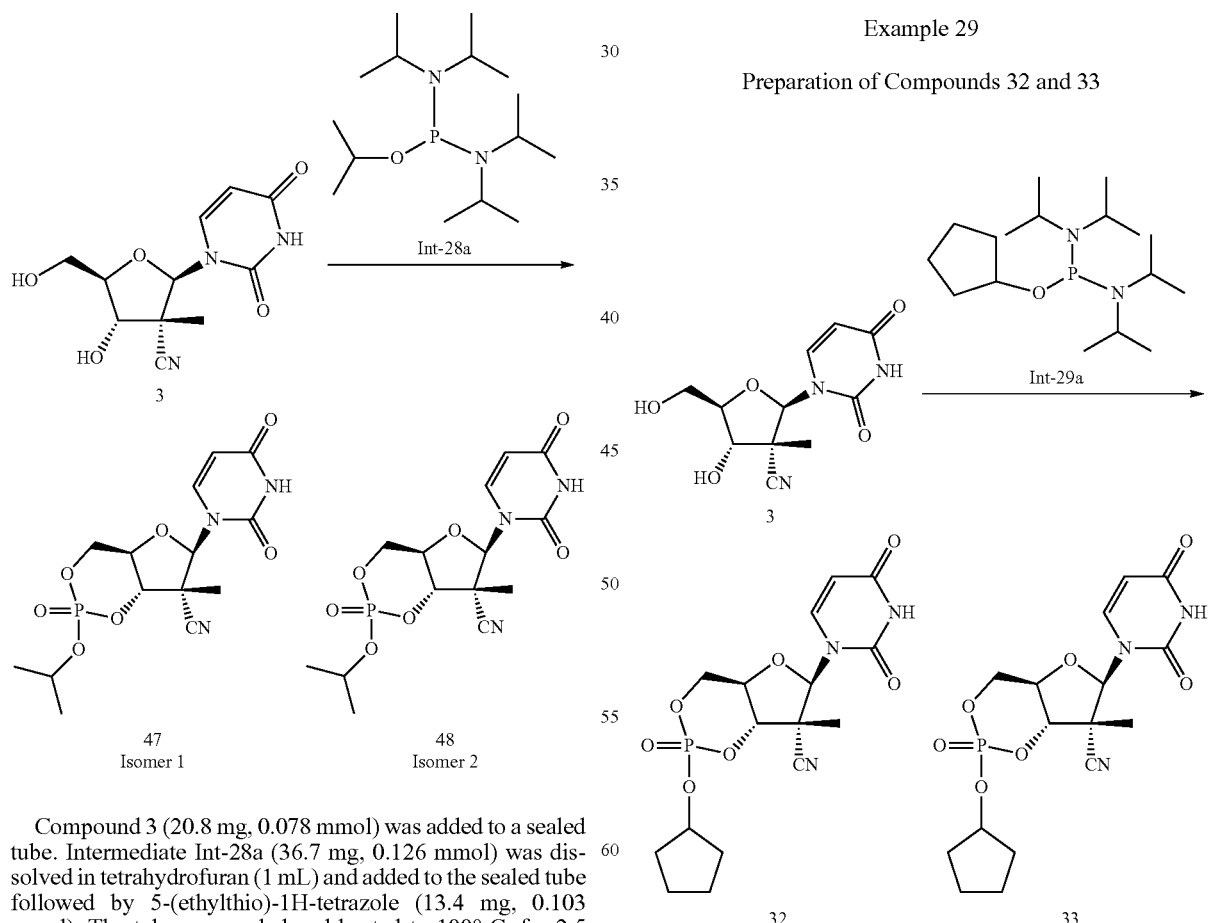 | 655 |

Example 28

Preparation of Compounds 47 and 48

Compound 3 (20.8 mg, 0.078 mmol) was added to a sealed tube. Intermediate Int-28a (36.7 mg, 0.126 mmol) was dissolved in tetrahydrofuran (1 mL) and added to the sealed tube followed by 5-(ethylthio)-1H-tetrazole (13.4 mg, 0.103 mmol). The tube was sealed and heated to 100° C. for 2.5 hours. The reaction was cooled to room temperature and t-butyl hydrogen peroxide (1 mL) was added to the reaction. The reaction continued to stir for 16 hours. The reaction was transferred to a round bottom flask and concentrated in vacuo.

The material was purified by reverse-phase HPLC using a solvent gradient of 10% H$_2$O (0.1% TFA)/CH$_3$CN to 90% CH$_3$CN/H$_2$O (0.1% TFA) over 20 minutes giving 47 (1.7 mg) and 48 (1.9 mg). $^1$H NMR: 47 (500 MHz, CD$_3$OD) δ 7.65 (d, J=8.0 Hz, 1H), 6.59 (s, 1H), 5.78 (d, J=8.0 Hz, 1H), 4.82-4.58 (m, 5H), 4.48-4.42 (m, 1H), 1.45-1.39 (m, 9H); LC-MS: 47: (ES, m/z): 371.1. $^1$H NMR: 48 (500 MHz, CD$_3$OD) δ 7.72 (d, J=8.0 Hz, 1H), 6.58 (s, 1H), 5.77 (d, J=8.0 Hz, 1H), 4.81-4.71 (m, 2H), 4.63-4.59 (m, 1H), 4.38 (d, J=9 Hz), 4.33-4.30 (m, 1H), 1.45-1.42 (m, 9H); LC-MS: 48: (ES, m/z): 371.1.

Example 29

Preparation of Compounds 32 and 33

Compound 3 (0.50 g, 1.89 mmol) was added to a sealed tube and dissolved in tetrahydrofuran (8.0 mL). Intermediate Int-29a (0.78 g, 2.48 mmol) was dissolved in tetrahydrofuran (8.0 mL) and added to the sealed tube. 5-(ethylthio)-1H-tetrazole (0.26 g, 1.99 mmol) was added to the tube which was sealed and heated to 100° C. for 3 hours. The reaction was cooled to room temperature and t-butyl hydroperoxide (15.0 mL, 120 mmol) was added to the reaction and stirred for 16 hours. The reaction was transferred to a round bottom flask and concentrated in vacuo. The material was purified via column chromatography with a gradient of 2-10% methanol/dichloromethane yielding a mixture of diastereomers, which were separated by SFC separation to afford compound 32 (64.2 mg) as a white solid and compound 33 (279 mg) as a white solid. Compound 32: $^1$H NMR (500 MHz, CD$_3$OD) δ 7.65 (d, J=8.0 Hz, 1H), 6.60 (s, 1H), 5.77 (d, J=8.5 Hz, 1H), 5.10-5.04 (m, 1H), 4.83-4.75 (m, 1H), 4.72-4.65 (m, 1H), 4.64-4.57 (m, 1H), 4.48-4.42 (m, 1H), 1.98-1.87 (m, 4H), 1.86-1.77 (m, 2H), 1.71-1.64 (m, 2H), 1.44 (s, 3H). LC-MS: 32: (ES, m/z): 371.1 [M−CN]$^+$. Compound 33: $^1$H NMR (500 MHz, CD$_3$OD) δ 7.72 (d, J=8.0 Hz, 1H), 6.58 (s, 1H), 5.77 (d, J=8.0 Hz, 1H), 5.05-5.01 (m, 1H), 4.83-4.76 (m, 1H), 4.62-4.57 (m, 2H), 4.34-4.32 (m, 1H), 2.02-1.93 (m, 4H), 1.87-1.82 (m, 2H), 1.73-1.66 (m, 2H), 1.44 (s, 3H). LC-MS: 33: (ES, m/z): 371.1 [M−CN]$^+$.

Example 30

Cell-Based HCV Replicon Assay

To measure cell-based anti-HCV activity of selected compounds of the present invention, replicon cells were seeded at 5000 cells/well in 96-well collagen I-coated Nunc plates in the presence of the test compound. Various concentrations of test compound, typically in 10 serial 2-fold dilutions, were added to the assay mixture, with the starting concentration ranging from 250 µM to 1 µM. The final concentration of dimethylsulfoxide was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA (SEQ ID. NO. 1); 5B.2R, TTGATGGGCAGCTTGGTTTC (SEQ ID. NO. 2); the probe sequence was FAM-labeled CACGCCATGCGCTGCGG (SEQ ID. NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 minutes, 95° C. for 10 minutes, 40 cycles of 95° C. for 15 sec, 60° C. for 1 minute. The ACT values (CT$_{5B}$−CT$_{GAPDH}$) were plotted against the concentration of test compound and fitted to the sigmoid dose-response model using XLfit4 (MDL). EC$_{50}$ was defined as the concentration of inhibitor necessary to achieve ΔCT=1 over the projected baseline; EC$_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from petroleum ether Applied Biosystems. Such an assay procedure was described in detail in e.g. Malcolm et al., *Antimicrobial Agents and Chemotherapy* 50: 1013-1020 (2006).

HCV replicon assay data was calculated for the compounds of the present invention using this method and replicon EC$_{50}$ data obtained is provided in the table below.

| Compound | 1b EC$_{50}$ (µM) |
|---|---|
| 1 | 14 |
| 2 | 12.6 |
| 3 | >66 |
| 4 | 100 |
| 5 | >100 |
| 6 | 1.4 |
| 7 | 1 |
| 8 | 11.7 |
| 9 | 0.7 |
| 10 | 15 |
| 11 | 17 |
| 12 | 1.7 |
| 13 | 1.5 |
| 14 | 11 |
| 15 | 5 |
| 16 | 51 |
| 17 | 13 |
| 18 | 1 |
| 19 | 15 |
| 20 | 16 |
| 21 | 25 |
| 22 | 18 |
| 23 | 6.7 |
| 24 | 7.9 |
| 25 | >100 |
| 26 | 62 |
| 27 | >100 |
| 28 | 2.7 |
| 29 | NS5b IC$_{50}$ = 0.5 µM |
| 30 | 571.2 |

Example 31

In Vitro Conversion of Prodrug to Nucleoside Triphosphate

The degree of conversion of a prodrug compound of the present invention to its corresponding nucleoside triphosphate is measured in vitro using the procedure described below.

A 2 mM stock solution of the prodrug test compound is prepared in 5% DMSO/95% MeOH to provide a final sample concentration of 10 µM. A 5 µL aliquot is removed from this stock solution and added to 1 mL of either a rat or human cryopreserved hepatocyte sample to provide a control sample at a concentration of 1 million cells/mL. This sample is assayed in triplicate and used as a test sample.

A 2 mM stock solution of Compound A is prepared in 5% DMSO/95% MeOH to provide a final sample concentration of 10 µM.

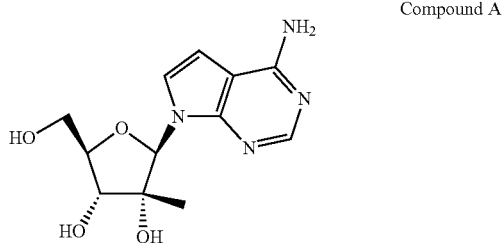 [SMILES: C[C@@]1(O)[C@H](O)[C@@H](CO)O[C@H]1n1ccc2c(N)ncnc21]

Compound A

A 5 µL aliquot is removed from this stock solution and added to 1 mL of either a rat or human cryopreserved hepatocyte sample to provide a control sample at a concentration of 1 million cells/mL. This sample is assayed in triplicate and used as a control standard.

Human and rat hepatocytes are removed from liquid nitrogen storage and thawed by submerging the hepatocyte tube into a pre-heated 37° C. waterbath and gently shaking the tube back & forth until thawed. The thawed hepatocytes are then gently poured into a container of Hepatocyte Basal Medium (50 mL, pre-warmed to 37° C.) and washed. The hepatocyte tube is then rinsed out with pre-warmed Hepatocyte Basal Medium and the washed hepatocytes and rinse are combined and centrifuged at 500 rpm for 4 minutes at room temperature. The supernatant is then discarded and the resulting hepatocyte pellet is resuspended with Hepatocyte Basal Medium (pre-warmed to 37° C.) and the final hepatocyte concentration is adjusted to 1 million cells/mL to provide the final hepatocyte suspension.

A 1 mL aliquot is removed from the 1 million cells/mL final hepatocyte suspension, analyzed in triplicate and placed into 20 mL scintillation vial without a cap. 2 mM of the prodrug test sample is then added into the hepatocyte suspension to provide a 10 µM final concentration in the 1 mL hepatocyte sample. The sample is then incubated at 37° C./5% $CO_2$ for 4 hours. A blank hepatocyte sample as well as the control standard are also incubated in this fashion.

The incubated hepatocyte suspension samples are transferred to a micro-centrifuge tube using a transfer pipette and centrifuged at 500 rpm for 4 minutes at room temperature. The supernatant is discarded and the resulting hepatocyte pellet was resuspended and the cells are extracted with 0.25 mL of a 4° C. solution of 70% methanol/30%(20 mM EDTA/20 mM EGTA) that has been adjusted to pH 8 using sodium hydroxide. The resulting extract solution is then stored in a refrigerator at 4° C. until ready for use, at which point the sample is first subjected to vortexing/sonication to ensure that all hepatocyte cells have burst. The sample is then centrifuged at 4000 rpm for 10 minutes at 4° C. and a 100 µL aliquot of the resulting supernatant is added into a bioanalytical plate (2 mL Square 96 well plate w/100 uL Tapered Reservoir), with the remaining supernatant immediately stored at −80° C. for re-assay if necessary. The blank control supernatant is transferred to a new tube for use as a control matrix in standard curves.

Alternatively, cryopreserved plateable hepatocytes are obtained from Celsis —In Vitro Technologies (Baltimore, Md.), and plated according to manufacturer's protocol at $0.7 \times 10^6$ cells/mL in InVitro GRO CP Medium ($1.75 \times 10^6$ cells/well in 6-well plates) three hours prior to inhibitor treatment. An inhibitor in DMSO at the indicated concentration in InVitro GRO CP Medium is added to the hepatocytes at t=0. At indicated times up to 48 hours post dosing, cells are washed in ice-cold PBS, extracted with ice-cold 1 mL 70% methanol: 30% 20 mM EDTA/EGTA and centrifuged. The supernatant is stored at −80° C. until analysis. For intracellular NTP analysis, an NTP calibration curve is first generated by spiking a blank extraction buffer with known concentrations of the NTP standard. LC/ESI-MS analysis is performed on a QTRAP 5500 LC/MS/MS system (Applied Biosystems, Foster City, Calif.) coupled to a Shimazu UFLC system, operated in the positive-ion mode. The HPLC system is consisted of solvent delivery module (LC20-AD XR), auto injector (SIL-20ACXR), and photodiode array detector (SPD-M20A PDA) (Shimadzu Corporation, Tokyo, Japan). All HPLC separations are performed at 40° C. The test samples are analyzed on a BioBasic AX column (5 µm particle size, 100×2.1 mm I.D., Thermo Scientific) using A (Acetonitrile: 10 mM $NH_4Ac$=30:70, v: v, pH=6) and B (Acetonitrile: 1 mM $NH_4Ac$=30:70, v: v, pH=10) as mobile phases at a flow rate of 1.0 mL/min. The injection volume is 50 µL. The mobile phase gradient starts at 0% B, and linearly increases to 100% B over 6 min. The MS analysis of all NTPs is performed on the same QTRAP 5500 MS instrument in the multiple ion monitoring mode (MRM), with Turbo-Ion-Spray ionization. The collision energy is 40 eV for all the analytes and standards. The quadrupole mass analyzer is set to unit resolution.

Results are reported in pmol of triphosphate per L of cells. To estimate µM intracellular concentration of nucleoside triphosphate, the following conversion is applied: $1 \times 10^6$ hepatocytes is 3 µL in volume.

Data was obtained using this method for selected compounds of the present invention, tested at 10 µM, and is presented in the table below. This data indicates that the compounds are efficiently converted to its corresponding NTP in vitro resulting in significant coverage over its intrinsic potency (Ki). Data is also presented for a comparative compound, labeled as Compound B.

| Compound | Human Hepatocyte (4 hour at 10 µM, NTP)/Ki |
|---|---|
| 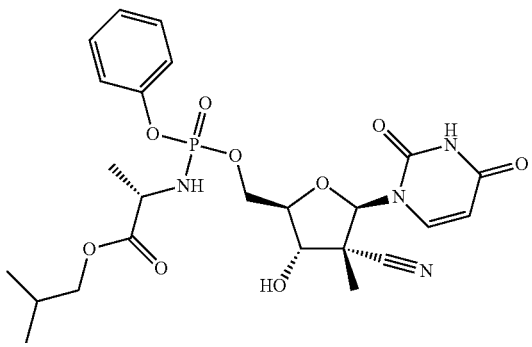 | 282x |

-continued
| Compound | Human Hepatocyte (4 hour at 10 μM, NTP)/Ki |
|---|---|
| 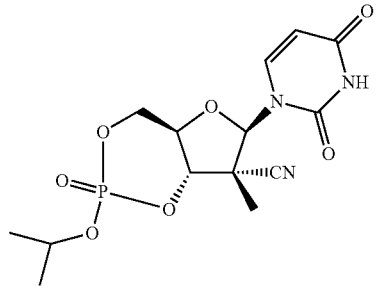  47 | 20x |
| 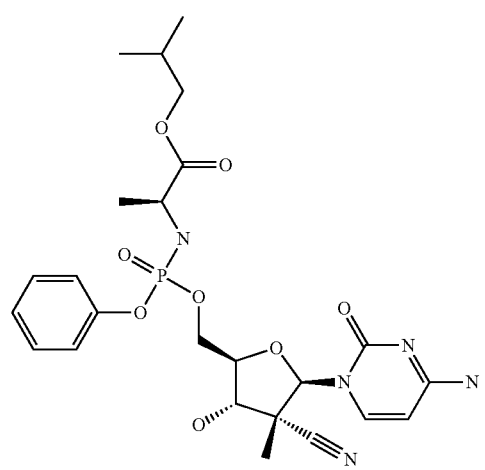  206 | 8277x |
| 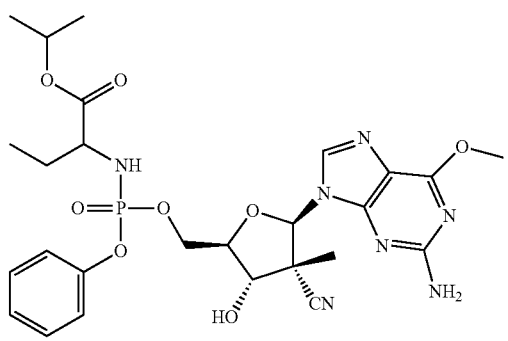  228 | 9x |

| Compound | Human Hepatocyte (4 hour at 10 μM, NTP)/Ki |
|---|---|
| 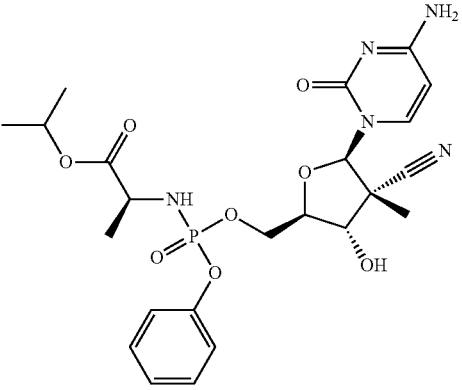 195 | 3333x |
| 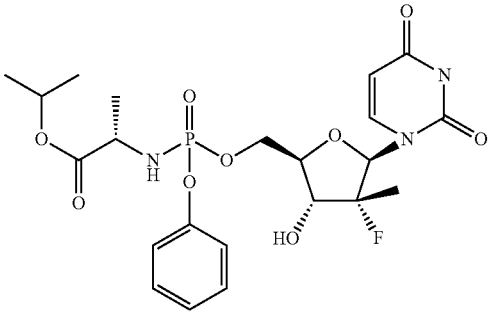 Compound B | ~80x |

Example 32

Determination of In Vivo Conversion of Prodrug to Nucleoside Triphosphate

The degree of conversion of a prodrug compound of the present invention to its corresponding nucleoside triphosphate is measured in vivo using the procedure described below.

Liver samples are collected from either Wistar Hannover Rats or Beagle Dogs dosed with the prodrug via the freeze clamp procedure (animals anesthetized via isofluorane, the liver is clamped with modified clamps that are frozen in liquid nitrogen, and then the clamped liver piece is placed in liquid nitrogen to ensure frozen completely; repeat liver clamp procedure to get a second piece of liver sample; samples stored at −80° C.). Liver samples are homogenized using a a Spex Sample Prep Freezer/Mill (Cryomill); settings for the cryomill operation are 1 Cycle, 2 minute pre-chill time, 2 minute run time, 1 minute cool time, and a rate of 15 cycles/second (cps). Control liver samples collected from rats dosed with vehicle are cryomilled in the same manner. During this process it is imperative that anything that will come into contact with the liver samples remain frozen on dry ice at all times, such as all Cryomill sample containers/lids and spatulas.

The cryomilled control liver sample is used to generate the standard curve. Weigh out an appropriate amount of cryomilled control liver sample into a conical tube, depending on how many standard curves are needed, place on wet ice and suspend with cold 70% Methanol/30% (20 mM EDTA/EGTA) that had been adjusted to pH 8 with sodium hydroxide at a ratio of 1:4 (liver:MeOH/EDTA-EGTA). The suspended liver homogenate is vortexed until a homogenous suspension is obtained. The standard curve ranges from 10 ng/mL to 50,000 ng/mL of NTP standard, as well as a QC sample at 10,000 ng/mL. A 500 μL aliquot of suspended control liver homogenate per each point on the standard curve and each QC is removed and placed into a 1.5 mL centrifuge tube, and 125 μL of each corresponding standard curve or QC standard solution is added to each individual control aliquot and re-vortexed. Liver sample aliquots are centrifuged at 4° C., 3645×g, for 10 minutes, and 450 μL of the supernatant is aliquoted into a 2 mL Square 96 well bioanalytical plate. Single and double blank samples are also generated from the suspended control liver homogenate using the procedure above, substituting the 125 μL of standard solution with 125 μL of water.

Approximately 1-2 grams of the cryomilled liver sample is weighed out into a 50 mL conical tube and placed on wet ice and suspended with cold 70% Methanol/30% (20 mM EDTA/EGTA) that had been adjusted to pH 8 with sodium hydroxide at a ratio of 1:4 (liver:MeOH/EDTA-EGTA); the remaining cryomilled liver sample is stored at −80° C. for possible re-assay if needed. The suspended liver homogenate is vortexed until a homogenous suspension is obtained. A 500 μL aliquot of each unknown liver sample is removed and placed into a 1.5 mL centrifuge tube, and 125 μL of water is added to each aliquot and re-vortexed. Standard curve/QC liver sample aliquots are centrifuged at 4° C., 3645×g, for 10 minutes, and 450 μL of the supernatant is aliquoted into a 2 mL square 96 well bioanalytical plate, and an appropriate internal standard is added to all sample wells, standard curve/QC wells, and the single blank well. The sample plate is stored at −80° C. until analysis and results are reported in M of NTP measured.

Data was obtained using this method for selected compounds of the present invention, tested at 10 µM, and is presented in the table below. This data indicates that the compounds are efficiently converted to their corresponding NTPs in vivo, resulting in significant coverage over their intrinsic potency (Ki). Data is also presented for comparative compounds, labeled as Compound B and Compound C.

| Compound | In Vivo Rat NTP (50 mpk, 4h)/Ki |
|---|---|
| 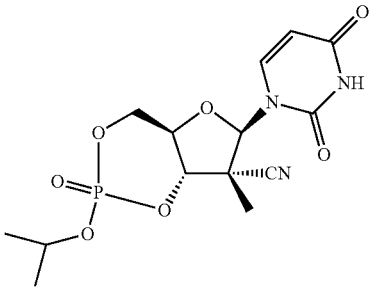 47 | 5x |
| 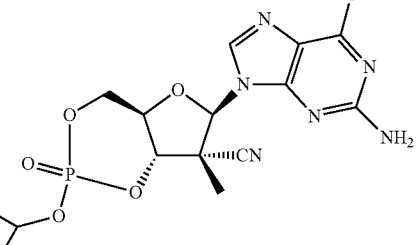 45 | 14x |
| 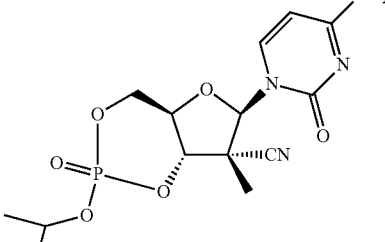 34 | 15x |
| 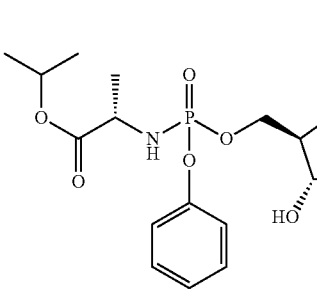 Compound B | 10x |
| 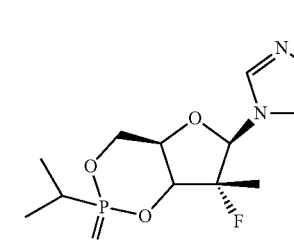 Compound C | 1400x |

Example 34

Inhibition of HCV NS5B Polymerase by Nucleoside Triphosphate Analogs

To measure inhibition of the enzymatic activity of the HCV NS5B RNA-dependent RNA polymerase by the nucleoside triphosphate compounds of the present invention, a radiolabeled nucleotide incorporation assay was used. This assay is a modified version of the assay described in International Publication No. WO2002/057287. Briefly, 50 µL reactions containing 20 mM HEPES (pH 7.3); 7.5 mM DTT; 20 units/ml RNasIN; 1 µM each of ATP, GTP, UTP and CTP; 20 µCi/mL [$^{33}$P]-CTP; 10 mM MgCl; 60 mM NaCl; 100 µg/ml BSA; 0.021 µM DCoH heteropolymer RNA template; and 5 nM NS5B (1b-BKΔ55) enzyme are incubated at room temperature for 1 hour. The assay is then terminated by the addition of 500 mM EDTA (50 µL). The reaction mixture is transferred to a Millipore DE81 filter plate and the incorporation of labeled CTP is determined using Packard TopCount. Compound $IC_{50}$ values can then be calculated from experiments with 10 serial 3-fold dilutions of the inhibitor in duplicate. The intrinsic potency (Ki) of an NTP inhibitor is derived from its NS5B $IC_{50}$ using the Cheng-Prusoff equation for a competitive inhibitor, as described in Cheng et al., *Biochem Pharmacol* 22:3099-3108 (1973): Ki=$IC_{50}/(1+[S]/K_m)$, where [S]=1 µM, and $K_m$ is the concentration of cognate NTP yielding half-maximal enzyme activity in the assay absent exogenous inhibitors.

Data was obtained using this method for the NTP analogs of selected compounds below of the present invention, and is set forth below. This data indicates that the nucleoside triphosphate (NTP) of the compounds are potent and effective inhibitors of HCV NS5B polymerase. Data is also presented for comparative compounds, labeled as Compound B and Compound C.

| Compound | NTP Ki (µM) |
|---|---|
| 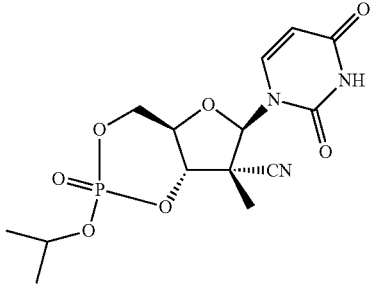<br>47 | 0.3 |
| 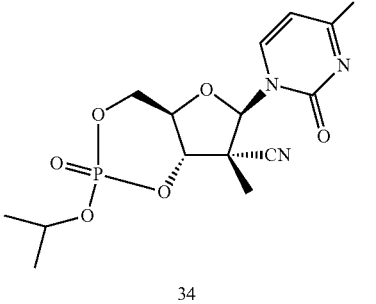<br>34 | 0.003 |
| 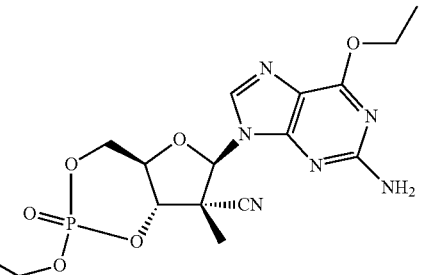<br>45 | 0.1 |

| Compound | NTP Ki (µM) |
|---|---|
| 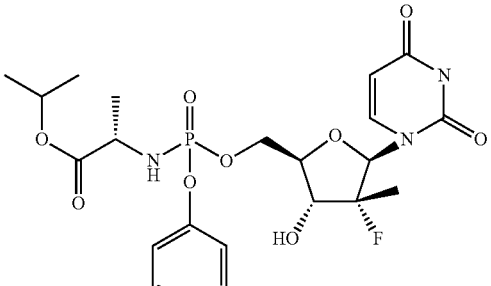<br>Compound B | 1.5 |
| 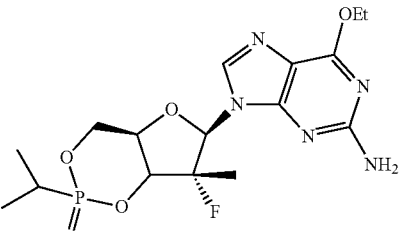<br>Compound C | 0.03 |

Example 35

Replicon Activity and Cytotoxicity Assays

To measure cell-based anti-HCV activity of the compounds of the present invention, replicon cells (1b-Con1) are seeded at 5000 cells/well in 96-well plates one day prior to treatment with a compound of the invention. Various concentrations of a test compound of the invention in DMSO are then added to the replicon cells, with the final concentration of DMSO at 0.5% and fetal bovine serum at 10% in the assay media. Cells are harvested three days post-dosing and the replicon RNA level is determined using real-time RT-PCR (Taqman assay) with GAPDH RNA as endogenous control. $EC_{50}$ values are calculated from experiments with 10 serial twofold dilutions of the inhibitor in triplicate. To measure cytotoxicity in replicon cells of an inhibitor, an MTS assay is performed according to the manufacturer's protocol for Cell-Titer 96 Aqueous One Solution Cell Proliferation Assay (Promega, Cat #G3580) three days post dosing on cells treated identically as in replicon activity assays. $CC_{50}$ is the concentration of inhibitor that yields 50% inhibition compared to vehicle-treated cells. Cytotoxicity in other types of cells can be measured using the same MTS protocol.

Data was obtained using this method for selected compounds of the present invention, and is set forth below. This data indicates that the compound possesses significant cytotoxicity windows over replicon activity.

| Compound | Replicon (1b) EC$_{50}$ (μM) | Cytotoxicity (μM) |
|---|---|---|
| 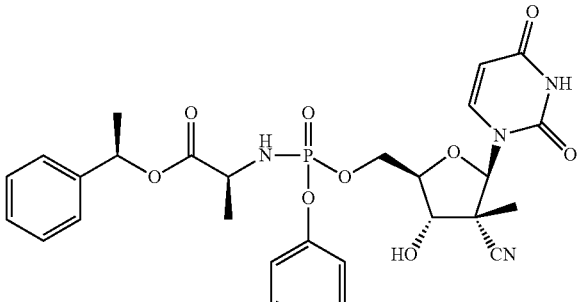 57 | 34 | >100 |
| 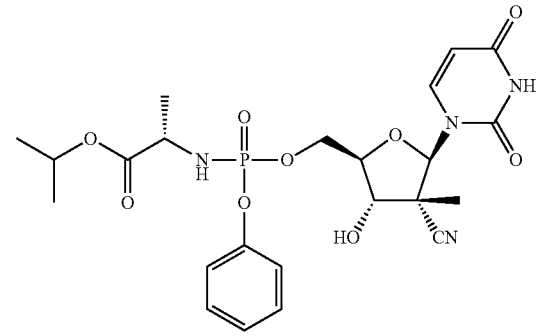 61 | 8.3 | >100 |
| 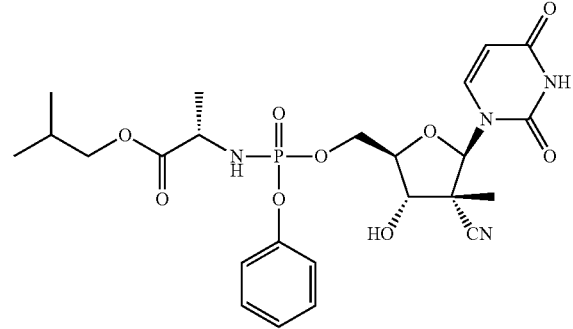 64 | 1.4 | >100 |
| 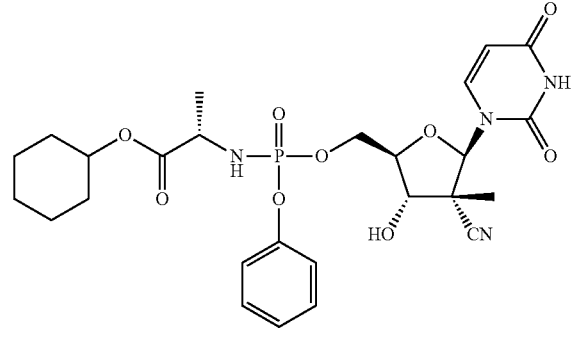 70 | 2.4 | NA |

-continued
| Compound | Replicon (1b) EC$_{50}$ (μM) | Cytotoxicity (μM) |
|---|---|---|
| 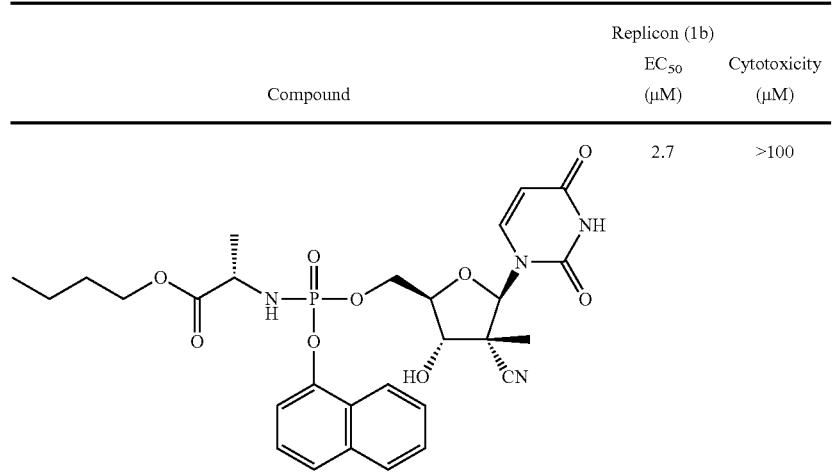 74 | 2.7 | >100 |
| 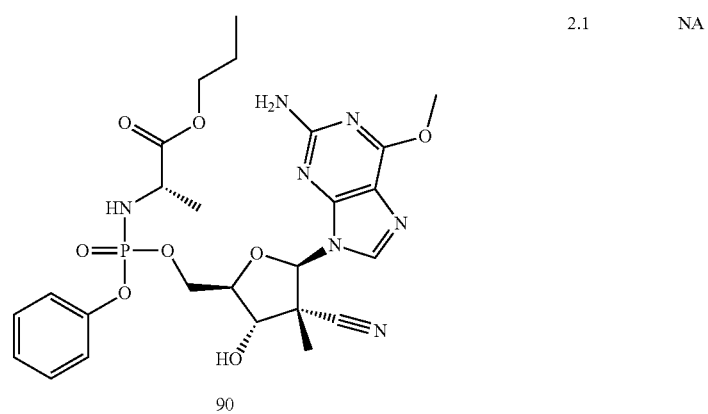 90 | 2.1 | NA |
| 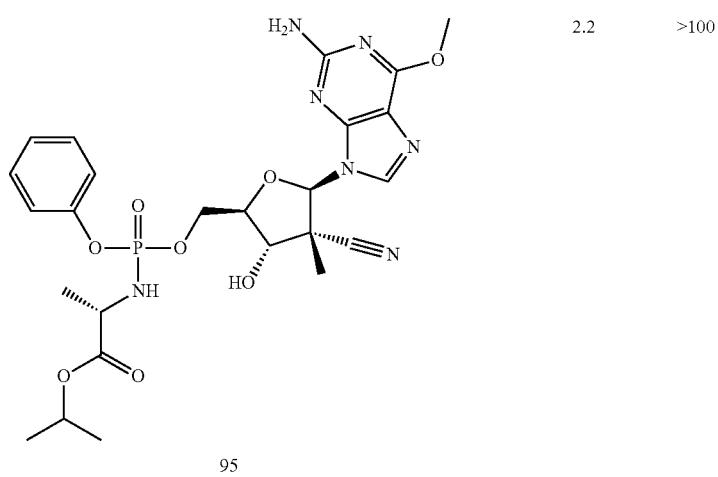 95 | 2.2 | >100 |

-continued
| Compound | Replicon (1b) EC$_{50}$ (μM) | Cytotoxicity (μM) |
|---|---|---|
| 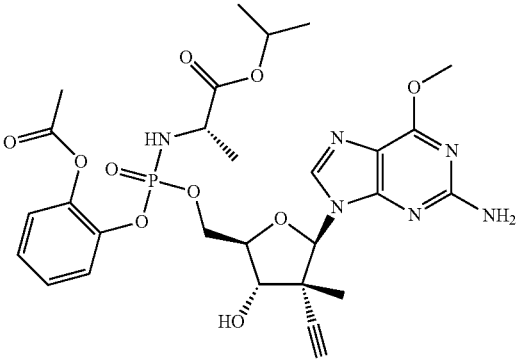<br>98 | 8.9 | 15 |
| 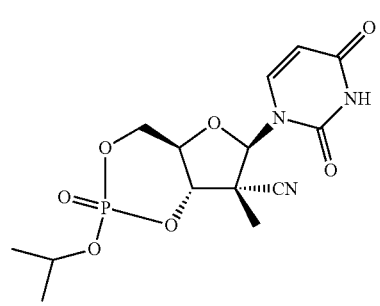<br>47 | 1.3 | >100 |
| 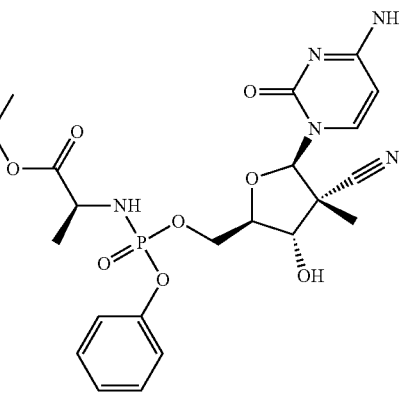<br>210 | 5.2 | >100 |
| 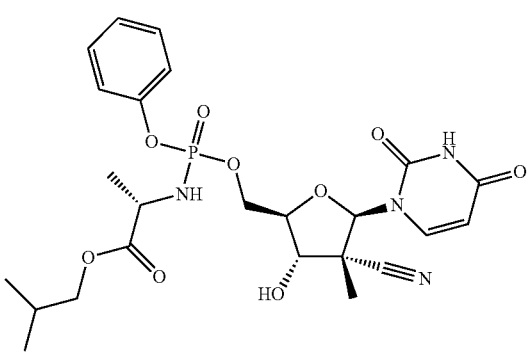<br>53 | 1.3 | >100 |

-continued
| Compound | Replicon (1b) EC$_{50}$ (µM) | Cytotoxicity (µM) |
|---|---|---|
| 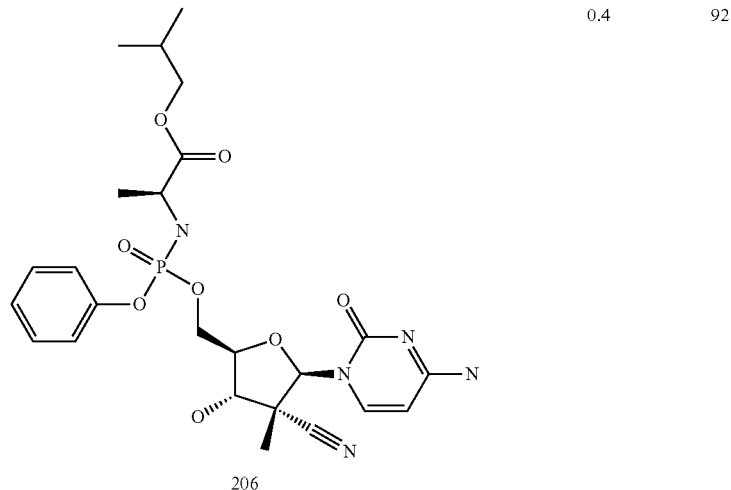 206 | 0.4 | 92 |
| 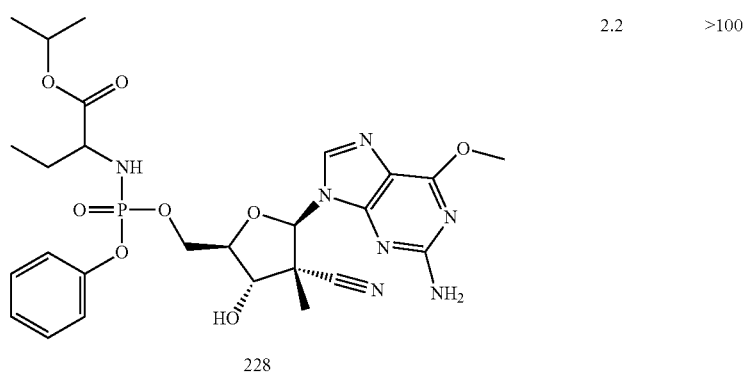 228 | 2.2 | >100 |
| 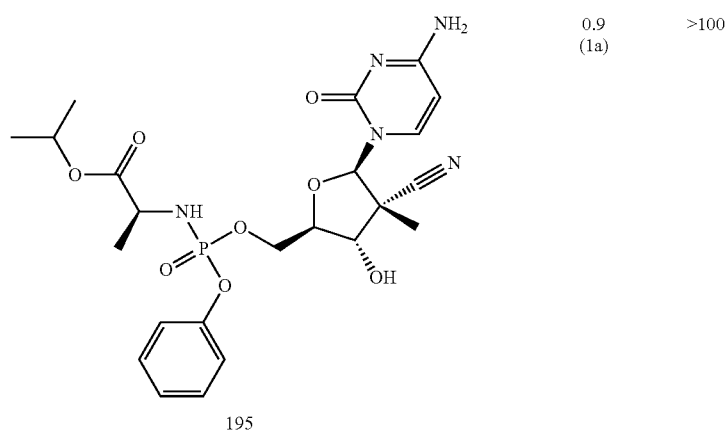 195 | 0.9 (1a) | >100 |

| Compound | Replicon (1b) EC$_{50}$ (µM) | Cytotoxicity (µM) |
|---|---|---|
| 45 | 1.2 | >100 |

NA = Not Available

Example 36

Mitochondrial Toxicity Assay

Mitochondrial toxicity in replicon cells of an inhibitor can be evaluated by its effect on the mitochondrial genome copy number relative to a nuclear gene control. Replicon cells are seeded at 60,000 cells/well in 6-well plates one day prior to inhibitor treatment. Various concentrations of an inhibitor in culture medium are added on the first day of treatment and dosing media are refreshed every three days thereafter. Cells are harvested at the indicated days post dosing; the total DNA is isolated using DNeasy Blood & Tissue Kit (Qiagen, Cat #69504) and quantitated by standard spectrophotometric methods. Two alternative sets of mitochondrial-specific DNA primer can be used: 1) 5'-CACCCAAGAACAGGGTTTGT-3' (SEQ. ID. NO. 3) (F3212, forward), 5'-TGGCCATGGG-TATGTTGTTAA-3' (SEQ. ID. NO. 4) (R3319, reverse), 6-FAM-5'-TTACCGGGCTCTGCCATCT-3'-TAMRA (SEQ. ID. NO. 5) (probe) (see Bai et al., *Ann NY Acad Sci* 1011:304-309 (2004)); or 2) 5'-TGCCCGCCATCATCCTA-3' (SEQ. ID. NO. 6) (COX II, forward), 5'-CGTCTGTTAT-GTAAAGGATGCGT-3' (SEQ. ID. NO. 7) (COX II, reverse), 6-FAM-5'-TCCTCATCGCCCTCCCATCCC-3'-TAMRA (SEQ. ID. NO. 8) (probe) (see Stuyver et al., *Antimicrob Agents Chemother* 46:3854-3860 (2002)). Primers are used at 500 nM and probes at 200 nM in the Taqman quantitative PCR assay. The nuclear gene control quantitation is run in parallel for 18S DNA using ABI PDAR part #4310875 (20×). The ACT value (CT difference between mt DNA and 18S DNA) from inhibitor-treated cells is compared to that of vehicle-treated cells. Mitochondrial toxicity in other types of cells can be measured using the same protocol.

Uses of the 2'-Cyano Substituted Nucleoside Derivatives

The 2'-Cyano Substituted Nucleoside Derivatives are useful in human and veterinary medicine for treating or preventing a viral infection in a patient. In one embodiment, the 2'-Cyano Substituted Nucleoside Derivatives can be inhibitors of viral replication. In another embodiment, the 2'-Cyano Substituted Nucleoside Derivatives can be inhibitors of HCV replication. Accordingly, the 2'-Cyano Substituted Nucleoside Derivatives are useful for treating viral infections, such as HCV. In accordance with the invention, the 2'-Cyano Substituted Nucleoside Derivatives can be administered to a patient in need of treatment or prevention of a viral infection.

Accordingly, in one embodiment, the invention provides methods for treating a viral infection in a patient comprising administering to the patient an effective amount of at least one 2'-Cyano Substituted Nucleoside Derivative or a pharmaceutically acceptable salt thereof.

Treatment or Prevention of a Flaviviridae Virus

The 2'-Cyano Substituted Nucleoside Derivatives can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The 2'-Cyano Substituted Nucleoside Derivatives are useful in the inhibition of HCV, the treatment of HCV infection and/or reduction of the likelihood or severity of symptoms of HCV infection and the inhibition of HCV viral replication and/or HCV viral production in a cell-based system. For example, the 2'-Cyano Substituted Nucleoside Derivatives are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one 2'-Cyano Substituted Nucleoside Derivative or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The 2'-Cyano Substituted Nucleoside Derivatives are also useful in the preparation and execution of screening assays for antiviral compounds. For example the 2'-Cyano Substituted Nucleoside Derivatives are useful for identifying resistant HCV replicon cell lines harboring mutations within NS5B, which are excellent screening tools for more powerful antiviral compounds. Furthermore, the 2'-Cyano Substituted Nucleoside Derivatives are useful in establishing or determining the binding site of other antivirals to the HCV NS5B polymerase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not 2'-Cyano Substituted Nucleoside Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one 2'-Cyano Substituted Nucleoside Derivative (which may include two or more different 2'-Substituted Nucleoside Derivatives), or a pharmaceutically acceptable salt thereof, and (ii) at least one additional therapeutic agent that is other than a 2'-Cyano Substituted Nucleoside Derivative, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 2'-Cyano Substituted Nucleoside Derivative and an additional therapeutic agent may be present in fixed amounts (dosage amounts) in a single dosage unit (e.g., a capsule, a tablet and the like).

In one embodiment, the at least one 2'-Cyano Substituted Nucleoside Derivative is administered during a time when the additional therapeutic agent(s) exert their prophylactic or therapeutic effect, or vice versa.

In another embodiment, the at least one 2'-Cyano Substituted Nucleoside Derivative and the additional therapeutic agent(s) are administered in doses commonly employed when such agents are used as monotherapy for treating a viral infection.

In another embodiment, the at least one 2'-Cyano Substituted Nucleoside Derivative and the additional therapeutic agent(s) are administered in doses lower than the doses commonly employed when such agents are used as monotherapy for treating a viral infection.

In still another embodiment, the at least one 2'-Cyano Substituted Nucleoside Derivative and the additional therapeutic agent(s) act synergistically and are administered in doses lower than the doses commonly employed when such agents are used as monotherapy for treating a viral infection.

In one embodiment, the at least one 2'-Cyano Substituted Nucleoside Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one 2'-Cyano Substituted Nucleoside Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one 2'-Cyano Substituted Nucleoside Derivative and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759/VX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development,* 7(4):446 (2004); Tan et al., *Nature Reviews,* 1:867 (2002); and Beaulieu et al., *Current Opinion in Investigational Drugs,* 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125; and the following compounds:

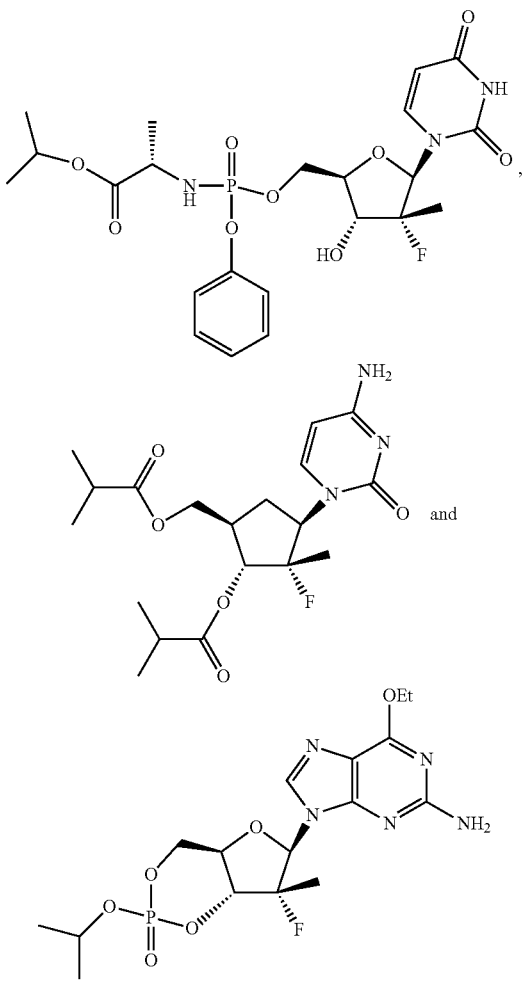

and pharmaceutically acceptable salts thereof.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J. in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, the following compounds:

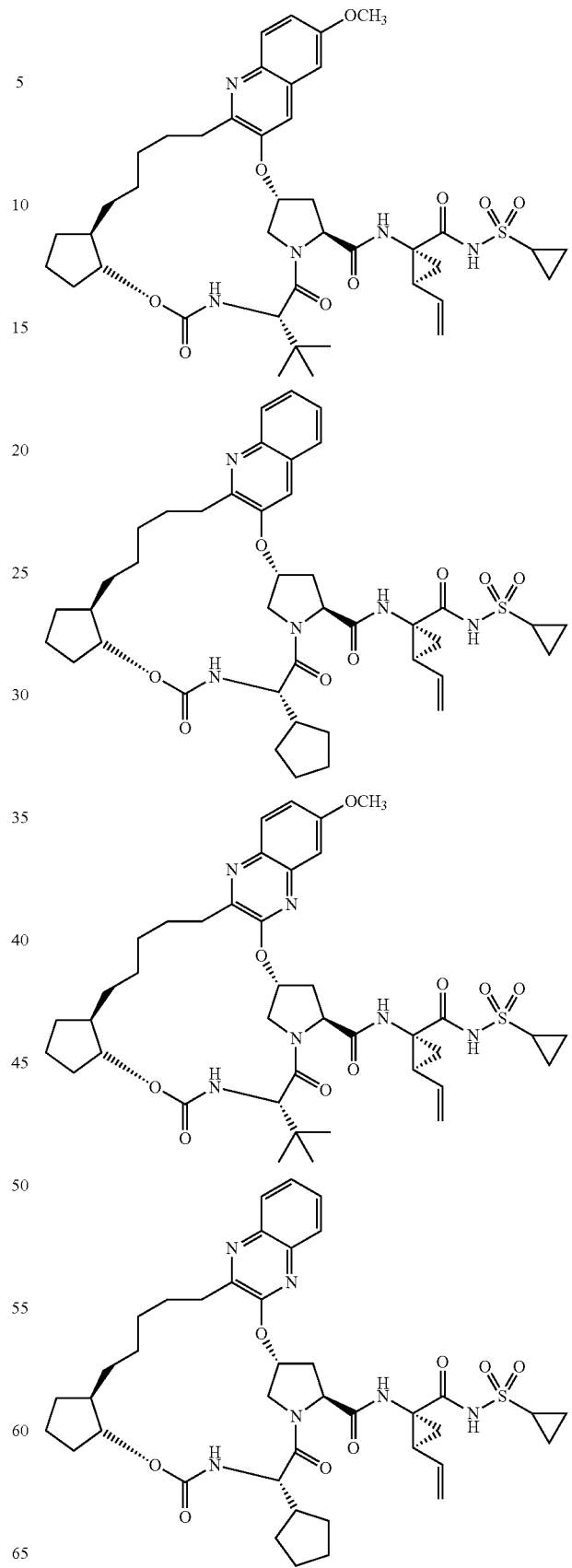

223
-continued
224
-continued
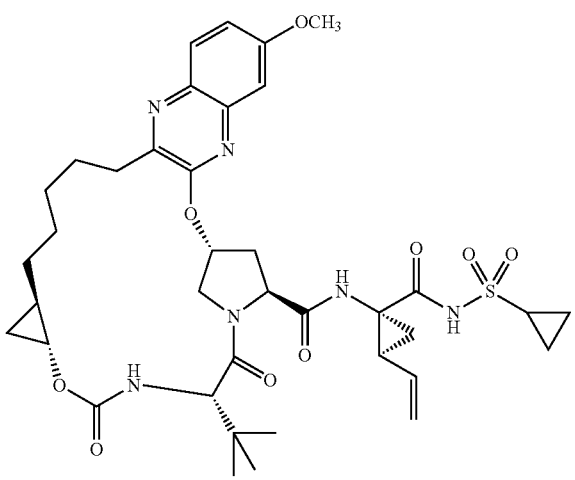
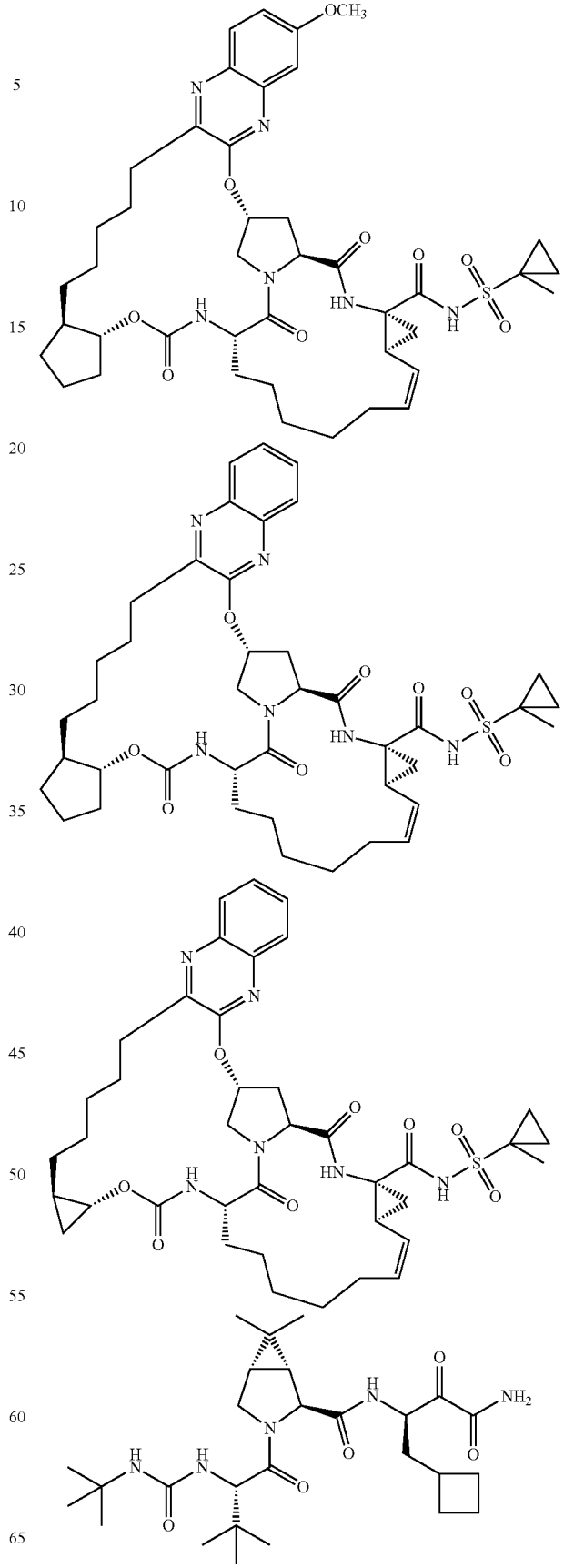

225
-continued
226
-continued
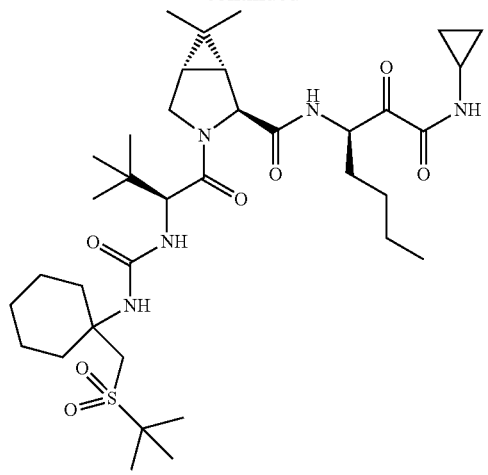
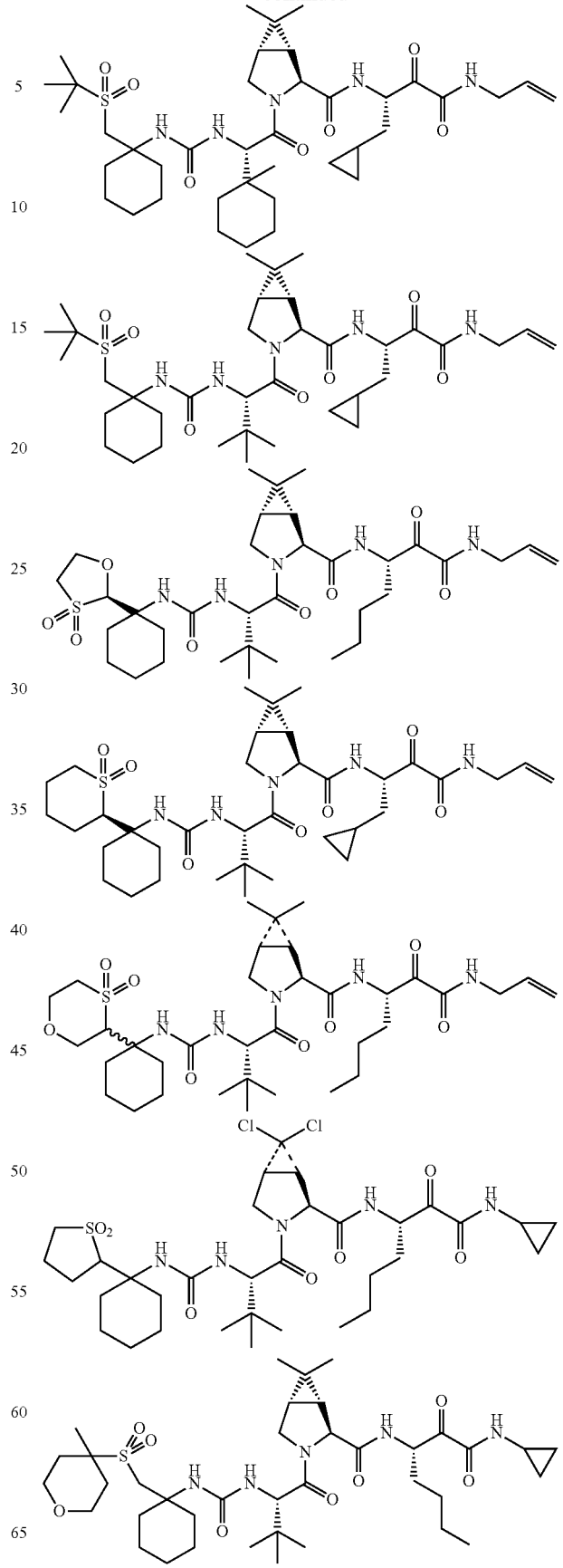

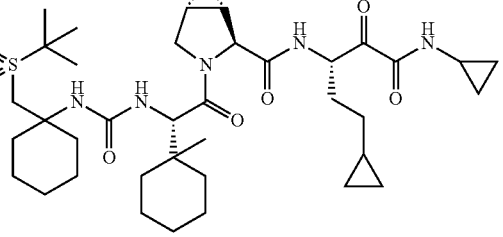

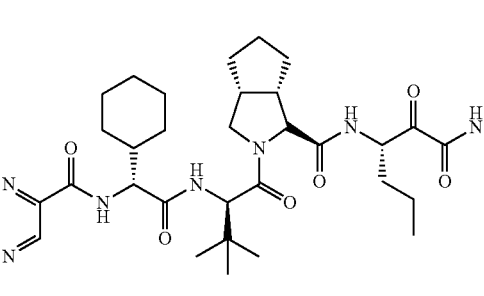

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

Viral entry inhibitors useful as second additional therapeutic agents in the present compositions and methods include, but are not limited to, PRO-206 (Progenics), REP-9C (REPICor), SP-30 (Samaritan Pharmaceuticals) and ITX-5061 (iTherx).

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful as second additional therapeutic agents in the present compositions and methods include, but are not limited to, AZD2836 (Astra Zeneca), ACH-1095 (Achillion) and ACH-806 (Achillion).

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), PPI-461 (Presidio), PPI-1301 (Presidio), BMS-824383 (Bristol-Myers Squibb) and BMS-790052 (Bristol-Myers Squibb). Additional HCV NS4A inhibitors useful as second additional therapeutic agents in the present compositions and methods include, but are not limited to those disclosed in International Publication No. WO 2010/111483 and the following compounds:

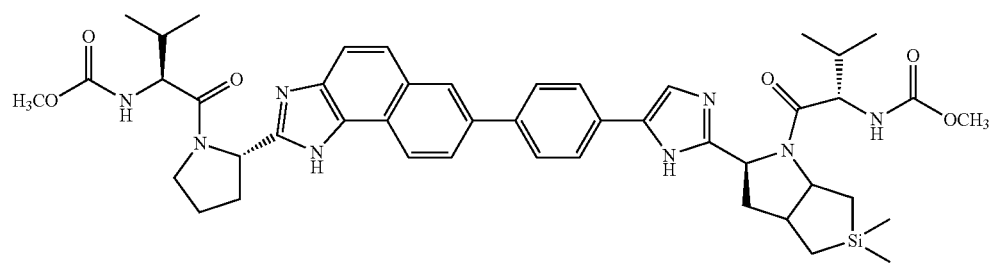
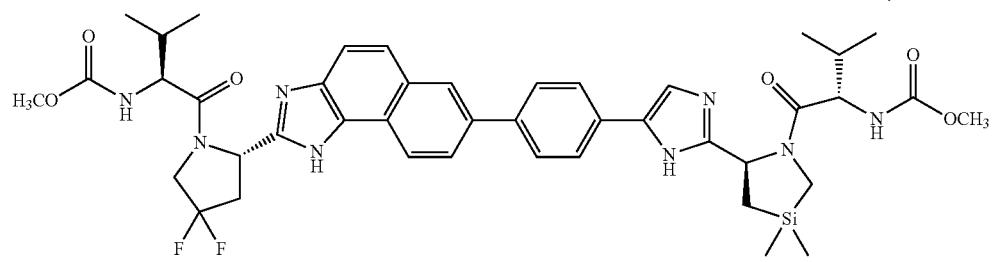
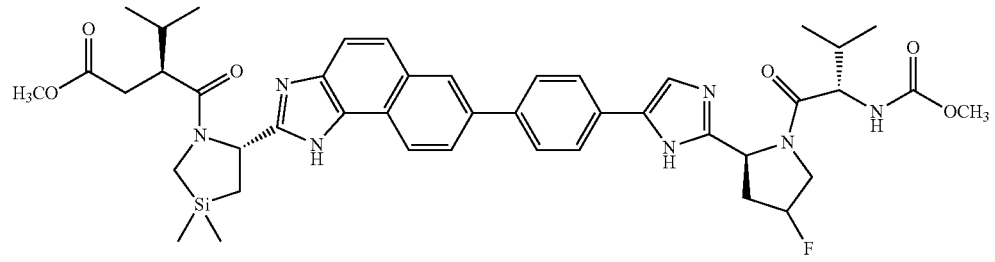
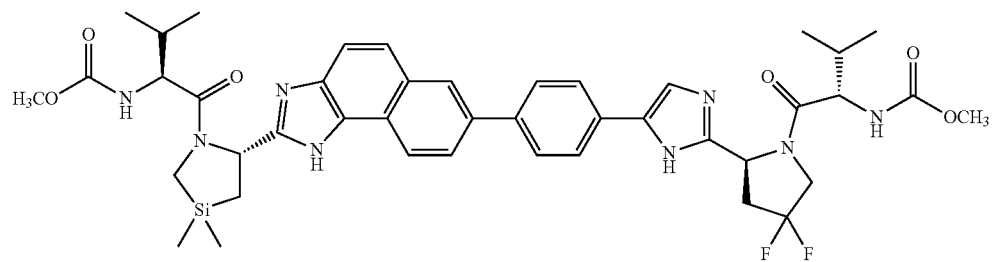
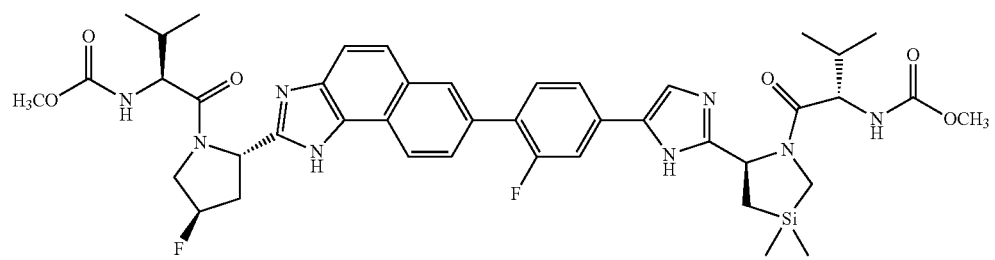
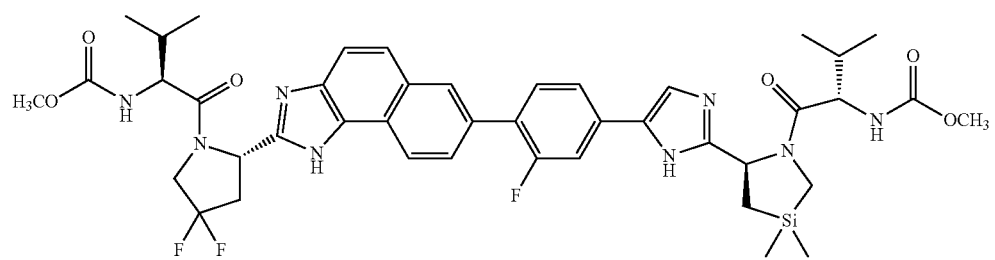

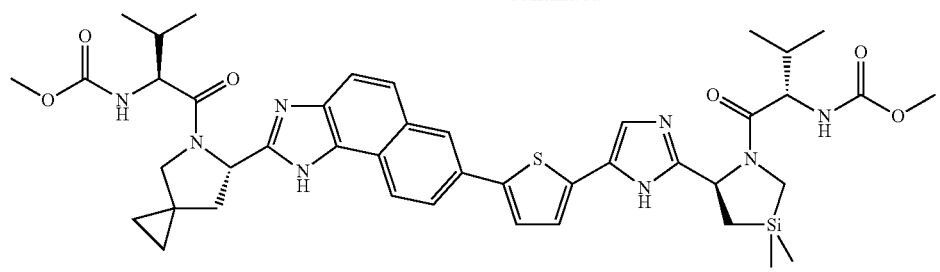
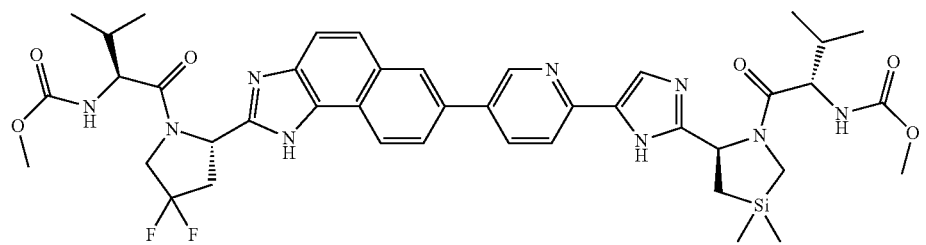
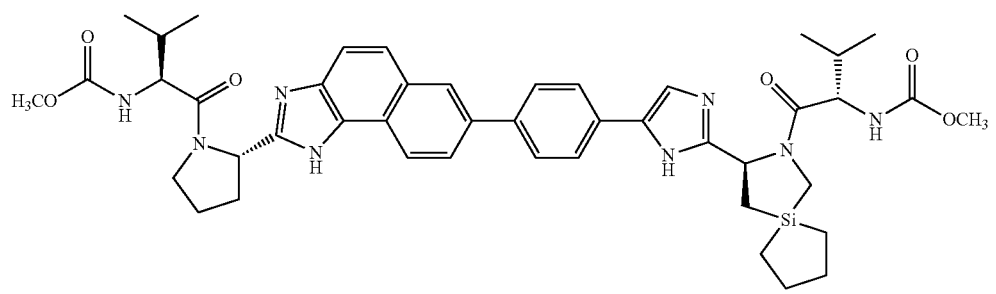
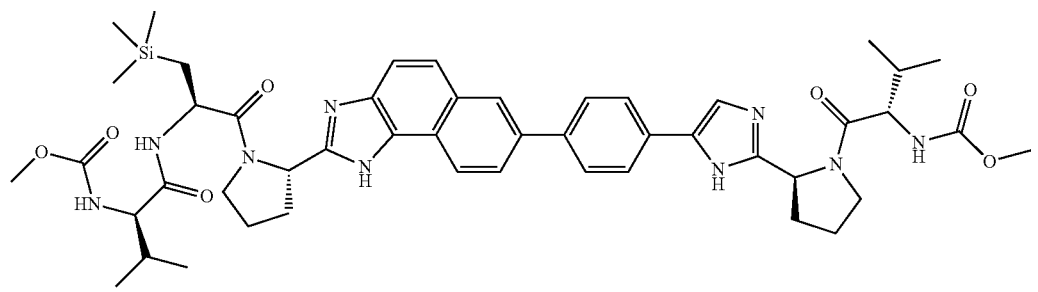
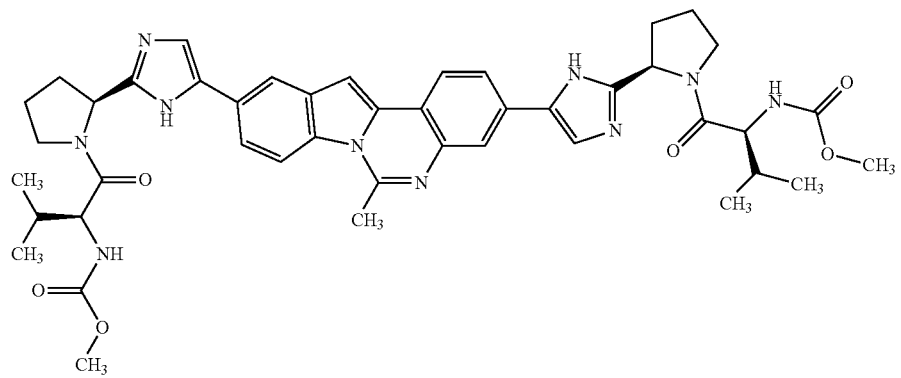

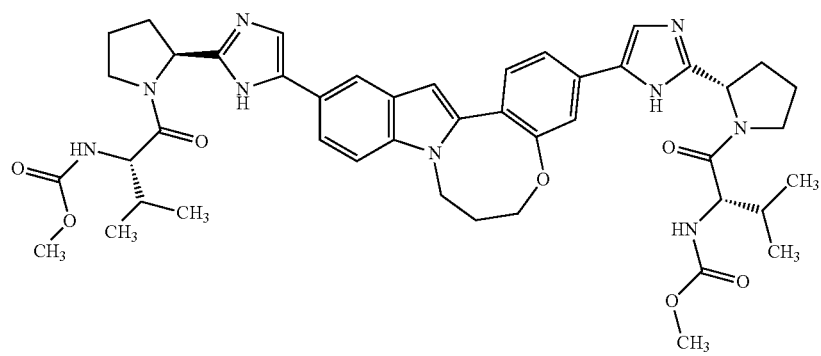
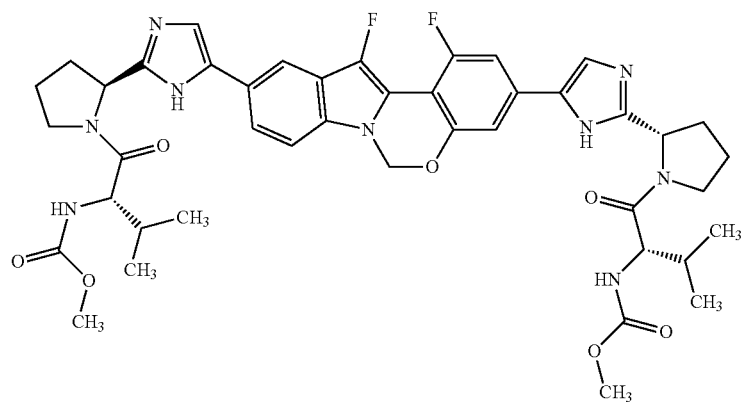
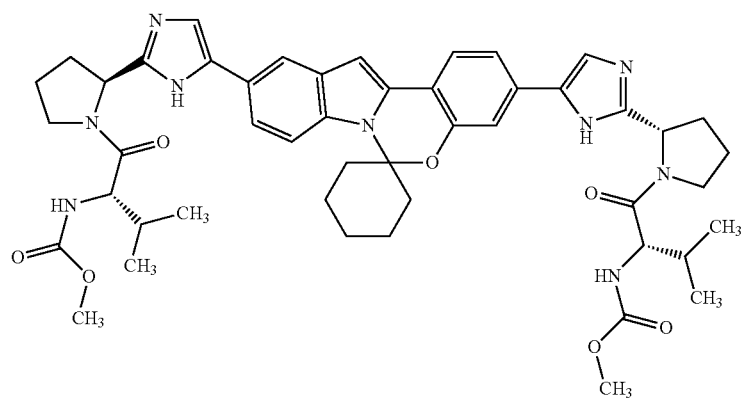
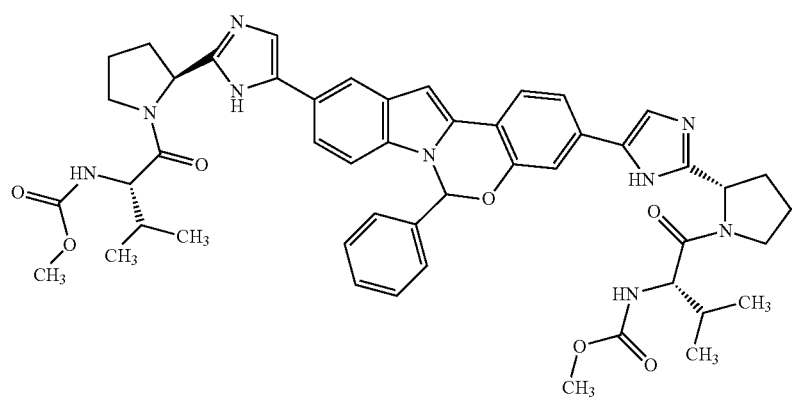

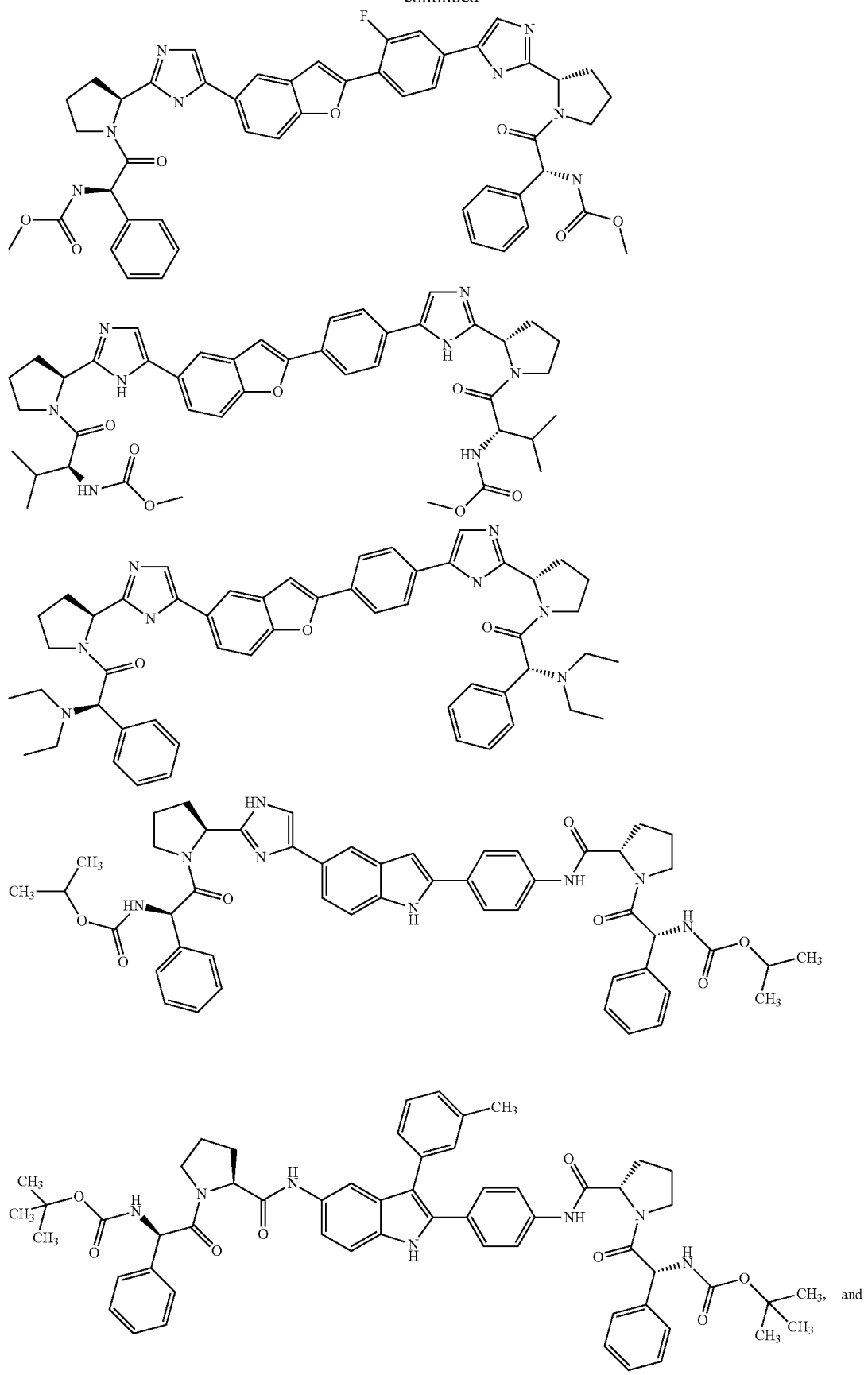

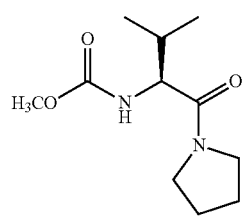 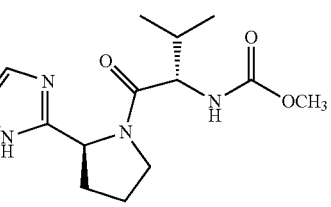

-continued and pharmaceutically acceptable salts thereof.

HCV replicase inhibitors useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis), MBL-HCV1 (MassBiologics), GI-5005 (GlobeImmune), CT-011 (CureTech/Teva) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO 206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the 2'-Cyano Substituted Nucleoside Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one 2'-Cyano Substituted Nucleoside Derivative(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3 MIU(12 mcg)/0.5 mL/TIW for 24 weeks or 48 weeks for first time treatment.

In another embodiment, when the additional therapeutic agent is petroleum etherG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3 MIU (11.1 mcg/mL)/TIW for at least 48 to 52 weeks, or alternatively 6 MIU/TIW for 12 weeks followed by 3 MIU/TIW for 36 weeks.

In still another embodiment, when the additional therapeutic agent is petroleum etherGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, an HCV NS5A inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

Compositions and Administration

Due to their activity, the 2'-Cyano Substituted Nucleoside Derivatives are useful in veterinary and human medicine. As described above, the 2'-Cyano Substituted Nucleoside Derivatives are useful for treating or preventing HCV infection in a patient in need thereof.

When administered to a patient, the 2'-Cyano Substituted Nucleoside Derivatives can be administered as a component of a composition that comprises a pharmaceutically acceptable carrier or vehicle. The present invention provides pharmaceutical compositions comprising an effective amount of at least one 2'-Cyano Substituted Nucleoside Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 2'-Cyano Substituted Nucleoside Derivatives are administered orally.

In another embodiment, the one or more 2'-Cyano Substituted Nucleoside Derivatives are administered intravenously.

In one embodiment, a pharmaceutical preparation comprising at least one 2'-Cyano Substituted Nucleoside Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the 2'-Cyano Substituted Nucleoside Derivative(s) by weight or volume. In various embodiments, the present compositions can contain, in one embodiment, from about 1% to about 70% or from about 5% to about 60% of the 2'-Cyano Substituted Nucleoside Derivative(s) by weight or volume.

The quantity of 2'-Cyano Substituted Nucleoside Derivative in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 2'-Cyano Substituted Nucleoside Derivatives will be regulated according to the judgment of the attending clinician considering such factors as age, condition and size of the patient as well as severity of the symptoms being treated. Generally, a total daily dosage of the 2'-Cyano Substituted Nucleoside Derivatives range from about 0.1 to about 2000 mg per day, although variations will necessarily occur depending on the target of therapy, the patient and the route of administration.

In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 2'-Cyano Substituted Nucleoside Derivative or a pharmaceutically acceptable salt thereof; (ii) one or more additional therapeutic agents that are not a 2'-Cyano Substituted Nucleoside Derivative; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and wto additional therapeutic agents, each of which are independently selected from the group consisting of HCV antiviral agents, immunomodulators, and anti-infective agents.

Kits

In one aspect, the present invention provides a kit comprising a therapeutically effective amount of at least one 2'-Cyano Substituted Nucleoside Derivative, or a pharmaceutically acceptable salt, solvate, ester or prodrug of said compound and a pharmaceutically acceptable carrier, vehicle or diluent.

In another aspect the present invention provides a kit comprising an amount of at least one 2'-Cyano Substituted Nucleoside Derivative, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more 2'-Cyano Substituted Nucleoside Derivatives and the one or more additional therapeutic agents are provided in the same container. In one embodiment, the one or more 2'-Cyano Substituted Nucleoside Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the structure:

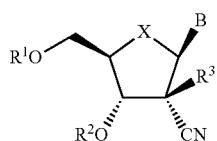

(I)

or a pharmaceutically acceptable salt thereof,
wherein:

X is O, S or $CH_2$;

B is selected from one of the following groups:

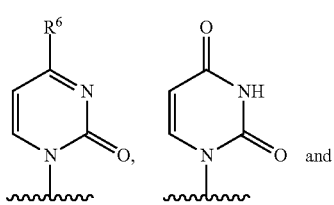 and

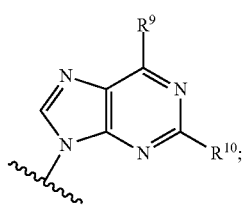

Y is N or $-C(R^{19})-$;

$R^1$ is H,

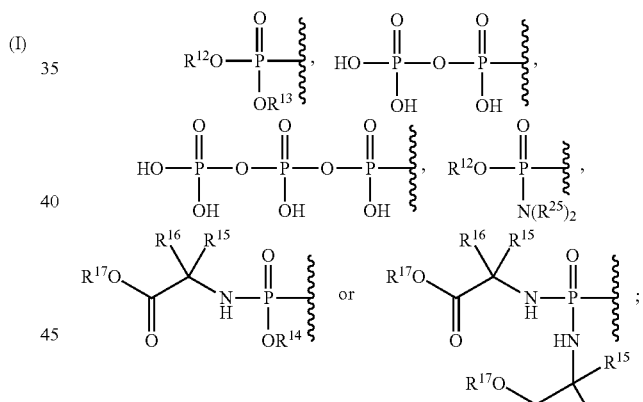

$R^2$ is H or

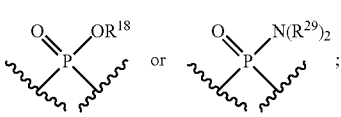

or $R^1$ and $R^2$ join to form a group having the formula:

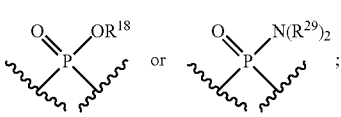

$R^3$ is $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl or $C_3$-$C_7$ cycloalkyl;

R$^4$, R$^5$, R$^7$ and R$^8$ are each independently H, C$_1$-C$_6$ alkyl, C$_1$-C$_6$ haloalkyl, C$_1$-C$_6$ hydroxyalkyl, halo, —OR$^{20}$, —SR$^{20}$ or —N(R$^{20}$)$_2$;

R$^6$, R$^9$ and R$^{10}$ are each independently selected from H, C$_1$-C$_6$ alkyl, C$_2$-C$_6$ alkenyl, C$_2$-C$_6$ alkynyl, C$_3$-C$_7$ cycloalkyl, 5- or 6-membered monocyclic heteroaryl, 9- or 10-membered bicyclic heteroaryl, halo, —OR$^{20}$, —SR$^{20}$, —S(O)R$^{20}$, —S(O)$_2$R$^{20}$, —S(O)$_2$N(R$^{20}$)$_2$, —NHC(O)OR$^{20}$, —NHC(O)N(R$^{20}$)$_2$, C$_1$-C$_6$ haloalkyl, C$_1$-C$_6$ hydroxyalkyl, —O—(C$_1$-C$_6$ haloalkyl), —CN, —NO$_2$, —N(R$^{20}$)$_2$, —NH(C$_1$-C$_6$ alkylene)-(5- or 6-membered monocyclic heteroaryl), —NH(C$_1$-C$_6$ alkylene)-(9- or 10-membered bicyclic heteroaryl), —C(O)R$^{20}$, —C(O)OR$^{20}$, —C(O)N(R$^{20}$)$_2$ and —NHC(O)R$^{20}$, wherein said C$_2$-C$_6$ alkenyl group and said C$_2$-C$_6$ alkynyl group can be optionally substituted a halo group;

R$^{12}$ is H or —(C$_1$-C$_6$ alkylene)-T-R$^{21}$;

R$^{13}$ is H or —(C$_1$-C$_6$ alkylene)-T-R$^{21}$, or R$^{12}$ and R$^{13}$ can join to form a C$_2$-C$_4$ alkylene group between the oxygen atoms that R$^{12}$ and R$^{13}$ are attached to, wherein said C$_2$-C$_4$ alkylene group is substituted with at least one C$_6$-C$_{10}$ aryl group;

R$^{14}$ is H, C$_6$-C$_{10}$ aryl, 5- or 6-membered monocyclic heteroaryl or 9- or 10-membered bicyclic heteroaryl, wherein said C$_6$-C$_{10}$ aryl group, said 5- or 6-membered monocyclic heteroaryl group and said 9- or 10-membered bicyclic heteroaryl group can be optionally substituted with R$^{22}$;

R$^{15}$ is H, C$_1$-C$_6$ alkyl, C$_3$-C$_7$ cycloalkyl, phenyl or benzyl, wherein said C$_1$-C$_6$ alkyl can be optionally substituted with a group selected from halo, —OR$^{20}$, —SR$^{20}$, guanidino, —N(R$^{20}$)$_2$, —C(O)OR$^{20}$, —C(O)N(R$^{20}$)$_2$, —NHC(O)R$^{20}$, 5- or 6-membered monocyclic heteroaryl and 9- or 10-membered bicyclic heteroaryl, and wherein said phenyl group and said benzyl group can be optionally substituted with up to 2 groups, each independently selected from C$_1$-C$_6$ alkyl, halo and —OR$^{20}$;

R$^{16}$ is H, C$_1$-C$_6$ alkyl, C$_3$-C$_7$ cycloalkyl, phenyl or benzyl, wherein said C$_1$-C$_6$ alkyl can be optionally substituted with a group selected from halo, —OR$^{20}$, —SR$^{20}$, guanidino, —N(R$^{20}$)$_2$, —C(O)OR$^{20}$, —C(O)N(R$^{20}$)$_2$, —NHC(O)R$^{20}$, 5- or 6-membered monocyclic heteroaryl and 9- or 10-membered bicyclic heteroaryl, and wherein said phenyl group and said benzyl group can be optionally substituted with up to 2 groups, each independently selected from C$_1$-C$_6$ alkyl, halo and —OR$^{20}$;

R$^{17}$ is H, C$_1$-C$_{20}$ alkyl, C$_2$-C$_{20}$ alkenyl, —(C$_1$-C$_3$ alkylene)$_m$-C$_3$-C$_7$ cycloalkyl), —(C$_1$-C$_3$ alkylene)$_m$-(C$_6$-C$_{10}$ aryl) or adamantyl, wherein said C$_1$-C$_{20}$ alkyl group, said C$_2$-C$_{20}$ alkenyl group, said C$_6$-C$_{10}$ aryl group and said adamantyl group can be optionally substituted with up to three groups, each independently selected from halo, —OR$^{20}$, —C(O)OR$^{20}$, CN, NO$_2$, C$_1$-C$_6$ haloalkyl, C$_1$-C$_6$ hydroxyalkyl, C$_3$-C$_7$ cycloalkyl, C$_6$-C$_{10}$ aryl, 5- or 6-membered monocyclic heteroaryl, 9- or 10-membered bicyclic heteroaryl, —N(R$^{20}$)$_2$, —C(O)N(R$^{20}$)$_2$—SR$^{20}$, —S(O)R$^{20}$, —S(O)$_{2R}$$^{20}$, —S(O)$_2$N(R$^{20}$)$_2$, —NHC(O)R$^{20}$, —NHC(O)OR$^{20}$ and —NHC(O)N(R$^{20}$)$_2$ and;

R$^{18}$ is H, C$_1$-C$_6$ alkyl, C$_3$-C$_7$ cycloalkyl, —(C$_1$-C$_3$ alkylene)$_m$-C$_6$-C$_{10}$ aryl, 5- or 6-membered monocyclic heteroaryl, 9- or 10-membered bicyclic heteroaryl or:

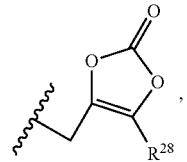

wherein said C$_6$-C$_{10}$ aryl group, said 5- or 6-membered monocyclic heteroaryl group and said 9- or 10-membered bicyclic heteroaryl group can be optionally substituted with up to five groups, each independently selected from C$_1$-C$_6$ alkyl, C$_2$-C$_6$ alkenyl, C$_2$-C$_6$ alkynyl, halo, —OR$^{20}$, —SR$^{20}$, C$_1$-C$_6$ haloalkyl, C$_1$-C$_6$ hydroxyalkyl, —O—(C$_1$-C$_6$ haloalkyl), —CN, —NO$_2$, —N(R$^{20}$)$_2$, —C(O)OR$^{20}$, —C(O)N(R$^{20}$)$_2$ and —NHC(O)R$^{20}$;

R$^{19}$ is H, C$_1$-C$_6$ alkyl, C$_1$-C$_6$ haloalkyl, C$_1$-C$_6$ hydroxyalkyl, halo, —OR$^{20}$, —SR$^{20}$, N(R$^{20}$)$_2$, C$_3$-C$_7$ cycloalkyl, C$_6$-C$_{10}$ aryl, 5- or 6-membered monocyclic heteroaryl or 9- or 10-membered bicyclic heteroaryl;

each occurrence of R$^{20}$ is independently H, C$_1$-C$_{10}$ alkyl, C$_1$-C$_6$ haloalkyl, C$_1$-C$_6$ hydroxyalkyl, —(C$_1$-C$_3$ alkylene)$_m$-(C$_3$-C$_7$ cycloalkyl), —(C$_1$-C$_3$ alkylene)$_m$-(C$_6$-C$_{10}$ aryl), —(C$_1$-C$_3$ alkylene)$_m$-(4 to 7-membered heterocycloalkyl), —(C$_1$-C$_3$ alkylene)$_m$-(5- or 6-membered monocyclic heteroaryl) or —(C$_1$-C$_3$ alkylene)$_m$-(9- or 10-membered bicyclic heteroaryl), wherein said C$_3$-C$_7$ cycloalkyl group, said C$_6$-C$_{10}$ aryl group, said 4 to 7-membered heterocycloalkyl group, said -(5- or 6-membered monocyclic heteroaryl group or said 9- or 10-membered bicyclic heteroaryl group can be optionally substituted with R$^{26}$;

each occurrence of R$^{21}$ is independently H, C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, C$_3$-C$_7$ cycloalkyl, C$_3$-C$_7$ cycloalkenyl, 5- or 6-membered monocyclic heteroaryl, 9- or 10-membered bicyclic heteroaryl, —OR$^{20}$, —O—(C$_1$-C$_6$ haloalkyl) or —N(R$^{20}$)$_2$, wherein said C$_2$-C$_6$ alkenyl group, said C$_2$-C$_6$ alkynyl group, said C$_3$-C$_7$ cycloalkyl group, said C$_3$-C$_7$ cycloalkenyl group, said C$_6$-C$_{10}$ aryl group, said 5- or 6-membered monocyclic heteroaryl group and said 9- or 10-membered bicyclic heteroaryl group can be optionally substituted with up to five groups, each independently selected from C$_1$-C$_6$ alkyl, C$_2$-C$_6$ alkenyl, C$_2$-C$_6$ alkynyl, halo, —OR$^{20}$, —SR$^{20}$, C$_1$-C$_6$ haloalkyl, C$_1$-C$_6$ hydroxyalkyl, —O—(C$_1$-C$_6$ haloalkyl), —CN, —NO$_2$, —N(R$^{20}$)$_2$, —C(O)R$^{20}$, —C(O)OR$^{20}$, —C(O)N(R$^{20}$)$_2$ and —NHC(O)R$^{20}$;

R$^{22}$ represents from one to five substituent groups, each independently selected from C$_1$-C$_6$ alkyl, halo, —OR$^{20}$, —SR$^{20}$, C$_1$-C$_6$ haloalkyl, C$_1$-C$_6$ hydroxyalkyl, —O—(C$_1$-C$_6$ haloalkyl), —CN, —NO$_2$, —N(R$^{20}$)$_2$, —C(O)OR$^{20}$, —C(O)N(R$^{20}$)$_2$ and —NHC(O)R$^{20}$, or any two R$^{22}$ groups on adjacent ring carbon atoms can combine to form —O—R$^{23}$—O—;

R$^{23}$ is —[C(R$^{24}$)$_2$]$_n$—;

each occurrence of R$^{24}$ is independently H or C$_1$-C$_6$ alkyl;

each occurrence of R$^{25}$ is independently H, C$_1$-C$_6$ alkyl, C$_2$-C$_6$ alkenyl, C$_2$-C$_6$ alkynyl, C$_3$-C$_7$ cycloalkyl, —(C$_1$-C$_3$ alkylene)$_m$-(C$_6$-C$_{10}$ aryl), 4 to 7-membered heterocycloalkyl, 5- or 6-membered monocyclic heteroaryl or 9- or 10-membered bicyclic heteroaryl, wherein said C$_1$-C$_6$ alkyl group, said C$_2$-C$_6$ alkenyl group, said C$_2$-C$_6$ alkynyl group, said C$_3$-C$_7$ cycloalkyl group, said C$_6$-C$_{10}$ aryl group, said 4 to 7-membered heterocycloalkyl group, said -(5- or 6-membered monocyclic heteroaryl group or said 9- or 10-membered bicyclic heteroaryl group can be optionally substituted with $R^{26}$; or two $R^{25}$ groups, together with the common nitrogen atom to which they are attached, join to form a 4- to 7-membered heterocycloalkyl group;

$R^{26}$ represents from one to five substituent groups, each independently selected from $C_1$-$C_6$ alkyl, $C_2$-$C_6$ alkenyl, $C_2$-$C_6$ alkynyl, halo, —$OR^{27}$, —$SR^{27}$, $C_1$-$C_6$ haloalkyl, $C_1$-$C_6$ hydroxyalkyl, —O—($C_1$-$C_6$ haloalkyl), —CN, —$NO_2$, —$N(R^{27})_2$, —$C(O)OR^{27}$, —$C(O)N(R^{27})_2$ and —$NHC(O)R^{27}$;

each occurrence of $R^{27}$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_{10}$ alkylene)$_m$-(5- or 6-membered monocyclic heteroaryl) or —($C_1$-$C_3$ alkylene)$_m$-(9- or 10-membered bicyclic heteroaryl);

$R^{28}$ is H, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_7$ cycloalkyl, $C_3$-$C_7$ cycloalkenyl, 5- or 6-membered monocyclic heteroaryl, 9- or 10-membered bicyclic heteroaryl, —$OR^{20}$, —O—($C_1$-$C_6$ haloalkyl) or —$N(R^{20})_2$, wherein said $C_2$-$C_6$ alkenyl group, said $C_2$-$C_6$ alkynyl group, said $C_3$-$C_7$ cycloalkyl group, said $C_3$-$C_7$ cycloalkenyl group, said $C_6$-$C_{10}$ aryl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —$OR^{20}$, —$SR^{20}$, $C_1$-$C_6$ haloalkyl, $C_1$-$C_6$ hydroxyalkyl, —O—($C_1$-$C_6$ haloalkyl), —CN, —$NO_2$, —$N(R^{20})_2$, —$C(O)R^{20}$, —$C(O)OR^{20}$, —$C(O)N(R^{20})_2$ and —$NHC(O)R^{20}$;

each occurrence of $R^{29}$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -(5- or 6-membered monocyclic heteroaryl group or said 9- or 10-membered bicyclic heteroaryl group can be optionally substituted with $R^{26}$;

each occurrence of T is independently —S—, —O—, —SC(O)—, —SC(S)—, —OC(O)— and —OC(S)—;

each occurrence of m is independently 0 or 1; and
each occurrence of n is independently 1 or 2.

2. The compound of claim 1, wherein X is O.
3. The compound of claim 1, wherein B is:

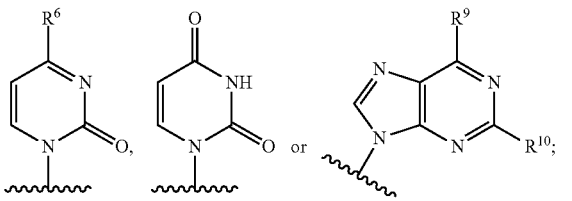

$R^6$ and $R^{10}$ are each independently —$NH_2$ or —$NHC(O)CH_3$; and $R^9$ is —OH or —O—($C_1$-$C_6$ alkyl).

4. The compound of claim 1, wherein $R^3$ is methyl.

5. The compound of claim 1 having the formula:

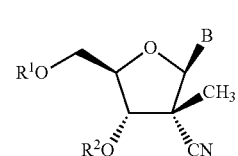

(Ia)

or a pharmaceutically acceptable salt thereof, wherein:

B is:

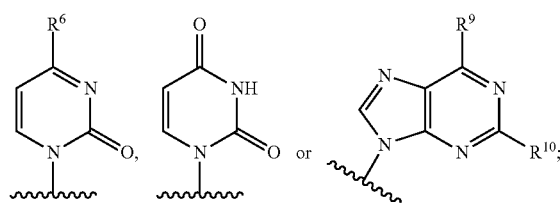

$R^1$ is H,

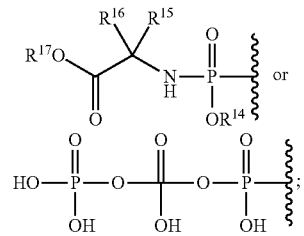

$R^2$ is H, or $R^1$ and $R^2$ join to form a group having the formula:

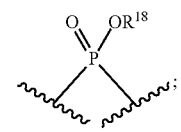

$R^6$ and $R^{10}$ are each independently —$N(R^{20})_2$;
$R^9$ is —OH or —O—($C_1$-$C_6$ alkyl);
$R^{14}$ is $C_6$-$C_{10}$ aryl, which can be optionally substituted with a halo group;
$R^{15}$ and $R^{16}$ are each independently H or $C_1$-$C_6$ alkyl;
$R^{17}$ is $C_1$-$C_6$ alkyl;
$R^{18}$ is $C_1$-$C_6$ alkyl, $C_3$-$C_7$ cycloalkyl or $C_6$-$C_{10}$ aryl; and
each occurrence of $R^{20}$ is independently H or —C(O)—($C_1$-$C_6$ alkyl).

6. The compound of claim 1 having the formula:

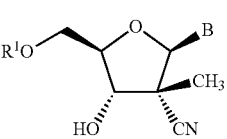

(Ib)

or a pharmaceutically acceptable salt thereof, wherein:

B is:

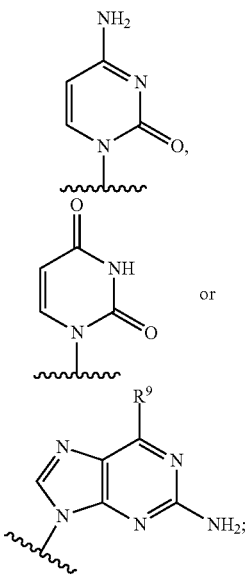

R¹ is:

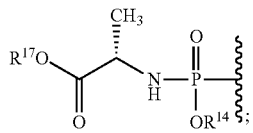

R⁹ is —OH or —O—($C_1$-$C_6$ alkyl);
R14 is phenyl, which can be optionally substituted with up to 2 halo groups, which can be the same or different; and
$R^{17}$ is $C_1$-$C_6$ alkyl.

7. The compound of claim 1 having the formula:

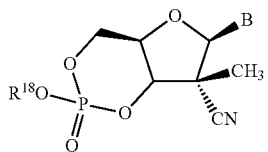 (Ic)

or a pharmaceutically acceptable salt thereof,
wherein:

B is:

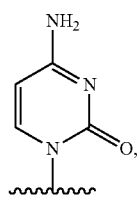

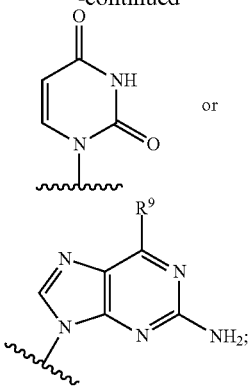

$R^9$ is —OH or —O—($C_1$-$C_6$ alkyl); and
$R^{18}$ is aryl or $C_1$-$C_6$ alkyl.

8. The compound of claim 1 having the formula:

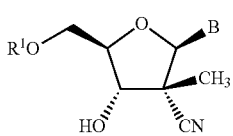 (Id)

or a pharmaceutically acceptable salt thereof,
wherein:

B is:

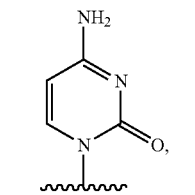

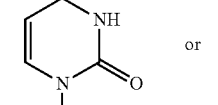

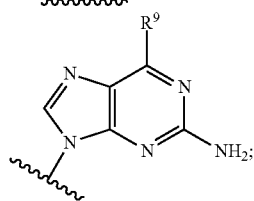

R¹ is:

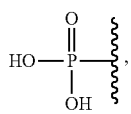

-continued

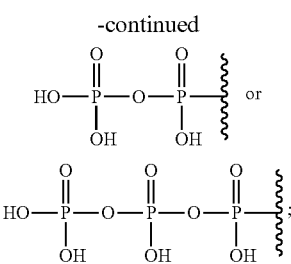

and

R$^9$ is —OH or —O—(C$_1$-C$_6$ alkyl).

9. The compound of claim 1, wherein B is:

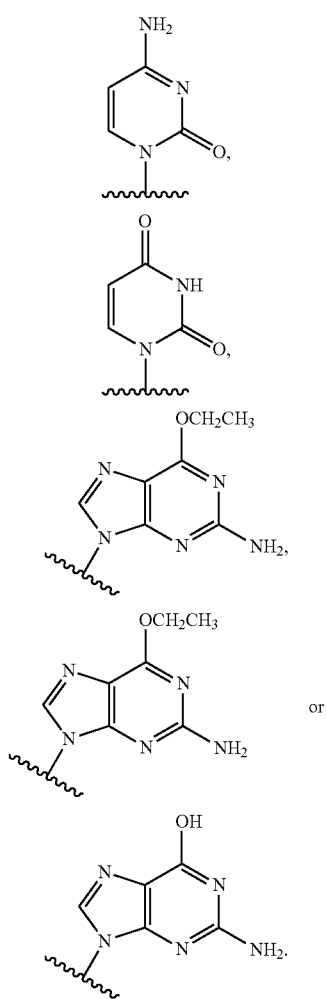

10. The compound of claim 1, wherein R$^1$ is H or

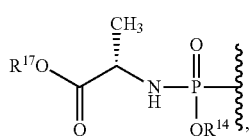

or R$^1$ and R$^2$ join to form a group having the formula:

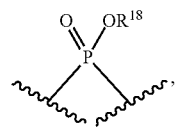

wherein R$^{14}$ is C$_6$-C$_{10}$ aryl, which can be optionally substituted as set forth in claim 1; R$^{17}$ is C$_1$-C$_6$ alkyl; and R$^{18}$ is C$_1$-C$_6$ alkyl, C$_3$-C$_7$ cycloalkyl or C$_6$-C$_{10}$ aryl.

11. The compound of claim 1, wherein R$^1$ is

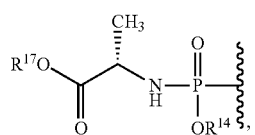

wherein R$^{14}$ is naphthyl or phenyl, which can be optionally substituted with F or Cl; and R$^{17}$ is methyl, ethyl, isopropyl, n-butyl or neopentyl.

12. The compound of claim 7, wherein R$^{18}$ is C$_1$-C$_6$ alkyl.

13. The compound of claim 1, wherein R$^1$ and R$^2$ join to form a group having the formula:

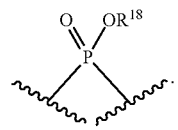

14. The compound of claim 1 being one of the compounds numbered 1-243 in the above specification.

15. The compound of claim 1 having the structure:

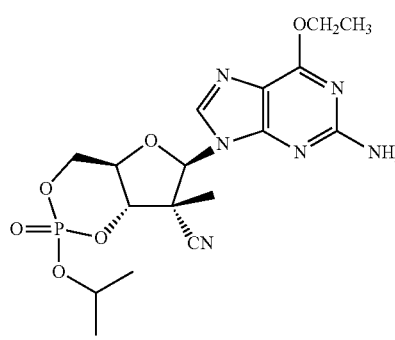

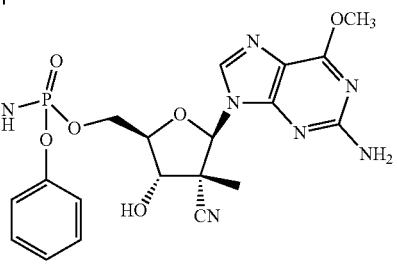

255
-continued

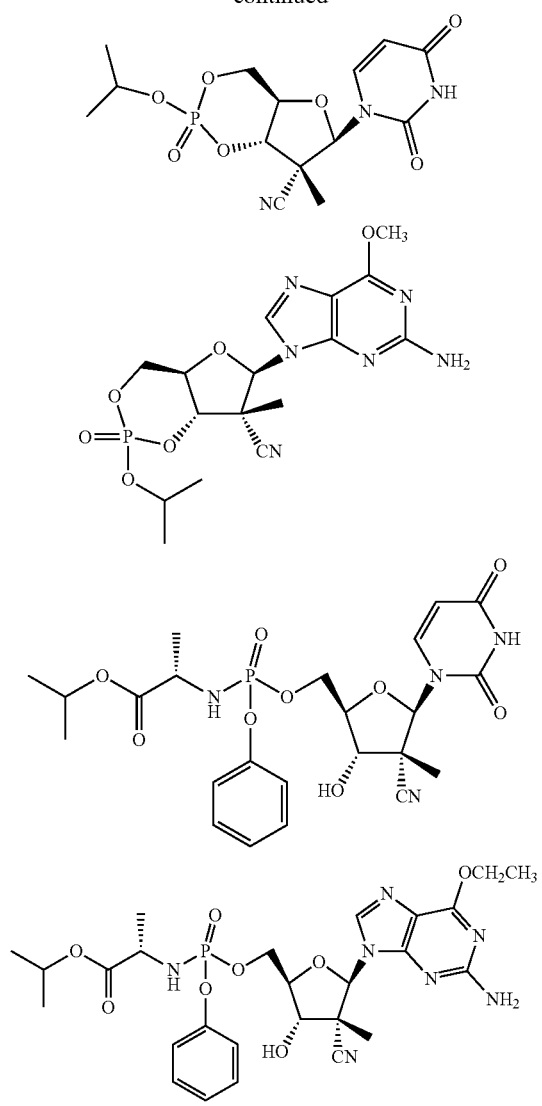

256
-continued

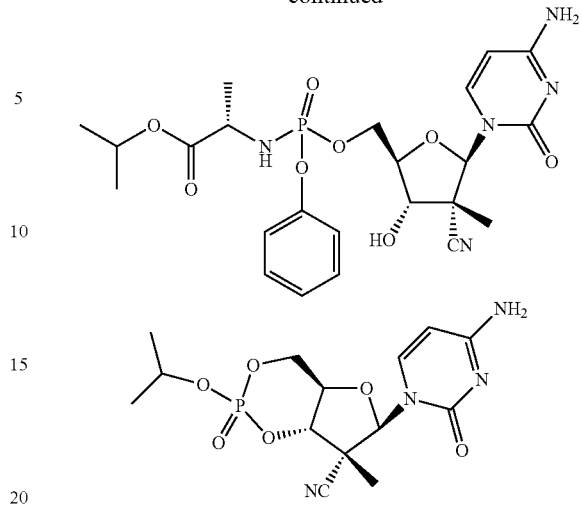

or a pharmaceutically acceptable salt thereof.

16. A pharmaceutical composition comprising an effective amount of the compound of claim 1, or a pharmaceutically acceptable salt thereof, and a pharmaceutically acceptable carrier.

17. The pharmaceutical composition according to claim 16, further comprising a second therapeutic agent selected from the group consisting of HCV antiviral agents, immuno-modulators, and anti-infective agents.

18. The pharmaceutical composition according to claim 17, further comprising a third therapeutic agent selected from the group consisting of HCV protease inhibitors, HCV NS5A inhibitors and HCV NS5B polymerase inhibitors.

19. A method of treating a patient infected with HCV comprising the step of administering an amount of the compound according to claim 1 effective to treat infection by HCV in said patient.

20. The method according to claim 19, further comprising the step of administering pegylated-interferon alpha and an HCV protease inhibitor to said patient.

21. The method according to claim 19, further comprising the step of administering ribavirin to said patient.

* * * * *

SEQUENCE LISTING

<160> NUMBER OF SEQ ID NOS: 9

<210> SEQ ID NO 1
<211> LENGTH: 17
<212> TYPE: DNA
<213> ORGANISM: Artificial Sequence
<220> FEATURE:
<223> OTHER INFORMATION: 5B.2F Primer

<400> SEQUENCE: 1
atggacaggc gccctga                                                17

<210> SEQ ID NO 2
<211> LENGTH: 20
<212> TYPE: DNA
<213> ORGANISM: Artificial Sequence
<220> FEATURE:
<223> OTHER INFORMATION: 5B.2R Primer

<400> SEQUENCE: 2
ttgatgggca gcttggtttc                                             20

<210> SEQ ID NO 3
<211> LENGTH: 17
<212> TYPE: DNA
<213> ORGANISM: Artificial Sequence
<220> FEATURE:
<223> OTHER INFORMATION: FAM labeled probe

<400> SEQUENCE: 3
cacgccatgc gctgcgg                                                17

<210> SEQ ID NO 4
<211> LENGTH: 20
<212> TYPE: DNA
<213> ORGANISM: Artificial Sequence
<220> FEATURE:
<223> OTHER INFORMATION: F3212, forward primer

<400> SEQUENCE: 4
cacccaagaa cagggtttgt                                             20

<210> SEQ ID NO 5
<211> LENGTH: 21
<212> TYPE: DNA
<213> ORGANISM: Artificial Sequence
<220> FEATURE:
<223> OTHER INFORMATION: R3319, reverse primer

<400> SEQUENCE: 5
tggccatggg tatgttgtta a                                           21

<210> SEQ ID NO 6
<211> LENGTH: 19
<212> TYPE: DNA
<213> ORGANISM: Artificial Sequence
<220> FEATURE:
<223> OTHER INFORMATION: FAM-TAMRA labeled probe 1

<400> SEQUENCE: 6
ttaccgggct ctgccatct                                              19

<210> SEQ ID NO 7
<211> LENGTH: 17
<212> TYPE: DNA
<213> ORGANISM: Artificial Sequence

```
<220> FEATURE:
<223> OTHER INFORMATION: COX II, forward primer

<400> SEQUENCE: 7
tgcccgccat catccta                                              17

<210> SEQ ID NO 8
<211> LENGTH: 23
<212> TYPE: DNA
<213> ORGANISM: Artificial Sequence
<220> FEATURE:
<223> OTHER INFORMATION: COX II, reverse primer

<400> SEQUENCE: 8
cgtctgttat gtaaaggatg cgt                                       23

<210> SEQ ID NO 9
<211> LENGTH: 21
<212> TYPE: DNA
<213> ORGANISM: Artificial Sequence
<220> FEATURE:
<223> OTHER INFORMATION: FAM-TAMRA labeled probe 2

<400> SEQUENCE: 9
tcctcatcgc cctcccatcc c                                         21
```